United States Patent
Burgard et al.

(10) Patent No.: US 9,982,281 B2
(45) Date of Patent: May 29, 2018

(54) MICROORGANISMS FOR PRODUCING 1,3-BUTANEDIOL AND METHODS RELATED THERETO

(71) Applicant: Genomatica, Inc., San Diego, CA (US)

(72) Inventors: Anthony P. Burgard, Bellefonte, PA (US); Mark J. Burk, San Diego, CA (US); Robin E. Osterhout, San Diego, CA (US); Jun Sun, San Diego, CA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days. days.

(21) Appl. No.: 14/692,630

(22) Filed: Apr. 21, 2015

(65) Prior Publication Data
US 2016/0076060 A1   Mar. 17, 2016

Related U.S. Application Data

(63) Continuation of application No. 13/528,593, filed on Jun. 20, 2012, now abandoned.

(60) Provisional application No. 61/502,702, filed on Jun. 29, 2011, provisional application No. 61/500,131, filed on Jun. 22, 2011.

(51) Int. Cl.
*C12P 7/18* (2006.01)
*C12N 15/52* (2006.01)

(52) U.S. Cl.
CPC .............. *C12P 7/18* (2013.01); *C12N 15/52* (2013.01)

(58) Field of Classification Search
CPC .................................. C12P 7/18; C12N 15/52
See application file for complete search history.

(56) References Cited

U.S. PATENT DOCUMENTS

| | | | | |
|---|---|---|---|---|
| 8,048,661 B2* | 11/2011 | Burgard | ............... | C12N 9/0006 435/183 |
| 8,268,607 B2* | 9/2012 | Burgard | ................. | C12N 15/52 435/158 |
| 8,445,244 B2* | 5/2013 | Burgard | ............... | C12N 9/0008 435/183 |
| 8,637,286 B2* | 1/2014 | Burgard | ............... | C12N 9/0008 435/183 |
| 9,017,983 B2* | 4/2015 | Burgard | ................. | C12N 15/52 435/158 |
| 9,284,581 B2* | 3/2016 | Burgard | ................. | C12N 15/52 |
| 2010/0330635 A1* | 12/2010 | Burgard | ................. | C12N 15/52 435/158 |
| 2011/0129899 A1* | 6/2011 | Haselbeck | ................ | C12P 7/18 435/243 |
| 2011/0129904 A1* | 6/2011 | Burgard | ................. | C12N 15/52 435/252.33 |

FOREIGN PATENT DOCUMENTS

WO   WO 2010/127319   * 11/2010

OTHER PUBLICATIONS

Ramos-Vera et al. Autotrophic Carbon Dioxide Assimilation in Thermoproteales Revisited J. Bacteriol. (2009), vol. 191(13), pp. 4286-4297.*
Kopke et al. 2,3-butanediol production by acetogenic bacteria, an alternative route to chemical synthesis, using industrial waste gas., Applied and Environmental Microbiology (Epub Jun. 17, 2011), vol. 77, pp. 5467-5475.*

* cited by examiner

*Primary Examiner* — Anand Desai
(74) *Attorney, Agent, or Firm* — Jones Day

(57) ABSTRACT

Provided herein is a non-naturally occurring microbial organism having a 1,3-butanediol (1,3-BDO) pathway and comprising at least one exogenous nucleic acid encoding a 1,3-BDO pathway enzyme expressed in a sufficient amount to produce 1,3-BDO. In some embodiments, the pathway includes reducing equivalents from CO or hydrogen. In certain embodiments, a 1,3-BDO pathway proceeds by way of central metabolites pyruvate, succinate or alpha-ketoglutarate. Also provided herein is a method for producing 1,3-BDO, includes culturing such microbial organisms under conditions and for a sufficient period of time to produce 1,3-BDO.

14 Claims, 24 Drawing Sheets

ATGGCAGTGGATTCACCGGATGAGCGGCTACAGCGCCGCATTGCACAGTTGTTTGCAGAAGATG
AGCAGGTCAAGGCCGCACGTCCGCTCGAAGCGGTGAGCGCGGCGGTGAGCGCGCCCGGTATGCG
GCTGGCGCAGATCGCCGCCACTGTTATGGCGGGTTACGCCGACCGCCCCGGCCGCCGGGCAGCGT
GCGTTCGAACTGAACACCGACGACGCGACGGGCCGCACCTCGCTGCGGTTACTTCCCCGATTCG
AGACCATCACCTATCGCGAACTGTGGCAGCGAGTCGGCGAGGTTGCCGCGGCCTGGCATCATGA
TCCCGAGAACCCCTTGCGCGCAGGTGATTTCGTCGCCCTGCTCGGCTTCACCAGCATCGACTAC
GCCACCCTCGACCTGGCCGATATCCACCTCGGCGCGGTTACCGTGCCGTTGCAGGCCAGCGCGG
CGGTGTCCCAGCTGATCGCTATCCTCACCGAGACTTCGCCGCGGCTGCTCGCCTCGACCCCGGA
GCACCTCGATGCGGCGGTCGAGTGCCTACTCGCGGGCACCACACCGGAACGACTGGTGGTCTTC
GACTACCACCCCGAGGACGACGACCAGCGTGCGGCCTTCGAATCCGCCCGCCGCCGCCCTTGCCG
ACGCGGGCAGCTTGGTGATCGTCGAAACGCTCGATGCCGTGCGTGCCCGGGGCCGCGACTTACC
GGCCGCGCCACTGTTCGTTCCCGACACCGACGACGACCCGCTGGCCCTGCTGATCTACACCTCC
GGCAGCACCGGAACGCCGAAGGGCGCGATGTACACCAATCGGTTGGCCGCCACGATGTGGCAGG
GGAACTCGATGCTGCAGGGGAACTCGCAACGGGTCGGGATCAATCTCAACTACATGCCGATGAG
CCACATCGCCGGTCGCATATCGCTGTTCGGCGTGCTCGCTCGCGGTGGCACCGCATACTTCGCG
GCCAAGAGCGACATGTCGACACTGTTCGAAGCATCGGCTTGGTACGTCCCACCGAGATCTTCT
TCGTCCCGCGCGTGTGCGACATGGTCTTCCAGCGCTATCAGAGCGAGCTGGACGGCGCTCGGT
GGCGGGCGCCGACCTGGACACGCTCGATCGGGAAGTGAAAGCCGACCTCCGGCAGAACTACCTC
GGTGGGCGCTTCCTGGTGGCGGTCGTCGGCAGCGCGCCCGCTGGCCGCGGAGATGAAGACGTTCA
TGGAGTCCGTCCTCGATCTGCCACTGCACGACGGGTACGGGTCGACCGAGGCGGGCGCAAGCGT
GCTGCTCGACAACCAGATCCAGCGGCCGCCGGTGCTCGATTACAAGCTCGTCGACGTGCCCGAA
CTGGGTTACTTCCGCACCGACCGGCCGCATCCGCGCGGTGAGCTGTTGTTGAAGGCGGAGACCA
CGGATTCCGGGCTACTACAAGCGGCCCGAGGTCACCGCGGAGATCTTCGACGAGGACGGCTTCTA
CAAGACCGGCGATATCGTGGCCGAGCTCGAGCACGATCGGCTGGTCTATGTCGACCGTCGCAAC
AATGTGCTCAAACTGTCGCAGGGCGAGTTCGTGACCGTCGCCCATCTCGAGGCCGTGTTCGCCA
GCAGCCCGCTGATCCGGCAGATCTTCATCTACGGCAGCAGCGAACGTTCCTATCTGCTCGCGGT
GATCGTCCCCACCGACGACGCGCTGCGCGGCCGCGACACCGCCACCTTGAAATCGGCACTGGCC
GAATCGATTCAGCGCATCGCCAAGGACGCGAACCTGCAGCCCTACGAGATTCCGCGCGATTTCC
TGATCGAGACCGAGCCGTTCACCATCGCCAACGGACTGCTCTCCGGCATCGCGAAGCTGCTGCG
CCCCAATCTGAAGGAACGCTACGGCGCTCAGCTGGAGCAGATGTACACCCGATCTCGCGACAGGC
CAGGCCGATGAGCTGCTCGCCCTGCGCCGGCGAAGCCGCCGACCTGCCGGTGCTCGAAACCGTCA
GCCGGGCAGCGAAAGCGATGCTCGGCGTCGCCTCCGCCGATATGCGTCCCGACGCGCACTTCAC
CGACCTGGGCGGCGATTCCCTTTCCGCGCTGTCGTTCTCGAACCTGCTGCACGAGATCTTCGGG
GTCGAGGTGCCCGGTGGGTGTCGTCGTCAGCCCGGCGAACGAGCTGCGCGATCTGGCGAATTACA
TTGAGGCGGAACGCAACTCGGCGCGGAAGCGTCCCACCTTCACCTCGGTGCACGGCGGCGGTTC
CGAGATCCGCGCCGCCGATCTGACCCTCGACAAGTTCATCGATGCCCGCACCCTGGCCGCCGCC
GACAGCATTCCGCACGCGCCGGTGCCAGCGCAGACGGTGCTGCTGACCGGCGCGAACGGCTACC
TCGGCCGGTTCCTGTGCCTGGAATGGCTGGAGCGGCTGGACAAGACGGGTGGCACGCTGATCTG
CGTCGTGCGCGGTAGTGACGCGGCCGCGGCCCGTAAACGGCTGGACTCGGCGTTCGACAGCGGC
GATCCCGGCCTGCTCGAGCACTACCAGCAACTGGCCGCACGGACCCTGGAAGTCCTCGCCGGTG
ATATCGGCGACCCGAATCTCGGTCTGGACGACGCGACTTGGCAGCGGTTGGCCGAAACCGTCGA
CCTGATCGTCCATCCCGCCGCGTTGGTCAACCACGTCCTTCCCTACACCCAGCTGTTCGGCCCC

FIG. 12A

```
AATGTCGTCGGCACCGCCGAAATCGTCCGGTTGGCGATCACGGCGCGGCGCAAGCCGGTCACCT
ACCTGTCGACCGTCGGAGTGGCCGACCAGGTCGACCCGGCGGAGTATCAGGAGGACAGCGACGT
CCGCGAGATGAGCGCGGTGCGCGTCGTGCGCGAGAGTTACGCCAACGGCTACGGCAACAGCAAG
TGGGCGGGGGAGGTCCTGCTGCGCAAGCACACGATCTGTGTGGCTTGCCGGTCGCGGTGTTCC
GTTCGGACATGATCCTGGCGCACAGCCGGTACGCGGGTCAGCTCAACGTCCAGGACTGTTCAC
CCGGCTGATCCTCAGCCTGGTCGCCACCGGCATCGCGCCGTACTCGTTCTACCGAACCGACGCG
GACGGCAACCGGCAGCGGGCCCACTATGACGGCTTGCCGGCGGACTTCACGGCGGCGGCGATCA
CCGCGCTCGGCATCCAAGCCACCGAAGGCTTCCGGACCTACGACGTGCTCAATCCGTACGACGA
TGGCATCTCCCTCGATGAATTCGTCGACTGGCTCGTCGAATCCGGCCACCCGATCCAGCGCATC
ACCGACTACAGCGACTGGTTCCACCGTTTCGAGACGGCGATCCGCGCGCTGCCGGAAAAGCAAC
GCCAGGCCTCGGTGCTGCCGTTGCTGGACGCCTACCGCAACCCCTGCCCGGCGGTCCGGCGGCGC
GATACTCCCGGCCAAGGGAGTTCCAAGCGGCGGTGCAAACAGCCAAAATCGGTCCGGAACAGGAC
ATCCCGCATTTGTCCGCGCCACTGATCGATAAGTACGTCAGCGATCTGGAACTGCTTCAGCTGC
TCTAA
```

FIG. 12A, cont.

```
mavdspderlqrriaqlfaedeqvkaarpleavsaavsapgmrlaqiaatvmagyadrpaagqr
afelntddatgrtslrllprfetityrelwqrvgevsaawhhdpenplragdfvallgftsidy
atldladihlgavtvplqassavsqliailtetsprllastpehldaaveellagttperlvvf
dyhpedddqrsafesarrrladagslvivetldavrargrdlpaaplfvpdtdddplalliyts
gstgtpkgamytnrlaatmwqgnsmiggnsqrvginlnympmshiagrislfgvlarggtayfa
aksdmstlfediglvrpteiffvprvcdmvfqryqseldrrsvagadldtldrevkadlrqnyl
ggrflvavvgsaplasemktfmssvldlplhdgygsteaqasvlldnqiqrppvldyklvdvpe
lgyfrtdrphprgelllkaettipgyykrpevtaeifdedgfyktgdivaelehdrlvyvdrrn
nvlklsqgefvtvahleavfassplirqifiygssersyllavivptddalrgrdtatlksala
esiqriakdanlqpyeiprdflietspftiangllsgiakllrpnlkerygaqleqmytdlatq
qadellalrreaadlpvletvsraakamlqvasadmrpdahftdlggdslsalsfsnllheifg
vevpvgvvvspanelrdlanyiesernsqakrptftsvhgqqseiraadltldkfidartlaaa
dsiphapvpaqtvlltganqylqrflclewlerldktgqtlicvvrgsdasaarkrldsafdsq
dpgllehyqqlaartlevlagdigdpnlglddatwqrlaetvdlivhpaalvmhvlpytqlfgp
nvvgtaeivrlaitarrkpvtylstvgvadqvdpaeyqedsdvremsavrvvresyangygnsk
wagevllreahdlcglpvavfrsdmilahsryagqlnvqdvftrlilslvatgiapysfyrtda
dgnrqrahydglpadftaaaitalgiqategfrtydvlnpyddgisldefvdwlvesghpiqri
tdysdwfhrfetairalpekgrqasvlplldayrnpcpavrgailpakefqaavqtakigpeqd
iphlsaplidkyvsdlellqll*
```

FIG. 12B

```
ATGATTGAAACCATTCTGCCTGCAGGCGTTGAAAGCGCAGAACTGCTGGAATATCCGGAAGATC
TGAAAGCACATCCGGCAGAAGAACATCTGATTGCCAAAAGCGTTGAAAAACGTCGTCGTGATTT
TATTGGTGCACGTCATTGTGCACGTCTGGCACTGGCAGAACTGGGTGAACCTCCGGTTGCAATT
GGTAAAGGTGAACGTGGTGCACCGATTTGGCCTCGTGGTGTTGTTGGTAGCCTGACCCATTGTG
ATGGTTATCGTGCAGCAGCAGTTGCACATAAAATGCGCTTTCGCAGCATTGGTATTGATGCAGA
ACCGCATGCAACCCTGCCGGAAGGTGTTCTGGATAGCGTTAGCCTGCCGCCGGAACGTGAATGG
CTGAAAACCACCGATAGCGCACTGCATCTGGATCGTCTGCTGTTTTGTGCAAAAGAAGCCACCT
ATAAAGCCTGGTGGCCGCTGACAGCACGTTGGCTGGGTTTTGAAGAAGCCCATATTACCTTTGA
AATTGAAGATGGTAGCGCAGATAGCGGTAATGGCACCTTTCATAGCGAACTGCTGGTTCCGGGT
CAGACCAATGATGGTGGTACACCGCTGCTGAGCTTTGATGGTCGTTGGCTGATTGCAGATGGTT
TTATTCTGACCGCAATTGCCTATGCCTAA
```

FIG. 13A

```
mietilpagvesaelleypedlkahpaeehliaksvekrrrdfigarhcarlalaelgeppvai
gkgergapiwprgvvgslthcdgyraaavahkmrfrsigidaephatlpegvldsvslpperew
lkttdsalhldrllfcakeatykawwpltarwlgfeeahitfeiedgsadsgngtfhsellvpg
qtndggtpllsfdgrwliadgfiltaiaya*
```

FIG. 13B atgaccagcgatgttcacgacgccacagacggcgtcaccgaaaccgcactcgacgacgagcagtcgacccgccgcat
cgccgagctgtacgccaccgatcccgagttccgcgccgccgcaccgttgcccgccgtggtcgacgcggcgcacaaac
ccgggctgcggctggcagagatcctgcagacctgttcaccggctacggtgacgccggcgctgggatacgcgcc
cgtgaactggccacgacgagggcgggcgcaccgtgacgcgtctgctgccgcggttcgacaccctcacctacgcca
ggtgtggtcgcgcgtgcaagcggtcgcgcgggccctgcgccacaacttcgcgcagcgatctaccggcgacgccg
tcgcacgatcggtttcgcgagtccgattacctgacgctggatctcgtatgcgcctacctggcctcgtgagtgtt
ccgctgcagcacaacgcaccggtcagccggctcgcccgatcctggccgaggtcgaaccgcggatcctcaccgtgag
cgccgaatccctcgacctgcagtcgaatccgtgcgggacgtcaactcggtgtcgcagctcgtggtgttcgaccatc
acccggaggtcgacgaccacgcgacgactggccgcgcgcgtgaacaactcgccggcaagggcatcgccgtcacc
accctggacgcgatcgccgacgaggcgccggctgccggccgaaccgatctacaccgccgaccatgatcagcgct
cgcgatgatcctgtacacctcgggttccacggcgcacccaagggtgcgatgtacaacgaggcgatggtggcgcggc
tgtggaccatgtcgttcatcacgggtgacccacgccggtcatcaacgtcaacttcatgccgtcaaccacctggc
gggcgcatcccccatttccaccgccgtgcagaacgtggaaccagttacttcgtaccggaatccgacatgtccacgct
gttcgaggatctcgcgctggtgcccgaccgaactcggctggttccgcgcgtcgcgacatgctctaccagcacc
acctcgccaccgtcgacgcctggtcacgcagggcgccgacgaactgaccgccgagaagcaggccggtgccgaactg
cgtgagcaggtgctcggcgacgcgtgatcaccggattcgtcagcaccgcaccgctggccgcggagatgaggcgtt
cctcgacatcaccctgggcgcacacatcgtcgacggctacgggctcaccgagacggcgccgtgacacgcgacggtg
tgatcgtgcggccaccggtgatcgactacaagctgatcgacgttccgaactcggctacttcagcaccgacaagcc
taccgcgtggcgaactgctggtcaggtcgcaaacgctgactcccgggtactacaagcgccgaggtcaccgcgag
cgtcttcgacggggacggctactaccacaacggcgacgtcatggccgagacggcacccgaccacctggtgtacgtgg
accgtcgcaacaacgtcctcaaactcgcgcagggcgagttcgtggcggtcgccaactggagggcgtgttctcggc
gcgggcgctggtgcgccagatcttcgtgtacggcaacagcgagcgcagtttccttctggccgtggtggtccgacgcc
ggaggcgctcgagcagtacgatcggccgccgctcaaggccgcgctggccgactcgctgcagcgcaccgcacgcacg
ccgaactgcaatcctacgaggtgccggccgatttcatcgtcgagaccgagccgttcagccgcgcaacgggctgctg
tgggtgtcggaaaactgctgcggcccaacctcaaagaccgctacgggcagcgcctggagcagatgtacgcgatat
cgcggccacgcaggccaaccagttgcgcgaactgcggcgcgcgggcgcacacaacggtgatcgacaccctcaccc
aggccgctgccacgatcctcggcaccgggagcgaggtggcatccgacgccacttcaccgacctggggcgggattcc
ctgtcggcgctgacactttcgaacctgctgagcgattcttcggtttcgaagttccgtcggcaccatcgtgaacc
ggccaccaacctcgcccaactcgccagcacatcgaggcgcagcgcaccgcgggtgaccgcaggccgagtttcacca
ccgtgcacggcgcggacgccaccgagatccgggcgagtgagctgaccctggacaagttcatcgacgccgaaacgctc
cgggccgcacccgggtctgccccaaggtcaccaccgagccaacggacggtgttgctctcgggcgccaacggctggctggg
ccggttcctcacgtgcagtggctgaacgcctggcacctcggcgcgcaccctcatcacgatcgtgcggggccgcg
acgacgccgcggcccgcgcacggctgaccaggcctacgacaccgatcccgagttgtccgccgcttcgcgagctg
gccgaccgccacctcgggtggtcgccggtgacatcggcgacccgaatctgggcctcacaccgagatctggcaccg
gctcgccgcgaggtcgacctggtggtgcatccgcagcgctggtcaaccacgtgctccctacggcagctgttcg
gcccaaacgtcgtgggcacggccgaggtgatcaagctggccctcacgaacggatcaagccgtcacgtacctgtcc
accgtgtcggtggccatggggatcccgacttcgaggaggacggcgacatccggacgtgagccggtgcgcccgct
cgaccgggatacgccaacggctacgcaacagcaagtggccggcgaggtgctgctgggaggccaccgatctgt
gcgggctgcccgtggcgacgttccgctcggacatgatcctggcgcatccgcgctacgcggtcaggtcaacgtgcca
gacatgttcacgcgactcctgttgagcctcttgatcaccggcgtcgcgcgcggtcgttctacatcggagacggtga
gcgccgcgggcgcactaccccgcctgacggtcgatttcgtggccgagcggtcacgacgctcggcgcgcagcag
gcgacggatacgtgtcctacgacgtgatgaaccgcacgacgacgggatctcctggatgtgttcgtcgactggctg
atccgggcgggccatccgatcgaccgggtcgacgactacgacgactgggtcgcgtggttcgagaccgcgttgaccgc
gcttcccgagaagcgccgcgcacagaccgtactgcgcgctgctgcacgcgttcgcgctcccggcaccgttgcgcg
gcgcaccgaacccacggaggtgttccacgccgcgggtgcgcaccgcgaaggtggcccgggagacatccgccacctc
gacgaggcgctgatcgacaagtacatacgcgatctgcgtgagttcggtctgatctaa MTSDVHDATDGVTETALDDEQSTRRIAELYATDPEFAAAAPLPAVVDAAHKPGLRLAEILQTLFTGYGDRPALGYRA
RELATDEGGRTVTRLLPRFDTLTYAQVWSRVQAVAAALRHNFAQPIYPGIAVATIGFASPDYLTLDLVCAYLGLVSV
PLQHNAPVSRLAPILAEVEPRILPVSAEYLELAVESVRDVNSVSQLVVFTSHHPEVDIHRDALARAREQLASKGIAVT
TLDAIADEGAGLPAEFIYTADHDQRLAMILYTSGSTSAPKGAMYTEAMVARLWTMSFITGDPTPVINVNFMPLNHLG
GRIPISTAVQMKGTSYFVPESDMSTLFEDLALVRPTELGLVPRVADMLYQHHLATVDRLVTQGADELTAEKQAGAEL
REQVLGGRVITGFVSTAPLAAEMRAFLDITLGAHIVDGYGLTETGAVTRDGVIVRPPVIDYKLIDVPELGYFSTDKP
YPRGELLVRSQTLTFGYYKRPEVTASVFDRDGYYHTGDVMAETAPDHLVYVDRRNNVLKLAQGEFVAVANLEAVFSG
AALVRQIFVYGNSERSFLLAVVVPTPEALEQYDPAALKAALADSLQRTAEDAELQSYEVPADFIVETEPFSAANGLL
SGVGKLLRPNLEDRYGQRLEQMYADIAATQANGLRELRRAAATQPVIDTLTQAAATILGTGSEVASDAHFTDLGGDS
LSALTLSNLLSDFFGFEVPVGTIVNPATNLAQLAQHIEAQRTAGDRRPSFTTVHGADATEIRASELTLDKFIDAETL
RAAPGLPKVTTEPRTVLLSGANGWLGRFLTLQWLERLAPVGGTLITIVRGKDAAARARLTQAYDTDPELGSRFAEL
ADRHLRVVAGDIGDPNLGLTPEINHRLAAEVDLVVHPAALVNHVLFYRQLFGPNVVGTAEVIKLALTERIKPVTYLS
TVSVAMGIPDFEEDGDIRTVSPVRPLDGGYANGYGNSKWAGEVLLREAHDLGGLPVATFRSDMILAHPRYRGQVNVP
DMFTRLLLSLLITSVAPRSFYIGDGERPRAHYPGLTVDFVAEAVTTLGSQQREGYVSYDVMNPHDDGISLDVFVDWL
IRAGHPIDRVDDYTDWVRKFETALTALPEKRRAQTVLPLLHAFRAPQAPLRGAPEPTEVFHAAVRTAKVGPGDIPHL
DEALIDKYIRDLRRFGLI

FIG. 14B

```
atgtcgactgccacccatgacgaacgactcgacgtcgcgtccacgaactcatcgccaccgacccgcaattcgcgc
cgcccaaccgaccggcgatcaccgccgccctcgaacagcccggctgcggctgccgcagatcatccgcaccgtgc
tcgacggctacgcgaccggccggcgctgggacagcgcgtggtggagttcgtcacggacgccaagaccggggcacg
tcggcgcagctgctccccgcttcgagaccatcacgtacagcgaagtagcgcagcgtgttccggcgctgggccgcgc
cctgtccgacgacgcggtgcacccggcgacccggtgtgcgtgctcggcttcaacagcgtcgactacgccaccatcg
acatggcgctgggcgccatcggcgccgtctcggtgccgctgcagaccagcgcggcaatcagctcgctgcagccgatc
gtggccgagaccgagcccaccctgatcgcgtccagcgtgaaccagctgtccgacgcggtgcagctgatcaccggcgc
cgacaggcgccaccggctggtggtgttcgactaccacccgcaggtcgacgaccagcgcgaggccgtccaggacg
ccgcggcggcgctgtccagcaccggcgtgccgtccagacgctggccgagctgctggagcgccggcaaggacctgccc
gccgtcgcggagccgccgccgacgaggactcgctggccctgctgatctacacctccgggtccacggcgcgcccaa
gggcgcgatgtaccacagagcaacgtcggcaagatgtggcgcgcggcagcaagaactggttcggcgagagcgcg
cgtcgatcacccctgaacttcatgccgatgagccaagtcgatgggccgaagcatcctctacggcacgctgggcaacggc
ggcaccgcctactcgccgccgcagcgacctgtccacccctgcttgaggacctcgagctggtgcggcccaccgagct
caacttcgtccgcgggatctgggagacgctgtacggcgaattccaccgtcaggtcgagcggcggctctccgaggcg
ggacgccgggcgaacgtcgcgcgcgtcgagccgaggtgctggccgagcagcgcagtacctgctggcgggcggtc
accttcgcgatgacgggctcggcgcccatctcgccggagctgcgcaactgggtcgagtcgctgctcgaaatgcacct
gatggacggctacggctccaccgaggccggaatggtgttgttcgacgggagattcagcgcccgccggtgatcgact
acaagctggtcgacgtgccggacctgggctacttcagcacgacccggcgcatccgcgcggcgagctgctgctgcgc
accgagaacatgttccggggctactacaagcgggccgaaaccaccgcgggcgtcttcgacgaggacggctactaccg
caccggcgacgtgttcgccgagatcgcccggaccggctggtctacgtcgacgcgcaacaacgtgctcaagctgg
cgcaggggcgaattcgtcacgctgcgcaagctggagcggtgttcggcaacagcccgctgatccgccagatctacgtc
tacggcaacagcgcccagcccctacctgctgcggtcgtggtgccccaccgaggaggcgctggcctcgggtgacccga
gacgctcaagcccaagatcgccgactcgctgcagcaggtcgccaagaggccggcctgcagctcctacgaggtgccgc
gcgacttcatcatcgagaccacccgttcagcctggaaaacggtctgctgaccgggatccggaagctggcgtggccg
aaactgaagcagcactacggggaacggctggagcagatgtacgccgacctggccgccgacaggccaacgagctggc
cgagctgcgccgcaacggtgccaggcgccggtgttcagacgtgagccgccgcgggcgccatgctgggttcgg
ccgcctccgacctgtccccgacgccccacttcacgatctcggccgagactcgttgtccgcggttgacattcggcaac
ctgctgcgcgagatcttcgacgtcgacgtgccggtaggcgtgatcgtcagcccggccaacgacctggcggccatcgc
gagctacatcgaggccgagcggcagggcagcaagcgcccgacgtttgcctcggtgcaaggccggacgcgacgtgg
tgcgccgccgacctgacgctggacaagttcctcgacgcgagacgctggccgccgccgaacctgccaagccg
gccaccgagtgcgccacccgtgctgctgaccggcgccacggcttcctgggccgctacctggccctggaatgctgga
gcggatggacatggtggacggcaaggtcatcgccctggtccgggccggctccgacgaggaggcacgcgccggctgg
acaagaccttcgacagcggcgacccgaaactgctcgcgcactaccagcagctggccgccgatcacctggaggtcatc
gccggcgacaagggcgaggccaatctgggcctgggccaagacgtttggcaaacgactggccgacacggtcgacgtgat
cgtcgaccccgccgcgctggtcaaccacgtgttgccgtacagcgagctgttcggcccaacgcctgggcacgcgg
agctgatccggctggcgctgacgtccaagcagaagccgtacctacgtgtccaccatggcgtgggcgaccagatc
gagccggcaagttcgtcgagaaacgccgacatccggcagatgagcgccaccggggcgatcaacgacagctacgccaa
cggctatggcaacagcaagtgggccgccgcgaggtgctgctgcgcgagtacgcacgacctgtgcgggctgccgtcgcgg
tgttccgctgcgacatgatcctggccgacaccacgtatgccggcagctcaacctgccggacatgttcaccggctg
atgctgagcctggtggccaccggggatcgcgccggctcgttctacgagctcgacgccgacggcaacggcagcggc
gcactacgacggcctgcgcggtcgagttcatcgccgcgggcgatctcgacgctggttcgcagatcaccgacagcgaca
ccggcttccagacctacacgtgatgaaccccctacgatgacggcgtcggtctggacgagtacgtcgattggctggtg
gacgccggctattcgatcgagcggatcgccgactactccgaatggctgcggcggttcgagacctcgctgcgggccct
gccggaccggcagcgccagtactcgctgctgccgctgctgcacaactaccgcacgccgagaagccgatcaacgggt
cgatagctccaccgacgtgttcggcagcggtgcaggaggcgaaaatcggcccgacaaagacattccgcaccgtg
tcgccgccggtcatcgtcaagtacatcaccgacctgcagctgctcggctgctctaa
```

FIG. 15A

MSTATHDERLDREVHELIAIDPQFAAAQPDPAITAALEQPGLRLPQIIRTVLDGYADRPALGQRVVEFVTDAKTGRT
SAQLLPRFETITYSEVAQRVSALGRALSDDAVHPGDRVCVLGPNSVDYATIDMALGAIGAVSVPLQTSAAISSLQPI
VAETEPTLIASSVNQLSDAVQLITGAEQAPTELVVFDYHPQVDEQREAVQDAAARLSSTGVAVQTLAELLERGKDLP
AVAEPPADEDSLALLIYTSGSTGAPKGAMYPQSNVGKMWRRGSKNWPGESAASITLNFMPMSHVMGRSILYGTLGNG
GTAYPAARSDLSTLLEDLELVRPTELNPVPRIWETLYGEFQRQVEERLSEAGDAGEREAVEAEVLAEQRQYLLGGRP
TPAMTGSAPISPELRNWVESLLEMHLMDGYGSTEAGMVLFDGEIQEPPVIDYKLVDVPDLGYPSTDRPHPRGELLLR
TENMFPGYYERAETTAGVPDEDGYYRTGDVPREIAPDRLVYVDRRNNVLEIAQGEFVTLAKLERVFGNSPLIRQIYV
YGRSAQPYLLAVVVPTEEALASGDPETLKPKIADSLQQVAKEAGLQSYEVPRDPIIETTPFSLENGLLTGIRKLAWP
KLKQHYGERLEQMYADLAAGQANELAELERNGAQAPVLQTVSRAAGAMLGSAASDLSPDAHFTDLGGDSLSALTFGN
LLREIPDVDVFVGVIVSPANDLAAIASYIEAERQGSKRPTFASVHGRDATVVRAADLTLDKFLDAETLAAAPNLPKP
ATEVRTVLLTGATGFLGRYLALEWLERMDMVDGKVIALVRARSDEEAFARLDKTPDSGDPKLLAHYQQLAADHLEVI
AGDKGEAMLGLGQDVWQRLADTVDVIVDPAALVNHVLPYSELPGPNALGTAELIRLALTSKQKPYTYVSTIGVGDQI
EPGKFVENADIRQMSATRAINDSYANGYGNSKWAGEVLLREAHDLCGLPVAVFRCDMILADTTYAGQLNLPDMPTRL
MLSLVATGIAPGSFYELDADGNRQRAHYIGLFVEFIAAAISTLASQITDSDTGPQTYHVMNFYIDGVGLDEYVDWLV
DACYSIERIADYSEWLRRFETSLRALPDRQRQYSLLPLLHNYRTPEKPINGSIAPTDVFRAAVQEAKIGPDKDIPHV
SPPVIVKYITDLQLLGLL

FIG. 15B

```
atgtcgccaatcacgcgtgaagagcgcctcgagcgccgcatccaggacctctacgccaacgaccgcagttcgccgc
cgccaaaccgccacgggcgatcacgcagcaatcgagcggccgggtctaccgctacccagatcatcgagaccgtca
tgaccggatacgccgatcggccggctctcgctcagcgctcggtcgaattcgtgaccgaccgcggcaccggccacacc
acgctgcgactgctccccccactccgaaaccatcagctacggcgagctttgggaccgcatcagcgcactggccgacgt
gctcagcaccgaacagaccggtgaaaccgggcgaccgggtctgcttgttgggcttcaacagcgtcgactacgcaacga
tcgacatgactttggcgcgggctgggcgcggtggccgtaccactgcagccgacgcgggcgataacccagctgcagccg
atcgtcgccgagaccagccaccatgatcgcggccagcgtcgacgcactcgctgacgccaccgaattggctctgtc
cggtcagaccgctaccggagtcctggtgttcgaccaccaccggcaggttgacgcacacggcgcagcggtcgaatccg
ccgggagcgcctggccggctcggccgtcgtcgaaaccctggccgaggccatcgcgcgcggggacgtgcccgcggt
ggtccgccggctcggcgccggcacgatgtgtccgacgactcgctcgcgctactgatctacacctcggcagcac
gggtgcgccaaggcgcgatgtaccccgacgcaacgttgcgaccttctggcgcaagcgcacctggttcgaaggcg
gctacgagccgtcgatcacgctgaactttcatgccaatgagccacgtcatgggccgcaaatcctgtacggcacgctg
tgcaatggcggcaccgcctacttcgtggcgaaaagcgatctctccaccttgttcgaagacctggcgctggtgcggcc
cacccgagctgaccttcgtgccgcgcgtgtgggacatggtgttcgacgagtttcagagtcgaggtcgaccgccgctgg
tcgaccgggcgccgaccgggtcgcgctcgaagccaggtcaaggccgagatacgcaacgacgtgctcggttggacggtat
accagcgcactgaccgcctccgccccctatctccgacgatgaaggcgtgggtcgaggagcgtgctcgacatgcatct
ggtcgaaggctacggctccaccgaggccgggatgatcctgatcgacgggaccattcggccgccgcggtactcgact
acaagctggtcgatgtttccgacctgggttacttcctgaccgaccggccacatccggcgggggagttgctggtcaag
accgatagtttgttcccgggctactaccagcgagccgaagtcaccgccgacgtgttcgatgctgacggcttctaccg
gaccggcgacatcatggcgaggtcggcccccgaacagttcgtgtacctcgacccgccgcaacaacgtgttgaagctgt
cgcaggcgagttcgtcacgtctccaaactcgaagcggtgtttggcgacagcccactggtacggcagatctacatc
tacggcaacagcgccgtgcctacctgttcgccggtgatcgtccccaccaggagcgcgctgacgccgtgcctcga
ggagctcaaggcgcggctggcgactcgctgcaagaggtcgcaaagccgccggcctgcagtcctacgagatcccgc
gcgacttcatcatcgaacaacaccatggacgctggagaacggcctgctcaccggcatcgcaagttcgccaggcccg
cagctgaaaagcattacggcgagcttctcgagcagatctacacggacctggcacacggccaggcgaccgactgcg
ctcgctgcgccaaagcgtgccgatgcgccggtgctggtgacggtgtgccgtgccgccgccgcgctgttggcggca
gcgcctctgacgtccagcccgatgcgcacttcaccgatttggcggcgactcgctgtcggcgctgtcgttcaccaac
ctgctgcacgagatctcgacatcgaagtgccggtgggcgtcatcgtcagccccgccaacgacttgcaggccctggc
cgactacgtcgaggcggctcgcaaaaccggctcgtcacggccgaccttcgcctcggtccacggcgcctcgaatgggc
aggtcacgaggtcgatgccggtgacctgtccctggacaaattcatcgatgccgaacctggccgaagctcccgg
ctgccggccgcaaaacaccaagtcgcgacgtgctgctgacccgcgccacggcttcctcgggcgctacctggccct
ggaatggctggagcggatggacctggtcgacggcaaactgatctgctggtccgggcaagtccgacaccgaagcac
ggcgcgggctggacaagacgttcgacagcggcgaccccgaactgctggccactaccgcgcactggccgcgaccac
ctcgaggtgctcgccggtgacaaggcgaagccgaccctcggactggaccggcagaccctggcacgcctggccgacac
ggtcgacctgatcgtcgaccccgcggcctggtcaaccactacgcatacagccagctgttcgggccaacgcgc
tggccacgccgagctgctgcggcggtggcgtcaccccaagatcaagcctacagctacacctcgacaatcggtgtc
gccgaccagatccgccgtcggcgttcaacgaggacgccgacatcccgggtcatcagcgccaccgcgcggtcgacga
cagctacgccaatggctactcgaacagcaagtggccggcgaggtgctgttgcgcgaggcgcatgacctgtgtggcc
tgccggttgcggtgttccgtgcgacatgatcctggccgacaccacatgcggggacagctcaatgtgccggacatg
ttcaccccggatgatcctgagcctggcggccacccgtatcgccgccggttcgttctatgagcttgccgccgacgcgcc
ccggcaacgcgccccactatgacggtctgcccgtcgagttcatcgccgagcgcgattcgactttgggtgcgcagagcc
aggatggtttccacacgtatcacgtgatgaaccccctacgacgacggcatcggactcgacgagttcgtcgactggctc
aaccgagtccggttgcccccatccagccgcatcgctgactatggcgactggctcagcgcttcgaaaccgcactgcgcgc
actgccgcatcggcagcggcacagctcactgctgcgcgctgttgcacaactatcggcagcggagcggccgtccgcg
ggtcgatcgccctaccgatcgcttccgggcagcggtcgaagaggccaagatcggccccgacaagacattccgcac
gtccggcgcgcgatcatcgtgaagtacgtcagcgacctgcgcctactcggcctgctctaa
```

FIG. 16A

MSPITREERLERRIQDLYANDPQFAAAKPATAITAAIERPGLPLPQIIETVMTGYADRPALAQRSVEFVTDAGTGHT
TLRLLPHPETISYGELWDRISALADVLSTEQTVKPGDRVCLLGFNSVDYATIDMTLARLGAVAVPLQTSAAITQLQP
IVAETQPTMIAASVDALADATELALSGQTATRVLVFDHHRQVDAHRAAVESARERLAGSAVVETLAEAIARGDVPRG
ASAGSAPGTDVSDDSLALLIYTSGSTGAPKGAMYPRRNVATFWRKRTWPEGGYEPSITLNFMPMSHVMGRQILYGTL
CNGGTAYFVAKSDLSTLPEDLALVRPTELTFVPRVWDNVFDEPQSEVDRELVDGADRVALEAQVKAEIRNDVLGGRY
TSALTGSAPISDEMKAWVEELLDMHLVSGYGSTEAGNILIDGAIRREPAVLDYKLVDVPDLGYFLTDRPHPRGELLVK
TDSLFPGYYQRAEVTADVFDADGFYRTGDIMAEVGPEQPVYLDRRNNVLKLSQGEPVTVSKLEAVFGDSPLVRQIYI
YGNSARAYLLAVIVPTQRALDAVPVEELKARLGDSLQEVAKAAGLQSYEIPRDFIIETTPWTLENGLLTGIRKLARP
QLKKHYSELLEQIYTDLARXQADELESLRQSGADAPVLVTVCRAAAALLGXSASDVQPDARFTDLXIDSLSALSFTN
LLHEIFDIEVPVGVIVSPANDLQALADYVEAARKPGSSRPTFASVBGRASNGQVTEVHAGDLSLDKFIDAATLAEAPR
LPAANTQVRTVLLTGATGFLGRYLALEWLERMDLVDGKLICLVRAKSDTEARARLDKTFDSGDPELLAHYRALAGDH
LEVLAGDRGEADLGLDRQTWQRLADTVDLIVDPAALVNHVLPYSQLFGPNALGTAELLRLALTSKIKPYSYTSTIGV
ADQIPPSAFTEDADIRVISATRAVDDSYANGYSNSKWAGEVLJREAHDLCGLPVAVPRCDMILADTTWAGQINVPDM
PTRMILSLAATGIAPGSFYELAADGARQRAHYDGLPVEFIAEAISTLGAQSQDGFHTYHVMNPYTRDSIGLDRPVDWL
NESGCPIQRIADTGDWLQRFETALRALPDRQRHSELLPLLHNYRQPERPVRGSIAPTDRPRAAVQEAKIGPDKDIPH
VGAPIIVKYVSDLRLLGLL
```

FIG. 16B atgagcaccgcaaccatgatgaacgtctggatcgtcgtgttcatgaactgattgcaaccgatc
cgcagtttgcagcagcacagccggatcctgcaattaccgcagcactggaacagcctggtctgcg
tctgccgcagattattcgtaccgttctggatggttatgcagatcgtccggcactgggtcagcgt
gttgttgaatttgttaccgatgcaaaaaccggtcgtaccagcgcacagctgctgcctcgttttg
aaaccattacctatagcgaagttgcacagcgtgttagcgcactgggtcgtgcactgagtgatga
tgcagttcatccgggtgatcgtgtttgtgttctgggttttaatagcgttgattatgccaccatt
gatatggcactgggtgcaattggtgcagttagccgttccgctgcagaccagcgcagcaattagca
gcctgcagccgattgttgcagaaaccgaaccgaccctgattgcaagcagcgttaatcagctgtc
agatgcagttcagctgattaccggtgcagaacaggcaccgacccgtctggttgttttttgattat
catccgcaggttgatgatcagcgtgaagcagttcaggatgcagcagcacgtctgagcagcaccg
gtgttgcagttcagaccctggcagaactgctggaacgtggtaaagatctgcctgcagttgcaga
accgcctgcagatgaagatagcctggcactgctgatttataccagcggtagcacaggtgcaccg
aaaggtgcaatgtatccgcagagcaatgttggtaaaatgtggcgtcgtggtagcaaaaattggt
ttggtgaaagcgcagcaagcattaccctgaatttcatgccgatgagccatgttatgggtcgtag
cattctgtatggcaccctgggtaatggtggcaccgcatattttgcagcacgtagcgatctgagc
accctgctggaagatctggaactggttcgtccgaccgaactgaatttgttccgcgtatttggg
aaaccctgtatgtgaatttcagcgtcaggttgaacgtcgtctgagcgagaagctggcgatgccgg
tgaacgtcgtgcagttgaagcagaagttctggcagaacagcgtcagtatctgctgggtggtcgt
tttaccttgcaatgaccggtagcgcaccgattagtccggaactgcgtaattgggttgaaagcc
tgctggaaatgcatctgatggatggctatggtagcaccgaagcaggtatggttctgtttgatgg
cgaaattcagcgtccgcctgtgattgattataaactggttgatgttccggatctgggttattt
agcaccgatcgtccgcatccgcgtggtgaactgctgctgcgtaccgaaaatatgtttccgggtt
attataaacgtgcagaaaccaccgcaggcgttttttgatgaagatggttattatcgtaccggtga
tgtgtttgcagaaattgcaccggatcgtctggtttatgttgatcgtcgtaataatgttctgaaa
ctggcacagggtgaatttgtgaccctggccaaactggaagcagttttttggtaatagtccgctga
ttcgtcagatttatgtgtatggtaatagcgcacagccgtatctgctggcagttgttgttccgac
cgaagaggcactggcaagcggtgatccggaaaccctgaaaccgaaaatgcagatagcctgcag
caggttgcaaaagaagcaggtctgcagagctatgaagttccgcgtgatttttattattgaaacca
cccgtttagcctggaaaatggtctgctgaccggtattcgtaaactggcatggccgaaactgaa
acagcattatggtgaacgcctggaacaaatgtatgcagatctggcagcaggtcaggcaaatgaa
ctggccgaactgctgctgtaatggtgcacaggcaccggtctgcagaccgttagccgtgcagccg
gtgcaatgctgggtagccagccagcgatctgagtccggatgcacattttaccgatctggtgg
tgatagcctgagcgcactgacccttggtaatctgctgcgtgaaattttttgatgttgatgtgccg
gttggtgttattgttagccggctaatgatctggcagccattgcaagctatattgaagcagaac
gtcagggtagcaaacgtccgacctttgcaagcgttcatggtcgtgatgcaaccgttgttcgtgc
agcagatctgaccctggataaatttctggatgcagaaaccctggcagcagcaccgaatctgccg
aaaccggcaaccgaagttcgtaccgtgctgctgacaggtgcaacggttttctgggtcgttatc
tggcactggatggctggaacgtatggatatggttgatggtaaagttattgcactgcgttcgtgc
ccgtagtgatgaagaagcaccgcacgtctggataaaaacctttgatagtggtgatcgcgaaactg
ctggcacattatcagcagctggctgcagatcatctggaagttattgccggtgataaaggtgaag
caaatctgggtctgggtcaggatgttggcagcgtctggcagataccgttgatgttattgtgga
tccggcagcactggttaatcatgttctgccgtatagcgaactgttttggtccgaatgcactgggc

```
accgcagaactgattcgtctggcactgaccagcaaacagaaaccgtatacctatgttagcacca
ttggtgttggcgatcagattgaaccgggtaaatttgttgaaaatgccgatattcgtcagatgag
cgcaacccgtgcaattaatgatagctatgcaaatggctacggcaatagcaaatgggcaggcgaa
gttctgctgcgcgaagcacatgatctgtgtggtctgccggttgcagttttccgttgtgatatga
ttctggccgataccaccatgcaggtcagctgaatctgccggatatgtttaccgtctgatgct
gagcctggttgcaaccggtattgcaccgggtagcttttatgaactggatgcagatggtaatcgt
cagcgtgcacattatgatggcctgccggttgaatttattgcagcagccattagcaccctgggtt
cacagattaccgatagcgataccggttttcagacctatcatgttatgaacccgtatgatgatgg
tgttggtctggatgaatatgttgattggctggttgatgccggttatagcattgaacgtattgca
gattatagcgaatggctgcgtcgctttgaaacctcactgcgtgcactgccggatcgtcagcgcc
agtatagcctgctgccgctgctgcacaattatcgtacaccggaaaaaccgattaatggtagcat
tgcaccgaccgatgtttttcgtgcagccgttcaagaagccaaaattggtccggataaagatatt
ccgcatgttagccctccggtgattgttaaatatattaccgatctgcagctgctgggtctgctgt
aa
```

FIG. 17A, cont.

```
MSTATHDERLDRRVHELIATDPQPAAAQPDPAITAALEQPGLRLPQIIRTVLDGYADRPALGQR
VVEFVTDAKTGETSAQLLPRFETITYSEVAQRVSALGEALSDDAVHPGDRVCVLGFNSVDYATI
DMALGAIGAVSVPLQTSAAISSLQPIVAETEPTLIASSVNQLSDAVQLITSAEQAPTRLVVFDY
HPQVDDQREAVQDAAARLSSTGVAVQTLAELLERGKDLPAVAEPPADEDSLALLIYTSGSTGAP
KGAMYPQSNVGKMWRRGSKNWPGESAASITLNFMPMSEVMGRSILYGTLGNGGTAYFAARSDLS
TLLEDLELVRPTELNFVPRIWETLYGEFQRQVERRLSEAGDAGERRAVEAEVLAEQRQYLLGGR
PTFAMTGSAPISPELENWVESLLEMHLMDGYGSTEASMVLPDGEIQRPPVIDYELVDVPDLGYF
STDRPHPRGELLLRTENMFPGYYKRAETTAGVFDEDGYYRTGDVFAEIAPDRLVYVDRRNNVLK
LAQGEFVTLAKLEAVFGNSPLIRQIYVYGNSAQPYLLAVVVPTEEALASGDPETLKPKIADSLQ
QVAKEAGLQSYEVPRDFIIETTPFSLENGLLTGIRKLANPKLKQHYGERLEQMYADLAAGQANE
LAELRRNGAQAPVLQTVSRAAGAMLGSAASDLSPDAHFTDLGGDSLSALTFGNLLREIFDVDP
VGVIVSPANDLAAIASYIEAERQGSKRPTPASVHGRDATVVRAADLTLDKFLDAETLAAAPNLP
KPATEVRTVLLTGATGFLGRYLALEWLERMDMVDGKVIALVRARSDEEARARLDKTFDSGDPKL
LAHYQQLAADHLEVIAGDKGEANLGLGQDVWQRLADTVDVIVDPAALVNHVLPYSELFGPNALG
TAELIRLALTSKQKPYTYVSTIGVGDQIEPGKFVENADIRQMSATRAINDSYANGYGNSKWAGE
VLLREAHDLCGLPVAVFRCDMILADTTYAGQLNLPDMFTRLMLSLVATGIAPGSFYELDADGNR
QRAHYDGLPVEFIAAAISTLGSQITDSDTGFQTYHVMNPYDDGVGLDEYVDWLVDAGYSIERIA
DYSEWLRRFETSLRALPDRQRQYSLLPLLHNYRTPEKFINGSIAPTDVPRAAVQEAKIGPDKDI
PHVSPPVIVKYITDLQLLGLL
```

MICROORGANISMS FOR PRODUCING 1,3-BUTANEDIOL AND METHODS RELATED THERETO

CROSS-REFERENCE TO RELATED APPLICATIONS

The present application is a continuation of U.S. Ser. No. 13/528,593 filed Jun. 20, 2012, which claims the benefit of priority to U.S. Ser. Nos. 61/500,131, filed Jun. 22, 2011, and 61/502,702, filed Jun. 29, 2011, the contents of which are herein incorporated by reference in their entirety.

BACKGROUND

The present invention relates generally to biosynthetic processes and organisms capable of producing organic compounds. More specifically, the invention relates to non-naturally occurring organisms that can produce the commodity chemical 1,3-butanediol.

1,3-butanediol (1,3-BDO) is a four carbon diol traditionally produced from acetylene via its hydration. The resulting acetaldehyde is then converted to 3-hydroxybutyraldehdye which is subsequently reduced to form 1,3-BDO. In more recent years, acetylene has been replaced by the less expensive ethylene as a source of acetaldehyde. 1,3-BDO is commonly used as an organic solvent for food flavoring agents. It is also used as a co-monomer for polyurethane and polyester resins and is widely employed as a hypoglycaemic agent. Optically active 1,3-BDO is a useful starting material for the synthesis of biologically active compounds and liquid crystals. A substantial commercial use of 1,3-butanediol is subsequent dehydration to afford 1,3-butadiene (Ichikawa et al., *J. of Molecular Catalysis A-Chemical*, 256:106-112 (2006); Ichikawa et al., *J. of Molecular Catalysis A-Chemical*, 231:181-189 (2005)), a 25 billion lb/yr petrochemical used to manufacture synthetic rubbers (e.g., tires), latex, and resins. The reliance on petroleum based feedstocks for either acetylene or ethylene warrants the development of a renewable feedstock based route to 1,3-butanediol and to butadiene.

Thus, there exists a need to develop microorganisms and methods of their use to produce 1,3-BDO. The present invention satisfies this need and provides related advantages as well.

SUMMARY

In some embodiments, the present invention is directed to a non-naturally occurring microbial organism that includes a microbial organism having a 1,3-butanediol (1,3-BDO) pathway having at least one exogenous nucleic acid encoding a 1,3-BDO pathway enzyme expressed in a sufficient amount to produce 1,3-BDO. The 1,3-BDO pathway includes an enzyme selected from the group consisting of a 2-amino-4-ketopentanoate (AKP) thiolase, an AKP dehydrogenase, a 2-amino-4-hydroxypentanoate aminotransferase, a 2-amino-4-hydroxypentanoate oxidoreductase (deaminating), a 2-oxo-4-hydroxypentanoate decarboxylase, a 3-hydroxybutyraldehyde reductase, an AKP aminotransferase, an AKP oxidoreductase (deaminating), a 2,4-dioxopentanoate decarboxylase, a 3-oxobutyraldehyde reductase (ketone reducing), a 3-oxobutyraldehyde reductase (aldehyde reducing), a 4-hydroxy-2-butanone reductase, an AKP decarboxylase, a 4-aminobutan-2-one aminotransferase, a 4-aminobutan-2-one oxidoreductase (deaminating), a 4-aminobutan-2-one ammonia-lyase, a butenone hydratase, an AKP ammonia-lyase, an acetylacrylate decarboxylase, an acetoacetyl-CoA reductase (CoA-dependent, aldehyde forming), an acetoacetyl-CoA reductase (CoA-dependent, alcohol forming), an acetoacetyl-CoA reductase (ketone reducing), a 3-hydroxybutyryl-CoA reductase (aldehyde forming), a 3-hydroxybutyryl-CoA reductase (alcohol forming), a 4-hydroxybutyryl-CoA dehydratase, and a crotonase.

In some embodiments, the present invention is directed to a method for producing 1,3-BDO that includes culturing such a non-naturally occurring microbial organism, under conditions and for a sufficient period of time to produce 1,3-BDO.

BRIEF DESCRIPTION OF THE DRAWINGS

FIG. 12A shows the nucleotide sequence (SEQ ID NO:1) of carboxylic acid reductase from *Nocardia iowensis* (GNM_720), and FIG. 12B shows the encoded amino acid sequence (SEQ ID NO:2).

FIG. 13A shows the nucleotide sequence (SEQ ID NO:3) of phosphpantetheine transferase, which was codon optimized, and FIG. 13B shows the encoded amino acid sequence (SEQ ID NO:4).

FIG. 14A shows the nucleotide sequence (SEQ ID NO:5) of carboxylic acid reductase from *Mycobacterium smegmatis* mc(2)155 (designated 890), and FIG. 14B shows the encoded amino acid sequence (SEQ ID NO:6).

FIG. 15A shows the nucleotide sequence (SEQ ID NO:7) of carboxylic acid reductase from *Mycobacterium avium* subspecies paratuberculosis K-10 (designated 891), and FIG. 15B shows the encoded amino acid sequence (SEQ ID NO:8).

FIG. 16A shows the nucleotide sequence (SEQ ID NO:9) of carboxylic acid reductase from *Mycobacterium marinum* M (designated 892), and FIG. 16B shows the encoded amino acid sequence (SEQ ID NO:10).

FIG. 17A shows the nucleotide sequence (SEQ ID NO:11) of carboxylic acid reductase designated 891GA, and FIG. 17B shows the encoded amino acid sequence (SEQ ID NO:12).

DETAILED DESCRIPTION

This invention is directed, in part, to non-naturally occurring microorganisms that express genes encoding enzymes that catalyze 1,3-butanediol (1,3-BDO) production. Pathways for the production of 1,3-butanediol disclosed herein are based on three precursors: (i) D-alanine, (ii) acetoacetyl-CoA, and (iii) 4-hydroxybutyryl-CoA. Successfully engineering these pathways entails identifying an appropriate set of enzymes with sufficient activity and specificity, cloning their corresponding genes into a production host, optimizing fermentation conditions, and assaying for product formation following fermentation.

Figure 1:
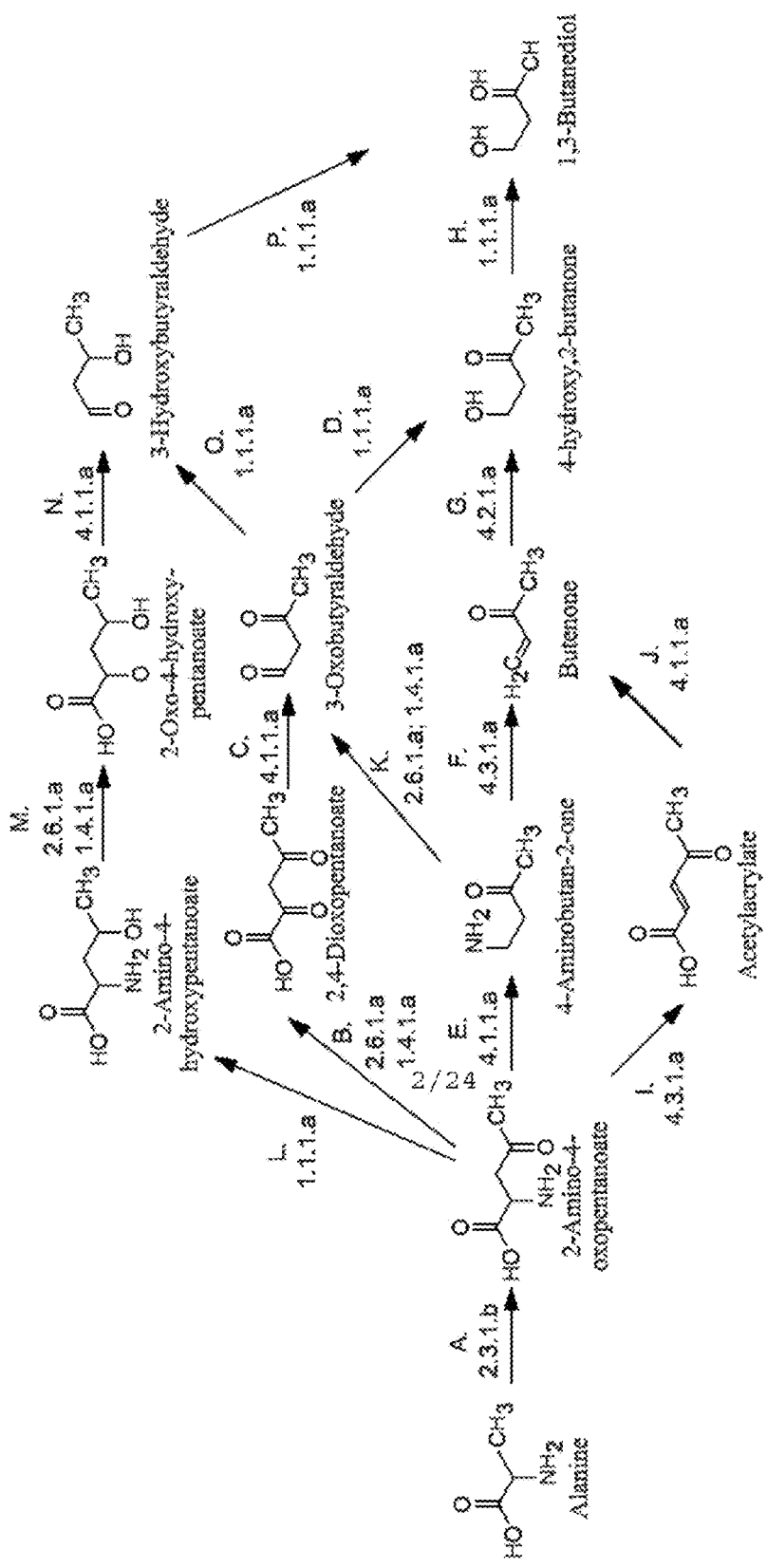
FIG. 1 shows pathways to 1,3-BDO from alanine. Enzymes are: A) AKP thiolase, B) AKP aminotransferase or AKP oxidoreductase (deaminating), C) 2,4-dioxopentanoate decarboxylase, D) 3-oxobutyraldehyde reductase (aldehyde reducing), E) AKP decarboxylase, F) 4-aminobutan-2-one ammonia-lyase, G) Butenone hydratase, H) 4-hydroxy,2-butanone reductase, I) AKP ammonia-lyase, J) acetylacrylate decarboxylase, K) 4-aminobutan-2-one aminotransferase or 4-aminobutan-2-one oxidoreductase (deaminating), L) AKP dehydrogenase, M) 2-amino-4-hydroxypentanoate aminotransferase or 2-amino-4-hydroxypentanoate oxidoreductase (deaminating), N) 2-oxo-4-hydroxypentanoate decarboxylase, O) 3-oxobutyraldehyde reductase (ketone reducing), and P) 3-hydroxybutyraldehyde reductase.

The conversion of alanine to 1,3-BDO can be accomplished by a number of pathways in about five enzymatic steps as shown in FIG. 1. In the first step of all pathways (Step A), alanine and acetyl-CoA are combined by 2-amino-4-ketopentanoate thiolase, a highly selective enzyme. The product of this reaction, 2-amino-4-oxopentanoate (AKP) can then be transaminated, reduced, decarboxylated or deaminated as shown in FIG. 1. Further synthetic steps for the production of 1,3-BDO are discussed in detail below. The theoretical yield of 1,3-BDO from each of these pathways is calculated to be about 1.09 mole/mole of glucose consumed.

Figure 2:
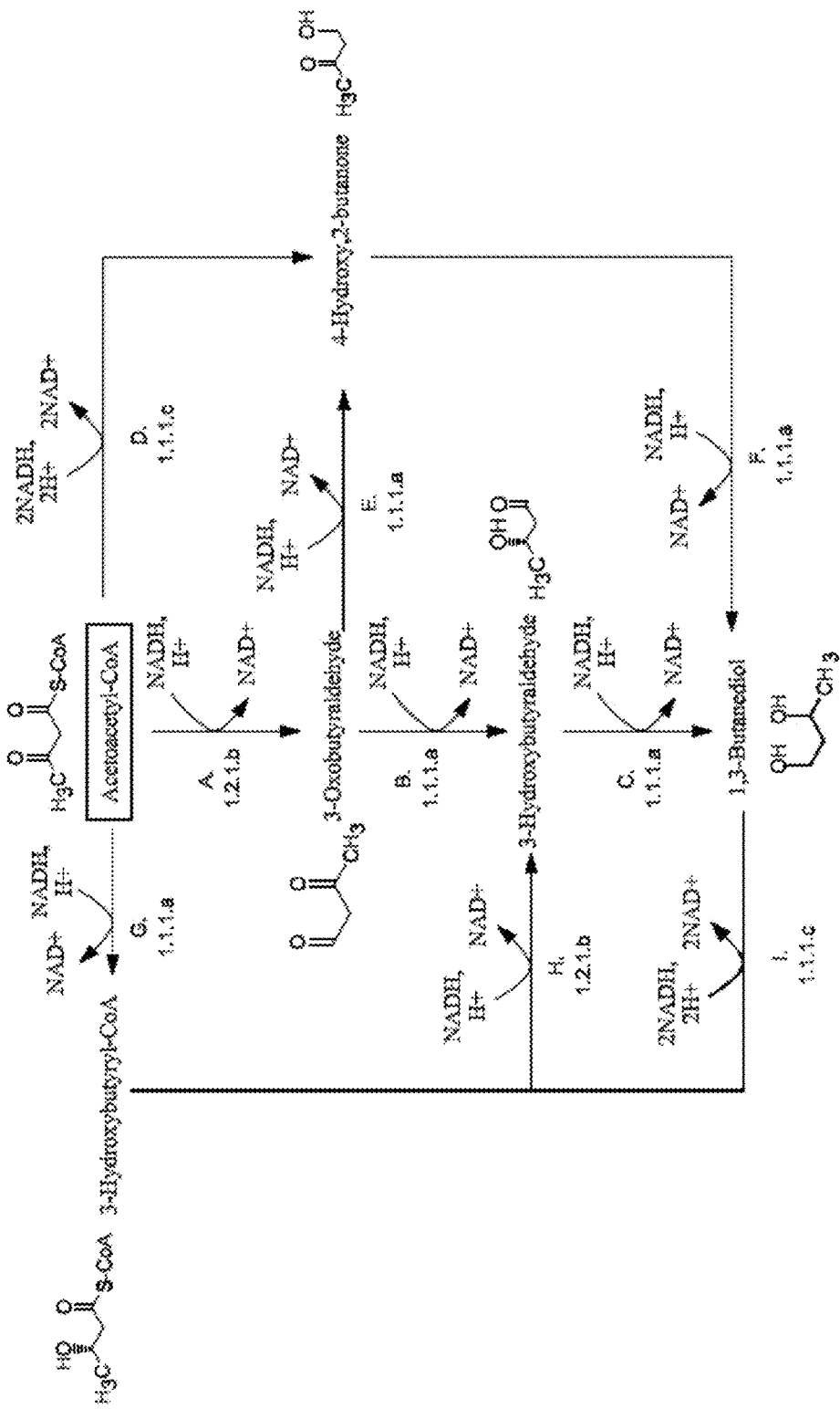
FIG. 2 shows pathways from acetoacetyl-CoA to 1,3-butanediol. Enzymes are: A) acetoacetyl-CoA reductase (CoA-dependent, aldehyde forming), B) 3-oxobutyraldehyde reductase (ketone reducing), C) 3-hydroxybutyraldehyde reductase, D) acetoacetyl-CoA reductase (CoA-dependent, alcohol forming), E) 3-oxobutyraldehyde reductase (aldehyde reducing), F) 4-hydroxy,2-butanone reductase, G) acetoacetyl-CoA reductase (ketone reducing), H) 3-hydroxybutyryl-CoA reductase (aldehyde forming), and I) 3-hydroxybutyryl-CoA reductase (alcohol forming).

FIG. 2 outlines multiple routes for producing 1,3-BDO from acetoacetyl-CoA. Each of these pathways from acetoacetyl-CoA to 1,3-BDO utilizes three reducing equivalents and provides a theoretical yield of 1 mole of 1,3-BDO per mole of glucose consumed. Other carbon substrates such as syngas can also be used for the production of acetoacetyl-CoA. Gasification of glucose to form syngas will result in the maximum theoretical yield of 1.09 moles of 1,3-BDO per mole of glucose consumed, assuming that 6 moles of CO and 6 moles of $H_2$ are obtained from glucose

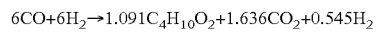

$$6CO+6H_2 \rightarrow 1.091C_4H_{10}O_2+1.636CO_2+0.545H_2$$

Figure 3:
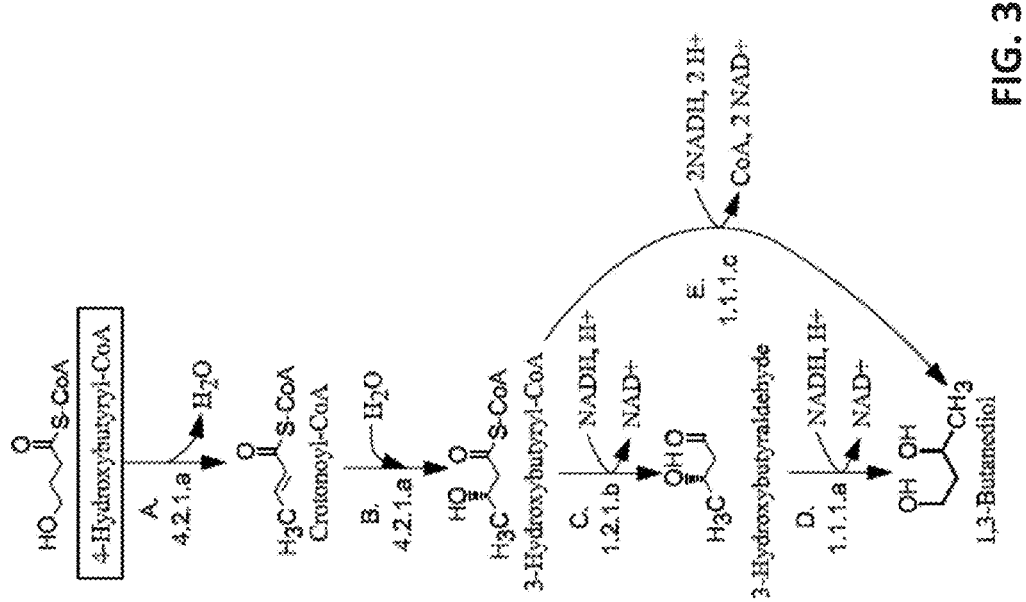
FIG. 3 shows pathways from 4-hydroxybutyryl-CoA to 1,3-butanediol. Enzymes are: A) 4-hydroxybutyryl-CoA dehydratase, B) crotonase, C) 3-hydroxybutyryl-CoA reductase (aldehyde forming), D) 3-hydroxybutyraldehyde reductase, and E) 3-hydroxybutyryl-CoA reductase (alcohol forming).

4-Hydroxybutyryl-CoA is an important starting metabolite from which a number of industrially useful compounds can be made, including 1,3-BDO as shown in FIG. 3. Although 4-hydroxybutyryl-CoA is not a highly common central metabolite, methods for engineering strains that synthesize 4-hydroxybutyryl-CoA have been described previously by Applicants in U.S. Patent Application No. 2009/0075351. The 4-hydroxybutyryl-CoA to 1,3-butanediol pathway has a theoretical yield of 1.09 mol/mol product yield assuming glucose as the carbohydrate feedstock.

This invention is also directed, in part, to methods for producing 1,3-BDO through culturing of these non-naturally occurring microbial organisms. Dehydration of 1,3-BDO produced by the organisms and methods described herein, provides an opportunity to produce renewable butadiene in small end-use facilities obviating the need to transport this flammable and reactive chemical.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a 1,3-butanediol biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbal organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of mycoplasma 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having 1,3-BDO biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

In some embodiments, the present invention provides a non-naturally occurring microbial organism that includes a microbial organism having a 1,3-butanediol (1,3-BDO) pathway with at least one exogenous nucleic acid encoding a 1,3-BDO pathway enzyme expressed in a sufficient amount to produce 1,3-BDO. The 1,3-BDO pathway includes an enzyme selected from the group consisting of a 2-amino-4-ketopentanoate (AKP) thiolase, an AKP dehydrogenase, a 2-amino-4-hydroxypentanoate aminotransferase, a 2-amino-4-hydroxypentanoate oxidoreductase (deaminating), a 2-oxo-4-hydroxypentanoate decarboxylase, a 3-hydroxybutyraldehyde reductase, an AKP aminotransferase, an AKP oxidoreductase (deaminating), a 2,4-dioxopentanoate decarboxylase, a 3-oxobutyraldehyde reductase (ketone reducing), a 3-oxobutyraldehyde reductase (aldehyde reducing), a 4-hydroxy-2-butanone reductase, an AKP decarboxylase, a 4-aminobutan-2-one aminotransferase, a 4-aminobutan-2-one oxidoreductase (deaminating), a 4-aminobutan-2-one ammonia-lyase, a butenone hydratase, an AKP ammonia-lyase, an acetylacrylate decarboxylase, an acetoacetyl-CoA reductase (CoA-dependent, aldehyde forming), an acetoacetyl-CoA reductase (CoA-dependent, alcohol forming), an acetoacetyl-CoA reductase (ketone reducing), a 3-hydroxybutyryl-CoA reductase (aldehyde forming), a 3-hydroxybutyryl-CoA reductase (alcohol forming), a 4-hydroxybutyryl-CoA dehydratase, and a crotonase.

Any combination and any number of the aforementioned enzymes can be introduced into a host microbial organism to complete a 1,3-BDO pathway, as exemplified in FIGS. 1-3. For example, the non-naturally occurring microbial organism can include one, two, three, four, five, up to all of the nucleic acids in a 1,3-BDO pathway, each nucleic acid encoding a 1,3-BDO pathway enzyme. Such nucleic acids can include heterologous nucleic acids, additional copies of existing genes, and gene regulatory elements, as explained further below. The pathways of the non-naturally occurring microbial organisms of the invention are also suitably engineered to be cultured in a substantially anaerobic culture medium.

In some embodiments, the non-naturally occurring microbial organisms having a 1,3-BDO pathway include a set of 1,3-BDO pathway enzymes. A set of 1,3-BDO pathway enzymes represents a group of enzymes that can convert alanine, acetoacetyl-CoA, or 4-hydroxybutyryl-CoA to 1,3-BDO, as show in FIGS. 1-3. Exemplary sets of 1,3-BDO pathway enzymes to convert alanine to 1,3-BDO, according to FIG. 1 include (a) (1) a 2-amino-4-ketopentanoate (AKP) thiolase; (2) an AKP dehydrogenase; (3) a 2-amino-4-hydroxypentanoate aminotransferase or oxidoreductase (deaminating); (4) a 2-oxo-4-hydroxypentanoate decarboxylase; and (5) a 3-hydroxybutyraldehyde reductase; (b) (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (ketone reducing); and (5) a 3-hydroxybutyraldehyde reductase; (c) (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (aldehyde reducing); and (5) a 4-hydroxy-2-butanone reductase; (d) (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (ketone reducing); and (5) a 3-hydroxybutyraldehyde reductase; (e) (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (aldehyde reducing); and (5) a 4-hydroxy-2-butanone reductase; (f) (1) a 2-amino-4-ketopentanoate (AKP) thiolase; (2) an AKP decarboxylase; (3) a 4-aminobutan-2-one ammonia-lyase; (4) a butenone hydratase; and (5) a 4-hydroxy-2-butanone reductase; and (g) (1) a 2-amino-4-ketopentanoate (AKP) thiolase; (2) an AKP ammonia-lyase; (3) an acetylacrylate decarboxylase; (4) a butenone hydratase; and (5) a 4-hydroxy-2-butanone reductase;

Exemplary sets of 1,3-BDO pathway enzymes to convert acetoacetyl-CoA to 1,3-BDO, according to FIG. 2 include (h) (1) an acetoacetyl-CoA reductase (CoA-dependent, aldehyde forming); (2) a 3-oxobutyraldehyde reductase (ketone reducing); and (3) a 3-hydroxybutyraldehyde reductase; (i) (1) an acetoacetyl-CoA reductase (CoA dependent, alcohol forming) and (2) a 4-hydroxy-2-butanone reductase; (j) (1) an acetoacetyl-CoA reductase (CoA-dependent, aldehyde forming); (2) a 3-oxobutyraldehyde reductase (aldehyde reducing); and (3) a 4-hydroxy-2-butanone reductase; (k) (1) an acetoacetyl-CoA reductase (ketone reducing) and (2) a 3-hydroxybutyryl-CoA reductase (alcohol forming); and (l) (1) an acetoacetyl-CoA reductase (ketone reducing); (2) a 3-hydroxybutyryl-CoA reductase (aldehyde forming); and (3) a 3-hydroxybutyraldehyde reductase;

Exemplary sets of 1,3-BDO pathway enzymes to convert 4-hydroxybutyryl-CoA to 1,3-BDO, according to FIG. 3 include (m) (1) a 4-hydroxybutyryl-CoA dehydratase; (2) a crotonase; and (3) a 3-hydroxybutyryl-CoA reductase (alcohol forming); and (n) (1) a 4-hydroxybutyryl-CoA dehydratase; (2) a crotonase; (3) a 3-hydroxybutyryl-CoA reductase (aldehyde forming); and (4) a 3-hydroxybutyraldehyde reductase.

The conversion of alanine to 1,3-BDO can be accomplished by a number of pathways involving about five enzymatic steps as shown in FIG. 1. In the first step of all pathways (Step A), alanine and acetyl-CoA are combined by 2-amino-4-ketopentanoate thiolase, a highly selective enzyme. The product of this reaction, 2-amino-4-oxopentanoate (AKP) can then be transaminated, reduced, decarboxylated or deaminated as shown in FIG. 1.

In one route, AKP converted to 2,4-dioxopentanoate, a 2-keto acid similar in structure to alpha-ketoglutarate, by an aminotransferase or deaminating oxidoreductase (Step B). 2,4-Dioxopentanoate is then converted to 3-oxobutyraldehyde by a 2-ketoacid decarboxylase (Step C). Reduction of the ketone and aldehyde groups to their corresponding alcohols yields 1,3-butanediol. These reductions can occur in either order to form the intermediates 3-hydroxybutyraldehyde (Steps O and P) or 4-hydroxy,2-butanone (Steps D and H).

In another route, the 4-oxo group of AKP is first reduced to a secondary alcohol by AKP dehydrogenase (Step L). The product, 2-amino-4-hydroxypentanoate, is then converted to 2-oxo-4-hydroxypentanoate (Step M). The resulting 2-ketoacid is decarboxylated to 3-hydroxybutyraldehyde (Step N). In the final step of this route, the aldehyde of 3-hydroxybutyraldehyde is reduced to a primary alcohol by 3-hydroxybutyraldehyde reductase, forming 1,3-butanediol (Step P).

Yet another route involves decarboxylation of AKP by an amino acid decarboxylase (Step E). The decarboxylation product, 4-aminobutan-2-one, can either be transaminated or oxidatively deaminated to 3-oxobutyraldehyde (Step K) or deaminated to butenone (Step F). When 3-oxobutyraldehyde is formed, two alcohol-forming reduction steps are used to form 1,3-butanediol, as described previously (Steps O and P, or Steps D and H). The deamination product, butenone, is then hydrolyzed to 4-hydroxy,2-butanone (Step G), which is reduced to 1,3-butanediol by 4-hydroxy-2-butanone reductase (Step H).

Yet another route involves the deamination of AKP to acetylacrylate (Step I). Acetylacrylate is decarboxylated to butenone (Step J), which is then converted to 1,3-butandiol by butenone hydratase (Step G) and 4-hydroxy,2-butanone reductase (Step H).

Based on the routes described above for the production 1,3-BDO from alanine, in some embodiments, the non-naturally occurring microbial organism has a set of 1,3-BDO pathway enzymes that includes (1) a 2-amino-4-ketopentanoate (AKP) thiolase; (2) an AKP dehydrogenase; (3) a 2-amino-4-hydroxypentanoate aminotransferase or oxidoreductase (deaminating); (4) a 2-oxo-4-hydroxypentanoate decarboxylase; and (5) a 3-hydroxybutyraldehyde reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

In other embodiments non-naturally occurring microbial organism has a set of 1,3-BDO pathway enzymes that includes (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (ketone reducing); and (5) a 3-hydroxybutyraldehyde reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

In still other embodiments, the non-naturally occurring microbial organism has a set of 1,3-BDO pathway enzymes that includes (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (aldehyde reducing); and (5) a 4-hydroxy-2-butanone reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

In yet further embodiments, the non-naturally occurring microbial organism has a set of 1,3-BDO pathway enzymes that includes (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (ketone reducing); and (5) a 3-hydroxybutyraldehyde reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

In yet still further embodiments, the non-naturally occurring microbial organism has a set of 1,3-BDO pathway enzymes that includes (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (aldehyde reducing); and (5) a 4-hydroxy-2-butanone reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

In still further embodiments, the non-naturally occurring microbial organism has a set of 1,3-BDO pathway enzymes that includes (1) a 2-amino-4-ketopentanoate (AKP) thiolase; (2) an AKP decarboxylase; (3) a 4-aminobutan-2-one ammonia-lyase; (4) a butenone hydratase; and (5) a 4-hydroxy-2-butanone reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

In yet still further embodiments, the non-naturally occurring microbial organism has a set of 1,3-BDO pathway enzymes that includes (1) a 2-amino-4-ketopentanoate (AKP) thiolase; (2) an AKP ammonia-lyase; (3) an acetylacrylate decarboxylase; (4) a butenone hydratase; and (5) a 4-hydroxy-2-butanone reductase. Any number of nucleic acids encoding these enzymes can be introduced into a host microbial organism including one, two, three, four, up to all five of the nucleic acids that encode these enzymes. Where one, two, three, or four exogenous nucleic acids are introduced, such nucleic acids can be any permutation of the five nucleic acids.

FIG. 2 outlines multiple routes for producing 1,3-butanediol from acetoacetyl-CoA. One route through steps A, B and C utilizes (i) CoA-dependent, aldehyde forming acetoacetyl-CoA reductase to convert acetoacetyl-CoA into 3-oxobutyraldehyde (FIG. 2, Step A), (ii) 3-oxobutyraldehyde reductase to reduce 3-oxobutyraldehyde to 3-hydroxybutyraldehyde (FIG. 2, Step B), and (iii) finally, 3-hydroxybutyraldehyde reductase to form 1,3-butanediol (FIG. 2, Step C).

Alternatively, acetoacetyl-CoA can be reduced via the aldehyde forming acetoacetyl-CoA reductase to form 4-hydroxy,2-butanone (FIG. 2, Step D). 4-hydroxy,2-butanone can also be formed by the reduction of 3-oxobutyraldehyde by the aldehyde reducing 3-oxobutyraldehyde reductase (FIG. 2, Step E). Eventually, 4-hydroxy,2-butanone can be reduced to form 1,3-BDO by 4-hydroxy-2-butanone reductase (FIG. 2, Step F).

Yet another set of 1,3-BDO forming routes rely on the reduction of acetoacetyl-CoA to 3-hydroxybutyryl-CoA by the ketone reducing acetoacetyl-CoA reductase (FIG. 2, Step G). This enzyme reduces the ketone function in acetoacetyl-CoA to a hydroxyl group. 3-hydroxybutyryl-CoA can be reduced by the bifunctional alcohol-forming 3-hydroxybutyryl-CoA reductase to form 1,3-butanediol (FIG. 2, Step I). Alternatively, it can first be reduced to 3-hydroxybutyraldehyde via the aldehyde forming 3-hydroxybutyryl-CoA reductase (Step H) and 3-hydroxybutyraldehyde can then be reduced as shown in Step C.

Based on the routes described above for the production 1,3-BDO from acetoacetyl-CoA, in some embodiments, the non-naturally occurring microbial organism has a set of 1,3-BDO pathway enzymes that includes (1) an acetoacetyl-CoA reductase (CoA-dependent, aldehyde forming); (2) a 3-oxobutyraldehyde reductase (ketone reducing); and (3) a 3-hydroxybutyraldehyde reductase. Any number of nucleic acids encoding these enzymes can be introduced into a host microbial organism including one, two up to all three of the nucleic acids that encode these enzymes. Where one or two exogenous nucleic acids are introduced, such nucleic acids can be any permutation of the three nucleic acids.

In other embodiments, the non-naturally occurring microbial organism has a set of 1,3-BDO pathway enzymes that includes (1) an acetoacetyl-CoA reductase (CoA dependent, alcohol forming) and (2) a 4-hydroxy-2-butanone reductase. Any number of nucleic acids encoding these enzymes can be introduced into a host microbial organism including one or both of the nucleic acids that encode these enzymes. Where one exogenous nucleic acid is introduced, such a nucleic acid can be either of the two nucleic acids.

In further embodiments, the non-naturally occurring microbial organism has a set of 1,3-BDO pathway enzymes that includes (1) an acetoacetyl-CoA reductase (CoA-dependent, aldehyde forming); (2) a 3-oxobutyraldehyde reductase (aldehyde reducing); and (3) a 4-hydroxy-2-butanone reductase. Any number of nucleic acids encoding these enzymes can be introduced into a host microbial organism including one, two up to all three of the nucleic acids that encode these enzymes. Where one or two exogenous nucleic acids are introduced, such nucleic acids can be any permutation of the three nucleic acids.

In yet further embodiments, the non-naturally occurring microbial organism has a set of 1,3-BDO pathway enzymes that includes (1) an acetoacetyl-CoA reductase (ketone reducing) and (2) a 3-hydroxybutyryl-CoA reductase (alcohol forming). Any number of nucleic acids encoding these enzymes can be introduced into a host microbial organism including one or both of the nucleic acids that encode these enzymes. Where one exogenous nucleic acid is introduced, such a nucleic acid can be either of the two nucleic acids.

In still further embodiments, the non-naturally occurring microbial organism has a set of 1,3-BDO pathway enzymes that includes (1) an acetoacetyl-CoA reductase (ketone reducing); (2) a 3-hydroxybutyryl-CoA reductase (aldehyde forming); and (3) a 3-hydroxybutyraldehyde reductase. Any number of nucleic acids encoding these enzymes can be introduced into a host microbial organism including one, two up to all three of the nucleic acids that encode these enzymes. Where one or two exogenous nucleic acids are introduced, such nucleic acids can be any permutation of the three nucleic acids.

4-hydroxybutyryl-CoA is an important starting metabolite from which a number of industrially useful compounds can be made. Although 4-hydroxybutyryl-CoA is not a highly common central metabolite, methods for engineering strains that synthesize 4-hydroxybutyryl-CoA have been described in Burk et al. (US 20090075351). An exemplary method involves synthesizing 4-hydroxybutyryl-CoA from succinyl-CoA by employing genes encoding succinic semialdehyde dehydrogenase (CoA-dependent), 4-hydroxybutyrate dehydrogenase, 4-hydroxybutyrate kinase, and phosphotransbutyrylase activities.

The first step in the pathway involves the dehydration of 4-hydroxybutyryl-CoA (Step A, FIG. 3) followed by the hydration of crotonoyl-CoA to form 3-hydroxybutyryl-CoA (Step B). 3-hydroxybutyryl-CoA then undergoes two reduction steps to form 1,3-butanediol carried out by either two enzymes (Steps C and D) or a single dual-function enzyme (Step E).

Thus, in some embodiments, the non-naturally occurring microbial organism has a set of 1,3-BDO pathway enzymes that includes (1) a 4-hydroxybutyryl-CoA dehydratase; (2) a crotonase; and (3) a 3-hydroxybutyryl-CoA reductase (alcohol forming). Any number of nucleic acids encoding these enzymes can be introduced into a host microbial organism including one, two up to all three of the nucleic acids that encode these enzymes. Where one or two exogenous nucleic acids are introduced, such nucleic acids can be any permutation of the three nucleic acids.

In other embodiments, the non-naturally occurring microbial organism has a set of 1,3-BDO pathway enzymes that includes (1) a 4-hydroxybutyryl-CoA dehydratase; (2) a crotonase; (3) a 3-hydroxybutyryl-CoA reductase (aldehyde forming); and (4) a 3-hydroxybutyraldehyde reductase. Any number of nucleic acids encoding these enzymes can be introduced into a host microbial organism including one, two, three up to all four of the nucleic acids that encode these enzymes. Where one, two, or three exogenous nucleic acids are introduced, such nucleic acids can be any permutation of the four nucleic acids.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to 2-amino-4-hydroxypentanoate, 2-amino-4-hydroxypentanoate to 2-oxo-4-hydroxypentanoate, 2-oxo-4-hydroxypentanoate to 3-hydroxybutyraldehyde, and 3-hydroxybutyraldehyde to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to 2,4-dioxopentanoate, 2,4-dioxopentanoate to 3-oxobutyraldehyde, 3-oxobutyraldehyde to 3-hydroxybutyraldehyde, and 3-hydroxybutyraldehyde to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to 2,4-dioxopentanoate, 2,4-dioxopentanoate to 3-oxobutyraldehyde, 3-oxobutyraldehyde to 4-hydroxy-2-butanone, and 4-hydroxy-2-butanone to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to 4-aminobutan-2-one, 4-aminobutan-2-one to 3-oxobutyraldehyde, 3-oxobutyraldehyde to 3-hydroxybutyraldehyde, and 3-hydroxybutyraldehyde to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to 4-aminobutan-2-one, 4-aminobutan-2-one to 3-oxobutyraldehyde, 3-oxobutyraldehyde to 4-hydroxy-2-butanone, and 4-hydroxy-2-butanone to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to 4-aminobutan-2-one, 4-aminobutan-2-one to butenone, butenone to 4-hydroxy-2-butanone, and 4-hydroxy-2-butanone to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of alanine to 2-amino-4-oxopentanoate, 2-amino-4-oxopentanoate to acetylacrylate, acetylacrylate to butenone, butenone to 4-hydroxy-2-butanone, and 4-hydroxy-2-butanone to 1,3-BDO.

Thus, the invention provides a non-naturally occurring microbial organism containing at least one exogenous nucleic acid encoding an enzyme or protein, where the enzyme or protein converts the substrates and products of a 1,3-BDO pathway converting alanine to 1,3-BDO, as exemplified by the pathways shown in FIG. 1.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of acetoacetyl-CoA to 4-hydroxy-2-butanone, and 4-hydroxy-2-butanone to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of acetoacetyl-CoA to 3-oxobutyraldehyde, 3-oxobutyraldehyde to 4-hydroxy-2-butanone, and 4-hydroxy-2-butanone to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of acetoacetyl-CoA to 3-oxobutyraldehyde, 3-oxobutyraldehyde to 3-hydroxybutyraldehyde, and 3-hydroxybutyraldehyde to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of acetoacetyl-CoA to 3-hydroxybutyryl-CoA, 3-hydroxybutyryl-CoA to 3-hydroxybutryaldehyde, and 3-hydroxybutyraldehyde to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of acetoacetyl-CoA to 3-hydroxybutyryl-CoA, and 3-hydroxybutyryl-CoA to 1,3-BDO.

Thus, the invention provides a non-naturally occurring microbial organism containing at least one exogenous nucleic acid encoding an enzyme or protein, where the enzyme or protein converts the substrates and products of a 1,3-BDO pathway converting acetoacetyl-CoA to 1,3-BDO, as exemplified by the pathways shown in FIG. 2.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of 4-hydroxy-butyryl-CoA to crotonoyl-CoA, crotonoyl-CoA to 3-hydroxybutyryl-CoA, 3-hydroxybutyryl-CoA to 3-hydroxybutryaldehyde, and 3-hydroxybutyraldehyde to 1,3-BDO.

In an additional embodiment, the invention provides a non-naturally occurring microbial organism having a 1,3-BDO pathway, wherein the non-naturally occurring microbial organism comprises at least one exogenous nucleic acid encoding an enzyme or protein that converts a substrate to a product selected from the group consisting of 4-hydroxy-butyryl-CoA to crotonoyl-CoA, crotonoyl-CoA to 3-hydroxybutyryl-CoA, and 3-hydroxybutyryl-CoA to 1,3-BDO.

Thus, the invention provides a non-naturally occurring microbial organism containing at least one exogenous nucleic acid encoding an enzyme or protein, where the enzyme or protein converts the substrates and products of a 1,3-BDO pathway, the pathway converting 4-hydroxybutyryl-CoA to 1,3-BDO, as exemplified by the pathways shown in FIG. 3.

This invention is also directed, in part to engineered biosynthetic pathways to improve carbon flux through a central metabolism intermediate en route to 1,3-butanediol. The present invention provides non-naturally occurring microbial organisms having one or more exogenous genes encoding enzymes that can catalyze various enzymatic transformations en route to 1,3-butanediol. In some embodiments, these enzymatic transformations are part of the reductive tricarboxylic acid (RTCA) cycle and are used to improve product yields, including but not limited to, from carbohydrate-based carbon feedstock.

In numerous engineered pathways, realization of maximum product yields based on carbohydrate feedstock is hampered by insufficient reducing equivalents or by loss of reducing equivalents and/or carbon to byproducts. In accordance with some embodiments, the present invention increases the yields of 1,3-butanediol by (i) enhancing carbon fixation via the reductive TCA cycle, and/or (ii) accessing additional reducing equivalents from gaseous carbon sources and/or syngas components such as CO, $CO_2$, and/or $H_2$. In addition to syngas, other sources of such gases include, but are not limited to, the atmosphere, either as found in nature or generated.

Figure 8A:
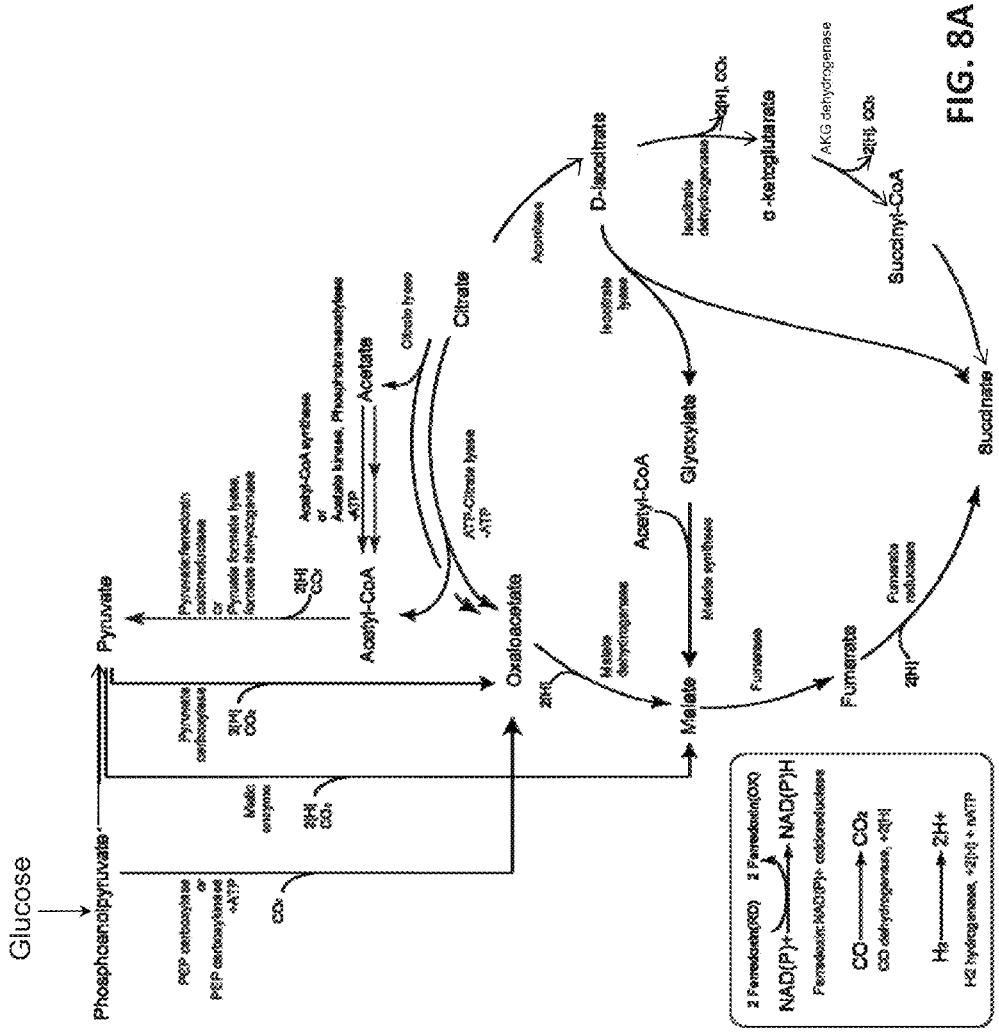
FIG. 8A shows the pathways for fixation of $CO_2$ to pyruvate using the reductive TCA cycle.
Figure 9A:
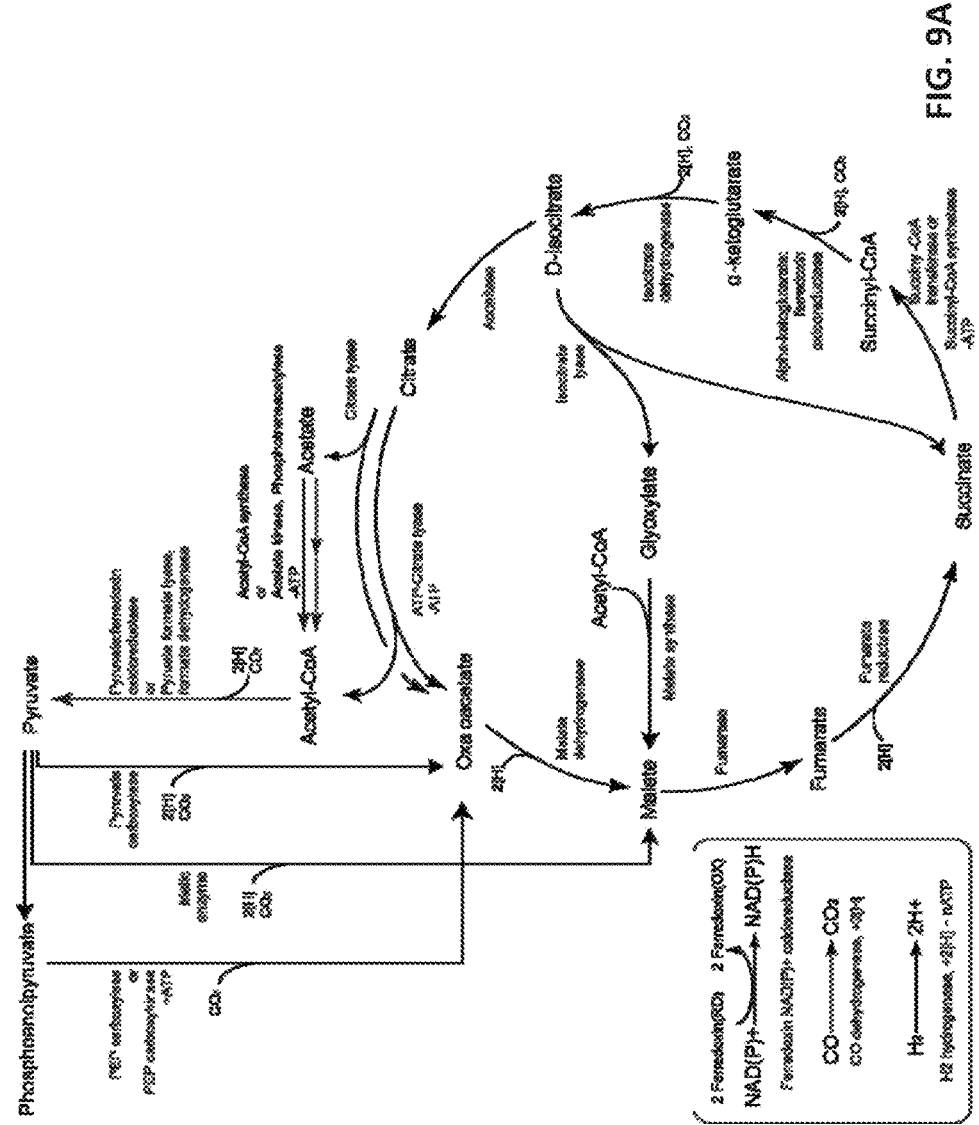
FIG. 9A shows the pathways for fixation of $CO_2$ to alpha-ketoglutarate, succinate and succinyl-CoA using the reductive TCA cycle.

The $CO_2$-fixing reductive tricarboxylic acid (RTCA) cycle is an endergenic anabolic pathway of $CO_2$ assimilation which uses reducing equivalents and ATP (FIGS. 8a and 9a). One turn of the RTCA cycle assimilates two moles of $CO_2$ into one mole of acetyl-CoA, or four moles of $CO_2$ into one mole of oxaloacetate. This additional availability of acetyl-CoA improves the maximum theoretical yield of product molecules derived from carbohydrate-based carbon feedstock. Exemplary carbohydrates include but are not limited to glucose, sucrose, xylose, arabinose and glycerol.

In some embodiments, the reductive TCA cycle, coupled with carbon monoxide dehydrogenase and/or hydrogenase enzymes (FIGS. 8a and 9a insert), can be employed to allow syngas, $CO_2$, CO, $H_2$, and/or other gaseous carbon source utilization by microorganisms. Synthesis gas (syngas), in particular is a mixture of primarily $H_2$ and CO, sometimes including some amounts of $CO_2$, that can be obtained via gasification of any organic feedstock, such as coal, coal oil, natural gas, biomass, or waste organic matter. Numerous gasification processes have been developed, and most designs are based on partial oxidation, where limiting oxygen avoids full combustion, of organic materials at high temperatures (500-1500° C.) to provide syngas as a 0.5:1-3:1 $H_2$/CO mixture. In addition to coal, biomass of many types has been used for syngas production and represents an inexpensive and flexible feedstock for the biological production of renewable chemicals and fuels. Carbon dioxide can be provided from the atmosphere or in condensed from, for example, from a tank cylinder, or via sublimation of solid $CO_2$. Similarly, CO and hydrogen gas can be provided in reagent form and/or mixed in any desired ratio. Other gaseous carbon forms can include, for example, methanol or similar volatile organic solvents.

The components of synthesis gas and/or other carbon sources can provide sufficient $CO_2$, reducing equivalents, and ATP for the reductive TCA cycle to operate. One turn of the RTCA cycle assimilates two moles of $CO_2$ into one mole of acetyl-CoA and requires 2 ATP and 4 reducing equivalents. CO and/or $H_2$ can provide reducing equivalents by means of carbon monoxide dehydrogenase and hydrogenase enzymes, respectively. Reducing equivalents can come in the form of NADH, NADPH, FADH, reduced quinones, reduced ferredoxins, thioredoxins, and reduced flavodoxins. The reducing equivalents, particularly NADH, NADPH, and reduced ferredoxin, can serve as cofactors for the RTCA cycle enzymes, for example, malate dehydrogenase, fumarate reductase, alpha-ketoglutarate:ferredoxin oxidoreductase (alternatively known as 2-oxoglutarate:ferredoxin oxidoreductase, alpha-ketoglutarate synthase, or 2-oxoglutarate synthase), pyruvate:ferredoxin oxidoreductase and isocitrate dehydrogenase. The electrons from these reducing equivalents can alternatively pass through an ion-gradient producing electron transport chain where they are passed to an acceptor such as oxygen, nitrate, oxidized metal ions, protons, or an electrode. The ion-gradient can then be used for ATP generation via an ATP synthase or similar enzyme.

In some embodiments, a non-naturally occurring microbial organism has a 1,3-butanediol pathway and includes at least one exogenous nucleic acid encoding a 1,3-butanediol pathway enzyme expressed in a sufficient amount to produce 1,3-butanediol; wherein the non-naturally occurring microbial organism further includes:

A non-naturally occurring microbial organism having a 1,3-butanediol pathway, wherein said microbial organism comprises at least one exogenous nucleic acid encoding a 1,3-butanediol pathway enzyme expressed in a sufficient amount to produce 1,3-butanediol; said non-naturally occurring microbial organism further comprising:

(i) a reductive TCA pathway, wherein said microbial organism comprises at least one exogenous nucleic acid encoding a reductive TCA pathway enzyme selected from the group consisting of an ATP-citrate lyase, citrate lyase, a fumarate reductase, and an alpha-ketoglutarate:ferredoxin oxidoreductase;

(ii) a reductive TCA pathway, wherein said microbial organism comprises at least one exogenous nucleic acid encoding a reductive TCA pathway enzyme selected from the group consisting of a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encodes an enzyme selected from the group consisting of a CO dehydrogenase, an $H_2$ hydrogenase, and combinations thereof;

wherein said 1,3-butanediol pathway comprises a pathway selected from the group consisting of:

(a) (1) a 2-amino-4-ketopentanoate (AKP) thiolase; (2) an AKP dehydrogenase; (3) a 2-amino-4-hydroxypentanoate aminotransferase or oxidoreductase (deaminating); (4) a 2-oxo-4-hydroxypentanoate decarboxylase; and (5) a 3-hydroxybutyraldehyde reductase;

(b) (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (ketone reducing); and (5) a 3-hydroxybutyraldehyde reductase;

(c) (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (aldehyde reducing); and (5) a 4-hydroxy-2-butanone reductase;

(d) (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (ketone reducing); and (5) a 3-hydroxybutyraldehyde reductase;

(e) (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (aldehyde reducing); and (5) a 4-hydroxy-2-butanone reductase;

(f) (1) a 2-amino-4-ketopentanoate (AKP) thiolase; (2) an AKP decarboxylase; (3) a 4-aminobutan-2-one ammonialyase; (4) a butenone hydratase; and (5) a 4-hydroxy-2-butanone reductase;

(g) (1) a 2-amino-4-ketopentanoate (AKP) thiolase; (2) an AKP ammonia-lyase; (3) an acetylacrylate decarboxylase; (4) a butenone hydratase; and (5) a 4-hydroxy-2-butanone reductase;

(h) (1) an acetoacetyl-CoA reductase (CoA-dependent, aldehyde forming); (2) a 3-oxobutyraldehyde reductase (ketone reducing); and (3) a 3-hydroxybutyraldehyde reductase;

(i) (1) an acetoacetyl-CoA reductase (CoA dependent, alcohol forming) and (2) a 4-hydroxy-2-butanone reductase;

(j) (1) an acetoacetyl-CoA reductase (CoA-dependent, aldehyde forming); (2) a 3-oxobutyraldehyde reductase (aldehyde reducing); and (3) a 4-hydroxy-2-butanone reductase;

(k) (1) an acetoacetyl-CoA reductase (ketone reducing) and (2) a 3-hydroxybutyryl-CoA reductase (alcohol forming);

(l) (1) an acetoacetyl-CoA reductase (ketone reducing); (2) a 3-hydroxybutyryl-CoA reductase (aldehyde forming); and (3) a 3-hydroxybutyraldehyde reductase;

(m) (1) a 4-hydroxybutyryl-CoA dehydratase; (2) a crotonase; and (3) a 3-hydroxybutyryl-CoA reductase (alcohol forming); and (n) (1) a 4-hydroxybutyryl-CoA dehydratase; (2) a crotonase; (3) a 3-hydroxybutyryl-CoA reductase (aldehyde forming); and (4) a 3-hydroxybutyraldehyde reductase;

(o) (1) a succinyl-CoA transferase, a succinyl-CoA synthetase or a succinyl-CoA ligase, (2) a succinyl-CoA reductase (aldehyde forming), (3) a 4-hydroxybutyrate dehydrogenase, (4) a 4-hydroxybutyrate kinase, (5) a phosphotrans-4-hydroxybutyrylase, (6) a 4-hydroxybutyryl-CoA dehydratase, (7) a crotonase, (8) a 3-hydroxybutyryl-CoA reductase (aldehyde forming), and (9) a 3-hydroxybutanal reductase;

(p) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase; (6) a crotonase, (7) a 3-hydroxybutyryl-CoA reductase (aldehyde forming), and (8) a 3-hydroxybutanal reductase;

(q) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA reductase (aldehyde forming), and (7) a 3-hydroxybutanal reductase;

(r) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, and (7) a 3-hydroxybutyryl-CoA reductase (alcohol forming);

(s) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, and (6) a 3-hydroxybutyryl-CoA reductase (alcohol forming);

(t) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA hydrolase, transferase or synthetase, and (8) a 3-hydroxybutyrate reductase;

(u) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA hydrolase, transferase or synthetase, and (7) a 3-hydroxybutyrate reductase.

(v) (1) a succinate reductase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA reductase (aldehyde forming), and (8) a 3-hydroxybutanal reductase;

(w) (1) a succinate reductase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA reductase (aldehyde forming), (7) a 3-hydroxybutanal reductase;

(x) (1) a succinate reductase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, and (7) a 3-hydroxybutyryl-CoA reductase (alcohol forming);

(y) (1) a succinate reductase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, and (6) a 3-hydroxybutyryl-CoA reductase (alcohol forming);

(z) (1) a succinate reductase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA hydrolase, transferase or synthetase, and (8) a 3-hydroxybutyrate reductase;

(aa) (1) a succinate reductase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA hydrolase, transferase or synthetase, and (7) a 3-hydroxybutyrate reductase;

(bb) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (5) a 4-hydroxybutyrate kinase, (6) a pPhosphotrans-4-hydroxybutyrylase, (7) a 4-hydroxybutyryl-CoA dehydratase, (8) a crotonase, and (9) a 3-hydroxybutyryl-CoA reductase (alcohol forming);

(cc) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (4) a 4-hydroxybutyrate kinase, (5) a phosphotrans-4-hydroxybutyrylase, (6) a 4-hydroxybutyryl-CoA dehydratase, (7) a crotonase, (8) a 3-hydroxybutyryl-CoA hydrolase, transferase or synthetase, and (9) a 3-hydroxybutyrate reductase;

(dd) (1) a succinyl-CoA transferase, succinyl-CoA synthetase or succinyl-CoA ligase, (2) a succinyl-CoA reductase (alcohol forming), (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA reductase (aldehyde forming), and (8) a 3-hydroxybutanal reductase;

(ee) (1) a succinyl-CoA transferase, succinyl-CoA synthetase or succinyl-CoA ligase, (2) a succinyl-CoA reductase (alcohol forming), (3) a 4-hydroxybutyrate kinase, (4) a phosphotrans-4-hydroxybutyrylase, (5) a 4-hydroxybutyryl-CoA dehydratase, (6) a crotonase, and (7) a 3-hydroxybutyryl-CoA reductase (alcohol forming);

(ff) (1) a succinyl-CoA transferase, succinyl-CoA synthetase or succinyl-CoA ligase, (2) a succinyl-CoA reductase (alcohol forming), (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA hydrolase, transferase or synthetase, and (8) a 3-hydroxybutyrate reductase;

(gg) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (4) a 4-hydroxybutyryl-CoA transferase, or 4-hydroxybutyryl-CoA synthetase, (5) a 4-hydroxybutyryl-CoA dehydratase, (6) a crotonase, (7) a 3-hydroxybutyryl-CoA reductase (aldehyde forming), and (8) a 3-hydroxybutanal reductase;

(hh) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (4) a 4-hydroxybutyryl-CoA transferase or 4-hydroxybutyryl-CoA synthetase, (5) a 4-hydroxybutyryl-CoA dehydratase, (6) a crotonase, and (7) a 3-hydroxybutyryl-CoA reductase (alcohol forming);

(ii) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (4) a 4-hydroxybutyryl-CoA transferase or 4-hydroxybutyryl-CoA synthetase, (5) a 4-hydroxybutyryl-CoA dehydratase, (6) a crotonase, (7) a 3-hydroxybutyryl-CoA hydrolase, transferase or synthetase, (8) a 3-hydroxybutyrate reductase;

(jj) (1) a succinyl-CoA transferase, succinyl-CoA synthetase or succinyl-CoA ligase, (2) a succinyl-CoA reductase (alcohol forming), (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA reductase (aldehyde forming), and (7) a 3-hydroxybutanal reductase;

(kk) (1) a succinyl-CoA transferase, succinyl-CoA synthetase or succinyl-CoA ligase, (2) a succinyl-CoA reductase (alcohol forming), (3) a 4-hydroxybutyryl-CoA transferase or 4-hydroxybutyryl-CoA synthetase, (4) a 4-hydroxybutyryl-CoA dehydratase, (5) a crotonase, and (6) a 3-hydroxybutyryl-CoA reductase (alcohol forming); and (ll) (1) a succinyl-CoA transferase, succinyl-CoA synthetase or succinyl-CoA ligase, (2) a succinyl-CoA reductase (alcohol forming), (3) a 4-hydroxybutyryl-CoA transferase or 4-hydroxybutyryl-CoA synthetase, (5) a 4-hydroxybutyryl-CoA dehydratase, (6) a crotonase, (7) a 3-hydroxybutyryl-CoA hydrolase, transferase or synthetase, and (8) a 3-hydroxybutyrate reductase.

In some embodiments, the non-naturally occurring microbial organism (e.g., having pathway (i)) further includes an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof.

In some embodiments, the non-naturally occurring microbial organism (e.g., having pathway (ii)) further includes an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

In some embodiments, the non-naturally occurring microbial organism includes two, three, four, five, six, seven, eight or nine exogenous nucleic acids, each encoding a 1,3-BDO pathway enzyme.

In some embodiments, the non-naturally occurring microbial organism comprises exogenous nucleic acids encoding each of the enzymes of at least one of the 1,3-butanediol pathways selected from the group consisting of (a)-(ll).

In some embodiments, the non-naturally occurring microbial organism has at least one exogenous nucleic acid is a heterologous nucleic acid.

In some embodiments, the non-naturally occurring microbial organism is in a substantially anaerobic culture medium.

The reductive TCA cycle was first reported in the green sulfur photosynthetic bacterium *Chlorobium limicola* (Evans et al., *Proc. Natl. Acad. Sci. U.S.A.* 55:928-934 (1966)). Similar pathways have been characterized in some prokaryotes (proteobacteria, green sulfur bacteria and thermophillic Knallgas bacteria) and sulfur-dependent archaea (Hugler et al., *J. Bacteriol.* 187:3020-3027 (2005; Hugler et al., *Environ. Microbiol.* 9:81-92 (2007). In some cases, reductive and oxidative (Krebs) TCA cycles are present in the same organism (Hugler et al., supra (2007); Siebers et al., *J. Bacteriol.* 186:2179-2194 (2004)). Some methanogens and obligate anaerobes possess incomplete oxidative or reductive TCA cycles that may function to synthesize biosynthetic intermediates (Ekiel et al., *J. Bacteriol.* 162:905-908 (1985); Wood et al., *FEMS Microbiol. Rev.* 28:335-352 (2004)).

The key carbon-fixing enzymes of the reductive TCA cycle are alpha-ketoglutarate:ferredoxin oxidoreductase, pyruvate:ferredoxin oxidoreductase and isocitrate dehydrogenase. Additional carbon may be fixed during the conversion of phosphoenolpyruvate to oxaloacetate by phosphoenolpyruvate carboxylase or phosphoenolpyruvate carboxykinase or during the conversion of pyruvate to malate by malic enzyme and during the conversion of pyruvate to oxaloacetate by pyruvate carboxylase.

Many of the enzymes in the TCA cycle are reversible and can catalyze reactions in the reductive and oxidative directions. However, some TCA cycle reactions are irreversible in vivo and thus different enzymes are used to catalyze these reactions in the directions required for the reverse TCA cycle. These reactions are: (1) conversion of citrate to oxaloacetate and acetyl-CoA, (2) conversion of fumarate to succinate, and (3) conversion of succinyl-CoA to alpha-ketoglutarate. In the TCA cycle, citrate is formed from the condensation of oxaloacetate and acetyl-CoA. The reverse reaction, cleavage of citrate to oxaloacetate and acetyl-CoA, is ATP-dependent and catalyzed by ATP-citrate lyase, or citryl-CoA synthetase and citryl-CoA lyase. Alternatively, citrate lyase can be coupled to acetyl-CoA synthetase, an acetyl-CoA transferase, or phosphotransacetylase and acetate kinase to form acetyl-CoA and oxaloacetate from citrate. The conversion of succinate to fumarate is catalyzed by succinate dehydrogenase while the reverse reaction is catalyzed by fumarate reductase. In the TCA cycle succinyl-CoA is formed from the $NAD(P)^+$ dependent decarboxylation of alpha-ketoglutarate by the alpha-ketoglutarate dehydrogenase complex. The reverse reaction is catalyzed by alpha-ketoglutarate:ferredoxin oxidoreductase.

An organism capable of utilizing the reverse tricarboxylic acid cycle to enable production of acetyl-CoA-derived products on 1) CO, 2) $CO_2$ and $H_2$, 3) CO and $CO_2$, 4) synthesis gas comprising CO and $H_2$, and 5) synthesis gas or other gaseous carbon sources comprising CO, $CO_2$, and $H_2$ can include any of the following enzyme activities: ATP-citrate lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, acetate kinase, phosphotransacetylase, acetyl-CoA synthetase, acetyl-CoA transferase, pyruvate:ferredoxin oxidoreductase, NAD(P)H:ferredoxin oxidoreductase, carbon monoxide dehydrogenase, hydrogenase, and ferredoxin (see FIGS. 8A and 9A). Enzymes and the corresponding genes required for these activities are described herein below.

Carbon from syngas or other gaseous carbon sources can be fixed via the reverse TCA cycle and components thereof. Specifically, the combination of certain carbon gas-utilization pathway components with the pathways for formation of 1,3-butanediol from acetyl-CoA results in high yields of these products by providing an efficient mechanism for fixing the carbon present in carbon dioxide, fed exogenously or produced endogenously from CO, into acetyl-CoA.

In some embodiments, a 1,3-butanediol pathway in a non-naturally occurring microbial organism of the invention can utilize any combination of (1) CO, (2) $CO_2$, (3) $H_2$, or mixtures thereof to enhance the yields of biosynthetic steps involving reduction, including addition to driving the reductive TCA cycle.

In some embodiments a non-naturally occurring microbial organism having a 1,3-butanediol pathway includes at least one exogenous nucleic acid encoding a reductive TCA pathway enzyme. The at least one exogenous nucleic acid is selected from an ATP-citrate lyase, citrate lyase, a fumarate reductase, an isocitrate dehydrogenase, an aconitase, an isocitrate dehydrogenase, and an alpha-ketoglutarate:ferredoxin oxidoreductase; and at least one exogenous enzyme selected from a carbon monoxide dehydrogenase, a hydrogenase, a NAD(P)H:ferredoxin oxidoreductase, and a ferredoxin, expressed in a sufficient amount to allow the utilization of (1) CO, (2) $CO_2$, (3) $H_2$, (4) $CO_2$ and $H_2$, (5) CO and $CO_2$, (6) CO and $H_2$, or (7) CO, $CO_2$, and $H_2$.

In some embodiments a method includes culturing a non-naturally occurring microbial organism having a 1,3-butanediol pathway also comprising at least one exogenous nucleic acid encoding a reductive TCA pathway enzyme. The at least one exogenous nucleic acid is selected from an ATP-citrate lyase, citrate lyase, a fumarate reductase, an isocitrate dehydrogenase, an aconitase, an isocitrate dehydrogenase, and an alpha-ketoglutarate:ferredoxin oxidoreductase. Additionally, such an organism can also include at least one exogenous enzyme selected from a carbon monoxide dehydrogenase, a hydrogenase, a NAD(P)H:ferredoxin oxidoreductase, and a ferredoxin, expressed in a sufficient amount to allow the utilization of (1) CO, (2) $CO_2$, (3) $H_2$, (4) $CO_2$ and $H_2$, (5) CO and $CO_2$, (6) CO and $H_2$, or (7) CO, $CO_2$, and $H_2$ to produce a product.

In some embodiments a non-naturally occurring microbial organism having a 1,3-butanediol pathway further includes at least one exogenous nucleic acid encoding a reductive TCA pathway enzyme expressed in a sufficient amount to enhance carbon flux through acetyl-CoA. The at least one exogenous nucleic acid is selected from an ATP-citrate lyase, citrate lyase, a fumarate reductase, an isocitrate dehydrogenase, an aconitase, an isocitrate dehydrogenase, a pyruvate:ferredoxin oxidoreductase and an alpha-ketoglutarate:ferredoxin oxidoreductase.

In some embodiments a non-naturally occurring microbial organism having a 1,3-butanediol pathway includes at least one exogenous nucleic acid encoding an enzyme expressed in a sufficient amount to enhance the availability of reducing equivalents in the presence of carbon monoxide and/or hydrogen, thereby increasing the yield of redox-limited products via carbohydrate-based carbon feedstock. The at least one exogenous nucleic acid is selected from a carbon monoxide dehydrogenase, a hydrogenase, an NAD(P)H:ferredoxin oxidoreductase, and a ferredoxin. In some embodiments, the present invention provides a method for enhancing the availability of reducing equivalents in the presence of carbon monoxide or hydrogen thereby increasing the yield of redox-limited products via carbohydrate-based carbon feedstock, such as sugars or gaseous carbon sources, the method includes culturing this non-naturally occurring microbial organism under conditions and for a sufficient period of time to produce 1,3-butanediol.

In some embodiments, the non-naturally occurring microbial organism having a 1,3-butanediol pathway includes two exogenous nucleic acids each encoding a reductive TCA pathway enzyme. In some embodiments, the non-naturally occurring microbial organism having a 1,3-butanediol pathway includes three exogenous nucleic acids each encoding a reductive TCA pathway enzyme. In some embodiments, the non-naturally occurring microbial organism includes three exogenous nucleic acids encoding an ATP-citrate lyase, a fumarate reductase, and an alpha-ketoglutarate:ferredoxin oxidoreductase. In some embodiments, any one of the three exogenous nucleic acids can be an isocitrate dehydrogenase. In some embodiments, the non-naturally occurring microbial organism includes three exogenous nucleic acids encoding a citrate lyase, a fumarate reductase, and an alpha-ketoglutarate:ferredoxin oxidoreductase. In some embodiments, the non-naturally occurring microbial organism includes four exogenous nucleic acids encoding a pyruvate:ferredoxin oxidoreductase; a phosphoenolpyruvate carboxylase or a phosphoenolpyruvate carboxykinase, a CO dehydrogenase; and an H2 hydrogenase. In some embodiments, the non-naturally occurring microbial organism includes two exogenous nucleic acids encoding a CO dehydrogenase and an H2 hydrogenase.

In some embodiments, the non-naturally occurring microbial organisms having a 1,3-butanediol pathway further include an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, and combinations thereof.

In some embodiments, the non-naturally occurring microbial organism having a 1,3-butanediol pathway further includes an exogenous nucleic acid encoding an enzyme selected from carbon monoxide dehydrogenase, acetyl-CoA synthase, ferredoxin, NAD(P)H:ferredoxin oxidoreductase and combinations thereof.

In some embodiments, the non-naturally occurring microbial organism having a 1,3-butanediol pathway utilizes a carbon feedstock selected from (1) CO, (2) $CO_2$, (3) $CO_2$ and $H_2$, (4) CO and $H_2$, or (5) CO, $CO_2$, and $H_2$. In some embodiments, the non-naturally occurring microbial organism having a 1,3-butanediol pathway utilizes hydrogen for reducing equivalents. In some embodiments, the non-naturally occurring microbial organism having a 1,3-butanediol pathway utilizes CO for reducing equivalents. In some embodiments, the non-naturally occurring microbial organism having a 1,3-butanediol pathway utilizes combinations of CO and hydrogen for reducing equivalents.

In some embodiments, the non-naturally occurring microbial organism having a 1,3-butanediol pathway further includes one or more nucleic acids encoding an enzyme selected from a phosphoenolpyruvate carboxylase, a phosphoenolpyruvate carboxykinase, a pyruvate carboxylase, and a malic enzyme.

In some embodiments, the non-naturally occurring microbial organism having a 1,3-butanediol pathway further includes one or more nucleic acids encoding an enzyme selected from a malate dehydrogenase, a fumarase, a fumarate reductase, a succinyl-CoA synthetase, and a succinyl-CoA transferase.

In some embodiments, the non-naturally occurring microbial organism having a 1,3-butanediol pathway further includes at least one exogenous nucleic acid encoding a citrate lyase, an ATP-citrate lyase, a citryl-CoA synthetase, a citryl-CoA lyase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an acetyl-CoA transferase, and a ferredoxin.

It is understood by those skilled in the art that the above-described pathways for increasing product yield can be combined with any of the pathways disclosed herein, including those pathways depicted in the figures. One skilled in the art will understand that, depending on the pathway to a desired product and the precursors and intermediates of that pathway, a particular pathway for improving product yield, as discussed herein above and in the examples, or combination of such pathways, can be used in combination with a pathway to a desired product to increase the yield of that product or a pathway intermediate.

In an additional embodiment, the invention provides a non-naturally occurring microbial organism having a 1,3-butanediol pathway, wherein the non-naturally occurring microbial organism comprises at least one exogenous nucleic acid encoding an enzyme or protein that converts a substrate to a product selected from the group consisting of pyruvate to alanine, alanine to 2-amino-4-oxopentanoate, 2-amino-4-oxopentanoate to 2-amino-4-hydroxypentanoate, 2-amino-4-oxopentanoate to 2,4-dioxopentanoate, 2-amino-4-oxopentanoate to 4-aminobutan-2-one, 2-amino-4-oxopentanoate to acetylacrylate, 2-amino-4-hydroxypentanoate to 2-oxo-4-hydroxypentanoate, 2-oxo-4-hydroxypentanoate to 3-hydroxybutyraldehyde, 2,4-dioxopentanoate to 3-oxobutyraldehyde, 3-oxobutyraldehyde to 3-hydroxybutryaldehyde, 3-oxobutyraldehdye to 4-hydroxy-2-butanone, 4-aminobutan-2-one to 3-oxobutyraldehyde, 4-aminobutan-2-one to butanone, butanone to 4-hydroxy-2-butanone and acetylacrylate to butenone. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a 1,3-butanediol pathway, such as that shown in FIG. 8B.

In an additional embodiment, the invention provides a non-naturally occurring microbial organism having a 1,3-butanediol pathway, wherein the non-naturally occurring microbial organism comprises at least one exogenous nucleic acid encoding an enzyme or protein that converts a substrate to a product selected from the group consisting of succinate to succinyl-CoA, succinate to succinic semialdehyde, succinyl-CoA to succinic semialdehyde, alpha-ketoglutarate to succinic semialdehyde, succinyl-CoA to 4-hydroxybutyrate, succinic semialdehyde to 4-hydroxybutyrate, 4-hydroxybutyrate to 4-hydroxybutyryl phosphate, 4-hydroxybutyrate to 4-hydroxybutyryl-CoA, 4-hydroxybutyryl phosphate to 4-hydroxybutyryl CoA, 4-hydroxybutyryl-CoA to crotonyl-CoA, crotonyl-CoA to 3-hydroxybutyryl-CoA, 3-hydroxybutyryl-CoA to 3-hydroxybutyrate, 3-hydroxybutyrate to 1,3-butanediol, 3-hydroxybutyryl-CoA to 1,3-butanediol, 3-hydroxybutyryl-CoA to 3-hydroxybutanal, 3-hydroxybutanal to 1,3-butanediol. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a 1,3-butanediol pathway, such as that shown in FIG. 9B.

While generally described herein as a microbial organism that contains a 1,3-butanediol pathway, it is understood that the invention additionally provides a non-naturally occurring microbial organism comprising at least one exogenous nucleic acid encoding a 1,3-butanediol pathway enzyme expressed in a sufficient amount to produce an intermediate of a 1,3-butanediol pathway. For example, as disclosed herein, a 1,3-butanediol pathway is exemplified in FIGS. 1-3, 8A/B, and 9A/B. Therefore, in addition to a microbial organism containing a 1,3-butanediol pathway that produces 1,3-butanediol, the invention additionally provides a non-naturally occurring microbial organism comprising at least one exogenous nucleic acid encoding a 1,3-butanediol pathway enzyme, where the microbial organism produces a 1,3-butanediol pathway intermediate, for example, alanine, 2-amino-4-pentanoate, 2-amino-4-hydroxypentanoate, 2-oxo-4-hydroxypentanoate, 3-hydroxybutyraldehyde, 2,4-dioxopentanoate, 3-oxobutyraldehyde, 4-aminobutan-2-one, acetylacrylate, butanone, 4-hydroxy-2-butanone, succinic semialdehyde, 4-hydroxybutyrate, 4-hydroxybutyryl phosphate, 4-hydroxybutyryl-CoA, crotonyl-CoA, 3-hydroxybutyryl-CoA, 3-hydroxybutyrate, and 3-hydroxybutanal.

It is understood that any of the pathways disclosed herein, as described in the Examples and exemplified in the Figures, including the pathways of FIGS. 1-3, 8A/B, and 9A/B can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a 1,3-butanediol pathway intermediate can be utilized to produce the intermediate as a desired product.

Successfully engineering any of these pathways entails identifying an appropriate set of enzymes with sufficient activity and specificity, cloning their corresponding genes into a production host, optimizing fermentation conditions, and assaying for product formation following fermentation. To engineer a production host for the production of any of the aforementioned products, one or more exogenous DNA sequence(s) can be expressed in microorganisms. In addition, the microorganisms can have endogenous gene(s) functionally deleted. These modifications will enable the production of 1,3-BDO using renewable feedstocks.

Below, are described a number of biochemically characterized genes capable of encoding enzymes that catalyze each of the steps shown in FIGS. 1, 2 3, 8B, and 9B. Although we describe this method for *E. coli*, one skilled in the art can apply these teachings to essentially any other organism. Specifically, genes are listed that are native to *E. coli* in addition to genes in other organisms that can be applied to catalyze the appropriate transformations when properly cloned and expressed.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

As disclosed herein, intermediates en route to 1,3-butanediol can be carboxylic acids or CoA esters thereof, such as 4-hydroxy butyrate, 3-hydroxybutyrate, their CoA esters, as well as crotonyl-CoA. Any carboxylic acid intermediate can occur in various ionized forms, including fully protonated, partially protonated, and fully deprotonated forms. Accordingly, the suffix "-ate," or the acid form, can be used interchangeably to describe both the free acid form as well as any deprotonated form, in particular since the ionized form is known to depend on the pH in which the compound is found. It is understood that carboxylate intermediates includes ester forms of carboxylate products or pathway intermediates, such as O-carboxylate and S-carboxylate esters. O- and S-carboxylates can include lower alkyl, that is C1 to C6, branched or straight chain carboxylates. Some such O- or S-carboxylates include, without limitation, methyl, ethyl, n-propyl, n-butyl, i-propyl, sec-butyl, and tert-butyl, pentyl, hexyl O- or S-carboxylates, any of which can further possess an unsaturation, providing for example, propenyl, butenyl, pentyl, and hexenyl O- or S-carboxylates. O-carboxylates can be the product of a biosynthetic pathway. Exemplary O-carboxylates accessed via biosynthetic pathways can include, without limitation, methyl 4-hydroxybutyrate, methyl-3-hydroxybutyrate, ethyl 4-hydroxybutyrate, ethyl 3-hydroxybutyrate, n-propyl 4-hydroxybutyrate, and n-propyl 3-hydroxybutyrate. Other biosynthetically accessible O-carboxylates can include medium to long chain groups, that is C7-C22, O-carboxylate esters derived from fatty alcohols, such heptyl, octyl, nonyl, decyl, undecyl, lauryl, tridecyl, myristyl, pentadecyl, cetyl, palmitolyl, heptadecyl, stearyl, nonadecyl, arachidyl, heneicosyl, and behenyl alcohols, any one of which can be optionally branched and/or contain unsaturations. O-carboxylate esters can also be accessed via a biochemical or chemical process, such as esterification of a free carboxylic acid product or transesterification of an O- or S-carboxylate. S-carboxylates are exemplified by CoA S-esters, cysteinyl S-esters, alkylthioesters, and various aryl and heteroaryl thioesters.

All transformations depicted in FIGS. 1-3, 8B and 9B fall into the 8 general categories of transformations shown in Table 1. Below is described a number of biochemically characterized genes in each category. Specifically listed are genes that can be applied to catalyze the appropriate transformations in FIGS. 1-3, 8B, and 9B when properly cloned and expressed. Exemplary genes for each of the steps in FIGS. 1-3, 8B and 9B are provided further below in Tables 35-37.

Table 1 shows the enzyme types useful to convert common central metabolic intermediates into 1,3-butanediol. The first three digits of each label correspond to the first three Enzyme Commission number digits which denote the general type of transformation independent of substrate specificity.

TABLE 1

| LABEL | FUNCTION |
| --- | --- |
| 1.1.1.a | Oxidoreductase (ketone to hydroxyl or aldehyde to alcohol) |
| 1.1.1.c | Oxidoreductase (2 step, acyl-CoA to alcohol) |
| 1.2.1.b | Oxidoreductase (acyl-CoA to aldehyde) |
| 1.4.1.a | Oxidoreductase (deaminating) |
| 2.3.1.b | Acyltransferase |
| 2.6.1.a | Aminotransferase |
| 4.1.1.a | Carboxy-lyase |
| 4.2.1.a | Hydro-lyase |
| 4.3.1.a | Ammonia-lyase |

Numerous transformation in FIGS. 1, 2 and 3 fall into the category of oxidoreductases that reduce an aldehyde to alcohol. For example, Steps D and P in FIG. 1 catalyzed by 3-oxobutyraldehyde reductase (aldehyde reducing) and 3-hydroxybutyraldehyde reductase respectively fall into this category. Similarly, Steps C and E in FIG. 2 catalyzed by 3-hydroxybutyraldehyde reductase and 3-oxobutyraldehyde reductase (aldehyde reducing) respectively are also oxidoreductases that convert the aldehyde functionality to alcohol. Pathways in FIG. 3 involve oxidoreductases such as 3-hydroxybutyraldehyde reductase in Step D.

Exemplary genes encoding enzymes that catalyze the conversion of an aldehyde to alcohol (i.e., alcohol dehydrogenase or equivalently aldehyde reductase) include alrA encoding a medium-chain alcohol dehydrogenase for C2-C14 (Tani et al., *Appl. Environ. Microbiol.*, 66:5231-5235 (2000)), ADH2 from *Saccharomyces cerevisiae* (Atsumi et al., *Nature*, 451:86-89 (2008)), yqhD from *E. coli* which has preference for molecules longer than C3 (Sulzenbacher et al., *J. of Molecular Biology*, 342:489-502 (2004)), and bdh I and bdh II from *C. acetobutylicum* which converts butyraldehyde into butanol (Walter et al., *J. of Bacteriology*, 174:7149-7158 (1992)). The gene product of yqhD catalyzes the reduction of acetaldehyde, malondialdehyde, propionaldehyde, butyraldehyde, and acrolein using NADPH as the cofactor (Perez et al., *J. Biol. Chem.*, 283:7346-7353 (2008)). The adhA gene product from *Zymomonas mobilis* has been demonstrated to have activity on a number of aldehydes including formaldehyde, acetaldehyde, propionaldehyde, butyraldehyde, and acrolein (Kinoshita et al., *Appl. Microbiol. Biotechnol*, 22:249-254 (1985)). Additional aldehyde reductase candidates are encoded by bdh in *C. saccharoperbutylacetonicum* and Cbei_/722, Cbei_2181 and Cbei_2421 in *C. beijerinckii*.

Data related to the sequences for each of these exemplary gene product can be found using the following GenBank accession numbers shown in Table 2.

TABLE 2

| Protein | GENBANK ID | GI NUMBER | ORGANISM |
|---|---|---|---|
| alrA | BAB12273.1 | 9967138 | Acinetobacter sp. strain M-1 |
| ADH2 | NP_014032.1 | 6323961 | Saccharomyces cerevisiae |
| yqhD | NP_417484.1 | 16130909 | Escherichia coli |
| bdh I | NP_349892.1 | 15896543 | Clostridium acetobutylicum |
| bdh II | NP_349891.1 | 15896542 | Clostridium acetobutylicum |
| adhA | YP_162971.1 | 56552132 | Zymomonas mobilis |
| bdh | BAF45463.1 | 124221917 | Clostridium saccharoperbutylacetonicum |
| Cbei_1722 | YP_001308850 | 150016596 | Clostridium beijerinckii |
| Cbei_2181 | YP_001309304 | 150017050 | Clostridium beijerinckii |
| Cbei_2421 | YP_001309535 | 150017281 | Clostridium beijerinckii |

Enzymes exhibiting 3-hydroxybutyraldehyde reductase activity (EC 1.1.1.61) also fall into this category. Such enzymes have been characterized in *Ralstonia eutropha* (Bravo et al., *J. Forensic Sci.*, 49:379-387 (2004)), *Clostridium kluyveri* (Wolff et al., *Protein Expr. Purif.*, 6:206-212 (1995)) and *Arabidopsis thaliana* (Breitkreuz et al., *J. Biol. Chem.*, 278:41552-41556 (2003)). Yet another gene is the alcohol dehydrogenase adh1 from *Geobacillus thermoglucosidasius* (Jeon et al., *J. Biotechnol.*, 135:127-133 (2008)). Data related to the sequences for each of these exemplary gene products can be found using the following GenBank accession numbers shown in Table 3.

TABLE 3

| PROTEIN | GENBANK ID | GI NUMBER | ORGANISM |
|---|---|---|---|
| 4hbd | YP_726053.1 | 113867564 | Ralstonia eutropha H16 |
| 4hbd | L21902.1 | 146348486 | Clostridium kluyveri DSM 555 |
| 4hbd | Q94B07 | 75249805 | Arabidopsis thaliana |
| adhI | AAR91477.1 | 40795502 | Geobacillus thermoglucosidasius M10EXG |

Another exemplary enzyme is 3-hydroxyisobutyrate dehydrogenase which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al., *J. Mol. Biol.*, 352:905-917 (2005)). The reversibility of the human 3-hydroxyisobutyrate dehydrogenase was demonstrated using isotopically-labeled substrate (Manning et al., *Biochem J.*, 231:481-484 (1985)). Additional genes encoding this enzyme include 3hidh in *Homo sapiens* (Hawes et al., *Methods Enzymol*, 324:218-228 (2000)) and *Oryctolagus cuniculus* (Hawes et al., supra; Chowdhury et al., *Biosci. Biotechnol Biochem.*, 60:2043-2047 (1996)), mmsB in *Pseudomonas aeruginosa* and *Pseudomonas putida* (Liao et al., US patent 20050221466), and dhat in *Pseudomonas putida* (Aberhart et al., *J. Chem. Soc.*, 6:1404-1406 (1979); Chowdhury et al., supra; Chowdhury et al., *Biosci. Biotechnol Biochem.*, 67:438-441 (2003)). Data related to the sequences for each of these exemplary gene products can be found using the following GenBank accession numbers shown in Table 4.

TABLE 4

| PROTEIN | GENBANK ID | GI NUMBER | ORGANISM |
|---|---|---|---|
| P84067 | P84067 | 75345323 | Thermus thermophilus |
| 3hidh | P31937.2 | 12643395 | Homo sapiens |
| 3hidh | P32185.1 | 416872 | Oryctolagus cuniculus |
| mmsB | P28811.1 | 127211 | Pseudomonas aeruginosa |
| mmsB | NP_746775.1 | 26991350 | Pseudomonas putida |
| dhat | Q59477.1 | 2842618 | Pseudomonas putida |

Oxidoreductases that convert a ketone functionality to the corresponding hydroxyl group are also synthetic steps in the disclosed pathways. Notably, Reactions L, O and H in FIG. 1 catalyzed by AKP dehydrogenase, 3-oxobutyraldehyde reductase (ketone reducing), 4-hydroxy-2-butanone reductase respectively are transformations of this category. The two latter transformations are also encountered in Steps B and F respectively in FIG. 2. On similar lines, the acetoacetyl-CoA reductase in Step G of FIG. 2 reduces acetoacetyl-CoA to 3-hydroxybutyryl-CoA.

The reduction of 4-oxo group of 2-amino-4-oxopentanoate (AKP) by a dehydrogenase yields 2-amino-4-hydroxypentanoate (FIG. 1, step L). This reaction is very similar to the NAD(P)H-dependent reduction of aspartate semialdehyde to homoserine catalyzed by homoserine dehydrogenase (EC 1.1.13). In many organisms, including *E. coli*, homoserine dehydrogenase is a bifunctional enzyme that also catalyzes the ATP-dependent conversion of aspartate to aspartyl-4-phosphate (Starnes et al., *Biochemistry*, 11:677-687 (1973)). The functional domains are catalytically independent and connected by a linker region (Sibilli et al., *J. Biol. Chem.*, 256:10228-10230 (1981)) and both domains are subject to allosteric inhibition by threonine. The homoserine dehydrogenase domain of the *E. coli* enzyme, encoded by thrA, was separated from the aspartate kinase domain, characterized, and found to exhibit high catalytic activity and reduced inhibition by threonine (James et al., *Biochemistry*, 41:3720-3725 (2002)). This can be applied to other bifunctional threonine kinases including, for example, hom1 of *Lactobacillus plantarum* (Cahyanto et al., *Microbiology*, 152:205-112 (2006)) and *Arabidopsis thaliana*. The monofunctional homoserine dehydrogenases encoded by hom6 in *S. cerevisiae* (Jacques et al., *Biochem. Biophys. Acta*, 1544:28-41 (2001)) and hom2 in *Lactobacillus plantarum* (Cahyanto et al., supra) have been functionally expressed and characterized in *E. coli*. Data related to the sequences for each of these exemplary gene products can be found using the following GenBank accession numbers shown in Table 5.

TABLE 5

| PROTEIN | GENBANK ID | GI NUMBER | ORGANISM |
|---|---|---|---|
| thrA | AAC73113.1 | 1786183 | Escherichia coli K12 |
| akthr2 | O81852 | 75100442 | Arabidopsis thaliana |
| hom6 | CAA89671 | 1015880 | Saccharomyces cerevisiae |
| hom1 | CAD64819 | 28271914 | Lactobacillus plantarum |
| hom2 | CAD63186 | 28270285 | Lactobacillus plantarum |

Acetoacetyl-CoA reductase (Step G, FIG. 2) catalyzing the reduction of acetoacetyl-CoA to 3-hydroxybutyryl-CoA participates in the acetyl-CoA fermentation pathway to butyrate in several species of Clostridia and has been studied in detail (Jones et al., Microbiol. Rev., 50:484-524 (1986)). The enzyme from Clostridium acetobutylicum, encoded by hbd, has been cloned and functionally expressed in E. coli (Youngleson et al., J. Bacteriol., 171:6800-6807 (1989)). Additionally, subunits of two fatty acid oxidation complexes in E. coli, encoded byfadB andfadJ, function as 3-hydroxyacyl-CoA dehydrogenases (Binstock et al., Methods Enzymol., 71C:403-411 (1981)). Yet other genes demonstrated to reduce acetoacetyl-CoA to 3-hydroxybutyryl-CoA are phbB from Zoogloea ramigera (Ploux et al., Eur. J. Biochem., 174:177-182 (1988)) and phaB from Rhodobacter sphaeroides (Alber et al., Mol. Microbiol., 61:297-309 (2006)). The former gene is NADPH-dependent, its nucleotide sequence has been determined (Peoples et al., Mol. Microbiol. 3:349-357 (1989)) and the gene has been expressed in E. coli. Substrate specificity studies on the gene led to the conclusion that it could accept 3-oxopropionyl-CoA as a substrate besides acetoacetyl-CoA (Ploux et al., supra). Additional genes include Hbd1 (C-terminal domain) and Hbd2 (N-terminal domain) in Clostridium kluyveri (Hillmer and Gottschalk, Biochim. Biophys. Acta 3334:12-23 (1974)) and HSD17B10 in Bos taurus (Wakil et al., J. Biol. Chem., 207:631-638 (1954)). Data related to the sequences for each of these exemplary gene products can be found using the following GenBank accession numbers shown in Table 6.

TABLE 6

| Protein | GENBANK ID | GI NUMBER | ORGANISM |
|---|---|---|---|
| fadB | P21177.2 | 119811 | Escherichia coli |
| fadJ | P77399.1 | 3334437 | Escherichia coli |
| Hbd2 | EDK34807.1 | 146348271 | Clostridium kluyveri |
| Hbd1 | EDK32512.1 | 146345976 | Clostridium kluyveri |
| hbd | P52041.2 | | Clostridium acetobutylicum |
| HSD17B10 | O02691.3 | 3183024 | Bos Taurus |
| phbB | P23238.1 | 130017 | Zoogloea ramigera |
| phaB | YP_353825.1 | 77464321 | Rhodobacter sphaeroides |

A number of similar enzymes have been found in other species of Clostridia and in Metallosphaera sedula (Berg et al., Archaea. Science, 318:1782-1786 (2007)) as shown in Table 7.

TABLE 7

| Protein | GenBank ID | GI number | Organism |
|---|---|---|---|
| Hbd | NP_349314.1 | NP_349314.1 | Clostridium acetobutylicum |
| Hbd | AAM14586.1 | AAM14586.1 | Clostridium beijerinckii |
| Msed_1423 | YP_001191505 | YP_001191505 | Metallosphaera sedula |
| Msed_0399 | YP_001190500 | YP_001190500 | Metallosphaera sedula |

TABLE 7-continued

| Protein | GenBank ID | GI number | Organism |
|---|---|---|---|
| Msed_0389 | YP_001190490 | YP_001190490 | Metallosphaera sedula |
| Msed_1993 | YP_001192057 | YP_001192057 | Metallosphaera sedula |

An exemplary alcohol dehydrogenase that converts a ketone to a hydroxyl group is the secondary alcohol dehydrogenase that was shown to convert acetone to isopropanol in C. beijerinckii (Ismaiel et al., J. Bacteriol., 175:5097-5105 (1993)) and T. brockii (Lamed et al., Biochem. J., 195:183-190 (1981); Peretz et al., Biochemistry, 28:6549-6555 (1989)). The gene product of adhA from Pyrococcus furiosus, which exhibits maximum activity on 2-pentanol and pyruvaldehyde, was shown to have very broad specificity which includes isopropanol and acetone (Van der et al., Eur. J. Biochem., 268:3062-3068 (2001)). Yet another secondary alcohol dehydrogenase with activity on isopropanol and acetone is encoded by the gene product of adh-A from Rhodococcus ruber (Edegger et al., Chem. Commun. (Camb), 2402-2404 (2006); Kosjek et al., Biotechnol. Bioeng., 86:55-62 (2004)). These genes along with others are listed below in Table 8.

TABLE 8

| Protein | GenBank ID | GI number | Organism |
|---|---|---|---|
| adh | AAA23199.2 | 60592974 | Clostridium beijerinckii NRRL B593 |
| adh | P14941.1 | 113443 | Thermoanaerobacter brockii HTD4 |
| adhA | AAC25556 | 3288810 | Pyrococcus furiosus |
| adh-A | CAD36475 | 21615553 | Rhodococcus ruber |

Alternatively, there exist several exemplary alcohol dehydrogenases that convert a ketone to a hydroxyl functional group. Two such enzymes from E. coli are encoded by malate dehydrogenase (mdh) and lactate dehydrogenase (ldhA). In addition, lactate dehydrogenase from Ralstonia eutropha has been shown to demonstrate high activities on substrates of various chain lengths such as lactate, 2-oxobutyrate, 2-oxopentanoate and 2-oxoglutarate (Steinbuchel et al., Eur. J. Biochem., 130:329-334 (1983)). Conversion of the oxo functionality to the hydroxyl group can also be catalyzed by 2-keto1,3-butanediol reductase, an enzyme reported to be found in rat and in human placenta (Suda et al., Arch. Biochem. Biophys., 176:610-620 (1976); Suda et al., Biochem. Biophys. Res. Commun., 77:586-591 (1977)). All of these enzymes can provide a 3-oxobutyraldehyde reductase, and a 4-hydroxy-2-butanone reductase. An additional enzyme for these steps is the mitochondrial 3-hydroxybutyrate dehydrogenase (bdh) from the human heart which has been cloned and characterized (Marks et al., J. Biol. Chem. 267:15459-15463 (1992)). This enzyme is a dehydrogenase that operates on a 3-hydroxyacid. Data related to the sequences for each of these exemplary gene products can be found using the following GenBank accession numbers shown in Table 9.

TABLE 9

| Protein | GenBank ID | GI number | Organism |
|---|---|---|---|
| mdh | AAC76268.1 | 1789632 | Escherichia coli |
| ldhA | NP_415898.1 | 16129341 | Escherichia coli |

TABLE 9-continued

| Protein | GenBank ID | GI number | Organism |
| --- | --- | --- | --- |
| ldh | YP_725182.1 | 113866693 | Ralstonia eutropha |
| bdh | AAA58352.1 | 177198 | Homo sapiens |

A number of organisms can catalyze the reduction of 4-hydroxy-2-butanone to 1,3-butanediol, including those belonging to the genus Bacillus, Brevibacterium, Candida, and Klebsiella among others, as described by Matsuyama et al. (1995).

Several transformations in FIGS. 2 and 3 rely on the two-step reduction of acyl-CoA to the corresponding alcohol. For example, Steps D and I in FIG. 2, involving the acetoacetyl-CoA reductase (CoA-dependent, alcohol forming) and 3-hydroxybutyryl-CoA reductase (alcohol forming), and Step E in FIG. 3 involving 3-hydroxybutyryl-CoA reductase (alcohol forming), shows such a transformation.

Exemplary two-step oxidoreductases that convert an acyl-CoA to alcohol include those that transform substrates such as acetyl-CoA to ethanol (e.g., adhE from *E. coli* (Kessler et al., *FEBS. Lett.*, 281:59-63 (1991)) and butyryl-CoA to butanol (e.g. adhE2 from *C. acetobutylicum* (Fontaine et al., *J. Bacteriol.*, 184:821-830 (2002)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., *J. Gen. Appl. Microbiol.*, 18:43-55 (1972); Koo et al., *Biotechnol. Lett.*, 27:505-510 (2005)). Data related to the sequences for each of these exemplary gene products can be found using the following GenBank accession numbers shown in Table 10.

TABLE 10

| Protein | GenBank ID | GI Number | Organism |
| --- | --- | --- | --- |
| adhE | NP_415757.1 | 16129202 | Escherichia coli |
| adhE2 | AAK09379.1 | 12958626 | Clostridium acetobutylicum |
| adhE | AAV66076.1 | 55818563 | Leuconostoc mesenteroides |

Another exemplary enzyme can convert malonyl-CoA to 3-HP. An NADPH-dependent enzyme with this activity has characterized in *Chloroflexus aurantiacus* where it participates in the 3-hydroxypropionate cycle (Hugler et al., *J. Bacteriol.*, 184:2404-2410 (2002); Strauss et al., *Eur. J. Biochem.*, 215:633-643 (1993)). This enzyme, with a mass of 300 kDa, is highly substrate-specific and shows little sequence similarity to other known oxidoreductases (Hugler et al., supra). No enzymes in other organisms have been shown to catalyze this specific reaction; however there is bioinformatic evidence that other organisms can have similar pathways (Klatt et al., *Environ. Microbiol.*, 9:2067-2078 (2007)). Enzymes in other organisms including *Roseiflexus castenholzii, Erythrobacter* sp. NAP1 and marine gamma proteobacterium HTCC2080 can be inferred by sequence similarity. Data related to the sequences for each of these exemplary gene products can be found using the following GenBank accession numbers shown in Table 11.

TABLE 11

| Protein | GenBank ID | GI Number | Organism |
| --- | --- | --- | --- |
| mcr | AAS20429.1 | 42561982 | Chloroflexus aurantiacus |

TABLE 11-continued

| Protein | GenBank ID | GI Number | Organism |
| --- | --- | --- | --- |
| Rcas_2929 | YP_001433009.1 | 156742880 | Roseiflexus castenholzii |
| NAP1_02720 | ZP_01039179.1 | 85708113 | Erythrobacter sp. NAP1 |
| MGP2080_00535 | ZP_01626393.1 | 119504313 | marine gamma proteobacterium HTCC2080 |

Longer chain acyl-CoA molecules can be reduced by enzymes such as the jojoba (*Simmondsia chinensis*) FAR which encodes an alcohol-forming fatty acyl-CoA reductase. Its overexpression in *E. coli* resulted in FAR activity and the accumulation of fatty alcohol (Metz et al., *Plant Physiology*, 122:635-644 (2000)) (FAR, AAD38039.1, 5020215, *Simmondsia chinensis*).

The pathways disclosed herein involve numerous oxidoreductase-type transformations that convert an acyl-CoA to an aldehyde. Specifically, Steps A and H in FIG. 2 catalyzed by acetoacetyl-CoA reductase (aldehyde forming) and 3-hydroxybutyryl-CoA reductase (aldehyde forming), and Step C from FIG. 3 showing the transformation catalyzed by 3-hydroxybutyryl-CoA reductase.

Several acyl-CoA dehydrogenases are capable of reducing an acyl-CoA to its corresponding aldehyde. Exemplary genes that encode such enzymes include the *Acinetobacter calcoaceticus* acr1 encoding a fatty acyl-CoA reductase (Reiser et al., *J. of Bacteriology*, 179:2969-2975 (1997)), the *Acinetobacter* sp. M-1 fatty acyl-CoA reductase (Ishige et al., *Appl. Environ. Microbiol.*, 68:1192-1195 (2002)), and a CoA- and NADP-dependent succinate semialdehyde dehydrogenase encoded by the sucD gene in *Clostridium kluyveri* (Sohling et al., *J. Bacteriol.*, 178:871-880 (1996)). SucD of *P. gingivalis* is another succinate semialdehyde dehydrogenase (Takahashi et al., *J. Bacteriol.*, 182:4704-4710 (2000)). The enzyme acylating acetaldehyde dehydrogenase in *Pseudomonas* sp, encoded by bphG, is yet another enzyme demonstrated to oxidize and acylate acetaldehyde, propionaldehyde, butyraldehyde, isobutyraldehyde and formaldehyde (Powlowski et al., *J. Bacteriol.*, 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., supra; Koo et al., supra). Butyraldehyde dehydrogenase catalyzes a similar reaction, conversion of butyryl-CoA to butyraldehyde, in solventogenic organisms such as *Clostridium saccharoperbutylacetonicum* (Kosaka et al., *Biosci. Biotechnol. Biochem.*, 71:58-61 (2007)). Additional aldehyde dehydrogenase enzyme candidates are found in *Desulfatibacillum alkenivorans, Citrobacter koseri, Salmonella enterica, Lactobacillus brevis* and *Bacillus selenitireducens*. Data related to the sequences for each of these exemplary gene products can be found using the following GenBank accession numbers shown in Table 12.

TABLE 12

| Protein | GenBank ID | GI Number | Organism |
|---|---|---|---|
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |
| bld | AAP42563.1 | 31075383 | *Clostridium saccharoperbutylacetonicum* |
| ald | ACL06658.1 | 218764192 | *Desulfatibacillum alkenivorans* AK-01 |
| ald | YP_001452373 | 157145054 | *Citrobacter koseri* ATCC BAA-895 |
| pduP | NP_460996.1 | 16765381 | *Salmonella enterica Typhimurium* |
| pduP | ABJ64680.1 | 116099531 | *Lactobacillus brevis* ATCC 367 |
| BselDRAFT_1651 | ZP_02169447 | 163762382 | *Bacillus selenitireducens* MLS10 |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., supra; Thauer, R. K., *Science*, 318:1732-1733 (2007)). The enzyme utilizes NADPH as a cofactor and has been characterized in *Metallosphaera* and *Sulfolobus* spp (Alber et al., *J. Bacteriol.*, 188:8551-8559 (2006); Hugler et al., supra). The enzyme is encoded by Msed_0709 in *Metallosphaera sedula* (Alber et al., supra; Berg et al., supra). A gene encoding a malonyl-CoA reductase from *Sulfolobus tokodaii* was cloned and heterologously expressed in *E. coli* (Alber et al., supra). This enzyme has also been shown to catalyze the conversion of methylmalonyl-CoA to its corresponding aldehyde (2007). Although the aldehyde dehydrogenase functionality of these enzymes is similar to the bifunctional dehydrogenase from *Chloroflexus aurantiacus*, there is little sequence similarity. Both malonyl-CoA reductase enzymes have high sequence similarity to aspartate-semialdehyde dehydrogenase, an enzyme catalyzing the reduction and concurrent dephosphorylation of aspartyl-4-phosphate to aspartate semialdehyde. Additional genes can be found by sequence homology to proteins in other organisms including *Sulfolobus solfataricus* and *Sulfolobus acidocaldarius* and have been listed below. Yet another enzyme for CoA-acylating aldehyde dehydrogenase is the ald gene from *Clostridium beijerinckii* (Toth et al., *Appl. Environ. Microbiol.*, 65:4973-4980 (1999)). This enzyme has been reported to reduce acetyl-CoA and butyryl-CoA to their corresponding aldehydes. This gene is very similar to cutE that encodes acetaldehyde dehydrogenase of *Salmonella typhimurium* and *E. coli* (Toth et al., supra). Data related to the sequences for each of these exemplary gene products can be found using the following GenBank accession numbers shown in Table 13.

TABLE 13

| Protein | GenBank ID | GI Number | Organism |
|---|---|---|---|
| MSED_0709 | YP_001190808.1 | 146303492 | *Metallosphaera sedula* |
| mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |

TABLE 13-continued

| Protein | GenBank ID | GI Number | Organism |
|---|---|---|---|
| Ald | AAT66436 | 9473535 | *Clostridium beijerinckii* |
| eutE | AAA80209 | 687645 | *Salmonella typhimurium* |
| eutE | P77445 | 2498347 | *Escherichia coli* |

The oxidative deamination of amino groups to their corresponding oxo groups is catalyzed by deaminating oxidoreductases in the EC class 1.4.1. Such enzymes utilize NAD$^+$, NADP$^+$ or FAD$^+$ as acceptor. Enzymes in this class can convert 2-amino-4-oxopentanoate to 2,4-dioxopentanoate (FIG. 1, Step B), 2-amino-4-hydroxypentanoate to 2-oxo-4-hydroxypentanoate (FIG. 1, Step M) and 4-aminobutan-2-one to 3-oxobutyraldehyde (FIG. 1, Step K). Exemplary oxidoreductases operating on similar substrates include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (McPherson et al., *Nucleic. Acids Res.* 11:5257-5266 (1983); Korber et al., *J. Mol. Biol.* 234:1270-1273 (1993)), gdh from *Thermotoga maritima* (Kort et al., *Extremophiles* 1:52-60 (1997); Lebbink et al., *J. Mol. Biol.* 280:287-296 (1998); Lebbink et al., *J. Mol. Biol.* 289:357-369 (1999)), and gdhA1 from *Halobacterium salinarum* (Ingoldsby et al., *Gene.* 349:237-244 (2005)) catalyze the reversible interconversion of glutamate to 2-oxoglutarate and ammonia, while favoring NADP(H), NAD(H), or both, respectively. Additional glutamate dehydrogenase gene candidates are found in *Bacillus subtilis* (Khan et al., *Biosci. Biotechnol Biochem.* 69:1861-1870 (2005)), *Nicotiana tabacum* (Purnell et al., *Planta* 222:167-180 (2005)), *Oryza sativa* (Abiko et al., *Plant Cell Physiol* 46:1724-1734 (2005)), *Haloferax mediterranei* (Diaz et al., *Extremophiles.* 10:105-115 (2006)), *Halobactreium salinarum* (Hayden et al., *FEMS Microbiol Lett.* 211:37-41 (2002)) and yeast (Roca et al., *Appl Environ. Microbiol* 69:4732-4736 (2003)). The *Nicotiana tabacum* enzyme is composed of alpha and beta subunits encoded by gdh1 and gdh2 (Purnell et al., *Planta* 222:167-180 (2005)). The ldh gene of *Bacillus cereus* encodes the LeuDH protein that accepts a wide of range of substrates including leucine, isoleucine, valine, and 2-aminobutanoate (Stoyan et al., *J. Biotechnol* 54:77-80 (1997); Ansorge et al., *Biotechnol Bioeng.* 68:557-562 (2000)). The nadX gene from *Thermo-* toga maritime encoding for the aspartate dehydrogenase is involved in the biosynthesis of NAD (Yang et al., *J. Biol. Chem.* 278:8804-8808 (2003)). Data related to the sequences for each of these exemplary gene products can be found using the GenBank accession numbers shown below in Table 14.

TABLE 14

| Protein | GenBank ID | GI Number | Organism |
|---|---|---|---|
| gdhA | P00370 | 118547 | *Escherichia coli* |
| gdh | P96110.4 | 6226595 | *Thermotoga maritima* |
| gdhA1 | NP_279651.1 | 15789827 | *Halobacterium salinarum* |
| rocG | NP_391659.1 | 16080831 | *Bacillus subtilis* |
| gdh1 | AAR11534.1 | 38146335 | *Nicotiana tabacum* |
| gdh2 | AAR11535.1 | 38146337 | *Nicotiana tabacum* |
| GDH | Q852M0 | 75243660 | *Oryza sativa* |
| GDH | Q977U6 | 74499858 | *Haloferax mediterranei* |
| GDH | P29051 | 118549 | *Halobactreium salinarum* |
| GDH2 | NP_010066.1 | 6319986 | *Saccharomyces cerevisiae* |
| ldh | P0A393 | 61222614 | *Bacillus cereus* |
| nadX | NP_229443.1 | 15644391 | *Thermotoga maritima* |

An enzyme with 4-aminobutan-2-one oxidoreductase (deaminating) activity is required to convert 4-aminobutan-2-one to its corresponding aldehyde (FIG. 1, Step K). Exemplary candidates include 3,5-diaminohexanoate dehydrogenase (EC 1.4.1.11) and lysine 6-dehydrogenase (EC 1.4.1.18). 3,5-Diaminohexanoate dehydrogenase interconverts 3-amino acids and 3-oxoacids and has been characterized in organisms that ferment lysine. The gene encoding 3,5-diaminohexanoate dehydrogenase, kdd, was recently identified in *Fusobacterium nucleatum* (Kreimeyer et al., *J Biol. Chem.* 282:7191-7197 (2007)). The enzyme has been purified and characterized in other organisms (Baker et al., *J Biol. Chem.* 247:7724-7734 (1972); Baker et al., *Biochemistry* 13:292-299 (1974)) but the genes associated with these enzymes are not known. Candidates in other sequenced organisms can be inferred by sequence homology. Lysine 6-dehydrogenase, encoded by the lysDH genes, catalyzes the conversion of primary amines to their corresponding aldehydes. This enzyme naturally catalyzes the reversible oxidative deamination of the 6-amino group of L-lysine to form 2-aminoadipate-6-semialdehyde (Misono et al., *J Bacteriol.* 150:398-401 (1982)). Exemplary enzymes are found in *Geobacillus stearothermophilus* (Heydari et al., *Appl Environ. Microbiol* 70:937-942 (2004)), *Agrobacterium tumefaciens* (Hashimoto et al., *J Biochem.* 106:76-80 (1989); Misono and Nagasaki, *J Bacteriol.* 150:398-401 (1982)), and *Achromobacter denitrificans* (Ruldeekulthamrong et al., *BMB. Rep.* 41:790-795 (2008)). Data related to the sequences for each of these exemplary gene products can be found using the following GenBank accession numbers shown in Table 15.

TABLE 15

| Protein | GenBank ID | GI Number | Organism |
|---|---|---|---|
| kdd | AAL93966.1 | 19713113 | *Fusobacterium nucleatum* |
| lysDH | BAB39707 | 13429872 | *Geobacillus stearothermophilus* |
| lysDH | NP_353966 | 15888285 | *Agrobacterium tumefaciens* |
| lysDH | AAZ94428 | 74026644 | *Achromobacter denitrificans* |

2-Amino-4-oxopentanoate (AKP) thiolase or AKP thiolase (AKPT) (Step 1, FIG. 1) is a pyridoxal phosphate-dependent enzyme participating in ornithine degradation in *Clostridium sticklandii* (Jeng et al., *A. Biochemistry*, 13:2898-2903 (1974); Kenklies et al., *Microbiology*, 145: 819-826 (1999)). A gene cluster encoding the alpha and beta subunits of AKPT (or-2 (ortA) and or-3 (ortB)) was recently identified and the biochemical properties of the enzyme were characterized (Fonknechten et al., *J. Bacteriol.*, In Press (2009)). The enzyme is capable of operating in both directions and reacts with the D-isomer of alanine Enzyme engineering can be performed to optimize function with L-alanine as a substrate. AKPT from *Clostridium sticklandii* has been characterized but its protein sequence has not yet been published. Enzymes with high sequence homology are found in *Clostridium difficile*, *Alkaliphilus metalliredigenes QYF*, *Thermoanaerobacter* sp. X514, and *Thermoanaerobacter tengcongensis* MB4 (Fonknechten et al, supra). Data related to the sequences for each of these exemplary gene products can be found using the following GenBank accession numbers shown in Table 16.

TABLE 16

| Protein | GenBank ID | GI Number | Organism |
|---|---|---|---|
| ortA (α) | YP_001086914.1 | 126698017 | *Clostridium difficile* 630 |
| ortB (β) | YP_001086915.1 | 126698018 | *Clostridium difficile* 630 |
| Amet_2368 (α) | YP_001320181.1 | 150390132 | *Alkaliphilus metalliredigenes* QYF |
| Amet_2369 (β) | YP_001320182.1 | 150390133 | *Alkaliphilus metalliredigenes* QYF |
| Teth514_1478 (α) | YP_001663101.1 | 167040116 | *Thermoanaerobacter* sp. X514 |
| Teth514_1479 (β) | YP_001663102.1 | 167040117 | *Thermoanaerobacter* sp. X514 |
| TTE1235 (α) | NP_622858.1 | 20807687 | *Thermoanaerobacter tengcongensis* MB4 |
| thrC (β) | NP_622859.1 | 20807688 | *Thermoanaerobacter tengcongensis* MB4 |

The conversion of 2-amino-4-oxopentanoate (AKP) to 2,4-dioxopentanoate (Step B, FIG. 1) is accomplished by 2-amino-4-oxopentanoate aminotransferase or oxidoreductase (deaminating). Selection of an appropriate enzyme for this transformation is dependent on the stereochemistry of the substrate. For example, if the substrate is in the D-configuration, a D-amino acid aminotransferase (EC 2.6.1.21) can be utilized, whereas the L-stereoisomer can utilize an L-aminotransferase such as aspartate aminotransferase (EC 2.6.1.1).

Aspartate aminotransferase transfers an amino group from aspartate to alpha-ketoglutarate, forming glutamate and oxaloacetate. Aspartate is similar in structure to 2-amino-4-oxopentanoate. This conversion is catalyzed by, for example, the gene products of aspC from *Escherichia coli* (Yagi et al., *FEBS Lett.*, 100:81-84 (1979); Yagi et al., *Methods Enzymol.*, 133:83-89 (1985)), AAT2 from *Saccharomyces cerevisiae* (Yagi et al., *J. Biochem.*, 92:35-43 (1982)) and ASP5 from *Arabidopsis thaliana* (Kwok et al., *J. Exp. Bot.*, 55:595-604 (2004); De la et al., *Plant J.*, 46:414-425 (2006); Wilkie et al., *Protein Expr. Purif.*, 12:381-389 (1998)). The enzyme from *Rattus norvegicus* has been shown to transaminate alternate substrates such as 2-aminohexanedioic acid and 2,4-diaminobutyric acid (Recasens et al., *Biochemistry*, 19:4583-4589 (1980)). Aminotransferases that work on other amino-acid-like substrates can also catalyze this transformation. Valine aminotransferase catalyzes the conversion of valine and pyruvate to 2-ketoisovalerate and alanine. The *E. coli* gene, avtA, encodes one such enzyme (Whalen et al., *J. Bacteriol.*, 150:739-746 (1982)). This gene product also catalyzes the amination of α-ketobutyrate to generate α-aminobutyrate, although the amine donor in this reaction has not been identified (Whalen et al., *J. Bacteriol.*, 158:571-574 (1984)). An additional candidate is alpha-aminoadipate transaminase (EC 2.6.1.39), an enzyme that participates in lysine biosynthesis and degradation in some organisms. The enzyme from *Thermus thermophilus*, encoded by lysN, is active with several alternate substrates including oxaloacetate, 2-oxoisocaproate, 2-oxoisovalerate, and 2-oxo-3-methylvalerate (Miyazaki et al., *Microbiol.* 150:2327-2334 (2004)). A similar enzyme from *Homo sapiens* has been characterized (Okuno et al., *Enz. Prot.* 47:136-148 (1993)). Data related to the sequences for each of these exemplary gene products can be found using the following GenBank accession numbers shown in Table 17.

TABLE 17

| Protein | GenBank ID | GI Number | Organism |
| --- | --- | --- | --- |
| aspC | NP_415448.1 | 16128895 | *Escherichia coli* |
| AAT2 | P23542.3 | 1703040 | *Saccharomyces cerevisiae* |
| ASP5 | P46248.2 | 20532373 | *Arabidopsis thaliana* |
| got2 | P00507 | 112987 | *Rattus norvegicus* |
| avtA | YP_026231.1 | 49176374 | *Escherichia coli* |
| lysN | BAC76939.1 | 31096548 | *Thermus thermophilus* |
| AadAT-II | Q8N5Z0.2 | 46395904 | *Homo sapiens* |

When the substrate is present as the D-stereoisomer, transamination can be catalyzed by D-aminotransferase (EC 2.6.1.21), also known as D-amino acid aminotransferase and D-alanine aminotransferase (DAAT). This class of enzymes is noted for its broad substrate specificity, which is species-specific. The D-aminotransferase from *Bacillus* species YM-1, encoded by dat, has been cloned, sequenced (Tanizawa et al., *J. Biol. Chem.*, 264:2450-2454 (1989)) and the crystal structure has been solved (Peisach et al., *Biochemistry*, 37:4958-4967 (1998)). This enzyme has also been the subject of protein engineering studies to alter the substrate specificity (Gutierrez et al., *Eur. J. Biochem*, 267:7218-7223 (2000); Gutierrez et al., *Protein Eng.*, 11:53-58 (1998)). Additional genes are found in *Bacillus licheniformis* ATCC 10716 (Taylor et al., *Biochim. Biophys. Acta.*, 1350:38-40 (1997)), *Staphylococcus haemolyticus* (Pucci et al., *J. Bacteriol.*, 177:336-342 (1995)) and *Bacillus subtilis* (Martinez-Carrion et al., *J. Biol. Chem.*, 240:3538-3546 (1965)). Data related to the sequences for each of these exemplary gene products can be found using the following GenBank accession numbers shown in Table 18.

TABLE 18

| Protein | GenBank ID | GI Number | Organism |
| --- | --- | --- | --- |
| dat | P19938 | 118222 | *Bacillus* sp. YM-1 |
| dat | P54692 | 1706292 | *Bacillus licheniformis* ATCC 10716 |
| dat | P54694 | 1706294 | *Staphylococcus haemolyticus* |
| dat | O07597.1 | 3121979 | *Bacillus subtilis* |

In reaction K of FIG. 1, 4-aminobutan-2-one is transaminated to form 3-oxobutanal. This transformation can likely be catalyzed by an aminotransferase that interconverts terminal amines and aldehydes. Exemplary candidate enzymes are beta-alanine/alpha-ketoglutarate aminotransferase, GABA aminotransferase, 3-amino-2-methylpropionate transaminase, lysine-6-aminotransferase, 2,4-diaminobutanoate transaminase, putrescine aminotransferase and diamine aminotransferase.

Cargill has developed and patented a beta-alanine/alpha-ketoglutarate aminotransferase for producing 3-HP from beta-alanine via malonyl-semialdehyde (Chandra et al., *ARch. Microbiol.*, 176:443-451 (2001)). The gene product of SkPYD4 in *Saccharomyces kluyveri* was also shown to preferentially use beta-alanine as the amino group donor (Aberhart et al., *J. Chem. Soc.* 6:1404-1406 (1979)). SkUGA1 encodes a homologue of *Saccharomyces cerevisiae* GABA aminotransferase, UGA1 (Ichikawa et al., *J. Mol. Catalysis A-Chem.*, 256:106-112 (2006)), whereas SkPYD4 encodes an enzyme involved in both β-alanine and GABA transamination (Aberthart et al., Supra). 3-amino-2-methylpropionate transaminase catalyzes the transformation from methylmalonate semialdehyde to 3-amino-2-methylpropionate. The enzyme has been characterized in *Rattus norvegicus* and *Sus scrofa* and is encoded by Abat (Chopra et al., *Protein Expr. Purif.*, 25:533-540 (2002), Kuznetsova et al., *FEMS Microbiol. Rev*, 29:263-279 (2005)). Enzyme candidates in other organisms with high sequence homology to 3-amino-2-methylpropionate transaminase include Gta-1 in *C. elegans* and gabT in *Bacillus subtilus*. Additionally, one of the native GABA aminotransferases in *E. coli*, encoded by gene gabT, has been shown to have broad substrate specificity (Fontaine et al., *J. Bacteriol.*, 184:821-830 (2002), Kanamasa et al., *Appl. Microbiol Biotechnol.*, 80:223-229 (2008)). The gene puuE encodes the other 4-aminobutyrate transaminase in *E. coli* (Drummond et al., *J. Biol. Chem.*, 235:318-325 (1960)).

Lysine-6-aminotransferase converts lysine to alpha-aminoadipate semialdehyde. Candidate enzymes have been characterized in *Candida utilis* (Hammer et al., *J Basic Microbiol* 32:21-27 (1992)), *Flavobacterium lutescens* (Fujii et al., *J Biochem.* 128:391-397 (2000)) and *Streptomyces clavuligenus* (Romero et al., *J Ind. Microbiol Biotechnol* 18:241-246 (1997)). A recombinant lysine-6-aminotransferase from *S. clavuligenus* was functionally expressed in *E. coli* (Tobin et al., *J Bacteriol.* 173:6223-6229 (1991)). The *F. lutescens* enzyme is specific to alpha-ketoglutarate as the amino acceptor (Soda et al., *Biochemistry* 7:4110-4119 (1968)). An enzyme with diaminobutanoate transaminase activity is encoded by the dat gene product in *Acinetobacter baumanii* (Ikai et al., *J Bacteriol.* 179:5118-5125 (1997)). In addition to its natural substrate, 2,4-diaminobutyrate, DAT transaminates the terminal amines of lysine, 4-aminobutyrate and ornithine. Candidate putrescine aminotransferase enzymes are encoded by ygjG in *E. coli* and spuC of *Pseudomonas aeruginosa* (Lu et al., *J Bacteriol.* 184:3765-3773 (2002)). The ygiG gene product reacts with the alternate substrates cadaverine, spermidine and 1,7-diaminoheptanoate (Samsonova et al., *BMC. Microbiol* 3:2 (2003); Kim, *J Biol. Chem.* 239:783-786 (1964)).

Data related to the sequences for each of these exemplary gene products can be found using the following GenBank accession numbers shown in Table 19.

TABLE 19

| Protein | GenBank ID | GI Number | Organism |
| --- | --- | --- | --- |
| SkyPYD4 | ABF58893.1 | 98626772 | *Saccharomyces kluyveri* |
| SkUGA1 | ABF58894.1 | 98626792 | *Saccharomyces kluyveri* |

TABLE 19-continued

| Protein | GenBank ID | GI Number | Organism |
|---|---|---|---|
| UGA1 | NP_011533.1 | 6321456 | Saccharomyces cerevisiae |
| Abat | P50554.3 | 122065191 | Rattus norvegicus |
| Abat | P80147.2 | 120968 | Sus scrofa |
| Gta-1 | Q21217.1 | 6016091 | Caenorhabditis elegans |
| gabT | P94427.1 | 6016090 | Bacillus subtilis |
| gabT | P22256.1 | 16130576 | Escherichia coli K12 |
| puuE | NP_415818.1 | 16129263 | Escherichia coli K12 |
| lat | BAB13756.1 | 10336502 | Flavobacterium lutescens |
| lat | AAA26777.1 | 153343 | Streptomyces clavuligenus |
| dat | P56744.1 | 6685373 | Acinetobacter baumanii |
| ygjG | NP_417544 | 145698310 | Escherichia coli |
| spuC | AAG03688 | 9946143 | Pseudomonas aeruginosa |

In FIG. 1, Step C, 2,4-dioxopentanoate is decarboxylated to form 3-oxobutyraldehyde by 2,4-dioxopentanoate decarboxylase. 2,4-dioxopentanoate is similar to the native substrates of pyruvate decarboxylase (EC 4.1.1.1) and benzoylformate decarboxylase (EC 4.1.1.7). Pyruvate decarboxylase (PDC), also termed keto-acid decarboxylase, is a key enzyme in alcoholic fermentation, catalyzing the decarboxylation of pyruvate to acetaldehyde. The enzyme from Saccharomyces cerevisiae has a broad substrate range for aliphatic 2-keto acids including 2-ketobutyrate, 2-ketovalerate, 3-hydroxypyruvate and 2-phenylpyruvate (Li et al., Biochemistry, 38:10004-10012 (1999)). This enzyme has been extensively studied, engineered for altered activity, and functionally expressed in E. coli (Killenberg-Jabs et al., Eur. J. Biochem., 268:1698-1704 (2001); Li et al., supra; Schure et al., Appl. Environ. Microbiol., 64:1303-1307 (1998)). The PDC from Zymomonas mobilus, encoded by pdc, also has a broad substrate range and has been a subject of directed engineering studies to alter the affinity for different substrates (Siegert et al., Protein Eng. Des. Sel., 18:345-357 (2005)). The crystal structure of this enzyme is available (Killenberg-Jabs, supra). Other well-characterized PDC enzymes include the enzymes from Acetobacter pasteurians (Chandra et al., Arch. Microbiol. 176:443-451 (2001)) and Kluyveromyces lactis (Krieger et al., Eur. J. Biochem., 269:3256-3263 (2002)). Data related to the sequences for each of these exemplary gene products can be found using the following GenBank accession numbers shown in Table 20.

TABLE 20

| Protein | GenBank ID | GI Number | Organism |
|---|---|---|---|
| pdc | P06672.1 | 118391 | Zymomonas mobilis |
| pdc1 | P06169 | 30923172 | Saccharomyces cerevisiae |
| pdc | Q8L388 | 20385191 | Acetobacter pasteurians |
| pdc1 | Q12629 | 52788279 | Kluyveromyces lactis |

Like PDC, benzoylformate decarboxylase (EC 4.1.1.7) has a broad substrate range and has been the target of enzyme engineering studies. The enzyme from Pseudomonas putida has been extensively studied and crystal structures of this enzyme are available (Polovnikova et al., Biochemistry 42:1820-1830 (2003); Hasson et al., Biochemistry, 37:9918-9930 (1998)). Site-directed mutagenesis of two residues in the active site of the Pseudomonas putida enzyme altered the affinity (Km) of naturally and non-naturally occuring substrates (Siegert et al., supra). The properties of this enzyme have been further modified by directed engineering (Lingen et al., Chembiochem, 4:721-726 (2003); Lingen et al., Protein Eng., 15:585-593 (2002)).

The enzyme from Pseudomonas aeruginosa, encoded by mdlC, has also been characterized experimentally (Barrowman et al., FEMS Microbiology Letters, 34:57-60 (1986)). Additional genes from Pseudomonas stutzeri, Pseudomonas fluorescens and other organisms can be inferred by sequence homology or identified using a growth selection system developed in Pseudomonas putida (Henning et al., Appl. Environ. Microbiol., 72:7510-7517 (2006)). Data related to the sequences for each of these exemplary gene products can be found using the following GenBank accession numbers shown in Table 21.

TABLE 21

| Protein | GenBank ID | GI Number | Organism |
|---|---|---|---|
| mdlC | P20906.2 | 3915757 | Pseudomonas putida |
| mdlC | Q9HUR2.1 | 81539678 | Pseudomonas aeruginosa |
| dpgB | ABN80423.1 | 126202187 | Pseudomonas stutzeri |
| ilvB-1 | YP_260581.1 | 70730840 | Pseudomonas fluorescens |

A third enzyme capable of decarboxylating 2-oxoacids is alpha-ketoglutarate decarboxylase (KGD). The substrate range of this class of enzymes has not been studied to date. The KDC from Mycobacterium tuberculosis (Tian et al., Proc. Natl. Acad. Sci. USA, 102:10670-10675 (2005)) has been cloned and has been functionally expressed in E. coli at Genomatica. KDC enzyme activity has been detected in several species of Rhizobia including Bradyrhizobium japonicum and Mesorhizobium loti (Green et al., J. Bacteriol., 182:2838-2844 (2000)). Although the KDC-encoding gene(s) have not been isolated in these organisms, the genome sequences are available and several genes in each genome are annotated as putative KDCs. A KDC from Euglena gracilis has also been characterized but the gene associated with this activity has not been identified to date (Shigeoka et al., Arch. Biochem. Biophys., 288:22-28 (1991)). The first twenty amino acids starting from the N-terminus were sequenced MTYKAPVKDVKFLLDK-VFKV (Shigeoka et al., supra). The gene can be identified by testing genes containing this N-terminal sequence for KDC activity. Data related to the sequences for each of these exemplary gene products can be found using the following GenBank accession numbers shown in Table 22.

TABLE 22

| Protein | GenBank ID | GI Number | Organism |
|---|---|---|---|
| kgd | O50463.4 | 160395583 | Mycobacterium tuberculosis |
| kgd | NP_767092.1 | 27375563 | Bradyrhizobium japonicum USDA110 |
| kgd | NP_105204.1 | 13473636 | Mesorhizobium loti |

A fourth enzyme for catalyzing this step is the branched chain alpha-ketoacid decarboxylase (BCKA). This class of enzymes has been shown to act on a variety of compounds varying in chain length from 3 to 6 carbons (Oku et al., J. Biol. Chem., 263:18386-18396 (1988); Smit et al., Appl. Environ. Microbiol., 71:303-311 (2005)). The enzyme in Lactococcus lactis has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., supra). The enzyme has been structurally characterized (Berthold et al., D. Biol. Crystallogr., 63:1217-1224 (2007)). Sequence alignments between the Lactococcus lactis enzyme and the pyruvate decarboxylase of Zymomonas mobilus indicate that the catalytic and substrate recognition residues are nearly identical (Siegert et al., supra), so this enzyme is readily amenable to directed engineering. Additional BCKA genes can be identified by homology to the *Lactococcus lactis* protein sequence (kdcA, AAS49166.1, 44921617, *Lactococcus lactis*). Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria.

2-amino-4-ketopentanoate is decarboxylated to form 4-aminobutan-2-one by AKP decarboxylase in Step E of FIG. 1. This transformation can be catalyzed by an amino acid decarboxylase. Selection of an appropriate decarboxylase depends on the stereochemical configuration of 4-amino-4-oxopentanoate. When this compound is in a D-configuration, a D-amino acid decarboxylase can be utilized. One such D-amino acid decarboxylase is diaminopimelate decarboxylase (DDC, EC 4.1.1.20). This enzyme decarboxylates the D-stereocenter of meso-diaminopimelate, catalyzing the final step of lysine biosynthesis. DDC has been studied in many organisms including *E. coli* (Momany et al., *D. Biol. Crystallogr.*, 58:549-552 (2002)), *Mycobacterium tuberculosis* (Kefala et al., *Acta. Crystallogr. Sect. F. Struct. Biol. Cryst. Commun.*, 61:782-784 (2005); Gokulan et al., *J. Biol. Chem.*, 278:18588-18596 (2003); Andersen et al., *Gene*, 124:105-109 (1993)), *Methylophilus methylotrophus* (Tsujimoto et al., *J. Biotechnol*, 124:327-337 (2006)), and *Helicobacter pylori* (Hu et al., *J. Biol. Chem.*, 283:21284-21293 (2008)). Alternately, the ornithine decarboxylase (EC 4.1.1.17) from *Homo sapiens* has a weak activity on the D-isomer of ornithine (Qu et al., *Biochem. J.*, 375:465-470 (2003); Fitzgerald et al., *DNA*, 8:623-634 (1989)) and can be used for the decarboxylation in step E. Data related to the sequences for each of these exemplary gene products can be found using the following GenBank accession numbers shown in Table 23.

TABLE 23

| Protein | GenBank ID | GI Number | Organism |
| --- | --- | --- | --- |
| lysA | NP_417315.1 | 16130742 | *Escherichia coli* |
| lysA | AAA25361.1 | 149964 | *Mycobacterium tuberculosis* |
| lysA | BAC92756.1 | 37196770 | *Methylophilus methylotrophus* |
| lysA | ABW70801.1 | 158523325 | *Helicobacter pylori* |
| odc1 | AA59969.1 | 386989 | *Homo sapiens* |

When 2-amino-4-ketopentanoate exhibits L-stereochemistry, an amino acid decarboxylase such as aspartate decarboxylase (EC 4.1.1.11), ornithine decarboxylase (EC 4.1.1.17) or lysine decarboxylase (EC 4.1.1.18) can be utilized. An exemplary enzyme is aspartate decarboxylase (EC 4.1.1.11). 2-Amino-4-ketopentanoate bears structural similarity to aspartate, the native substrate of this enzyme. Aspartate decarboxylase participates in pantothenate biosynthesis and is encoded by panD in *Escherichia coli* (Dusch et al., *Appl. Environ. Microbiol.*, 65:1530-1539 (1999); Ramjee et al., *Biochem. J.*, 323:661-669 (1997); Merkel et al., *FEMS Microbiol. Lett.*, 143:247-252 (1996); Schmitzberger et al., *EMBO J.*, 22:6193-6204 (2003)). The enzymes from *Mycobacterium tuberculosis* (Chopra et al., *Protein Expr. Purif.*, 25:533-540 (2002)) and *Corynebacterium glutamicum* (Dusch et al., supra) have been expressed and characterized in *E. coli*. Lysine decarboxylase enzymes are encoded in the *E. coli* genome by genes cadA and ldcC. A lysine decarboxylase analogous to CadA was recently identified in *Vibrio parahaemolyticus* (Tanaka et al., *J. Appl. Microbiol.* 104:1283-1293 (2008)). The lysine decarboxylase from *Selenomonas ruminantium*, encoded by ldc, bears sequence similarity to eukaryotic ornithine decarboxylases, and accepts both L-lysine and L-ornithine as substrates (Takatsuka et al., *Biosci. Biotechnol Biochem.* 63:1843-1846 (1999)). Ornithine decarboxylase enzyme candidates are found in *Nicotiana glutinosa* (Lee et al., *Biochem. J.* 360:657-665 (2001)), *Lactobacillus* sp. 30a (Guirard et al., *J Biol. Chem.* 255:5960-5964 (1980)) and *Vibrio vulnificus* (Lee et al., *J Biol. Chem.* 282:27115-27125 (2007)). The residues involved in substrate specificity *Vibrio vulnificus* have been elucidated (Lee et al., supra).

Data related to the sequences for each of these exemplary gene products can be found using the following GenBank accession numbers shown in Table 24.

TABLE 24

| Protein | GenBank ID | GI Number | Organism |
| --- | --- | --- | --- |
| panD | P0A790 | 67470411 | *Escherichia coli* |
| panD | Q9X4N0 | 18203593 | *Corynebacterium glutanicum* |
| panD | P65660.1 | 54041701 | *Mycobacterium tuberculosis* |
| cadA | AAA23536. | 145458 | *Escherichia coli* |
| ldcC | AAC73297.1 | 1786384 | *Escherichia coli* |
| ldc | O50657.1 | 13124043 | *Selenomonas ruminantium* |
| cadA | AB124819.1 | 44886078 | *Vibrio parahaemolyticus* |
| AF323910.1:1 . . . 1299 | AAG45222.1 | 12007488 | *Nicotiana glutinosa* |
| odc1 | P43099.2 | 1169251 | *Lactobacillus* sp. 30a |
| VV2_1235 | NP_763142.1 | 27367615 | *Vibrio vulnificus* |

In reaction J (FIG. 1), acetylacrylate is decarboxylated to 2-oxobutene by acetoacrylate decarboxylase. An enzyme catalyzing this transformation has not been identified to date, but similar reactions are catalyzed by the enzymes aconitate decarboxylase, 4-oxalocrotonate decarboxylase and cinnamate decarboxylase.

Aconitate decarboxylase catalyzes the final step in itaconate biosynthesis in a strain of *Candida* and also in the filamentous fungus *Aspergillus terreus* (Bonnarme et al., *J. Bacteriol.*, 177:3573-3578 (1995); Willke et al., *Appi. Microbiol. Biotechnol.*, 56:289-295 (2001)). A cis-aconitate decarboxylase (CAD) (EC 4.1.16), encoded by ATEG_09971, has been identified and extensively studied in *Aspergillus terreus* and other related fungi. Recently, the gene has been cloned and functionally characterized (Kanamasa et al., *Appl. Microbiol. Biotechnol.*, 80:223-229 (2008)) and (WO/2009/014437).

4-oxalocronate decarboxylase has been isolated from numerous organisms and characterized. Genes encoding this enzyme include dmpH and dmpE in *Pseudomonas* sp. (strain 600) (Shingler et al., *J. Bacteriol.*, 174:711-724 (1992)), xylII and xylIII from *Pseudomonas putida* (Kato et al., *Arch. Microbiol.*, 168:457-463 (1997); Stanley et al., *Biochemistry*, 39:3514 (2000); Lian et al., *J. Am. Chem. Soc.*, 116:10403-10411 (1994)) and Reut_B5691 and Reut_B5692 from *Ralstonia eutropha* JMP134 (Hughes et al., *J. Bacteriol.*, 158:79-83 (1984)). The genes encoding the enzyme from *Pseudomonas* sp. (strain 600) have been cloned and expressed in *E. coli* (Shingler et al., supra). Data related to the sequences for each of these exemplary gene products can be found using the following GenBank accession numbers shown in Table 25.

TABLE 25

| Protein | GenBank ID | GI Number | Organism |
| --- | --- | --- | --- |
| dmpH | CAA43228.1 | 45685 | Pseudomonas sp. CF600 |
| dmpE | CAA43225.1 | 45682 | Pseudomonas sp. CF600 |
| xylII | YP_709328.1 | 111116444 | Pseudomonas putida |
| xylIII | YP_709353.1 | 111116469 | Pseudomonas putida |
| Reut_B5691 | YP_299880.1 | 73539513 | Ralstonia eutropha JMP134 |
| Reut_B5692 | YP_299881.1 | 73539514 | Ralstonia eutropha JMP134 |
| ATEG_09971 | EAU29420.1 | 114187720 | Aspergillus terreus |

An additional class of decarboxylases has been characterized that catalyze the conversion of cinnamate (phenylacrylate) and substituted cinnamate derivatives to the corresponding styrene derivatives. These enzymes are common in a variety of organisms and specific genes encoding these enzymes that have been cloned and expressed in E. coli are: pad 1 from Saccharomyces cerevisae (Clausen et al., Gene, 142:107-112 (1994)), pdc from Lactobacillus plantarum (Barthelmebs et al., Appl. Environ. Microbiol., 67:1063-1069 (2001); Rodriguez et al., J. Agric. Food Chem., 56:3068-3072 (2008); Qi et al., Biochem. J., 375:465-470 (2007)), pofK (pad) from Klebsiella oxytoca (Uchiyama et al., Biosci. Biotechnol. Biochem., 72:116-123 (2008); Hashidoko et al., Biosci. Biotech. Biochem., 58:217-218 (1994)), Pedicoccus pentosaceus (Barthelmebs et al., supra) and padC from Bacillus subtilis and Bacillus pumilus (Cavin et al., Appl. Environ. Microbiol., 64:1466-1471 (1998)). A ferulic acid decarboxylase from Pseudomonas fluorescens also has been purified and characterized (Huang et al., J. Bacteriol., 176:5912-5918 (1994)). Importantly, this class of enzymes has been shown to be stable and does not require either exogenous or internally bound co-factors, thus making these enzymes ideally suitable for biotransformations (Sariaslani, F. S., Annu. Rev. Microbiol., 61:51-69 (2007)). Data related to the sequences for each of these exemplary gene products can be found using the following GenBank accession numbers shown in Table 26.

TABLE 26

| Protein | GenBank ID | GI Number | Organism |
| --- | --- | --- | --- |
| pad1 | AAB64980.1 | 1165293 | Saccharomyces cerevisae |
| pdc | AAC45282.1 | 1762616 | Lactobacillus plantarum |
| pad | BAF65031.1 | 149941608 | Klebsiella oxytoca |
| padC | NP_391320.1 | 16080493 | Bacillus subtilis |
| pad | YP_804027.1 | 116492292 | Pedicoccus pentosaceus |
| pad | CAC18719.1 | 11691810 | Bacillus pumilus |

An additional enzyme for decarboxylation is acetoacetate decarboxylase (EC 4.1.1.4), an enzyme that decarboxylates acetoacetate to acetone and has therefore been studied for its role in bacterial solventogenesis. Exemplary bacterial enzymes have been characterized from Clostridium acetobutylicum (Benner et al., J. Am. Chem. So. 103:993-994 (1981); Hlghbarger et al., Biochemistry 35:41-46 (1996); Petersen et al., Appl. Environ. Microbiol. 56:3491-3498 (1990); Rozzel et al. J. Am. Chem. Soc. 106:4937-4941 (1984)) Clostridium saccharoperbutylacetonicum (Kosaka, et al., Biosci. Biotechnol Biochem. 71:58-68 (2007)) and Clostridium beijerinckii (Ravagnani et al. Mol. Microbiol. 37:1172-1185 (2000)). Acetoacetate decarboxylase activity has also been demonstrated in Pseudomonas putida and Bacillus polymyxa but genes are not associated with this activity to date (Matiasek et al., Curr. Microbiol. 42: 276-281 (2001)). Bacterial genes in other organisms such as Clostridium botulinum and Bacillus amyloliquefaciens can be identified by sequence homology. In humans and other mammals, acetoacetate decarboxylase catalyzes the final step of the ketone-body pathway (Kalapos, Biochim. Biophys. Acta 1621:122-139 (2003)), but genes associated with this activity have not been identified to date. Data related to the sequences for each of these exemplary gene products can be found using the following GenBank accession numbers shown in Table 27.

TABLE 27

| Protein | GenBank ID | GI Number | Organism |
| --- | --- | --- | --- |
| adc | NP_149328.1 | 15004868 | Clostridium acetobutylicum |
| adc | AAP42566.1 | 31075386 | Clostridium saccharoperbutylacetonicum |
| cbei_3835 | YP_001310906.1 | 150018652 | Clostridium beijerinckii |
| CLL_A2135 | YP_001886324.1 | 187933144 | Clostridium botulinum |
| RBAM_030030 | YP_001422565.1 | 154687404 | Bacillus amyloliquefaciens |

All the aforementioned gene candidates can also be used to catalyze the decarboxylation of 2-oxo-4-hydroxypentanoate to 3-hydroxybutyraldehyde in Step N of FIG. 1.

Butenone hydratase (Step G, FIG. 1), 4-hydroxybutyryl-CoA dehydratase (Step A, FIG. 3) and crotonase (Step A, FIG. 3) are hydrolyase-type transformations. Specifically, the hydration of butenone to 4-hydroxy-2-butanone (Step G, FIG. 1) can be accomplished by an enzyme in the hydratase family of enzymes. Enzymes that can carry out this transformation include fumarate hydratase (EC 4.2.1.2), 2-(hydroxymethyl)glutarate dehydratase (EC 4.2.1.-), dimethylmaleate hydratase (EC 4.2.1.85) and citramalate hydrolyase (EC 4.2.1.34).

Fumarate hydratase enzymes naturally catalyze the reversible hydration of fumarate to malate. Although the ability of fumarate hydratase to react with butanone as a substrate has not been described in the literature, a wealth of structural information is available for this enzyme and other researchers have successfully engineered the enzyme to alter activity, inhibition and localization (Weaver, T., B. Biol. Crystallogr., 61:1395-1401 (2005)). E. coli has three fumarases: FumA, FumB, and FumC that are regulated by growth conditions. FumB is oxygen sensitive and only active under anaerobic conditions. FumA is active under microanaerobic conditions, and FumC is the only active enzyme in aerobic growth (Tseng et al., J. Bacteriol., 183:461-467 (2001); Woods et al., Biochem. Biophys. Acta., 954:14-26 (1988); Guest et al., J. Gen. Microbiol., 131: 2971-2984 (1985)). Additional enzymes are found in Campylobacter jejuni (Smith et al., Int. J. Biochem. Cell Biol., 31:961-975 (1999)), Thermus thermophilus (Mizobata et al., Arch. Biochem. Biophys., 355:49-55 (1998)) and Rattus norvegicus (Kobayashi et al., J. Biochem., 89:1923-1931 (1981)). Similar enzymes with high sequence homology include fum1 from Arabidopsis thaliana and fumC from Corynebacterium glutamicum. The MmcBC fumarase from Pelotomaculum thermopropionicum is another class of fumarase with two subunits (Shimoyama et al., *FEMS Microbiol. Lett.,* 270:207-213 (2007)). Data related to the sequences for each of these exemplary gene products can be found using the following GenBank accession numbers shown in Table 28.

TABLE 28

| Protein | GenBank ID | GI Number | Organism |
|---|---|---|---|
| fumA | NP_416129.1 | 16129570 | *Escherichia coli* |
| fumB | NP_418546.1 | 16131948 | *Escherichia coli* |
| fumC | NP_416128.1 | 16129569 | *Escherichia coli* |
| fumC | O69294 | 9789756 | *Campylobacter jejuni* |
| fumC | P84127 | 75427690 | *Thermus thermophilus* |
| fumH | P14408 | 120605 | *Rattus norvegicus* |
| fum1 | P93033 | 39931311 | *Arabidopsis thaliana* |
| fumC | Q8NRN8 | 39931596 | *Corynebacterium glutamicum* |
| MmcB | YP_001211906 | 147677691 | *Pelotomaculum thermopropionicum* |
| MmcC | YP_001211907 | 147677692 | *Pelotomaculum thermopropionicum* |

Two additional hydratase enzymes are 2-(hydroxymethyl) glutarate dehydratase and dimethylmaleate hydratase, enzymes studied for their role in nicontinate catabolism in *Eubacterium barkeri* (formerly *Clostridium barkeri*) (Alhapel et al., *Proc. Natl. Acad. Sci. USA,* 103:12341-12346 (2006)). 2-(Hydroxymethyl)glutarate dehydratase is a [4Fe-4S]-containing enzyme that dehydrates 2-(hydroxymethyl) glutarate to 2-methylene-glutarate. This enzyme is encoded by hmd in *Eubacterium barkeri* (Alhapel et al., supra). Similar enzymes with high sequence homology are found in *Bacteroides capillosus, Anaerotruncus colihominis,* and *Natranaerobius thermophilus.* These enzymes are homologous to the alpha and beta subunits of [4Fe-4S]-containing bacterial serine dehydratases (e.g., *E. coli* enzymes encoded by tdcG, sdhB, and sdaA). Dimethylmaleate hydratase (EC 4.2.1.85) is a reversible $Fe^{2+}$-dependent and oxygen-sensitive enzyme in the aconitase family that hydrates dimethylmaeate to form (2R,3S)-2,3-dimethylmalate. This enzyme is encoded by dmdAB in *Eubacterium barkeri* (Alhapel, et al., supra; Kollmann-Koch et al., *Physiol. Chem.,* 365:847-857 (1984)). Data related to the sequences for each of these exemplary gene products can be found using the following GenBank accession numbers shown in Table 29.

TABLE 29

| Protein | GenBank ID | GI Number | Organism |
|---|---|---|---|
| hmd | ABC88407.1 | 86278275 | *Eubacterium barkeri* |
| BACCAP_02294 | ZP_02036683.1 | 154498305 | *Bacteroides capillosus* ATCC 29799 |
| ANACOL_02527 | ZP_02443222.1 | 167771169 | *Anaerotruncus colihominis* DSM 17241 |
| NtherDRAFT_2368 | ZP_02852366.1 | 169192667 | *Natranaerobius thermophilus* JW/NM-WN-LF |
| dmdA | ABC88408 | 86278276 | *Eubacterium barkeri* |
| dmdB | ABC88409.1 | 86278277 | *Eubacterium barkeri* |

An additional enzyme is 2-methylmalate dehydratase, also called citramalate hydrolyase, a reversible hydrolyase that catalyzes the alpha, beta elimination of water from citramalate to form mesaconate. This enzyme has been purified and characterized in *Clostridium tetanomorphum* (Wang et al., *J. Biol. Chem.,* 244:2516-2526 (1969)). The activity of this enzyme has also been detected in several bacteria in the genera *Citrobacter* and *Morganella* in the context of the glutamate degradation VI pathway (Kato et al., supra). Genes encoding this enzyme have not been identified in any organism to date.

Hydration of crotonyl-CoA to form 3-hydroxybutyryl-CoA (Step B, FIG. 3) is catalyzed by a crotonase (EC 4.2.1.55). These enzymes are required for n-butanol formation in some organisms, particularly *Clostridial* species, and also comprise one step of the 3-hydroxypropionate/4-hydroxybutyrate cycle in thermoacidophilic Archaea of the genera *Sulfolobus, Acidianus,* and *Metallosphaera.* Exemplary genes encoding crotonase enzymes can be found in *C. acetobutylicum* (Boynton et al., *J. Bacteria,* 178:3015-3024 (1996)), *C. kluyveri* (Hillmer et al., *FEBS Lett.,* 21:351-354 (1972)), and *Metallosphaera sedula* (Berg et al., supra). Enoyl-CoA hydratases, which are involved in fatty acid beta-oxidation and/or the metabolism of various amino acids, can also catalyze the hydration of crotonyl-CoA to form 3-hydroxybutyryl-CoA (Roberts et al., *Arch. Microbiol.,* 117:99-108 (1978); Agnihotri et al., *Bioorg. Med. Chem.,* 11:9-20 (2003); Conrad et al., *J. Bacteriol.,* 118:103-111 (1974)). An exemplary enoyl-CoA hydratase is the gene product of ech from *Pseudomonas putida* (Roberts et al., supra). The enoyl-CoA hydratases, phaA and phaB, of *P. putida* have been indicated to carry out the hydroxylation of double bonds during phenylacetate catabolism (Olivera et al., *Proc. Natl. Acad. Sci USA,* 95:6419-6424 (1998)). The paaA and paaB from *P. fluorescens* catalyze analogous transformations (Olivera et al., supra). Lastly, a number of *Escherichia coli* genes have been shown to demonstrate enoyl-CoA hydratase functionality including maoC (Park et al., *J. Bacteriol.,* 185:5391-5397 (2003)), paaF (Ismail et al., *Eur. J. Biochem.,* 270:3047-3054 (2003); Park et al., *Appl. Biochem. Biotechnol.,* 113-116:335-346 (2004); Park et al., *Biotechnol Bioeng.,* 86:681-686 (2004)) and paaG (Ismail et al., supra; Park et al., supra; Park et al., supra). Data related to the sequences for each of these exemplary gene products can be found using the following GenBank accession numbers shown in Table 30.

TABLE 30

| Protein | GenBank ID | GI Number | Organism |
|---|---|---|---|
| crt | NP_349318.1 | 15895969 | *Clostridium acetobutylicum* |
| crt1 | YP_001393856 | 153953091 | *Clostridium kluyveri* DSM 555 |
| ech | NP_745498.1 | 26990073 | *Pseudomonas putida* |
| phaA | ABF82233.1 | 26990002 | *Pseudomonas putida* |
| phaB | ABF82234.1 | 26990001 | *Pseudomonas putida* |
| paaA | NP_745427.1 | 106636093 | *Pseudomonas fluorescens* |
| paaB | NP_745426.1 | 106636094 | *Pseudomonas fluorescens* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

Alternatively, the *E. coli* gene products of fadA and fadB encode a multienzyme complex involved in fatty acid oxidation that exhibits enoyl-CoA hydratase activity (Haller et al., *Biochemistry* 39:4622-4629 (2000); Martinez-Carrion et a., *J. Biol. Chem.* 240:3538-3546 (1965); Matthies et al., *Appl. Environ. Micriobiol.* 58:1435-1439 (1992)). Knocking out a negative regulator encoded by fadR can be utilized to activate the fadB gene product (Jeng et al., *A. Biochemistry* 13:2898-2903 (1974)). The fadI and fadJ genes encode similar functions and are naturally expressed under anaerobic conditions (Atsumi et al., *Nature* 451:86-89 (2008)).

Data related to the sequences for each of these exemplary gene products can be found using the following GenBank accession numbers shown in Table 31.

TABLE 31

| Protein | GenBank ID | GI Number | Organism |
|---|---|---|---|
| fadA | YP_026272.1 | 49176430 | Escherichia coli |
| fadB | NP_418288.1 | 16131692 | Escherichia coli |
| fadI | NP_416844.1 | 16130275 | Escherichia coli |
| fadJ | NP_416843.1 | 16130274 | Escherichia coli |
| fadR | NP_415705.1 | 16129150 | Escherichia coli |

The reversible condensation of 4-hydroxybutyryl-CoA to crotonyl-CoA (Step A, FIG. 3) is catalyzed by the bifunctional enzyme 4-hydroxybutyryl-CoA dehydratase/vinylacetyl-CoA Δ-isomerase. This enzyme first dehydrates 4-hydroxybutyryl-CoA to vinylacetyl-CoA, which subsequently rearranges to form crotonoyl-CoA. The enzymes from Clostridium kluyveri and C. aminobutyrium have been purified, characterized, and sequenced at the N-terminal domain (Scherf et al., Eur. J. Biochem., 215:421-429 (1993); Scherf et al., Arch. Microbiol., 161:239-245 (1994)). The abfD genes from C. aminobutyrium and C. kluyveri match exactly with these N-terminal amino acid sequences, and have been indicated to encode the 4-hydroxybutyrul-CoA dehydratases/vinylacetyl-CoA Δ-isomerase activities. Similar genes are identified through homology from genome projects, including abfD from Porphyromonas gingivalis and Msed_1220 from Metallosphaera sedula. Data related to the sequences for each of these exemplary gene products can be found using the following GenBank accession numbers shown in Table 32.

TABLE 32

| Protein | GenBank ID | GI Number | Organism |
|---|---|---|---|
| abfD | YP_001396399.1 | 153955634 | Clostridium kluyveri |
| abfD | P55792 | 84028213 | Clostridium aminobutyricum |
| abfD | YP_001928843 | 188994591 | Porphyromonas gingivalis |
| Msed_1220 | YP_001191305.1 | 146303989 | Metallosphaera sedula |

Deamination of 2-amino-4-ketopentanoate (FIG. 1, Reaction I) and of 4-aminobutan-2-one (Step F, FIG. 1) can be accomplished by AKP ammonia-lyase and 4-aminobutan-2-one ammonia-lyase respectively. These deaminations are very similar to the deamination of aspartate to fumarate by aspartase. The enzyme has been extensively studied and several crystal structures are available. The E. coli enzyme has been shown to react with alternate substrates such as aspartatephenylmethylester, asparagine, benzyl-aspartate and malate (Ma et al., Ann. N.Y. Acad. Sci., 672:60-65 (1992). In a separate study, directed evolution has been implemented on this enzyme to alter substrate specificity (Asano et al., Biomol. Eng., 22:95-101 (2005)). Enzymes with aspartase functionality have also been characterized in Haemophilus influenzae (Sjostrom et al., Biochem. Biophys. Acta., 1324:182-190 (1997)), Pseudomonas fluorescens (Takagi et al., J. Biochem., 96:545-552 (1984)), Bacillus subtilus (Sjostrom et al., supra) and Serratia marcescens (Takagi et al., J. Bacteriol., 161:1-6 (1985)). Data related to the sequences for each of these exemplary gene products can be found using the following GenBank accession numbers shown in Table 33.

TABLE 33

| Protein | GenBank ID | GI Number | Organism |
|---|---|---|---|
| aspA | NP_418562 | 90111690 | Escherichia coli |
| aspA | P44324.1 | 1168534 | Haemophilus influenzae |
| aspA | P07346.1 | 114273 | Pseudomonas fluorescens |
| ansB | P26899.1 | 251757243 | Bacillus subtilus |
| aspA | P33109.1 | 416661 | Serratia marcescens |

A similar ammonia lyase reaction is catalyzed by methylaspartase (EC 4.3.1.2), an enzyme participating in the glutamate fermentation route via mesaconate (Kato et al., supra). This enzyme, also known as beta-methylaspartase and 3-methylaspartate ammonia-lyase, naturally catalyzes the deamination of threo-3-methylasparatate to mesaconate. The 3-methylaspartase from Clostridium tetanomorphum has been cloned, functionally expressed in E. coli, and crystallized (Asuncion et al., 57:731-733 (2001); Asuncion et al., J Biol Chem. 277:8306-8311 (2002); Botting et al., 27:2953-2955 (1988); Goda et al., 31:10747-10756 (1992)). In Citrobacter amalonaticus, this enzyme is encoded by BAA28709 (Kato et al., Arch. Microbiol 168:457-463 (1997)). 3-Methylaspartase has also been crystallized from E. coli YG1002 (Asano et al., FEMS Microbiol Lett. 118: 255-258 (1994)) although the protein sequence is not listed in public databases such as GenBank. Data related to the sequences for each of these exemplary gene products can be found using the following GenBank accession numbers shown in Table 34.

TABLE 34

| Protein | GenBank ID | GI Number | Organism |
|---|---|---|---|
| mal | AAB24070.1 | 259429 | Clostridium tetanomorphum |
| BAA28709 | BAA28709.1 | 3184397 | Citrobacter amalonaticus |

Figure 8B:
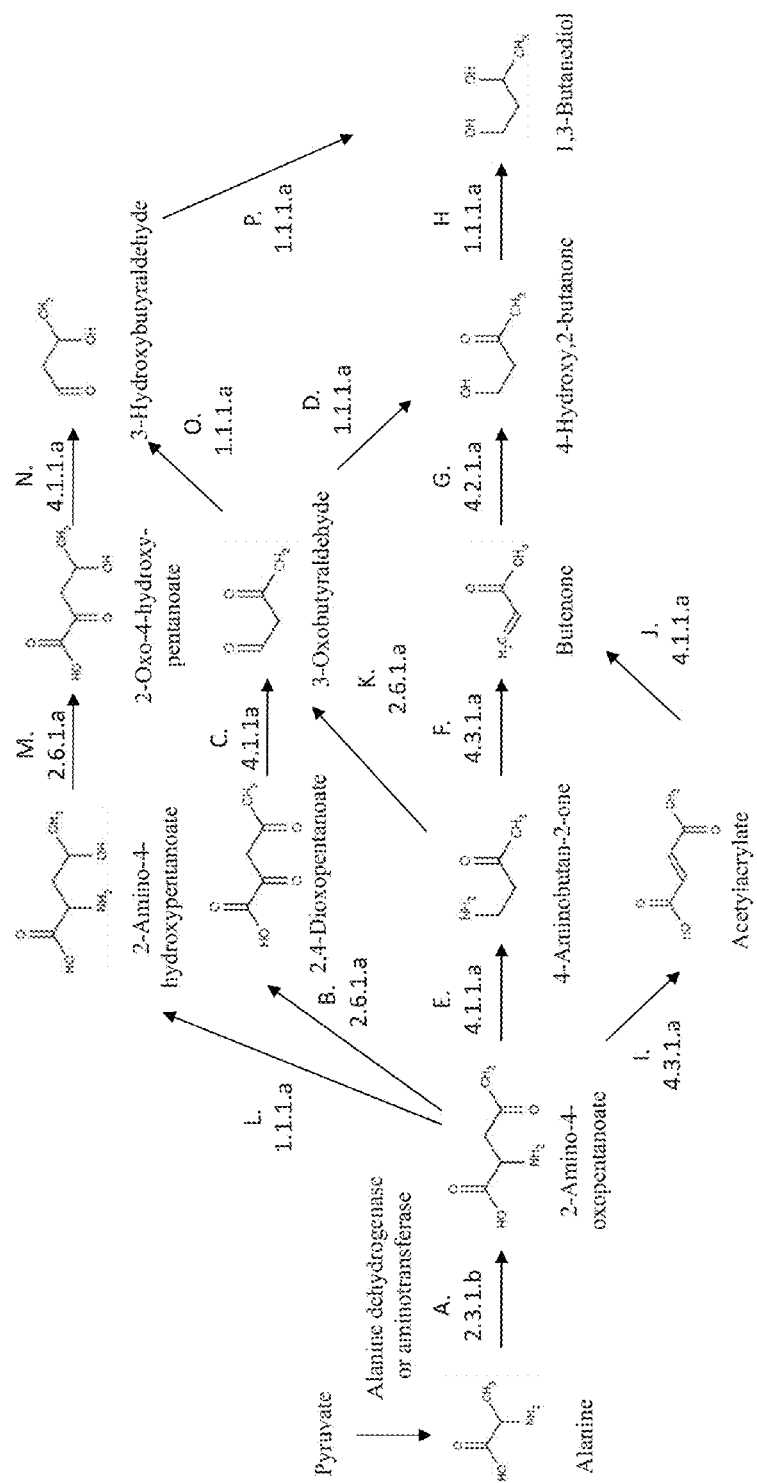
FIG. 8B shows exemplary pathways for the biosynthesis of 1,3-butanediol from pyruvate; pyruvate is converted to alanine by alanine dehydrogenase alanine aminotransferase; the remaining enzymatic transformations shown are carried out by the following enzymes: A) AKP thiolase, B) AKP aminotransferase or AKP oxidoreductase (deaminating), C) 2,4-dioxopentanoate decarboxylase, D) 3-oxobutyraldehyde reductase (aldehyde reducing), E) AKP decarboxylase, F) 4-aminobutan-2-one ammonia-lyase, G) Butenone hydratase, H) 4-hydroxy,2-butanone reductase, I) AKP ammonia-lyase, J) acetylacrylate decarboxylase, K) 4-aminobutan-2-one aminotransferase or 4-aminobutan-2-one oxidoreductase (deaminating), L) AKP dehydrogenase, M) 2-amino-4-hydroxypentanoate aminotransferase or 2-amino-4-hydroxypentanoate oxidoreductase (deaminating), N) 2-oxo-4-hydroxypentanoate decarboxylase, O) 3-oxobutyraldehyde reductase (ketone reducing), and P) 3-hydroxybutyraldehdye reductase.

Referring now to FIG. 8B, gene candidates for alanine dehydrogenase alanine aminotransferase are shown below which convert pyruvate to alanine

TABLE 35

| | | |
|---|---|---|
| glutamate-pyruvate aminotransferase (alaB) | Escherichia coli K-12 substr. MG1655 | Accession: AAC76384.1 GI: 1789759 |
| glutamate-pyruvate aminotransferase (alaA) | Escherichia coli K-12 substr. MG1655 | Accession: AAC75350.1 GI: 1788627 |
| glutamate-pyruvate aminotransferase (alaC) | Escherichia coli K-12 substr. MG1655 | Accession: AAC75438.1 GI: 1788722 |
| alanine transaminase (AOAT1) | Arabidopsis thaliana col | Accession: AEE30370.1 GI: 332192249 |
| alanine transaminase (AOAT2) | Arabidopsis thaliana col | Accession: AEE35084.1 GI: 332196963 |
| tryptophan aminotransferase (TAA1) | Arabidopsis thaliana col | Accession: NP_177213.1 GI: 15223183 |
| alanine aminotransferase (GPT2) | Homo sapiens | Accession: NP_597700.1 GI: 19263340 |
| alanine aminotransferase (GPT) | Homo sapiens | Accession: AAB20194.1 GI: 238134 |
| alanine aminotransferase | Clostridium propionicum | |
| alanine dehydrogenase (ald) | Phormidium lapideum | Accession: BAA24455.1 GI: 2804515 |
| alanine dehydrogenase (aladh) | Enterobacter aerogenes | Accession: BAA77513.1 GI: 4803749 |
| L-alanine dehydrogenase | Bacillus cereus | |

TABLE 35-continued

| L-alanine dehydrogenase (ald) | *Bacillus subtilis* | Accession: NP_391071.1 GI: 16080244 |
| alanine dehydrogenase | *Bilophila wadsworthia* RZATAU | Accession: AF269148.1 GI: 13661832 |

Figure 9B:
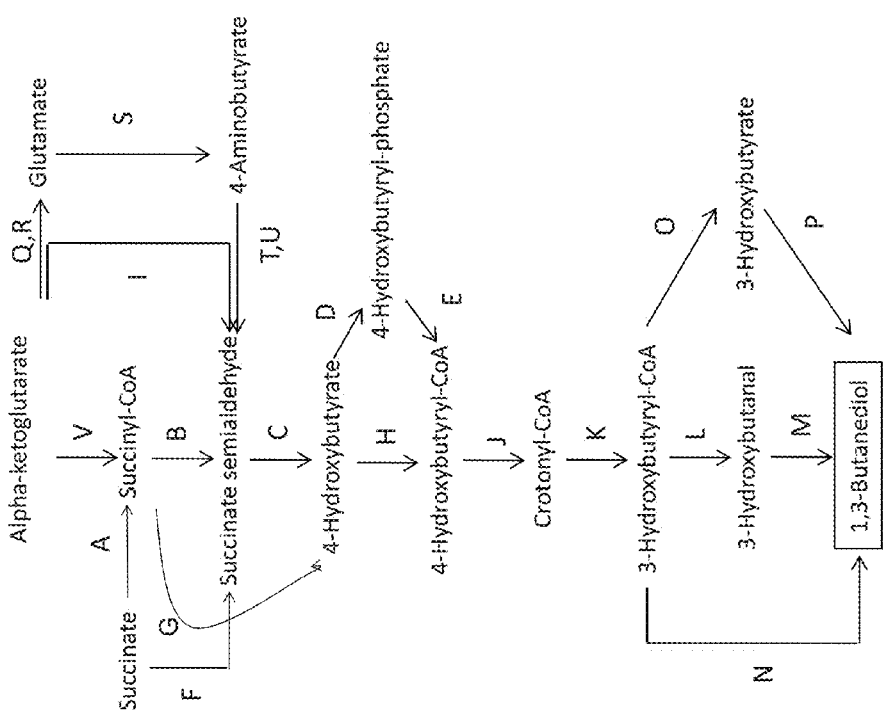
FIG. 9B shows exemplary pathways for the biosynthesis of 1,3-butanediol from alpha-ketoglutarate, succinate and succinyl-CoA; the enzymatic transformations shown are carried out by the following enzymes: A. Succinyl-CoA transferase, or Succinyl-CoA synthetase (or succinyl-CoA ligase), B. Succinyl-CoA reductase (aldehyde forming), C. 4-Hydroxybutyrate dehydrogenase, D. 4-Hydroxybutyrate kinase, E. Phosphotrans-4-hydroxybutyrylase, F. Succinate reductase, G. Succinyl-CoA reductase (alcohol forming), H. 4-Hydroxybutyryl-CoA transferase, or 4-Hydroxybutyryl-CoA synthetase, or 4-Hydroxybutyryl-CoA ligase I. Alpha-ketoglutarate decarboxylase, J. 4-hydroxybutyryl-CoA dehydratase, K. crotonase, L. 3-hydroxybutyryl-CoA reductase (aldehyde forming), M. 3-hydroxybutanal reductase, N. 3-hydroxybutyryl-CoA reductase (alcohol forming), O. 3-hydroxybutyryl-CoA hydrolase, transferase, or synthetase, P. 3-hydroxybutyrate reductase, Q. Glutamate dehydrogenase and/or R. Glutamate transaminase; S. Glutamate decarboxylase; T. 4-aminobutyrate dehydrogenase and/or U. 4-aminobutyrate transaminase and V. Alpha-ketoglutarate dehydrogenase.
Figure 10:
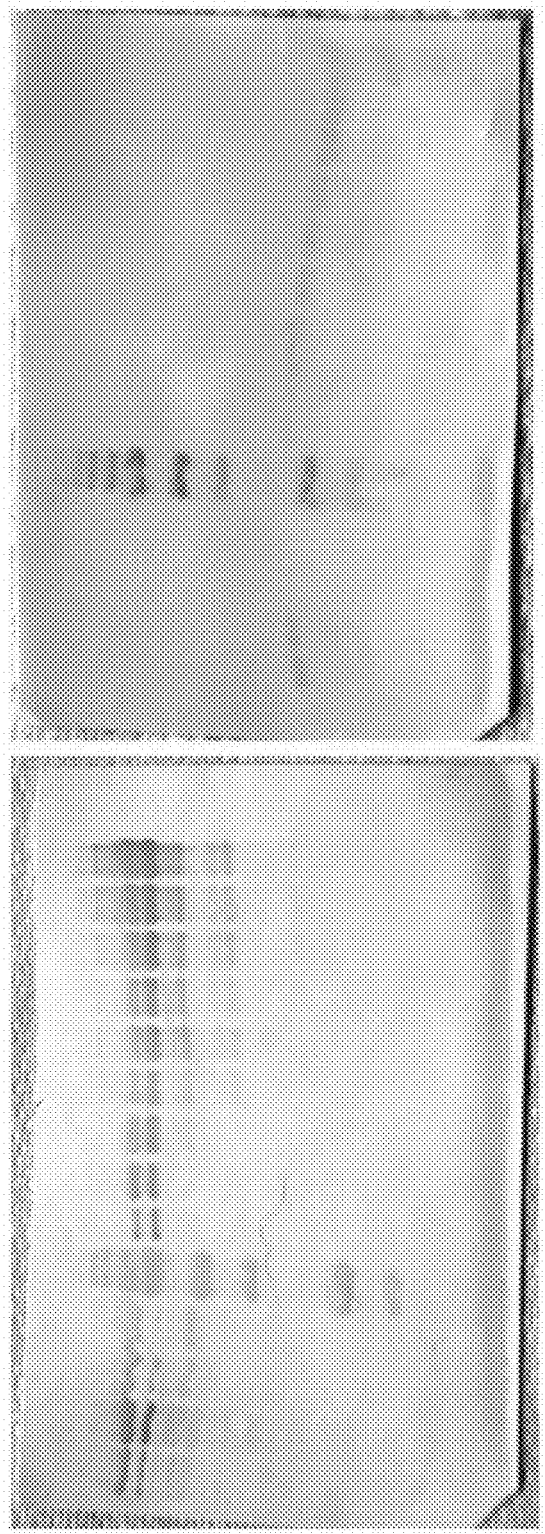
FIG. 10 shows Western blots of 10 micrograms ACS90 (lane 1), ACS91 (lane 2), Mta98/99 (lanes 3 and 4) cell extracts with size standards (lane 5) and controls of *M. thermoacetica* CODH (Moth_1202/1203) or Mtr (Moth_1197) proteins (50, 150, 250, 350, 450, 500, 750, 900, and 1000 ng).

Five requisite pathways to achieve the biosynthesis of 4-HB are exemplified herein and shown for purposes of illustration in FIG. 9B. One requisite 4-HB biosynthetic pathway includes the biosynthesis of 4-HB from succinate (the succinate pathway). The enzymes participating in this 4-HB pathway include succinate reductase, 4-hydroxybutanoate dehydrogenase (Steps F and C, FIG. 9B). Another requisite 4-HB biosynthetic pathway includes the biosynthesis from succinate through succinyl-CoA (the succinyl-CoA pathway). The enzymes participating in this 4-HB pathway include succinyl-CoA synthetase, CoA-dependent succinic semialdehyde dehydrogenase, and 4-hydroxybutanoate dehydrogenase (Steps A, I and K, FIG. 9B). Three other requisite 4-HB biosynthetic pathways include the biosynthesis of 4-HB from α-ketoglutarate (the α-ketoglutarate pathways). Hence, a third requisite 4-HB biosynthetic pathway is the biosynthesis of succinic semialdehyde through succinyl-CoA (Steps V, B, and C, FIG. 9B). AKG can be converted into succinyl-CoA by alpha-ketoglutarate dehydrogenase. This is then transformed into succinate semialdehyde and 4-HB as described earlier. Yet another pathway (Steps Q, R, S, T, U, FIG. 9B) for synthesizing 4-HB entails conversion of AKG into glutamate via glutamate dehydrogenase or glutamate transaminase. Glutamate is decarboxylated to form 4-aminobutyrate by glutamate decarboxylase and then 4-aminobutyrate dehydrogenase or 4-aminobutyrate transaminase can convert it into succinate semialdehyde. The final 4-HB biosynthetic pathway described here also includes the biosynthesis of 4-HB from α-ketoglutarate (Steps I and C, FIG. 9B), but utilizes α-ketoglutarate decarboxylase to catalyze succinic semialdehyde synthesis. 4-hydroxybutanoate dehydrogenase catalyzes the conversion of succinic semialdehyde to 4-HB. 4-hydroxybutanoate dehydrogenase catalyzes the conversion of succinic semialdehyde to 4-HB. 4HB can further be converted into 4-HB-CoA by 4-HB-CoA ligase, 4-HB-CoA synthetase or 4-HB-CoA transferase. Alternatively, the conversion of 4-HB to 4-HB CoA can be carried out by 4-Hydroxybutyrate kinase and Phosphotrans-4-hydroxybutyrylase (Steps D and E, FIG. 9B). Each of these 4-HB and 4HB-CoA biosynthetic pathways, their substrates, reactants and products are described further below in the Examples.

The non-naturally occurring microbial organisms of the invention can be produced by introducing expressible nucleic acids encoding one or more of the enzymes participating in one or more 4-HB biosynthetic pathways. Depending on the host microbial organism chosen for biosynthesis, nucleic acids for some or all of a particular 4-HB biosynthetic pathway can be expressed. For example, if a chosen host is deficient in both enzymes in the succinate to 4-HB pathway and this pathway is selected for 4-HB biosynthesis, then expressible nucleic acids for both succinate reductase and 4-hydroxybutanoate dehydrogenase are introduced into the host for subsequent exogenous expression. Alternatively, if the chosen host exhibits endogenous succinate reductase, but is deficient in 4-hydroxybutanoate dehydrogenase then an encoding nucleic acid is needed for this enzyme to achieve 4-HB biosynthesis.

In like fashion, where 4-HB biosynthesis is selected to occur through the succinate to succinyl-CoA pathway (the succinyl-CoA pathway), encoding nucleic acids for host deficiencies in the enzymes succinyl-CoA synthetase, CoA-dependent succinic semialdehyde dehydrogenase and/or 4-hydroxybutanoate dehydrogenase are to be exogenously expressed in the recipient host. Selection of 4-HB biosynthesis through the α-ketoglutarate to succinic semialdehyde pathway (the α-ketoglutarate pathway) can utilize exogenous expression for host deficiencies in one or more of the enzymes for glutamate dehydrogenase, glutamate transaminase, glutamate decarboxylase, 4-aminobutyrate dehydrogenase, 4-aminobutyrate transaminase, and/or 4-hydroxybutanoate dehydrogenase.

Depending on the 4-HB biosynthetic pathway constituents of a selected host microbial organism, the non-naturally occurring microbial 4-HB biocatalysts of the invention will include at least one exogenously expressed 4-HB pathway-encoding nucleic acid and up to all encoding nucleic acids for one or more 4-HB biosynthetic pathways. For example, 4-HB-CoA biosynthesis can be established from all five pathways in a host deficient in 4-hydroxybutanoate dehydrogenase through exogenous expression of a 4-hydroxybutanoate dehydrogenase encoding nucleic acid. In contrast, 4-HB biosynthesis can be established from all five pathways in a host deficient in all eleven enzymes through exogenous expression of all eight of CoA-independent succinic semialdehyde dehydrogenase, succinyl-CoA synthetase, CoA-dependent succinic semialdehyde dehydrogenase, glutamate: succinic semialdehyde transaminase, glutamate decarboxylase, α-ketoglutarate decarboxylase and 4-hydroxybutanoate dehydrogenase.

Given the teachings and guidance provided herein, those skilled in the art will understand that the number of encoding nucleic acids to introduce in an expressible form will, at least, parallel the 4-HB pathway deficiencies of the selected host microbial organism. Therefore, a non-naturally occurring microbial organism of the invention can have one, two, three, four, five, six or seven or up to eleven nucleic acids encoding the above enzymes constituting one or more 4-HB biosynthetic pathways. In some embodiments, the non-naturally occurring microbial organisms also can include other genetic modifications that facilitate or optimize 4-HB-CoA biosynthesis or that confer other useful functions onto the host microbial organism. One such other functionality can include, for example, augmentation of the synthesis of one or more of the 4-HB-CoA pathway precursors such as succinate, succinyl-CoA and/or α-ketoglutarate.

In some embodiments, a non-naturally occurring microbial organism of the invention is generated from a host that contains the enzymatic capability to synthesize 4-HB. In this specific embodiment it can be useful to increase the synthesis or accumulation of a 4-HB pathway product to, for example, drive 4-HB pathway reactions toward 4-HB production. Increased synthesis or accumulation can be accomplished by, for example, overexpression of nucleic acids encoding one or more of the above-described 4-HB pathway enzymes. Over expression of the 4-HB pathway enzyme or enzymes can occur, for example, through exogenous expression of the endogenous gene or genes, or through exogenous expression of the heterologous gene or genes. Therefore, naturally occurring organisms can be readily generated to be non-naturally 4-HB producing microbial organisms of the invention through overexpression of one, two, three, four, five, six or seven nucleic or all eleven acids encoding 4-HB biosynthetic pathway enzymes. In addition, a non-naturally occurring organism can be generated by mutagenesis of an endogenous gene that results in an increase in activity of an enzyme in the 4-HB biosynthetic pathway.

Non-naturally occurring microbial organisms also can be generated which biosynthesize 1,3-BDO. As with the 4-HB producing microbial organisms of the invention, the 1,3-BDO producing microbial organisms also can produce intracellularly or secret the 1,3-BDO into the culture medium. Following the teachings and guidance provided previously for the construction of microbial organisms that synthesize 4-HB, additional 1,3-BDO pathways can be incorporated into the 4-HB producing microbial organisms to generate organisms that also synthesize 1,3-BDO and other 1,3-BDO family compounds. The non-naturally occurring microbial organisms of the invention capable of 1,3-BDO biosynthesis circumvent these chemical synthesis using 4-HB as an entry point as illustrated in FIG. 9B.

The additional 1,3-BDO pathways to introduce into 4-HB producers include, for example, the exogenous expression in a host deficient background or the overexpression of one or more of the enzymes exemplified in FIG. 9B. An initial step in the entry pathway to 1,3-BDO is the conversion of 4-hydroxybutyrate to 4-hydroxybutyryl-CoA using 4-hydroxybutyrate:CoA transferase or 4-hydroxybutyryl-CoA synthetase (or ligase) the combination of butyrate kinase and phosphotransbutyrylase. Accordingly, the additional initial 1,3-BDO pathways to introduce into 4-HB producers to produce 4-hydroxybutyryl-CoA include, for example, the exogenous expression in a host deficient background or the overexpression of one or more of a 4-hydroxybutyrate:CoA transferase, 4-hydroxybutyryl-CoA synthetase (or ligase), butyrate kinase or phosphotransbutyrylase. In the absence of endogenous acyl-CoA synthetase capable of modifying 4-HB, the non-naturally occurring 1,3-BDO producing microbial organisms can further include an exogenous acyl-CoA synthetase selective for 4-HB, or the combination of multiple enzymes that have as a net reaction conversion of 4-HB into 4-HB-CoA. As exemplified further below in the Examples, butyrate kinase and phosphotransbutyrylase exhibit 1,3-BDO pathway activity and catalyze the conversions illustrated in FIG. 9B with a 4-HB substrate. Therefore, these enzymes also can be referred to herein as 4-hydroxybutyrate kinase and phosphotranshydroxybutyrylase respectively. Once 4-hydroxybutyryl-CoA is generated it can then be utilized for the biosynthesis of 1,3-BDO following the subsequent steps shown FIG. 9B.

Step A of FIG. 9B involves CoA synthetase or ligase reactions for succinate as the substrate. Exemplary genes encoding enzymes likely to carry out these transformations include the sucCD genes of *E. coli* which naturally form a succinyl-CoA synthetase complex. This enzyme complex naturally catalyzes the formation of succinyl-CoA from succinate with the contaminant consumption of one ATP, a reaction which is reversible in vivo (Buck et al., *Biochem.* 24:6245-6252 (1985)).

TABLE 36

| Gene | Accession No. | GI No. | Organism |
|------|---------------|--------|----------|
| sucC | NP_415256.1 | 16128703 | *Escherichia coli* |
| sucD | AAC73823.1 | 1786949 | *Escherichia coli* |

Additional exemplary CoA-ligases include the rat dicarboxylate-CoA ligase for which the sequence is yet uncharacterized (Vamecq et al., *Biochemical Journal* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacillus subtilis* (Bower et. al., *J. Bacteriol.* 178(14):4122-4130 (1996)). Additional candidate enzymes are acetoacetyl-CoA synthetases from *Mus musculus* (Hasegawa et al., *Biochim Biophys Acta* 1779:414-419 (2008)) and *Homo sapiens* (Ohgami et al., *Biochem Pharmacol* 65:989-994 (2003)) which naturally catalyze the ATP-dependant conversion of acetoacetate into acetoacetyl-CoA. 4-hydroxybutyryl-CoA synthetase activity has been demonstrated in *Metallosphaera sedula* (Berg et al., *Science* 318:1782-1786 (2007)). This function has been tentatively assigned to the Msed_1422 gene.

TABLE 37

| Gene | Accession No. | GI No. | Organism |
|------|---------------|--------|----------|
| phl | CAJ15517.1 | 77019264 | *Penicillium chrysogenum* |
| phlB | ABS19624.1 | 152002983 | *Penicillium chrysogenum* |
| paaF | AAC24333.2 | 22711873 | *Pseudomonas putida* |
| bioW | NP_390902.2 | 50812281 | *Bacillus subtilis* |
| AACS | NP_084486.1 | 21313520 | *Mus musculus* |
| AACS | NP_076417.2 | 31982927 | *Homo sapiens* |
| Msed_1422 | YP_001191504 | 146304188 | *Metallosphaera sedula* |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyrate, isovalerate, succinate, fumarate, phenylacetate, indoleacetate (Musfeldt et al., *J Bacteriol* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra). The enzymes from *A. fulgidus, H. marismortui* and *P. aerophilum* have all been cloned, functionally expressed, and characterized in *E. coli* (Musfeldt et al., supra; Brasen et al., supra).

TABLE 38

| Gene | Accession No. | GI No. | Organism |
|------|---------------|--------|----------|
| AF1211 | NP_070039.1 | 11498810 | *Archaeoglobus fulgidus* DSM 4304 |
| scs | YP_135572.1 | 55377722 | *Haloarcula marismortui* ATCC 43049 |
| PAE3250 | NP_560604.1 | 18313937 | *Pyrobaculum aerophilum* str. IM2 |

The conversion of succinate to succinate semialdehyde (Step F) can be catalyzed by a carboxylic acid reductase. One notable carboxylic acid reductase can be found in *Nocardia iowensis* which catalyzes the magnesium, ATP and NADPH-dependent reduction of carboxylic acids to their corresponding aldehydes (Venkitasubramanian et al., J Biol.

Chem. 282:478-485 (2007)). This enzyme is encoded by the car gene and was cloned and functionally expressed in *E. coli* (Venkitasubramanian et al., J Biol. Chem. 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid and the enzyme exhibits broad acceptance of aromatic and aliphatic substrates (Venkitasubramanian et al. "Biocatalytic Reduction of Carboxylic Acids: Mechanism and Applications" Chapter 15 in Biocatalysis in the Pharmaceutical and Biotechnology Industires, ed. R. N. Patel, CRC Press LLC, Boca Raton, Fla. (2006)). Additional car and npt genes can be identified based on sequence homology.

TABLE 39A

| Gene | Accession No. | GI No. | Organism |
| --- | --- | --- | --- |
| car | AAR91681.1 | 40796035 | *Nocardia iowensis* (sp. NRRL 5646) |
| npt | ABI83656.1 | 114848891 | *Nocardia iowensis* (sp. NRRL 5646) |

TABLE 39B

| Gene | Accession No. | GI No. | Organism |
| --- | --- | --- | --- |
| fadD9 | YP_978699.1 | 121638475 | *Mycobacterium bovis* BCG |
| BCG_2812c | YP_978898.1 | 121638674 | *Mycobacterium bovis* BCG |
| nfa20150 | YP_118225.1 | 54023983 | *Nocardia farcinica* IFM 10152 |
| nfa40540 | YP_120266.1 | 54026024 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., J. Antibiot. 60(6):380-387 (2007)). Co-expression of griC and griD with SGR_665, an enzyme similar in sequence to the *Nocardia iowensis* npt, may be beneficial.

TABLE 40

| Gene | Accession No. | GI No. | Organism |
| --- | --- | --- | --- |
| griC | 182438036 | YP_001825755.1 | *Streptomyces griseus* subsp. *griseus* NBRC 13350 |
| griD | 182438037 | YP_001825756.1 | *Streptomyces griseus* subsp. *griseus* NBRC 13350 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., Gene 98:141-145 (1991)), *Candida albicans* (Guo et al., Mol. Genet. Genomics 269:271-279 (2003)), and *Schizosaccharomyces pombe* (Ford et al., Curr. Genet. 28:131-137 (1995)). The AAR from *S. pombe* exhibited significant activity when expressed in *E. coli* (Guo et al., Yeast 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., J Biol. Chem 278:8250-8256 (2003)). The gene encoding the *P. chrysogenum* PPTase has not been identified to date and no high-confidence hits were identified by sequence comparison homology searching.

TABLE 41

| Gene | Accession No. | GI No. | Organism |
| --- | --- | --- | --- |
| LYS2 | AAA34747.1 | 171867 | *Saccharomyces cerevisiae* |
| LYS5 | P50113.1 | 1708896 | *Saccharomyces cerevisiae* |
| LYS2 | AAC02241.1 | 2853226 | *Candida albicans* |
| LYS5 | AAO26020.1 | 28136195 | *Candida albicans* |
| Lys1p | P40976.3 | 13124791 | *Schizosaccharomyces pombe* |
| Lys7p | Q10474.1 | 1723561 | *Schizosaccharomyces pombe* |
| Lys2 | CAA74300.1 | 3282044 | *Penicillium chrysogenum* |

The conversion of succinyl-CoA to succinate semialdehyde (Step B, FIG. 9B) is catalyzed by an aldehyde forming succinyl-CoA reductase. Several acyl-CoA dehydrogenases are capable of reducing an acyl-CoA to its corresponding aldehyde. Exemplary genes that encode such enzymes include the *Acinetobacter calcoaceticus* acr1 encoding a fatty acyl-CoA reductase (Reiser and Somerville, J. Bacteriology 179:2969-2975 (1997)), the *Acinetobacter* sp. M-1 fatty acyl-CoA reductase (Ishige et al. Appl. Environ. Microbiol. 68:1192-1195 (2002)), and a CoA- and NADP-dependent succinate semialdehyde dehydrogenase encoded by the sucD gene in *Clostridium kluyveri* (Sohling and Gottschalk J Bacteriol 178:871-80 (1996); Sohling and Gottschalk J Bacteriol. 178:871-880 (1996)). SucD of *P. gingivalis* is another aldehyde-forming succinyl-CoA reductase (Takahashi et al. J. Bacteriol. 182:4704-4710 (2000)). The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski et al. J Bacteriol. 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Koo et al., Biotechnol Lett. 27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., Biosci. Biotechnol Biochem. 71:58-68 (2007)).

TABLE 42

| Gene | Accession No. | GI No. | Organism |
| --- | --- | --- | --- |
| acr1 | YP_047869.1 | 50086359 | *Acinetobacter calcoaceticus* |
| acr1 | AAC45217 | 1684886 | *Acinetobacter baylyi* |
| acr1 | BAB85476.1 | 18857901 | *Acinetobacter* sp. Strain M-1 |
| sucD | P38947.1 | 730847 | *Clostridium kluyveri* |
| sucD | NP_904963.1 | 34540484 | *Porphyromonas gingivalis* |

TABLE 42-continued

| Gene | Accession No. | GI No. | Organism |
|---|---|---|---|
| bphG | BAA03892.1 | 425213 | Pseudomonas sp |
| adhE | AAV66076.1 | 55818563 | Leuconostoc mesenteroides |
| bld | AAP42563.1 | 31075383 | Clostridium saccharoperbutylacetonicum |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al. *Science* 318:1782-1786 (2007); Thauer, R. K. *Science* 318:1732-1733 (2007)). The enzyme utilizes NADPH as a cofactor and has been characterized in *Metallosphaera* and *Sulfolobus* spp (Alber et al. *J. Bacteriol.* 188:8551-8559 (2006); Hugler et al. *J. Bacteriol.* 184:2404-2410 (2002)). The enzyme is encoded by Msed_0709 in *Metallosphaera sedula* (Alber et al. *J. Bacteriol.* 188:8551-8559 (2006); Berg et al. *Science* 318:1782-1786 (2007)). A gene encoding a malonyl-CoA reductase from *Sulfolobus tokodaii* was cloned and heterologously expressed in *E. coli* (Alber et al. *J. Bacteriol.* 188:8551-8559 (2006)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius*. Yet another candidate for CoA-acylating aldehyde dehydrogenase is the ald gene from *Clostridium beijerinckii* (Toth et al., *Appl Environ. Microbiol* 65:4973-4980 (1999)). This enzyme has been reported to reduce acetyl-CoA and butyryl-CoA to their corresponding aldehydes. This gene is very similar to cutE that encodes acetaldehyde dehydrogenase of *Salmonella typhimurium* and *E. coli* (Toth et al., *Appl Environ. Microbiol* 65:4973-4980 (1999)).

TABLE 43

| Gene | Accession No. | GI No. | Organism |
|---|---|---|---|
| Msed_0709 | YP_001190808.1 | 146303492 | Metallosphaera sedula |
| mcr | NP_378167.1 | 15922498 | Sulfolobus tokodaii |
| asd-2 | NP_343563.1 | 15898958 | Sulfolobus solfataricus |
| Saci_2370 | YP_256941.1 | 70608071 | Sulfolobus acidocaldarius |
| Ald | AAT66436 | 49473535 | Clostridium beijerinckii |
| eutE | AAA80209 | 687645 | Salmonella typhimurium |
| eutE | P77445 | 2498347 | Escherichia coli |

Glutamate dehydrogenase (Step Q, FIG. 9B) and 4-aminobutyrate dehydrogenase (Step T, FIG. 9B) can be catalyzed by aminating oxidoreductases. Enzymes in this EC class (1.4.1.a) catalyze the oxidative deamination of alpha-amino acids with NAD$^+$ or NADP$^+$ as acceptor, and the reactions are typically reversible. Exemplary oxidoreductases operating on amino acids include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (Korber et al. *J. Mol. Biol.* 234:1270-1273 (1993); McPherson and Wootton *Nucleic. Acids Res.* 11:5257-5266 (1983)), gdh from *Thermotoga maritima* (Kort et al. *Extremophiles* 1:52-60 (1997); Lebbink, et al. *J. Mol. Biol.* 280:287-296 (1998)); Lebbink et al. *J. Mol. Biol.* 289:357-369 (1999)), and gdhA1 from *Halobacterium salinarum* (Ingoldsby et al. *Gene* 349:237-244 (2005)) catalyze the reversible interconversion of glutamate to 2-oxoglutarate and ammonia, while favoring NADP(H), NAD(H), or both, respectively. The ldh gene of *Bacillus cereus* encodes the LeuDH protein that has a wide of range of substrates including leucine, isoleucine, valine, and 2-aminobutanoate (Ansorge and Kula *Biotechnol Bioeng.* 68:557-562 (2000); Stoyan et al. *J. Biotechnol* 54:77-80 (1997)). The nadX gene from *Thermotoga* maritime encoding for the aspartate dehydrogenase is involved in the biosynthesis of NAD (Yang et al. *J. Biol. Chem.* 278:8804-8808 (2003)).

TABLE 44

| Gene | Accession No. | GI No. | Organism |
|---|---|---|---|
| gdhA | P00370 | 118547 | Escherichia coli |
| gdh | P96110.4 | 6226595 | Thermotoga maritima |
| gdhA1 | NP_279651.1 | 15789827 | Halobacterium salinarum |
| ldh | P0A393 | 61222614 | Bacillus cereus |
| nadX | NP_229443.1 | 15644391 | Thermotoga maritima |

Additional glutamate dehydrogenase gene candidates are found in *Bacillus subtilis* (Khan et al., *Biosci. Biotechnol Biochem.* 69:1861-1870 (2005)), *Nicotiana tabacum* (Purnell et al., *Planta* 222:167-180 (2005)), *Oryza sativa* (Abiko et al., *Plant Cell Physiol* 46:1724-1734 (2005)), *Haloferax mediterranei* (Diaz et al., *Extremophiles.* 10:105-115 (2006)) and *Halobactreium salinarum* (Hayden et al., *FEMS Microbiol Lett.* 211:37-41 (2002)). The *Nicotiana tabacum* enzyme is composed of alpha and beta subunits encoded by gdh1 and gdh2 (Purnell et al., *Planta* 222:167-180 (2005)). Overexpression of the NADH-dependent glutamate dehydrogenase was found to improve ethanol production in engineered strains of *S. cerevisiae* (Roca et al., *Appl Environ. Microbiol* 69:4732-4736 (2003)).

TABLE 45

| Gene | Accession No. | GI No. | Organism |
|---|---|---|---|
| rocG | NP_391659.1 | 16080831 | Bacillus subtilis |
| gdh1 | AAR11534.1 | 38146335 | Nicotiana tabacum |
| gdh2 | AAR11535.1 | 38146337 | Nicotiana tabacum |
| GDH | Q852M0 | 75243660 | Oryza sativa |
| GDH | Q977U6 | 74499858 | Haloferax mediterranei |
| GDH | P29051 | 118549 | Halobactreium salinarum |
| GDH2 | NP_010066.1 | 6319986 | Saccharomyces cerevisiae |

An exemplary enzyme for catalyzing the conversion of aldehydes to their corresponding primary amines is lysine 6-dehydrogenase (EC 1.4.1.18), encoded by the lysDH genes. The lysine 6-dehydrogenase (deaminating), encoded by lysDH gene, catalyze the oxidative deamination of the ε-amino group of L-lysine to form 2-aminoadipate-6-semialdehyde, which in turn nonenzymatically cyclizes to form Δ1-piperideine-6-carboxylate (Misono and Nagasaki *J. Bacteriol.* 150:398-401 (1982)). The lysDH gene from *Geobacillus stearothermophilus* encodes a thermophilic NAD-dependent lysine 6-dehydrogenase (Heydari et al. *Appl Environ. Microbiol* 70:937-942 (2004)). The lysDH gene from *Aeropyrum pernix* K1 is identified through homology from genome projects. Additional enzymes can be found in *Agrobacterium tumefaciens* (Hashimoto et al., *J Biochem.* 106:76-80 (1989); Misono et al., *J Bacteriol.* 150:398-401

(1982)) and *Achromobacter denitrificans* (Ruldeekultham-rong et al., *BMB. Rep.* 41:790-795 (2008)).

TABLE 46

| Gene | Accession No. | GI No. | Organism |
|---|---|---|---|
| lysDH | BAB39707 | 13429872 | *Geobacillus stearothermophilus* |
| lysDH | NP_147035.1 | 14602185 | *Aeropyrum pernix* K1 |
| lysDH | NP_353966 | 15888285 | *Agrobacterium tumefaciens* |
| lysDH | AAZ94428 | 74026644 | *Achromobacter denitrificans* |

An enzyme that converts 3-oxoacids to 3-amino acids is 3,5-diaminohexanoate dehydrogenase (EC 1.4.1.11), an enzyme found in organisms that ferment lysine. The gene encoding this enzyme, kdd, was recently identified in *Fusobacterium nucleatum* (Kreimeyer et al., 282:7191-7197 (2007)). The enzyme has been purified and characterized in other organisms (Baker et al., 247:7724-7734 (1972); Baker et al., 13:292-299 (1974)) but the genes associated with these enzymes are not known. Candidates in *Myxococcus xanthus, Porphyromonas gingivalis* W83 and other sequenced organisms can be inferred by sequence homology.

TABLE 47

| Gene | Accession No. | GI No. | Organism |
|---|---|---|---|
| kdd | AAL93966.1 | 19713113 | *Fusobacterium nucleatum* |
| mxan_439 | ABF87267.1 | 108462082 | *Myxococcus xanthus* |
| pg_1069 | AAQ66183.1 | 34397119 | *Porphyromonas gingivalis* |

Steps R and U in FIG. 9B can be catalyzed by aminotransferases that reversibly convert an aldehyde or ketone to an amino group. Common amino donor/acceptor combinations include glutamate/alpha-ketoglutarate, alanine/pyruvate, and aspartate/oxaloacetate. Several enzymes have been shown to convert aldehydes to primary amines, and vice versa. Lysine-6-aminotransferase (EC 2.6.1.36) is one exemplary enzyme capable of forming a primary amine. This enzyme function, converting lysine to alpha-aminoadipate semialdehyde, has been demonstrated in yeast and bacteria. Candidates from *Candida utilis* (Hammer et al., *J Basic Microbiol* 32:21-27 (1992)), *Flavobacterium lutescens* (Fujii et al., *J Biochem.* 128:391-397 (2000)) and *Streptomyces clavuligenus* (Romero et al., *J Ind. Microbiol Biotechnol* 18:241-246 (1997)) have been characterized. A recombinant lysine-6-aminotransferase from *S. clavuligenus* was functionally expressed in *E. coli* (Tobin et al., *J Bacteriol.* 173:6223-6229 (1991)). The *F. lutescens* enzyme is specific to alpha-ketoglutarate as the amino acceptor (Soda et al., 7:4110-4119 (1968)). Other enzymes which convert aldehydes to terminal amines include the dat gene product in *Acinetobacter baumanii* encoding 2,4-diaminobutanoate:2-ketoglutarate 4-transaminase (Ikai et al., *J Bacteriol.* 179: 5118-5125 (1997)). In addition to its natural substrate, 2,4-diaminobutyrate, DAT transaminates the terminal amines of lysine, 4-aminobutyrate and ornithine.

TABLE 48

| Gene | Accession No. | GI No. | Organism |
|---|---|---|---|
| lat | BAB13756.1 | 10336502 | *Flavobacterium lutescens* |
| lat | AAA26777.1 | 153343 | *Streptomyces clavuligenus* |
| dat | P56744.1 | 6685373 | *Acinetobacter baumanii* |

The conversion of an aldehyde to a terminal amine can also be catalyzed by gamma-aminobutyrate transaminase (GABA transaminase or 4-aminobutyrate transaminase). This enzyme naturally interconverts succinic semialdehyde and glutamate to 4-aminobutyrate and alpha-ketoglutarate and is known to have a broad substrate range (Schulz et al., 56:1-6 (1990); Liu et al., 43:10896-10905 (2004)). The two GABA transaminases in *E. coli* are encoded by gabT (Bartsch et al., *J Bacteriol.* 172:7035-7042 (1990)) and puuE (Kurihara et al., *J. Biol. Chem.* 280:4602-4608 (2005)). GABA transaminases in *Mus musculus, Pseudomonas fluorescens*, and *Sus scrofa* have been shown to react with a range of alternate substrates including 6-aminocaproic acid (Cooper, 113:80-82 (1985); SCOTT et al., 234: 932-936 (1959)).

TABLE 49

| Gene | Accession No. | GI No. | Organism |
|---|---|---|---|
| gabT | NP_417148.1 | 16130576 | *Escherichia coli* |
| puuE | NP_415818.1 | 16129263 | *Escherichia coli* |
| Abat | NP_766549.2 | 37202121 | *Mus musculus* |
| gabT | YP_257332.1 | 70733692 | *Pseudomonas fluorescens* |
| abat | NP_999428.1 | 47523600 | *Sus scrofa* |

Additional enzyme candidates for interconverting aldehydes and primary amines are putrescine transaminases or other diamine aminotransferases. The *E. coli* putrescine aminotransferase is encoded by the ygjG gene and the purified enzyme also was able to transaminate cadaverine and spermidine (Samsonova et al., *BMC. Microbiol* 3:2 (2003)). In addition, activity of this enzyme on 1,7-diaminoheptane and with amino acceptors other than 2-oxoglutarate (e.g., pyruvate, 2-oxobutanoate) has been reported (Samsonova et al., *BMC. Microbiol* 3:2 (2003); KIM, 239:783-786 (1964)). A putrescine aminotransferase with higher activity with pyruvate as the amino acceptor than alpha-ketoglutarate is the spuC gene of *Pseudomonas aeruginosa* (Lu et al., *J Bacteriol.* 184:3765-3773 (2002)).

TABLE 50

| Gene | Accession No. | GI No. | Organism |
|---|---|---|---|
| ygjG | NP_417544 | 145698310 | *Escherichia coli* |
| spuC | AAG03688 | 9946143 | *Pseudomonas aeruginosa* |

Enzymes that transaminate 3-oxoacids include GABA aminotransferase (described above), beta-alanine/alpha-ketoglutarate aminotransferase and 3-amino-2-methylpropionate aminotransferase. Beta-alanine/alpha-ketoglutarate aminotransferase (WO08027742) reacts with beta-alanine to form malonic semialdehyde, a 3-oxoacid. The gene product of SkPYD4 in *Saccharomyces kluyveri* was shown to preferentially use beta-alanine as the amino group donor (Andersen et al., *Gene* 124:105-109 (1993)). SkUGAJ encodes a homologue of *Saccharomyces cerevisiae* GABA aminotransferase, UGA1 (Ramos et al., *Eur. J. Biochem.* 149:401-404 (1985)), whereas SkPYD4 encodes an enzyme involved in both beta-alanine and GABA transamination (Andersen and Hansen, *Gene* 124:105-109 (1993)). 3-Amino-2-methylpropionate transaminase catalyzes the transformation from methylmalonate semialdehyde to 3-amino-2-methylpropionate. The enzyme has been characterized in *Rattus norvegicus* and *Sus scrofa* and is encoded by Abat (Tamaki et al., 324:376-389 (2000); Kakimoto et al., 156:374-380 (1968)).

TABLE 51

| Gene | Accession No. | GI No. | Organism |
|---|---|---|---|
| SkyPYD4 | ABF58893.1 | 98626772 | Lachancea kluyveri |
| SkUGA1 | ABF58894.1 | 98626792 | Lachancea kluyveri |
| UGA1 | NP_011533.1 | 6321456 | Saccharomyces cerevisiae |
| Abat | P50554.3 | 122065191 | Rattus norvegicus |
| Abat | P80147.2 | 120968 | Sus scrofa |

Several aminotransferases transaminate the amino groups of amino acids to form 2-oxoacids. Aspartate aminotransferase is an enzyme that naturally transfers an oxo group from oxaloacetate to glutamate, forming alpha-ketoglutarate and aspartate. Aspartate is similar in structure to OHED and 2-AHD. Aspartate aminotransferase activity is catalyzed by, for example, the gene products of aspC from *Escherichia coli* (Yagi et al., 100:81-84 (1979); Yagi et al., 113:83-89 (1985)), AAT2 from *Saccharomyces cerevisiae* (Yagi et al., 92:35-43 (1982)) and ASP5 from *Arabidopsis thaliana* (Kwok et al., 55:595-604 (2004); de la et al., 46:414-425 (2006); Wilkie et al., *Protein Expr. Purif.* 12:381-389 (1998)). The enzyme from *Rattus norvegicus* has been shown to transaminate alternate substrates such as 2-aminohexanedioic acid and 2,4-diaminobutyric acid (Recasens et al., 19:4583-4589 (1980)). Aminotransferases that work on other amino-acid substrates may also be able to catalyze this transformation. Valine aminotransferase catalyzes the conversion of valine and pyruvate to 2-ketoisovalerate and alanine. The *E. coli* gene, avtA, encodes one such enzyme (Whalen et al., *J. Bacteriol.* 150:739-746 (1982)). This gene product also catalyzes the transamination of alpha-ketobutyrate to generate α-aminobutyrate, although the amine donor in this reaction has not been identified (Whalen et al., *J. Bacteriol.* 158:571-574 (1984)). The gene product of the *E. coli* serC catalyzes two reactions, phosphoserine aminotransferase and phosphohydroxythreonine aminotransferase (Lam et al., *J. Bacteriol.* 172:6518-6528 (1990)), and activity on non-phosphorylated substrates could not be detected (Drewke et al., *FEBS. Lett.* 390:179-182 (1996)).

TABLE 52

| Gene | Accession No. | GI No. | Organism |
|---|---|---|---|
| aspC | NP_415448.1 | 16128895 | Escherichia coli |
| AAT2 | P23542.3 | 1703040 | Saccharomyces cerevisiae |
| ASP5 | P46248.2 | 20532373 | Arabidopsis thaliana |
| Got2 | P00507 | 112987 | Rattus norvegicus |
| avtA | YP_026231.1 | 49176374 | Escherichia coli |
| serC | NP_415427.1 | 16128874 | Escherichia coli |

Another enzyme candidate is alpha-aminoadipate aminotransferase (EC 2.6.1.39), an enzyme that participates in lysine biosynthesis and degradation in some organisms. This enzyme interconverts 2-aminoadipate and 2-oxoadipate, using alpha-ketoglutarate as the amino acceptor. Gene candidates are found in *Homo sapiens* (Okuno et al., *Enzyme Protein* 47:136-148 (1993)) and *Thermus thermophilus* (Miyazaki et al., 150:2327-2334 (2004)). The *Thermus thermophilus* enzyme, encoded by lysN, is active with several alternate substrates including oxaloacetate, 2-oxoisocaproate, 2-oxoisovalerate, and 2-oxo-3-methylvalerate.

TABLE 53

| Gene | Accession No. | GI No. | Organism |
|---|---|---|---|
| lysN | BAC76939.1 | 31096548 | Thermus thermophilus |
| AadAT-II | Q8N5Z0.2 | 46395904 | Homo sapiens |

Alpha-ketoglutarate decarboxylase (Step I, FIG. 9B) and glutamate decarboxylase (Step S, FIG. 9B) all involve the decarboxylation of an alpha-ketoacid. The decarboxylation of keto-acids is catalyzed by a variety of enzymes with varied substrate specificities, including pyruvate decarboxylase (EC 4.1.1.1), benzoylformate decarboxylase (EC 4.1.1.7), alpha-ketoglutarate decarboxylase and branched-chain alpha-ketoacid decarboxylase.

Pyruvate decarboxylase (PDC), also termed keto-acid decarboxylase, is a key enzyme in alcoholic fermentation, catalyzing the decarboxylation of pyruvate to acetaldehyde. The enzyme from *Saccharomyces cerevisiae* has a broad substrate range for aliphatic 2-keto acids including 2-ketobutyrate, 2-ketovalerate, 3-hydroxypyruvate and 2-phenylpyruvate. This enzyme has been extensively studied, engineered for altered activity, and functionally expressed in *E. coli* (Killenberg-Jabs et al., 268:1698-1704 (2001); Li et al., *Biochemistry.* 38:10004-10012 (1999); ter Schure et al., *Appl. Environ. Microbiol.* 64:1303-1307 (1998)). The PDC from *Zymomonas mobilis*, encoded by pdc, also has a broad substrate range and has been a subject of directed engineering studies to alter the affinity for different substrates (Siegert et al., 18:345-357 (2005)). The crystal structure of this enzyme is available (Killenberg-Jabs et al., 268:1698-1704 (2001)). Other well-characterized PDC candidates include the enzymes from *Acetobacter pasteurians* (Chandra et al., 176:443-451 (2001)) and *Kluyveromyces lactis* (Krieger et al., 269:3256-3263 (2002)).

TABLE 54

| Gene | Accession No. | GI No. | Organism |
|---|---|---|---|
| pdc | P06672.1 | 118391 | Zymomonas mobilis |
| pdc1 | P06169 | 30923172 | Saccharomyces cerevisiae |
| pdc | AM21208 | 20385191 | Acetobacter pasteurians |
| pdc1 | Q12629 | 52788279 | Kluyveromyces lactis |

Like PDC, benzoylformate decarboxylase (EC 4.1.1.7) has a broad substrate range and has been the target of enzyme engineering studies. The enzyme from *Pseudomonas putida* has been extensively studied and crystal structures of this enzyme are available (Polovnikova et al., 42:1820-1830 (2003); Hasson et al., 37:9918-9930 (1998)). Site-directed mutagenesis of two residues in the active site of the *Pseudomonas putida* enzyme altered the affinity (Km) of naturally and non-naturally occurring substrates (Siegert et al., 18:345-357 (2005)). The properties of this enzyme have been further modified by directed engineering (Lingen et al., *Chembiochem.* 4:721-726 (2003); Lingen et al., *Protein Eng* 15:585-593 (2002)). The enzyme from *Pseudomonas aeruginosa*, encoded by mdlC, has also been characterized experimentally (Barrowman et al., 34:57-60 (1986)). Additional gene candidates from *Pseudomonas stutzeri*, *Pseudomonas fluorescens* and other organisms can be inferred by sequence homology or identified using a growth selection system developed in *Pseudomonas putida* (Henning et al., *Appl. Environ. Microbiol.* 72:7510-7517 (2006)).

TABLE 55

| Gene | Accession No. | GI No. | Organism |
|---|---|---|---|
| mdlC | P20906.2 | 3915757 | *Pseudomonas putida* |
| mdlC | Q9HUR2.1 | 81539678 | *Pseudomonas aeruginosa* |
| dpgB | ABN80423.1 | 126202187 | *Pseudomonas stutzeri* |
| ilvB-1 | YP_260581.1 | 70730840 | *Pseudomonas fluorescens* |

A third enzyme capable of decarboxylating 2-oxoacids is alpha-ketoglutarate decarboxylase (KGD). The substrate range of this class of enzymes has not been studied to date. The KDC from *Mycobacterium tuberculosis* (Tian et al., 102:10670-10675 (2005)) has been cloned and functionally expressed in other internal projects at Genomatica. However, it is not an ideal candidate for strain engineering because it is large (~130 kDa) and GC-rich. KDC enzyme activity has been detected in several species of *rhizobia* including *Bradyrhizobium japonicum* and *Mesorhizobium loti* (Green et al., 182:2838-2844 (2000)). Although the KDC-encoding gene(s) have not been isolated in these organisms, the genome sequences are available and several genes in each genome are annotated as putative KDCs. A KDC from *Euglena gracilis* has also been characterized but the gene associated with this activity has not been identified to date (Shigeoka et al., 288:22-28 (1991)). The first twenty amino acids starting from the N-terminus were sequenced MTYKAPVKDVKFLLDKVFKV (Shigeoka and Nakano, 288:22-28 (1991)). The gene could be identified by testing candidate genes containing this N-terminal sequence for KDC activity.

TABLE 56

| Gene | Accession No. | GI No. | Organism |
|---|---|---|---|
| kgd | O50463.4 | 160395583 | *Mycobacterium tuberculosis* |
| kgd | NP_767092.1 | 27375563 | *Bradyrhizobium japonicum* |
| kgd | NP_105204.1 | 13473636 | *Mesorhizobium loti* |

A fourth candidate enzyme for catalyzing this reaction is branched chain alpha-ketoacid decarboxylase (BCKA). This class of enzyme has been shown to act on a variety of compounds varying in chain length from 3 to 6 carbons (Oku et al., 263:18386-18396 (1988); Smit et al., 71:303-311 (2005)). The enzyme in *Lactococcus lactis* has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., 71:303-311 (2005)). The enzyme has been structurally characterized (Berg et al., 318:1782-1786 (2007)). Sequence alignments between the *Lactococcus lactis* enzyme and the pyruvate decarboxylase of *Zymomonas mobilus* indicate that the catalytic and substrate recognition residues are nearly identical (Siegert et al., 18:345-357 (2005)), so this enzyme would be a promising candidate for directed engineering. Decarboxylation of alpha-ketoglutarate by a BCKA was detected in *Bacillus subtilis*; however, this activity was low (5%) relative to activity on other branched-chain substrates (Oku and Kaneda, 263:18386-18396 (1988)) and the gene encoding this enzyme has not been identified to date. Additional BCKA gene candidates can be identified by homology to the *Lactococcus lactis* protein sequence. Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria.

| Gene | Accession No. | GI No. | Organism |
|---|---|---|---|
| kdcA | AAS49166.1 | 44921617 | *Lactococcus lactis* |

Recombinant branched chain alpha-keto acid decarboxylase enzymes derived from the E1 subunits of the mitochondrial branched-chain keto acid dehydrogenase complex from *Homo sapiens* and *Bos taurus* have been cloned and functionally expressed in *E. coli* (Davie et al., 267:16601-16606 (1992); Wynn et al., 267:12400-12403 (1992); Wynn et al., 267:1881-1887 (1992)). In these studies, the authors found that co-expression of chaperonins GroEL and GroES enhanced the specific activity of the decarboxylase by 500-fold (Wynn et al., 267:12400-12403 (1992)). These enzymes are composed of two alpha and two beta subunits.

TABLE 57

| Gene | Accession No. | GI No. | Organism |
|---|---|---|---|
| BCKDHB | NP_898871.1 | 34101272 | *Homo sapiens* |
| BCKDHA | NP_000700.1 | 11386135 | *Homo sapiens* |
| BCKDHB | P21839 | 115502434 | *Bos taurus* |
| BCKDHA | P11178 | 129030 | *Bos taurus* |

Conversion of succinate semialdehyde to 4-hydroxybutyrate (Step C, FIG. 9B) can be catalyzed by an oxidoreductase that converts an aldehyde to alcohol. Exemplary genes encoding enzymes that catalyze the conversion of an aldehyde to alcohol, that is, alcohol dehydrogenase or equivalently aldehyde reductase, include alrA encoding a medium-chain alcohol dehydrogenase for C2-C14 (Tani et al. *Appl. Environ. Microbiol.* 66:5231-5235 (2000)), ADH2 from *Saccharomyces cerevisiae* (Atsumi et al. *Nature* 451:86-89 (2008)), yqhD from *E. coli* which has preference for molecules longer than C3 (Sulzenbacher et al. *Journal of Molecular Biology* 342:489-502 (2004)), and bdh I and bdh II from *C. acetobutylicum* which converts butyrylaldehyde into butanol (Walter et al. *Journal of Bacteriology* 174:7149-7158 (1992)). The protein sequences for each of these exemplary gene products, if available, can be found using the following GenBank accession numbers:

TABLE 58

| Gene | Accession No. | GI No. | Organism |
|---|---|---|---|
| alrA | BAB12273.1 | 9967138 | *Acinetobacter* sp. Strain M-1 |
| ADH2 | NP_014032.1 | 6323961 | *Saccharomyces cerevisiae* |
| yqhD | NP_417484.1 | 16130909 | *Escherichia coli* |
| bdh I | NP_349892.1 | 15896543 | *Clostridium acetobutylicum* |
| bdh II | NP_349891.1 | 15896542 | *Clostridium acetobutylicum* |

Enzymes exhibiting 4-hydroxybutyrate dehydrogenase activity (EC 1.1.1.61) have been characterized in *Ralstonia eutropha* (Bravo et al. *J. Forensic Sci.* 49:379-387 (2004), *Clostridium kluyveri* (Wolff et al. *Protein Expr. Purif.* 6:206-212 (1995)) and *Arabidopsis thaliana* (Breitkreuz et al. *J. Biol. Chem.* 278:41552-41556 (2003)).

TABLE 59

| Gene | Accession No. | GI No. | Organism |
|---|---|---|---|
| 4-HBd | YP_726053.1 | 113867564 | *Ralstonia eutropha* H16 |
| 4-HBd | EDK35022.1 | 146348486 | *Clostridium kluyveri* DSM 555 |
| 4-HBd | Q94B07 | 75249805 | *Arabidopsis thaliana* |

The adh1 gene from *Geobacillus thermoglucosidasius* M10EXG (Jeon et al., *J Biotechnol* 135:127-133 (2008)) has been indicated to exhibit high activity on both 4-hydroxybutanal and butanal. Thus this enzyme exhibits 1,4-butanediol dehydrogenase activity.

TABLE 60

| Gene | Accession No. | GI No. | Organism |
|------|---------------|--------|----------|
| adh1 | AAR91477.1 | 40795502 | *Geobacillus thermoglucosidasius* M10EXG |

Another exemplary enzyme is 3-hydroxyisobutyrate dehydrogenase which catalyzes the reversible oxidation of 3-hydroxyisobutyrate to methylmalonate semialdehyde. This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al. *J Mol Biol* 352:905-17 (2005)). The reversibility of the human 3-hydroxyisobutyrate dehydrogenase was demonstrated using isotopically-labeled substrate (Manning et al. *Biochem J* 231:481-484 (1985)). Additional genes encoding this enzyme include 3hidh in *Homo sapiens* (Hawes et al. *Methods Enzymol.* 324:218-228 (2000)) and *Oryctolagus Cuniculus* (Chowdhury et al. *Biosci. Biotechnol Biochem.* 60:2043-2047 (1996); Hawes et al. *Methods Enzymol.* 324:218-228 (2000)), mmsb in *Pseudomonas aeruginosa*, and dhat in *Pseudomonas putida* (Aberhart et al. *J Chem. Soc.* [Perkin 1] 6:1404-1406 (1979); Chowdhury et al. *Biosci. Biotechnol Biochem.* 67:438-441 (2003); Chowdhury et al. *Biosci. Biotechnol Biochem.* 60:2043-2047 (1996)).

TABLE 61

| Gene | Accession No. | GI No. | Organism |
|------|---------------|--------|----------|
| P84067 | P84067 | 75345323 | *Thermus thermophilus* |
| mmsb | P28811.1 | 127211 | *Pseudomonas aeruginosa* |
| dhat | Q59477.1 | 2842618 | *Pseudomonas putida* |
| 3hidh | P31937.2 | 12643395 | *Homo sapiens* |
| 3hidh | P32185.1 | 416872 | *Oryctolagus cuniculus* |

Several 3-hydroxyisobutyrate dehydrogenase enzymes have also been shown to convert malonic semialdehyde to 3-hydroxyproprionic acid (3-HP). Three gene candidates exhibiting this activity are mmsB from *Pseudomonas aeruginosa* PAO1(62), mmsB from *Pseudomonas putida* KT2440 (Liao et al., US Publication 2005/0221466) and mmsB from *Pseudomonas putida* E23 (Chowdhury et al., *Biosci. Biotechnol. Biochem.* 60:2043-2047 (1996)). An enzyme with 3-hydroxybutyrate dehydrogenase activity in *Alcaligenes faecalis* M3A has also been identified (Gokam et al., U.S. Pat. No. 7,393,676; Liao et al., US Publication No. 2005/0221466). Additional gene candidates from other organisms including *Rhodobacter spaeroides* can be inferred by sequence similarity.

TABLE 62

| Gene | Accession No. | GI No. | Organism |
|------|---------------|--------|----------|
| mmsB | AAA25892.1 | 151363 | *Pseudomonas aeruginosa* |
| mmsB | NP_252259.1 | 15598765 | *Pseudomonas aeruginosa* PAO1 |
| mmsB | NP_746775.1 | 26991350 | *Pseudomonas putida* KT2440 |
| mmsB | JC7926 | 60729613 | *Pseudomonas putida* E23 |
| orfB1 | AAL26884 | 16588720 | *Rhodobacter spaeroides* |

The conversion of malonic semialdehyde to 3-HP can also be accomplished by two other enzymes: NADH-dependent 3-hydroxypropionate dehydrogenase and NADPH-dependent malonate semialdehyde reductase. An NADH-dependent 3-hydroxypropionate dehydrogenase is thought to participate in beta-alanine biosynthesis pathways from propionate in bacteria and plants (Rathinasabapathi, B. *Journal of Plant Pathology* 159:671-674 (2002); Stadtman, E. R. *J. Am. Chem. Soc.* 77:5765-5766 (1955)). This enzyme has not been associated with a gene in any organism to date. NADPH-dependent malonate semialdehyde reductase catalyzes the reverse reaction in autotrophic $CO_2$-fixing bacteria. Although the enzyme activity has been detected in *Metallosphaera sedula*, the identity of the gene is not known (Alber et al. *J. Bacteriol.* 188:8551-8559 (2006)).

Step V in FIG. 9B depicts the conversion of alpha-ketoglutarate to succinyl-CoA. This reaction is catalyzed by alpha-ketoglutarate dehydrogenase, These enzymes are multi-enzyme complexes that catalyze a series of partial reactions which result in acylating oxidative decarboxylation of 2-keto-acids. This 2-keto-acid dehydrogenase complex occupies key positions in intermediary metabolism, and enzyme activity is typically tightly regulated (Fries et al. *Biochemistry* 42:6996-7002 (2003)). The enzyme shares a complex but common structure composed of multiple copies of three catalytic components: alpha-ketoacid decarboxylase (E1), dihydrolipoamide acyltransferase (E2) and dihydrolipoamide dehydrogenase (E3). The E3 component is shared among all 2-keto-acid dehydrogenase complexes in an organism, while the E1 and E2 components are encoded by different genes. The enzyme components are present in numerous copies in the complex and utilize multiple cofactors to catalyze a directed sequence of reactions via substrate channeling. The overall size of these dehydrogenase complexes is very large, with molecular masses between 4 and 10 million Da (that is, larger than a ribosome).

Activity of enzymes in the 2-keto-acid dehydrogenase family is normally low or limited under anaerobic conditions in *E. coli*. Increased production of NADH (or NADPH) could lead to a redox-imbalance, and NADH itself serves as an inhibitor to enzyme function. Engineering efforts have increased the anaerobic activity of the *E. coli* pyruvate dehydrogenase complex (Kim et al. *Appl. Environ. Microbiol.* 73:1766-1771 (2007); Kim et al. *J. Bacteriol.* 190: 3851-3858) 2008); Zhou et al. *Biotechnol. Lett.* 30:335-342 (2008)). For example, the inhibitory effect of NADH can be overcome by engineering an H322Y mutation in the E3 component (Kim et al. *J. Bacteriol.* 190:3851-3858 (2008)). Structural studies of individual components and how they work together in complex provide insight into the catalytic mechanisms and architecture of enzymes in this family (Aevarsson et al. *Nat. Struct. Biol.* 6:785-792 (1999); Zhou et al. *Proc. Natl. Acad. Sci. U.S.A.* 98:14802-14807 (2001)). The substrate specificity of the dehydrogenase complexes varies in different organisms, but generally branched-chain ketoacid dehydrogenases have the broadest substrate range.

Alpha-ketoglutarate dehydrogenase (AKGD) converts alpha-ketoglutarate to succinyl-CoA and is the primary site of control of metabolic flux through the TCA cycle (Hansford, R. G. *Curr. Top. Bioenerg.* 10:217-278 (1980)). Encoded by genes sucA, sucB and lpd in *E. coli*, AKGD gene expression is downregulated under anaerobic conditions and during growth on glucose (Park et al. *Mol. Microbiol.* 15:473-482 (1995)). Structural studies of the catalytic core of the E2 component pinpoint specific residues responsible for substrate specificity (Knapp et al. *J. Mol. Biol.* 280:655-668 (1998)). The *Bacillus subtilis* AKGD, encoded by odhAB (E1 and E2) and pdhD (E3, shared domain), is regulated at the transcriptional level and is dependent on the carbon source and growth phase of the organism (Resnekov et al. *Mol. Gen. Genet.* 234:285-296 (1992)). In yeast, the LPD1 gene encoding the E3 component is regulated at the transcriptional level by glucose (Roy and Dawes *J. Gen. Microbiol.* 133:925-933 (1987)). The E1 component, encoded by KGDJ, is also regulated by glucose and activated by the products of HAP2 and HAP3 (Repetto and Tzagoloff *Mol. Cell Biol.* 9:2695-2705 (1989)). The AKGD enzyme complex, inhibited by products NADH and succinyl-CoA, is well-studied in mammalian systems, as impaired function of has been linked to several neurological diseases (Tretter and dam-Vizi *Philos. Trans. R. Soc. Lond B Biol. Sci.* 360:2335-2345 (2005)).

TABLE 63

| Gene | Accession No. | GI No. | Organism |
|---|---|---|---|
| sucA | NP_415254.1 | 16128701 | *Escherichia coli* str. K12 |
| sucB | NP_415255.1 | 16128702 | *Escherichia coli* str. K12 |
| lpd | NP_414658.1 | 16128109 | *Escherichia coli* str. K12 |
| odhA | P23129.2 | 51704265 | *Bacillus subtilis* |
| odhB | P16263.1 | 129041 | *Bacillus subtilis* |
| pdhD | P21880.1 | 118672 | *Bacillus subtilis* |
| KGD1 | NP_012141.1 | 6322066 | *Saccharomyces cerevisiae* |
| KGD2 | NP_010432.1 | 6320352 | *Saccharomyces cerevisiae* |
| LPD1 | NP_116635.1 | 14318501 | *Saccharomyces cerevisiae* |

Steps A and H in FIG. 9B involve CoA transferase activities. The gene products of cat1, cat2, and cat3 of *Clostridium kluyveri* have been shown to exhibit succinyl-CoA, 4-hydroxybutyryl-CoA, and butyryl-CoA acetyltransferase activities (Seedorf et al. *Proc Natl Acad Sci U.S.A.* 105(6):2128-2133 (2008); Sohling and Gottschalk *J Bacteriol* 178(3):871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)).

TABLE 64

| Gene | Accession No. | GI No. | Organism |
|---|---|---|---|
| cat1 | P38946.1 | 729048 | *Clostridium kluyveri* |
| cat2 | P38942.2 | 1705614 | *Clostridium kluyveri* |
| cat3 | EDK35586.1 | 146349050 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |

An additionally useful enzyme for this type of transformation is acyl-CoA:acetate-CoA transferase, also known as acetate-CoA transferase (EC 2.8.3.8), which has been shown to transfer the CoA moiety to acetate from a variety of branched and linear acyl-CoA substrates, including isobutyrate (Matthies and Schink *Appl Environ Microbiol* 58:1435-1439 (1992)), valerate (Vanderwinkel et al. *Biochem. Biophys. Res Commun.* 33:902-908 (1968)) and butanoate (Vanderwinkel, supra (1968)). This enzyme is encoded by atoA (alpha subunit) and atoD (beta subunit) in *E. coli* sp. K12 (Korolev et al. *Acta Crystallogr. D Biol Crystallogr.* 58:2116-2121 (2002); Vanderwinkel, supra (1968)). Similar enzymes exist in *Corynebacterium glutamicum* ATCC 13032 (Duncan et al., 68:5186-5190 (2002)), *Clostridium saccharoperbutylacetonicum* (Kosaka et al., *Biosci. Biotechnol Biochem.* 71:58-68 (2007)), and *Clostridium acetobutylicum* (Cary et al., 56:1576-1583 (1990); Wiesenborn et al., 55:323-329 (1989)).

TABLE 65

| Gene | Accession No. | GI No. | Organism |
|---|---|---|---|
| atoA | P76459.1 | 2492994 | *Escherichia coli* K12 |
| atoD | P76458.1 | 2492990 | *Escherichia coli* K12 |
| actA | YP_226809.1 | 62391407 | *Corynebacterium glutamicum* |
| cg0592 | YP_224801.1 | 62389399 | *Corynebacterium glutamicum* |
| ctfA | NP_149326.1 | 15004866 | *Clostridium acetobutylicum* |
| ctfB | NP_149327.1 | 15004867 | *Clostridium acetobutylicum* |
| ctfA | AAP42564.1 | 31075384 | *Clostridium saccharoperbutylacetonicum* |
| ctfB | AAP42565.1 | 31075385 | *Clostridium saccharoperbutylacetonicum* |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack and Buckel *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al. *Eur. J. Biochem.* 118:315-321 (1981)). The enzyme has been cloned and expressed in *E. coli* (Mac et al. *Eur. J. Biochem.* 226:41-51 (1994)).

TABLE 66

| Gene | Accession No. | GI No. | Organism |
|---|---|---|---|
| gctA | CAA57199.1 | 559392 | *Acidaminococcus fermentans* |
| gctB | CAA57200.1 | 559393 | *Acidaminococcus fermentans* |

Step H of FIG. 9B involves CoA synthetase or ligase reactions for 4-HB as the substrate. Exemplary CoA-ligases include the rat dicarboxylate-CoA ligase for which the sequence is yet uncharacterized (Vamecq et al., *Biochemical Journal* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacillus subtilis* (Bower et. al., J. Bacteriol. 178(14):4122-4130 (1996)). Additional candidate enzymes are acetoacetyl-CoA synthetases from *Mus musculus* (Hasegawa et al., *Biochim Biophys Acta* 1779:414-419 (2008)) and *Homo sapiens* (Ohgami et al., *Biochem Pharmacol* 65:989-994 (2003)) which naturally catalyze the ATP-dependant conversion of acetoacetate into acetoacetyl-CoA. 4-hydroxybutyryl-CoA synthetase activity has been demonstrated in *Metallosphaera sedula* (Berg et al., *Science* 318:1782-1786 (2007)). This function has been tentatively assigned to the Msed_1422 gene.

TABLE 67

| Gene | Accession No. | GI No. | Organism |
|---|---|---|---|
| phl | CAJ15517.1 | 77019264 | *Penicillium chrysogenum* |
| phlB | ABS19624.1 | 152002983 | *Penicillium chrysogenum* |

TABLE 67-continued

| Gene | Accession No. | GI No. | Organism |
|------|---------------|--------|----------|
| paaF | AAC24333.2 | 22711873 | Pseudomonas putida |
| bioW | NP_390902.2 | 50812281 | Bacillus subtilis |
| AACS | NP_084486.1 | 21313520 | Mus musculus |
| AACS | NP_076417.2 | 31982927 | Homo sapiens |
| Msed_1422 | YP_001191504 | 146304188 | Metallosphaera sedula |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyrate, isovalerate, succinate, fumarate, phenylacetate, indoleacetate (Musfeldt et al., *J Bacteriol* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra). The enzymes from *A. fulgidus*, *H. marismortui* and *P. aerophilum* have all been cloned, functionally expressed, and characterized in *E. coli* (Musfeldt et al., supra; Brasen et al., supra).

TABLE 68

| Gene | Accession No. | GI No. | Organism |
|------|---------------|--------|----------|
| AF1211 | NP_070039.1 | 11498810 | Archaeoglobus fulgidus DSM 4304 |
| scs | YP_135572.1 | 55377722 | Haloarcula marismortui ATCC 43049 |
| PAE3250 | NP_560604.1 | 18313937 | Pyrobaculum aerophilum str. IM2 |

Exemplary phosphate transferring acyltransferases that transform 4-hydroxybutyryl-CoA to 4-hydroxybutyryl-phosphate include phosphotransacetylase, encoded by pta, and phosphotransbutyrylase, encoded by ptb. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Similarly, the ptb gene from *C. acetobutylicum* encodes an enzyme that can convert butyryl-CoA into butyryl-phosphate (Walter et al. *Gene* 134(1): p. 107-11 (1993)); Huang et al. *J Mol Microbiol Biotechnol* 2(1): p. 33-38 (2000). Additional ptb genes can be found in butyrate-producing bacterium L2-50 (Louis et al. *J. Bacteriol.* 186: 2099-2106 (2004)) and *Bacillus megaterium* (Vazquez et al. *Curr. Microbiol* 42:345-349 (2001)).

TABLE 69

| Gene | Accession No. | GI No. | Organism |
|------|---------------|--------|----------|
| pta | NP_416800.1 | 16130232 | Escherichia coli |
| ptb | NP_349676 | 15896327 | Clostridium acetobutylicum |

TABLE 69-continued

| Gene | Accession No. | GI No. | Organism |
|------|---------------|--------|----------|
| ptb | AAR19757.1 | 38425288 | butyrate-producing bacterium L2-50 |
| ptb | CAC07932.1 | 10046659 | Bacillus megaterium |

The conversion of 4-hydroxybutyryl-phosphate to 4-hydroxybutanal can be catalyzed by an oxidoreductase in the EC class 1.2.1. Aspartate semialdehyde dehydrogenase (ASD, EC 1.2.1.11) catalyzes the NADPH-dependent reduction of 4-aspartyl phosphate to aspartate-4-semialdehyde. ASD participates in amino acid biosynthesis and recently has been studied as an antimicrobial target (Hadfield et al., 40:14475-14483 (2001)). The *E. coli* ASD structure has been solved (Hadfield et al., 289:991-1002 (1999)) and the enzyme has been shown to accept the alternate substrate beta-3-methylaspartyl phosphate (Shames et al., 259:15331-15339 (1984)). The *Haemophilus influenzae* enzyme has been the subject of enzyme engineering studies to alter substrate binding affinities at the active site (Blanco et al., *Acta Crystallogr. D. Biol. Crystallogr.* 60:1388-1395 (2004); Blanco et al., *Acta Crystallogr. D. Biol. Crystallogr.* 60:1808-1815 (2004)). Other ASD candidates are found in *Mycobacterium tuberculosis* (Shafiani et al., *J Appl Microbiol* 98:832-838 (2005)), *Methanococcus jannaschii* (Faehnle et al., 353:1055-1068 (2005)), and the infectious microorganisms *Vibrio cholera* and *Heliobacter pylori* (Moore et al., *Protein Expr. Purif.* 25:189-194 (2002)). A related enzyme candidate is acetylglutamylphosphate reductase (EC 1.2.1.38), an enzyme that naturally reduces acetylglutamylphosphate to acetylglutamate-5-semialdehyde, found in *S. cerevisiae* (Pauwels et al., *Eur. J Biochem.* 270:1014-1024 (2003)), *B. subtilis* (O'Reilly et al., 140 (Pt 5):1023-1025 (1994)) and other organisms.

TABLE 70

| Gene | Accession No. | GI No. | Organism |
|------|---------------|--------|----------|
| asd | NP_417891.1 | 16131307 | Escherichia coli |
| asd | YP_248335.1 | 68249223 | Haemophilus influenzae |
| asd | AAB49996 | 1899206 | Mycobacterium tuberculosis |
| VC2036 | NP_231670 | 15642038 | Vibrio cholera |
| asd | YP_002301787.1 | 210135348 | Heliobacter pylori |
| ARG5,6 | NP_010992.1 | 6320913 | Saccharomyces cerevisiae |
| argC | NP_389001.1 | 16078184 | Bacillus subtilis |

Other exemplary enzymes in this class include glyceraldehyde 3-phosphate dehydrogenase which converts glyceraldehyde-3-phosphate into D-glycerate 1,3-bisphosphate (e.g., *E. coli* gapA (Branlant et al., *Eur. J. Biochem.* 150: 61-66 (1985))), N-acetyl-gamma-glutamyl-phosphate reductase which converts N-acetyl-L-glutamate-5-semialdehyde into N-acetyl-L-glutamyl-5-phosphate (e.g., *E. coli* argC (Parsot et al., *Gene.* 68:275-283 (1988))), and glutamate-5-semialdehyde dehydrogenase which converts L-glutamate-5-semialdehyde into L-glutamyl-5-phospate (e.g., *E. coli* proA (Smith et al., *J. Bacteriol.* 157:545-551 (1984a))). Genes encoding glutamate-5-semialdehyde dehydrogenase enzymes from *Salmonella typhimurium* (Mahan et al., *J Bacteriol.* 156:1249-1262 (1983)) and *Campylobacter jejuni* (Louie et al., 240:29-35 (1993)) were cloned and expressed in *E. coli*.

TABLE 71

| Gene | Accession No. | GI No. | Organism |
|------|---------------|--------|----------|
| gapA | P0A9B2.2 | 71159358 | *Escherichia coli* |
| argC | NP_418393.1 | 16131796 | *Escherichia coli* |
| proA | NP_414778.1 | 16128229 | *Escherichia coli* |
| proA | NP_459319.1 | 16763704 | *Salmonella typhimurium* |
| proA | P53000.2 | 9087222 | *Campylobacter jejuni* |

In some embodiments, the 2-amino-4-ketopentanoate (AKP) thiolase encoded by one or more genes selected from the group consisting of ortA (α), ortB (β), Amet_2368 (α), Amet_2369 (β), Teth514_1478 (α), Teth514_1479 (β), TTE1235 (α), and thrC (β).

In some embodiments, the AKP dehydrogenase is encoded by one or more genes selected from the group consisting of thrA, akthr2, hom6, hom1, hom2, fadB, fadJ, Hbd2, Hbd1, hbd, HSD17B10, phbB, phaB, Msed_1423, Msed_0399, Msed_0389, Msed_1993, adh, adhA, adh-A, mdh, ldhA, ldh, and bdh.

In some embodiments, the 2-amino-4-hydroxypentanoate aminotransferase is encoded by one or more genes selected from the group consisting of aspC, AAT2, ASP5, got2, avtA, lysN, AadAT-II, dat, lat, ygjG, spuC, SkyPYD4, SkUGA1, UGA1, Abat, Abat, Gta-1, gabT, and puuE.

In some embodiments, the 2-amino-4-hydroxypentanoate oxidoreductase (deaminating) is encoded by one or more genes selected from the group consisting of gdhA, gdh, gdhA1, rocG, gdh1, gdh2, GDH, GDH2, ldh and nadX.

In some embodiments, the 2-oxo-4-hydroxypentanoate decarboxylase is encoded by one or more genes selected from the group consisting of pdc, pdc1, mdlC, dpgB, ilvB-1, kgd, kdcA, lysA, panD, cadA, ldc, ldcC, AF323910.1:1 . . . 1299, odc1, VV2_1235, dmpH, dmpE, xylII, xylIII, Reut_B5691, Reut_B5692, CAD, pad1, pofK (pad), padC, pad, adc, cbei_3835, CLL_A2135, RBAM_030030, In some embodiments, the 3-hydroxybutyraldehdye reductase is encoded by one or more genes selected from the group consisting of alrA, ADH2, yqhD, bdh I, bdh II, adhA, 4hbd, adhI, P84067, mmsb, dhat, and 3hidh.

In some embodiments, the AKP aminotransferase is encoded by one or more genes selected from the group consisting of aspC, AAT2, ASP5, got2, avtA, lysN, AadAT-II, dat, lat, ygjG, spuC, SkyPYD4, SkUGA1, UGA1, Abat, Gta-1, gabT, and puuE.

In some embodiments, the AKP oxidoreductase (deaminating) is encoded by one or more genes selected from the group consisting of gdhA, gdh, gdhA1, rocG, gdh1, gdh2, GDH, GDH2, ldh and nadX. In some embodiments, the 2,4-dioxopentanoate decarboxylase is encoded by one or more genes selected from the group consisting of pdc, pdc1, mdlC, dpgB, ilvB-1, kgd, kdcA, lysA, panD, cadA, ldc, ldcC, AF323910.1:1 . . . 1299, odc1, VV2_1235, dmpH, dmpE, xylII, xylIII, Reut_B5691, Reut_B5692, CAD, pad1, padC, and pad, adc, cbei_3835, CLL_A2135, RBAM_030030.

In some embodiments, the 3-oxobutyraldehyde reductase (ketone reducing) is encoded by one or more genes selected from the group consisting of thrA, akthr2, hom6, hom1, hom2, fadB, fadJ, Hbd2, Hbd1, hbd, HSD17B10, phbB, phaB, Msed_1423, Msed_0399, Msed_0389, Msed_1993, adh, adhA, adh-A, mdh, ldhA, ldh, and bdh.

In some embodiments, the 3-oxobutyraldehyde reductase (aldehyde reducing) is encoded by one or more genes selected from the group consisting of alrA, ADH2, yqhD, bdh I, bdh II, adhA, 4hbd, adhI, P84067, mmsb, dhat, and 3hidh.

In some embodiments, the 4-hydroxy-2-butanone reductase is encoded by one or more genes selected from the group consisting of thrA, akthr2, hom6, hom1, hom2, fadB, fadJ, Hbd2, Hbd1, hbd, HSD17B10, phbB, phaB, Msed_1423, Msed_0399, Msed_0389, Msed_1993, adh, adhA, adh-A, mdh, ldhA, ldh, and bdh.

In some embodiments, the AKP decarboxylase is encoded by one or more genes selected from the group consisting of pdc, pdc1, mdlC, dpgB, ilvB-1, kgd, kdcA, lysA, panD, cadA, ldc, ldcC, AF323910.1:1 . . . 1299, odc1, VV2_1235, dmpH, dmpE, xylII, xylIII, Reut_B5691, Reut_B5692, CAD, pad1, pofK(pad), padC, pad.

In some embodiments, the 4-aminobutan-2-one aminotransferase is encoded by one or more genes selected from the group consisting of aspC, AAT2, ASP5, got2, avtA, lysN, AadAT-II, dat, lat, ygjG, spuC, SkyPYD4, SkUGA1, UGA1, Abat, Gta-1, gabT, and puuE.

In some embodiments, the 4-aminobutan-2-one oxidoreductase (deaminating) is encoded by one or more genes selected from the group consisting of gdhA, gdh, gdhA1, rocG, gdh1, gdh2, GDH, GDH2, ldh, nadX, kdd and lysDH.

In some embodiments, the 4-aminobutan-2-one ammonia-lyase is encoded by one or more genes selected from the group consisting of aspA, ansB, mal and BAA28709.

In some embodiments, the butenone hydratase is encoded by one or more genes selected from the group consisting of fumA, fumB, fumC, fumH, fum1, MmcB, MmcC, hmd, BACCAP_02294, ANACOL_02527, NtherDRAFT_2368, dmdA, dmdB, crt, crt1, ech paaA, paaB, phaA, phaB, maoC, paaF, paaG, abfD, Msed_1220, fadA, fadB, fadI, fadJ, and fadR.

In some embodiments, the AKP ammonia-lyase is encoded by one or more genes selected from the group consisting of aspA, ansB, mal and BAA28709.

In some embodiments, the acetylacrylate decarboxylase is encoded by one or more genes selected from the group consisting of pdc, pdc1, mdlC, dpgB, ilvB-1, kgd, kdcA, lysA, panD, cadA, ldc, ldcC, AF323910.1:1 . . . 1299, odc1, VV2_1235, dmpH, dmpE, xylII, xylIII, Reut_B5691, Reut_B5692, CAD, pad1, pofK (pad), padC, pad, adc, cbei_3835, CLL_A2135, RBAM_030030,)

In some embodiments, the acetoacetyl-CoA reductase (CoA-dependent, aldehyde forming) is encoded by one or more genes selected from the group consisting of acr1, sucD, bphG, bld, adhE, Msed_0709, mcr, asd-2, Saci_2370, Ald, and eutE.

In some embodiments, the acetoacetyl-CoA reductase (CoA-dependent, alcohol forming) is encoded by one or more genes selected from the group consisting of adhE, adhE2, mcr, Rcas_2929, NAP1_02720, MGP2080_00535, and FAR.

In some embodiments, the acetoacetyl-CoA reductase (ketone reducing) is encoded by one or more genes selected from the group consisting of thrA, akthr2, hom6, hom1, hom2, fadB, fadJ, Hbd2, Hbd1, hbd, HSD17B10, phbB, phaB, Msed_1423, Msed_0399, Msed_0389, Msed_1993, adh, adhA, adh-A, mdh, ldhA, ldh, and bdh.

In some embodiments, the 3-hydroxybutyryl-CoA reductase (aldehyde forming) is encoded by one or more genes selected from the group consisting of acr1, sucD, bphG, bld, adhE, Msed_0709, mcr, asd-2, Saci_2370, Ald, and eutE.

In some embodiments, the 3-hydroxybutyryl-CoA reductase (alcohol forming) is encoded by one or more genes selected from the group consisting of adhE, adhE2, mcr, Rcas_2929, NAP1_02720, MGP2080_00535, and FAR.

In some embodiments, the 4-hydroxybutyryl-CoA dehydratase is encoded by one or more genes selected from the group consisting of fumA, fumB, fumC, fumH, fum1, MmcB, MmcC, hmd, BACCAP_02294, ANACOL_02527, NtherDRAFT_2368, dmdA, dmdB, crt, crt1, ech, paaA, paaB, phaA, phaB, maoC, paaF, paaG, abfD, Msed_1220, fadA, fadB, fadI, fadJ, and fadR.

In some embodiments, the crotonase is encoded by one or more genes selected from the group consisting of fumA, fumB, fumC, fumH, fum1, MmcB, MmcC, hmd, BACCAP_02294, ANACOL_02527, NtherDRAFT_2368, dmdA, dmdB, crt, crt1, ech paaA, paaB, phaA, phaB, maoC, paaF, paaG, abfD, Msed_1220, fadA, fadB, fadI, fadJ, and fadR.

In some embodiments, the 3-hydroxybutyryl-CoA hydrolase, transferase, or synthetase is encoded by one or more genes selected from a group consisting of acot12, ACH1, acot8, tesB, acot8, teas, ybgC, paaI, pbdB, gctA, gctB, and hibCH.

In some embodiments, 3-hydroxybutyrate reductase is encoded by one or more genes selected from a group consisting of car, npt, fadD9, BCG_2812c, nfa20150, nfa40540, SGR_6790, SGR_665, griC, griD.

The non-naturally occurring microbial organisms of the invention can be produced by introducing expressible nucleic acids encoding one or more of the enzymes or proteins participating in one or more 1,3-butanediol biosynthetic pathways. Depending on the host microbial organism chosen for biosynthesis, nucleic acids for some or all of a particular 1,3-butanediol biosynthetic pathway can be expressed. For example, if a chosen host is deficient in one or more enzymes or proteins for a desired biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve 1,3-butanediol biosynthesis. Thus, a non-naturally occurring microbial organism of the invention can be produced by introducing exogenous enzyme or protein activities to obtain a desired biosynthetic pathway or a desired biosynthetic pathway can be obtained by introducing one or more exogenous enzyme or protein activities that, together with one or more endogenous enzymes or proteins, produces a desired product such as 1,3-butanediol.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica*, and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Depending on the 1,3-butanediol biosynthetic pathway constituents of a selected host microbial organism, the non-naturally occurring microbial organisms of the invention will include at least one exogenously expressed 1,3-butanediol pathway-encoding nucleic acid and up to all encoding nucleic acids for one or more 1,3-butanediol biosynthetic pathways. For example, 1,3-butanediol biosynthesis can be established in a host deficient in a pathway enzyme or protein through exogenous expression of the corresponding encoding nucleic acid. In a host deficient in all enzymes or proteins of a 1,3-butanediol pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of 1,3-butanediol can be included.

Given the teachings and guidance provided herein, those skilled in the art will understand that the number of encoding nucleic acids to introduce in an expressible form will, at least, parallel the 1,3-butanediol pathway deficiencies of the selected host microbial organism. Therefore, a non-naturally occurring microbial organism of the invention can have one, two, three, four, five, up to all nucleic acids encoding the enzymes or proteins constituting a 1,3-butanediol biosynthetic pathway disclosed herein. In some embodiments, the non-naturally occurring microbial organisms also can include other genetic modifications that facilitate or optimize 1,3-butanediol biosynthesis or that confer other useful functions onto the host microbial organism. One such other functionality can include, for example, augmentation of the synthesis of one or more of the 1,3-butanediol pathway precursors such as acetyl-CoA.

Generally, a host microbial organism is selected such that it produces the precursor of a 1,3-butanediol pathway, either as a naturally produced molecule or as an engineered product that either provides de novo production of a desired precursor or increased production of a precursor naturally produced by the host microbial organism. For example, acetyl-CoA is produced naturally in a host organism such as *E. coli*. A host organism can be engineered to increase production of a precursor, as disclosed herein. In addition, a microbial organism that has been engineered to produce a desired precursor can be used as a host organism and further engineered to express enzymes or proteins of a 1,3-butanediol pathway.

In some embodiments, a non-naturally occurring microbial organism of the invention is generated from a host that contains the enzymatic capability to synthesize 1,3-butanediol. In this specific embodiment it can be useful to increase the synthesis or accumulation of a 1,3-butanediol pathway product to, for example, drive 1,3-butanediol pathway reactions toward 1,3-butanediol production. Increased synthesis or accumulation can be accomplished by, for example, overexpression of nucleic acids encoding one or more of the above-described 1,3-butanediol pathway enzymes or proteins. Overexpression of the enzyme or enzymes and/or protein or proteins of the 1,3-butanediol pathway can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing 1,3-butanediol, through overexpression of one, two, three, four, five, that is, up to all nucleic acids encoding 1,3-butanediol biosynthetic pathway enzymes or proteins. In addition, a non-naturally occurring organism can be generated by mutagenesis of an endogenous gene that results in an increase in activity of an enzyme in the 1,3-butanediol biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

It is understood that, in methods of the invention, any of the one or more exogenous nucleic acids can be introduced into a microbial organism to produce a non-naturally occurring microbial organism of the invention. The nucleic acids can be introduced so as to confer, for example, 1,3-butanediol biosynthetic pathway onto the microbial organism. Alternatively, encoding nucleic acids can be introduced to produce an intermediate microbial organism having the biosynthetic capability to catalyze some of the required reactions to confer 1,3-butanediol biosynthetic capability. For example, a non-naturally occurring microbial organism having 1,3-butanediol biosynthetic pathway can comprise at least two exogenous nucleic acids encoding desired enzymes or proteins. For example, the non-naturally occurring microbial organism can comprise at least two exogenous nucleic acids encoding an acetoacetyl-CoA reductase (CoA-dependent, alcohol forming) and a 4-hydroxy,2-butanone reductase (FIG. 2, steps D and F). Thus, it is understood that any combination of two or more enzymes or proteins of a biosynthetic pathway can be included in a non-naturally occurring microbial organism of the invention. Similarly, it is understood that any combination of three or more enzymes or proteins of a biosynthetic pathway can be included in a non-naturally occurring microbial organism of the invention and so forth, as desired, so long as the combination of enzymes and/or proteins of the desired biosynthetic pathway results in production of the corresponding desired product. For example, the non-naturally occurring microbial organism can comprise at least three exogenous nucleic acids encoding an acetoacetyl-CoA reductase (CoA-dependent, aldehyde forming), a 3-oxobutyraldehyde reductase (ketone reducing), and a 3-hydroxybutyraldehyde reductase (FIG. 2, steps A, B and C). Similarly, any combination of four, or more enzymes or proteins of a biosynthetic pathway as disclosed herein can be included in a non-naturally occurring microbial organism of the invention, as desired, so long as the combination of enzymes and/or proteins of the desired biosynthetic pathway results in production of the corresponding desired product. For example, the non-naturally occurring microbial organism can comprise at least five exogenous nucleic acids encoding an AKP thiolase, an AKP decarboxylase, a 4-aminobutan-2-one ammonia-lyase, a butenone hydratase, and a 4-hydroxy,2-butanone reductase, (FIG. 8B, steps A, E, F, G and H). Other individual pathways depicted in the figures are also contemplated embodiments of the compositions and methods provided herein.

In addition to the biosynthesis of 1,3-butanediol as described herein, the non-naturally occurring microbial organisms and methods of the invention also can be utilized in various combinations with each other and with other microbial organisms and methods well known in the art to achieve product biosynthesis by other routes. For example, one alternative to produce 1,3-butanediol other than use of the 1,3-butanediol producers is through addition of another microbial organism capable of converting 1,3-butanediol pathway intermediate to 1,3-butanediol. One such procedure includes, for example, the fermentation of a microbial organism that produces 1,3-butanediol pathway intermediate. The 1,3-butanediol pathway intermediate can then be used as a substrate for a second microbial organism that converts the 1,3-butanediol pathway intermediate to 1,3-butanediol. The 1,3-butanediol pathway intermediate can be added directly to another culture of the second organism or the original culture of the 1,3-butanediol pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, 1,3-butanediol. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of 1,3-butanediol can be accomplished by constructing a microbial organism that contains biosynthetic pathways for conversion of one pathway intermediate to another pathway intermediate or the product. Alternatively, 1,3-butanediol also can be biosynthetically produced from microbial organisms through co-culture or co-fermentation using two organisms in the same vessel, where the first microbial organism produces 1,3-butanediol intermediate and the second microbial organism converts the intermediate to 1,3-butanediol.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce 1,3-butanediol.

Sources of encoding nucleic acids for 1,3-butanediol pathway enzyme or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli*, as well as other exemplary species disclosed herein or available as source organisms for corresponding genes. However, with the complete genome sequence available for now more than 550 species (with more than half of these available on public databases such as the NCBI), including 395 microorganism genomes and a variety of yeast, fungi, plant, and mammalian genomes, the identification of genes encoding the requisite 1,3-butanediol biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of 1,3-butanediol described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative 1,3-butanediol biosynthetic pathway exists in an unrelated species, 1,3-butanediol biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms can differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize 1,3-butanediol.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger* and *Pichia pastoris*. *E. coli* is a particularly useful host organism since it is a well characterized microbial organism suitable for genetic engineering. Other particularly useful host organisms include yeast such as *Saccharomyces cerevisiae*.

Methods for constructing and testing the expression levels of a non-naturally occurring 1,3-butanediol-producing host can be performed, for example, by recombinant and detection methods well known in the art. Such methods can be found described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999).

Exogenous nucleic acid sequences involved in a pathway for production of 1,3-butanediol can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., J. Biol. Chem. 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more 1,3-butanediol biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The invention provides a method for producing 1,3-BDO that includes culturing the non-naturally occurring microbial organism disclosed herein, under conditions and for a sufficient period of time to produce 1,3-BDO, including organisms that incorporate one, two, three, four, five, up to all exogenous nucleic acids encoding enzymes that complete a 1,3-BDO pathway. The 1,3-BDO pathways include a set of 1,3-BDO pathway enzymes, where the set of 1,3-BDO pathway enzymes are identified as above, namely: (a) (1) a 2-amino-4-ketopentanoate (AKP) thiolase; (2) an AKP dehydrogenase; (3) a 2-amino-4-hydroxypentanoate aminotransferase or oxidoreductase (deaminating); (4) a 2-oxo-4-hydroxypentanoate decarboxylase; and (5) a 3-hydroxybutyraldehyde reductase; (b) (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (ketone reducing); and (5) a 3-hydroxybutyraldehyde reductase; (c) (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (aldehyde reducing); and (5) a 4-hydroxy-2-butanone reductase; (d) (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (ketone reducing); and (5) a 3-hydroxybutyraldehyde reductase; (e) (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (aldehyde reducing); and (5) a 4-hydroxy-2-butanone reductase; (f) (1) a 2-amino-4-ketopentanoate (AKP) thiolase; (2) an AKP decarboxylase; (3) a 4-aminobutan-2-one ammonia-lyase; (4) a butanone hydratase; and (5) a 4-hydroxy-2-butanone reductase; (g) (1) a 2-amino-4-ketopentanoate (AKP) thiolase; (2) an AKP ammonia-lyase; (3) an acetylacrylate decarboxylase; (4) a butanone hydratase; and (5) a 4-hydroxy-2-butanone reductase; (h) (1) an acetoacetyl-CoA reductase (CoA-dependent, aldehyde forming); (2) a 3-oxobutyraldehyde reductase (ketone reducing); and (3) a 3-hydroxybutyraldehyde reductase; (i) (1) an acetoacetyl-CoA reductase (CoA dependent, alcohol forming) and (2) a 4-hydroxy-2-butanone reductase; (j) (1) an acetoacetyl-CoA reductase (CoA-dependent, aldehyde forming); (2) a 3-oxobutyraldehyde reductase (aldehyde reducing); and (3) a 4-hydroxy-2-butanone reductase; (k) (1) an acetoacetyl-CoA reductase (ketone reducing) and (2) a 3-hydroxybutyryl-CoA reductase (alcohol forming); (l) (1) an acetoacetyl-CoA reductase (ketone reducing); (2) a 3-hydroxybutyryl-CoA reductase (aldehyde forming); and (3) a 3-hydroxybutyraldehyde reductase; (m) (1) a 4-hydroxybutyryl-CoA dehydratase; (2) a crotonase; and (3) a 3-hydroxybutyryl-CoA reductase (alcohol forming); and (n) (1) a 4-hydroxybutyryl-CoA dehydratase; (2) a crotonase; (3) a 3-hydroxybutyryl-CoA reductase (aldehyde forming); and (4) a 3-hydroxybutyraldehyde reductase.

In some embodiments, a method for producing 1,3-BDO includes culturing a non-naturally occurring microbial organism provided herein under conditions and for a sufficient period of time to produce 1,3-BDO. In some embodiments, the non-naturally occurring microbial organism has a 1,3-butanediol pathway, wherein said microbial organism comprises at least one exogenous nucleic acid encoding a 1,3-butanediol pathway enzyme expressed in a sufficient amount to produce 1,3-butanediol. In some embodiments, the non-naturally occurring microbial organism includes at least one of (i) a reductive TCA pathway, wherein said microbial organism comprises at least one exogenous nucleic acid encoding a reductive TCA pathway enzyme selected from the group consisting of an ATP-citrate lyase, citrate lyase, a fumarate reductase, and an alpha-ketoglutarate:ferredoxin oxidoreductase;

(ii) a reductive TCA pathway, wherein said microbial organism comprises at least one exogenous nucleic acid encoding a reductive TCA pathway enzyme selected from the group consisting of a pyruvate:ferredoxin oxidoreductase, a phosphoenolpyruvate carboxylase, a phosphoenolpyruvate carboxykinase, a CO dehydrogenase, and an $H_2$ hydrogenase; or (iii) at least one exogenous nucleic acid encodes an enzyme selected from the group consisting of a CO dehydrogenase, an $H_2$ hydrogenase, and combinations thereof;

wherein said 1,3-butanediol pathway comprises a pathway selected from the group consisting of:

(a) (1) a 2-amino-4-ketopentanoate (AKP) thiolase; (2) an AKP dehydrogenase; (3) a 2-amino-4-hydroxypentanoate aminotransferase or oxidoreductase (deaminating); (4) a 2-oxo-4-hydroxypentanoate decarboxylase; and (5) a 3-hydroxybutyraldehyde reductase;

(b) (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (ketone reducing); and (5) a 3-hydroxybutyraldehyde reductase;

(c) (1) a 2-amino-4-ketopentanoate (AKP) thiolase; (2) an AKP aminotransferase or oxidoreductase (deaminating); (3) a 2,4-dioxopentanoate decarboxylase; (4) a 3-oxobutyraldehyde reductase (aldehyde reducing); and (5) a 4-hydroxy-2-butanone reductase;

(d) (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (ketone reducing); and (5) a 3-hydroxybutyraldehyde reductase;

(e) (1) a 2-amino-4-ketopentanoate (AKP) thiolase; (2) an AKP decarboxylase; (3) a 4-aminobutan-2-one aminotransferase or oxidoreductase (deaminating); (4) a 3-oxobutyraldehyde reductase (aldehyde reducing); and (5) a 4-hydroxy-2-butanone reductase;

(f) (1) a 2-amino-4-ketopentanoate (AKP) thiolase; (2) an AKP decarboxylase; (3) a 4-aminobutan-2-one ammonia-lyase; (4) a butenone hydratase; and (5) a 4-hydroxy-2-butanone reductase;

(g) (1) a 2-amino-4-ketopentanoate (AKP) thiolase; (2) an AKP ammonia-lyase; (3) an acetylacrylate decarboxylase; (4) a butenone hydratase; and (5) a 4-hydroxy-2-butanone reductase;

(h) (1) an acetoacetyl-CoA reductase (CoA-dependent, aldehyde forming); (2) a 3-oxobutyraldehyde reductase (ketone reducing); and (3) a 3-hydroxybutyraldehyde reductase;

(i) (1) an acetoacetyl-CoA reductase (CoA dependent, alcohol forming) and (2) a 4-hydroxy-2-butanone reductase;

(j) (1) an acetoacetyl-CoA reductase (CoA-dependent, aldehyde forming); (2) a 3-oxobutyraldehyde reductase (aldehyde reducing); and (3) a 4-hydroxy-2-butanone reductase;

(k) (1) an acetoacetyl-CoA reductase (ketone reducing) and (2) a 3-hydroxybutyryl-CoA reductase (alcohol forming);

(l) (1) an acetoacetyl-CoA reductase (ketone reducing); (2) a 3-hydroxybutyryl-CoA reductase (aldehyde forming); and (3) a 3-hydroxybutyraldehyde reductase;

(m) (1) a 4-hydroxybutyryl-CoA dehydratase; (2) a crotonase; and (3) a 3-hydroxybutyryl-CoA reductase (alcohol forming); and (n) (1) a 4-hydroxybutyryl-CoA dehydratase; (2) a crotonase; (3) a 3-hydroxybutyryl-CoA reductase (aldehyde forming); and (4) a 3-hydroxybutyraldehyde reductase;

(o) (1) a succinyl-CoA transferase, a succinyl-CoA synthetase or a succinyl-CoA ligase, (2) a succinyl-CoA reductase (aldehyde forming), (3) a 4-hydroxybutyrate dehydrogenase, (4) a 4-hydroxybutyrate kinase, (5) a phosphotrans-4-hydroxybutyrylase, (6) a 4-hydroxybutyryl-CoA dehydratase, (7) a crotonase, (8) a 3-hydroxybutyryl-CoA reductase (aldehyde forming), and (9) a 3-hydroxybutanal reductase;

(p) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase; (6) a crotonase, (7) a 3-hydroxybutyryl-CoA reductase (aldehyde forming), and (8) a 3-hydroxybutanal reductase;

(q) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA reductase (aldehyde forming), and (7) a 3-hydroxybutanal reductase;

(r) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, and (7) a 3-hydroxybutyryl-CoA reductase (alcohol forming);

(s) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, and (6) a 3-hydroxybutyryl-CoA reductase (alcohol forming);

(t) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA hydrolase, transferase or synthetase, and (8) a 3-hydroxybutyrate reductase;

(u) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA hydrolase, transferase or synthetase, and (7) a 3-hydroxybutyrate reductase.

(v) (1) a succinate reductase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA reductase (aldehyde forming), and (8) a 3-hydroxybutanal reductase;

(w) (1) a succinate reductase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA reductase (aldehyde forming), (7) a 3-hydroxybutanal reductase;

(x) (1) a succinate reductase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, and (7) a 3-hydroxybutyryl-CoA reductase (alcohol forming);

(y) (1) a succinate reductase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, and (6) a 3-hydroxybutyryl-CoA reductase (alcohol forming);

(z) (1) a succinate reductase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA hydrolase, transferase or synthetase, and (8) a 3-hydroxybutyrate reductase;

(aa) (1) a succinate reductase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA hydrolase, transferase or synthetase, and (7) a 3-hydroxybutyrate reductase;

(bb) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (5) a 4-hydroxybutyrate kinase, (6) a pPhosphotrans-4-hydroxybutyrylase, (7) a 4-hydroxybutyryl-CoA dehydratase, (8) a crotonase, and (9) a 3-hydroxybutyryl-CoA reductase (alcohol forming);

(cc) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (4) a 4-hydroxybutyrate kinase, (5) a phosphotrans-4-hydroxybutyrylase, (6) a 4-hydroxybutyryl-CoA dehydratase, (7) a crotonase, (8) a 3-hydroxybutyryl-CoA hydrolase, transferase or synthetase, and (9) a 3-hydroxybutyrate reductase;

(dd) (1) a succinyl-CoA transferase, succinyl-CoA synthetase or succinyl-CoA ligase, (2) a succinyl-CoA reductase (alcohol forming), (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA reductase (aldehyde forming), and (8) a 3-hydroxybutanal reductase;

(ee) (1) a succinyl-CoA transferase, succinyl-CoA synthetase or succinyl-CoA ligase, (2) a succinyl-CoA reductase (alcohol forming), (3) a 4-hydroxybutyrate kinase, (4) a phosphotrans-4-hydroxybutyrylase, (5) a 4-hydroxybutyryl-CoA dehydratase, (6) a crotonase, and (7) a 3-hydroxybutyryl-CoA reductase (alcohol forming);

(ff) (1) a succinyl-CoA transferase, succinyl-CoA synthetase or succinyl-CoA ligase, (2) a succinyl-CoA reductase (alcohol forming), (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA hydrolase, transferase or synthetase, and (8) a 3-hydroxybutyrate reductase;

(gg) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (4) a 4-hydroxybutyryl-CoA transferase, or 4-hydroxybutyryl-CoA synthetase, (5) a 4-hydroxybutyryl-CoA dehydratase, (6) a crotonase, (7) a 3-hydroxybutyryl-CoA reductase (aldehyde forming), and (8) a 3-hydroxybutanal reductase;

(hh) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (4) a 4-hydroxybutyryl-CoA transferase or 4-hydroxybutyryl-CoA synthetase, (5) a 4-hydroxybutyryl-CoA dehydratase, (6) a crotonase, and (7) a 3-hydroxybutyryl-CoA reductase (alcohol forming);

(ii) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (4) a 4-hydroxybutyryl-CoA transferase or 4-hydroxybutyryl-CoA synthetase, (5) a 4-hydroxybutyryl-CoA dehydratase, (6) a crotonase, (7) a 3-hydroxybutyryl-CoA hydrolase, transferase or synthetase, (8) a 3-hydroxybutyrate reductase;

(jj) (1) a succinyl-CoA transferase, succinyl-CoA synthetase or succinyl-CoA ligase, (2) a succinyl-CoA reductase (alcohol forming), (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA reductase (aldehyde forming), and (7) a 3-hydroxybutanal reductase;

(kk) (1) a succinyl-CoA transferase, succinyl-CoA synthetase or succinyl-CoA ligase, (2) a succinyl-CoA reductase (alcohol forming), (3) a 4-hydroxybutyryl-CoA transferase or 4-hydroxybutyryl-CoA synthetase, (4) a 4-hydroxybutyryl-CoA dehydratase, (5) a crotonase, and (6) a 3-hydroxybutyryl-CoA reductase (alcohol forming); and (ll) (1) a succinyl-CoA transferase, succinyl-CoA synthetase or succinyl-CoA ligase, (2) a succinyl-CoA reductase (alcohol forming), (3) a 4-hydroxybutyryl-CoA transferase or 4-hydroxybutyryl-CoA synthetase, (5) a 4-hydroxybutyryl-CoA dehydratase, (6) a crotonase, (7) a 3-hydroxybutyryl-CoA hydrolase, transferase or synthetase, and (8) a 3-hydroxybutyrate reductase.

In some embodiments, the method includes a non-naturally occurring microbial organism (e.g., having pathway (i)) that further includes an exogenous nucleic acid encoding an enzyme selected from a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof.

In some embodiments, the method includes a non-naturally occurring microbial organism (e.g., having pathway (ii)) that further includes an exogenous nucleic acid encoding an enzyme selected from an aconitase, an isocitrate dehydrogenase, a succinyl-CoA synthetase, a succinyl-CoA transferase, a fumarase, a malate dehydrogenase, and combinations thereof.

In some embodiments, the method includes a microbial organism that includes two, three, four, five, six, seven, eight or nine exogenous nucleic acids, each encoding a 1,3-BDO pathway enzyme.

In some embodiments, the method includes a microbial organism that comprises exogenous nucleic acids encoding each of the enzymes of at least one of the 1,3-butanediol pathways selected from the group consisting of (a)-(ll).

In some embodiments, the method includes at least one exogenous nucleic acid that is a heterologous nucleic acid.

In some embodiments, the method includes the non-naturally occurring microbial organism in a substantially anaerobic culture medium.

Suitable purification and/or assays to test for the production of 1,3-butanediol can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme or protein activities from the exogenous DNA sequences can also be assayed using methods well known in the art (see, for example, WO/2008/115840 and Hanai et al., Appl. Environ. Microbiol. 73:7814-7818 (2007)).

The 1,3-butanediol can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the 1,3-butanediol producers can be cultured for the biosynthetic production of 1,3-butanediol.

For the production of 1,3-butanediol, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic conditions can be applied by perforating the septum with a small hole for limited aeration. Exemplary anaerobic conditions have been described previously and are well-known in the art. Exemplary aerobic and anaerobic conditions are described, for example, in United States Publication No. US-2009-0047719, filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

In addition to renewable feedstocks such as those exemplified above, the 1,3-butanediol microbial organisms of the invention also can be modified for growth on syngas as its source of carbon. In this specific embodiment, one or more proteins or enzymes are expressed in the 1,3-butanediol producing organisms to provide a metabolic pathway for utilization of syngas or other gaseous carbon source.

Organisms of the present invention can utilize, and the growth medium can include, for example, any carbohydrate source which can supply a source of carbon to the non-naturally occurring microorganism. Such sources include, for example, sugars such as glucose, xylose, arabinose, galactose, mannose, fructose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of 1,3-butanediol.

In addition to renewable feedstocks such as those exemplified above, the 1,3-butanediol microbial organisms of the invention also can be modified for growth on syngas as its source of carbon. In this specific embodiment, one or more proteins or enzymes are expressed in the 1,3-butanediol producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

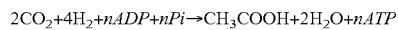

$$2CO_2 + 4H_2 + nADP + nPi \rightarrow CH_3COOH + 2H_2O + nATP$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes or proteins: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a 1,3-butanediol pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the 1,3-butanediol precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a 1,3-butanediol pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains a reductive TCA pathway can confer syngas utilization ability.

Accordingly, given the teachings and guidance provided herein, those skilled in the art will understand that a non-naturally occurring microbial organism can be produced that secretes the biosynthesized compounds of the invention when grown on a carbon source such as a carbohydrate, syngas, CO and/or CO2. Such compounds include, for example, 1,3-butanediol and any of the intermediate metabolites in the 1,3-butanediol pathway. All that is required is to engineer in one or more of the required enzyme or protein activities to achieve biosynthesis of the desired compound or intermediate including, for example, inclusion of some or all of the 1,3-butanediol biosynthetic pathways. Accordingly, the invention provides a non-naturally occurring microbial organism that produces and/or secretes 1,3-butanediol when grown on a carbohydrate or other carbon source and produces and/or secretes any of the intermediate metabolites shown in the 1,3-butanediol pathway when grown on a carbohydrate or other carbon source. The 1,3-butanediol producing microbial organisms of the invention can initiate synthesis from an intermediate, for example, acetyl-CoA.

The non-naturally occurring microbial organisms of the invention are constructed using methods well known in the art as exemplified herein to exogenously express at least one nucleic acid encoding a 1,3-butanediol pathway enzyme or protein in sufficient amounts to produce 1,3-butanediol. It is understood that the microbial organisms of the invention are cultured under conditions sufficient to produce 1,3-butanediol. Following the teachings and guidance provided herein, the non-naturally occurring microbial organisms of the invention can achieve biosynthesis of 1,3-butanediol resulting in intracellular concentrations between about 0.1-200 mM or more. Generally, the intracellular concentration of 1,3-butanediol is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic or substantially anaerobic conditions, the 1,3-butanediol producers can synthesize 1,3-butanediol at intracellular concentrations of 5-10 mM or more as well as all other concentrations exemplified herein. It is understood that, even though the above description refers to intracellular concentrations, 1,3-butanediol producing microbial organisms can produce 1,3-butanediol intracellularly and/or secrete the product into the culture medium.

In addition to the culturing and fermentation conditions disclosed herein, growth condition for achieving biosynthesis of 1,3-butanediol can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

In some embodiments, the carbon feedstock and other cellular uptake sources such as phosphate, ammonia, sulfate, chloride and other halogens can be chosen to alter the isotopic distribution of the atoms present in 1,3-butanediol or any 1,3-butanediol pathway intermediate. The various carbon feedstock and other uptake sources enumerated above will be referred to herein, collectively, as "uptake sources." Uptake sources can provide isotopic enrichment for any atom present in the product 1,3-butanediol or 1,3-butanediol pathway intermediate including any 1,3-butanediol impurities, or for side products generated in reactions diverging away from a 1,3-butanediol pathway. Isotopic enrichment can be achieved for any target atom including, for example, carbon, hydrogen, oxygen, nitrogen, sulfur, phosphorus, chloride or other halogens.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can be selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, a target isotopic ratio of an uptake source can be obtained via synthetic chemical enrichment of the uptake source. Such isotopically enriched uptake sources can be purchased commercially or prepared in the laboratory. In some embodiments, a target isotopic ratio of an uptake source can be obtained by choice of origin of the uptake source in nature. In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target atom isotopic ratio of an uptake source can be achieved by selecting a desired origin of the uptake source as found in nature. For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as CO2, which can possess a larger amount of carbon-14 than its petroleum-derived counterpart.

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}$N). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}$C) to carbon-12 ($^{12}$C). Specifically, the Fraction Modern (Fm) is computed from the expression: Fm=(S−B)/(M−B), where B, S and M represent the $^{14}$C/$^{12}$C ratios of the blank, the sample and the modern reference, respectively. Fraction Modern is a measurement of the deviation of the $^{14}$C/$^{12}$C ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil. (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950)$^{14}$C/$^{12}$C ratio of 1.176±0.010×10$^{-12}$ (Karlen et al., *Arkiv Geofysik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid II standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mille. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products that utilize of the invention having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable 1,4-butanediol and renewable terephthalic acid resulted in bio-based content exceeding 90% (Colonna et al., supra, 2011).

Accordingly, in some embodiments, the present invention provides 1,3-butanediol or a 1,3-butanediol intermediate that has a carbon-12, carbon-13, and carbon-14 ratio that reflects an atmospheric carbon, also referred to as environmental carbon, uptake source. For example, in some aspects the 1,3-butanediol or a 1,3-butanediol intermediate can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides 1,3-butanediol or a 1,3-butanediol intermediate that has a carbon-12, carbon-13, and carbon-14 ratio that reflects petroleum-based carbon uptake source. In this aspect, the 1,3-butanediol or a 1,3-butanediol intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides 1,3-butanediol or a 1,3-butanediol intermediate that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates to the biologically produced 1,3-butanediol or 1,3-butanediol intermediate as disclosed herein, and to the products derived therefrom, wherein the 1,3-butanediol or a 1,3-butanediol intermediate has a carbon-12, carbon-13, and carbon-14 isotope ratio of about the same value as the $CO_2$ that occurs in the environment. For example, in some aspects the invention provides: bioderived 1,3-butanediol or a bioderived 1,3-butanediol intermediate having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived 1,3-butanediol or a bioderived 1,3-butanediol intermediate as disclosed herein, wherein the bioderived product is chemically modified to generate a final product. Methods of chemically modifying a bioderived product of 1,3-butanediol, or an intermediate thereof, to generate a desired product are well known to those skilled in the art, as described herein. The invention further provides organic solvents, polyurethane resins, polyester resins, hypoglycaemic agents, butadiene and/or butadiene-based products having a carbon-12 versus carbon-13 versus carbon-14 isotope ratio of about the same value as the $CO_2$ that occurs in the environment, wherein the organic solvents, polyurethane resins, polyester resins, hypoglycaemic agents, butadiene and/or butadiene-based products are generated directly from or in combination with bioderived 1,3-butanediol or a bioderived 1,3-butanediol intermediate as disclosed herein.

1,3-butanediol is a chemical used in commercial and industrial applications and is also used as a raw material in the production of a wide range of products. Non-limiting examples of such applications and products include organic solvents, polyurethane resins, polyester resins, hypoglycaemic agents, butadiene and/or butadiene-based products organic solvents, polyurethane resins, polyester resins, hypoglycaemic agents, butadiene and/or butadiene-based products. Accordingly, in some embodiments, the invention provides biobased used as a raw material in the production of a wide range of products comprising one or more bioderived 1,3-butanediol or bioderived 1,3-butanediol intermediate produced by a non-naturally occurring microorganism of the invention or produced using a method disclosed herein.

As used herein, the term "bioderived" means derived from or synthesized by a biological organism and can be considered a renewable resource since it can be generated by a biological organism. Such a biological organism, in particular the microbial organisms of the invention disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound of the invention. A biobased or bioderived product is in contrast to a petroleum derived product, wherein such a product is derived from or synthesized from petroleum or a petrochemical feedstock.

In some embodiments, the invention provides organic solvents, polyurethane resins, polyester resins, hypoglycaemic agents, butadiene and/or butadiene-based products comprising bioderived 1,3-butanediol or bioderived 1,3-butanediol intermediate, wherein the bioderived 1,3-butanediol or bioderived 1,3-butanediol intermediate includes all or part of the 1,3-butanediol or 1,3-butanediol intermediate used in the production of organic solvents, polyurethane resins, polyester resins, hypoglycaemic agents, butadiene and/or butadiene-based products. Thus, in some aspects, the invention provides biobased organic solvents, polyurethane resins, polyester resins, hypoglycaemic agents, butadiene and/or butadiene-based products comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived 1,3-butanediol or bioderived 1,3-butanediol intermediate as disclosed herein. Additionally, in some aspects, the invention provides biobased organic solvents, polyurethane resins, polyester resins, hypoglycaemic agents, butadiene and/or butadiene-based products wherein the 1,3-butanediol or 1,3-butanediol intermediate used in its production is a combination of bioderived and petroleum derived 1,3-butanediol or 1,3-butanediol intermediate. For example, biobased organic solvents, polyurethane resins, polyester resins, hypoglycaemic agents, butadiene and/or butadiene-based products can be produced using 50% bioderived 1,3-butanediol and 50% petroleum derived 1,3-butanediol or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing organic solvents, polyurethane resins, polyester resins, hypoglycaemic agents, butadiene and/or butadiene-based products using the bioderived 1,3-butanediol or bioderived 1,3-butanediol intermediate of the invention are well known in the art.

The non-naturally occurring microbial organisms of the invention are constructed using methods well known in the art as exemplified herein to exogenously express at least one nucleic acid encoding a 1,3-butanediol pathway enzyme or protein in sufficient amounts to produce 1,3-butanediol. It is understood that the microbial organisms of the invention are cultured under conditions sufficient to produce 1,3-butanediol. Following the teachings and guidance provided herein, the non-naturally occurring microbial organisms of the invention can achieve biosynthesis of 1,3-butanediol resulting in intracellular concentrations between about 0.1-2000 mM or more. Generally, the intracellular concentration of 1,3-butanediol is between about 3-1800 mM, particularly between about 5-1700 mM and more particularly between about 8-1600 mM, including about 100 mM, 200 mM, 500 mM, 800 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. patent application No. US 2009/0047719, filed Aug. 10, 2007. Any of these conditions can be employed with the non-naturally occurring microbial organisms as well as other anaerobic conditions well known in the art. Under such anaerobic conditions, the 1,3-butanediol producers can synthesize 1,3-butanediol at intracellular concentrations of 5-10 mM or more as well as all other concentrations exemplified herein. It is understood that, even though the above description refers to intracellular concentrations, 1,3-butanediol producing microbial organisms can produce 1,3-butanediol intracellularly and/or secrete the product into the culture medium.

In addition to the culturing and fermentation conditions disclosed herein, growth condition for achieving biosynthesis of 1,3-butanediol can include the addition of an osmoprotectant to the culturing conditions. In certain embodiments, the non-naturally occurring microbial organisms of the invention can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopropionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of 1,3-butanediol includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an N2/CO2 mixture or other suitable non-oxygen gas or gases.

The culture conditions described herein can be scaled up and grown continuously for manufacturing of 1,3-butanediol. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of 1,3-butanediol. Generally, and as with non-continuous culture procedures, the continuous and/or near-continuous production of 1,3-butanediol will include culturing a non-naturally occurring 1,3-butanediol producing organism of the invention in sufficient nutrients and medium to sustain and/or nearly sustain growth in an exponential phase. Continuous culture under such conditions can include, for example, growth for 1 day, 2, 3, 4, 5, 6 or 7 days or more. Additionally, continuous culture can include longer time period of 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of 1,3-butanediol can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the 1,3-butanediol producers of the invention for continuous production of substantial quantities of 1,3-butanediol, the 1,3-butanediol producers also can be, for example, simultaneously subjected to chemical synthesis procedures to convert the product to other compounds or the product can be separated from the fermentation culture and sequentially subjected to chemical or enzymatic conversion to convert the product to other compounds, if desired. For example, 1,3-butanediol can be dehydrated to provide 1,3-butadiene.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 1,3-butadiene.

In some embodiments, syngas can be used as a carbon feedstock. Important process considerations for a syngas fermentation are high biomass concentration and good gas-liquid mass transfer (Bredwell et al., Biotechnol Prog., 15:834-844 (1999). The solubility of CO in water is somewhat less than that of oxygen. Continuously gas-sparged fermentations can be performed in controlled fermenters with constant off-gas analysis by mass spectrometry and periodic liquid sampling and analysis by GC and HPLC. The liquid phase can function in batch mode. Fermentation products such as alcohols, organic acids, and residual glucose along with residual methanol are quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids. The growth rate is determined by measuring optical density using a spectrophotometer (600 nm). All piping in these systems is glass or metal to maintain anaerobic conditions. The gas sparging is performed with glass fits to decrease bubble size and improve mass transfer. Various sparging rates are tested, ranging from about 0.1 to 1 vvm (vapor volumes per minute). To obtain accurate measurements of gas uptake rates, periodic challenges are performed in which the gas flow is temporarily stopped, and the gas phase composition is monitored as a function of time.

In order to achieve the overall target productivity, methods of cell retention or recycle are employed. One method to increase the microbial concentration is to recycle cells via a tangential flow membrane from a sidestream. Repeated batch culture can also be used, as previously described for production of acetate by *Moorella* (Sakai et al., J Biosci. Bioeng, 99:252-258 (2005)). Various other methods can also be used (Bredwell et al., Biotechnol Prog., 15:834-844 (1999); Datar et al., Biotechnol Bioeng, 86:587-594 (2004)). Additional optimization can be tested such as overpressure at 1.5 atm to improve mass transfer (Najafpour et al., Enzyme and Microbial Technology, 38[1-2], 223-228 (2006)).

Once satisfactory performance is achieved using pure H2/CO as the feed, synthetic gas mixtures are generated containing inhibitors likely to be present in commercial syngas. For example, a typical impurity profile is 4.5% CH4, 0.1% C2H2, 0.35% C2H6, 1.4% C2H4, and 150 ppm nitric oxide (Datar et al., Biotechnol Bioeng, 86:587-594 (2004)). Tars, represented by compounds such as benzene, toluene, ethylbenzene, p-xylene, o-xylene, and naphthalene, are added at ppm levels to test for any effect on production. For example, it has been shown that 40 ppm NO is inhibitory to *C. carboxidivorans* (Ahmed et al., Biotechnol Bioeng, 97:1080-1086 (2007)). Cultures are tested in shake-flask cultures before moving to a fermentor. Also, different levels of these potential inhibitory compounds are tested to quantify the effect they have on cell growth. This knowledge is used to develop specifications for syngas purity, which is utilized for scale up studies and production. If any particular component is found to be difficult to decrease or remove from syngas used for scale up, an adaptive evolution procedure is utilized to adapt cells to tolerate one or more impurities.

Advances in the field of protein engineering make it feasible to alter any of the enzymes disclosed herein to act efficiently on substrates not known to be natural to them. Below are several examples of broad-specificity enzymes from diverse classes of interest and methods that have been used for evolving such enzymes to act on non-natural substrates.

One class of enzymes in the pathways disclosed herein is the oxidoreductases that interconvert ketones or aldehydes to alcohols (1.1.1). Enzymes in this class that can operate on a wide range of substrates. An alcohol dehydrogenase (1.1.1.1) purified from the soil bacterium *Brevibacterium* sp KU 1309 (Hirano et al., J. Biosci. Bioeng. 100:318-322 (2005)) was shown to operate on a plethora of aliphatic as well as aromatic alcohols with high activities. Table 72 shows the activity of the enzyme and its Km on different alcohols. The enzyme is reversible and has very high activity on several aldehydes also as shown in Table 73.

TABLE 72

| SUBSTRATE | RELATIVE ACTIVITY (%) | $K_M$ (MM) |
|---|---|---|
| 2-Phenylethanol | 100 | 0.025 |
| (S)-2-Phenylpropanol | 156 | 0.157 |
| (R)-2-Phenylpropanol | 63 | 0.020 |
| Benzyl alcohol | 199 | 0.012 |
| 3-Phenylpropanol | 135 | 0.033 |
| Ethanol | 76 | |
| 1-Butanol | 111 | |
| 1-Octanol | 101 | |
| 1-Dodecanol | 68 | |
| 1-Phenylethanol | 46 | |
| 2-Propanol | 54 | |

In this Table, the activity of 2-phenylethanol, corresponding to 19.2 U/mg, was taken as 100%.

TABLE 73

| SUBSTRATE | RELATIVE ACTIVITY (%) | $K_M$ (MM) |
|---|---|---|
| Phenylacetaldehyde | 100 | 0.261 |
| 2-Phenylpropionaldehyde | 188 | 0.864 |
| 1-Octylaldehyde | 87 | |
| Acetophenone | 0 | |

Lactate dehydrogenase (1.1.1.27) from *Ralstonia eutropha* is another enzyme that has been demonstrated to have high activities on several 2-oxoacids such as 2-oxobutyrate, 2-oxopentanoate and 2-oxoglutarate (a C5 compound analogous to 2-oxoadipate) (Steinbuchel et al., supra). Column 2 in Table 74 demonstrates the activities of ldhA from *R. eutropha* (formerly *A. eutrophus*) on different substrates (Steinbuchel et al., supra).

TABLE 74

| | Activity of | | |
|---|---|---|---|
| Substrate | L(+)-lactate dehydrogenase from *A. eustrophus* % | L(+)-lactate dehydrogenase from rabbit muscle | D(−)-lactate dehydrogenase from *L. leischmanii* |
| Glyoxylate | 8.7 | 23.9 | 5.0 |
| Pyruvate | 100.0 | 100.0 | 100.0 |
| 2-Oxobutyrate | 107.0 | 18.6 | 1.1 |
| 2-Oxovalerate | 125.0 | 0.7 | 0.0 |
| 3-Methyl-2-oxobutyrate | 28.5 | 0.0 | 0.0 |
| 3-Methyl-2-oxovalerate | 5.3 | 0.0 | 0.0 |

TABLE 74-continued

| | Activity of | | |
|---|---|---|---|
| Substrate | L(+)-lactate dehydrogenase from A. eustrophus % | L(+)-lactate dehydrogenase from rabbit muscle | D(−)-lactate dehydrogenase from L. leischmanii |
| 4-Methyl-2-oxopentanoate | 39.0 | 1.4 | 1.1 |
| Oxaloacetate | 0.0 | 33.1 | 23.1 |
| 2-Oxoglutarate | 79.6 | 0.0 | 0.0 |
| 3-Fluoropyruvate | 33.6 | 74.3 | 40.0 |

Oxidoreductases that can convert 2-oxoacids to their acyl-CoA counterparts (1.2.1) have been shown to accept multiple substrates as well. For example, branched-chain 2-keto-acid dehydrogenase complex (BCKAD), also known as 2-oxoisovalerate dehydrogenase (1.2.1.25), participates in branched-chain amino acid degradation pathways, converting 2-keto acids derivatives of valine, leucine and isoleucine to their acyl-CoA derivatives and CO2. In some organisms including *Rattus norvegicus* (Paxton et al., Biochem. J. 234:295-303 (1986)) and *Saccharomyces cerevisiae* (Sinclair et al., Biochem. Mol. Biol. Int. 31:911-922 (1993)), this complex has been shown to have a broad substrate range that includes linear oxo-acids such as 2-oxobutanoate and alpha-ketoglutarate, in addition to the branched-chain amino acid precursors.

Members of yet another class of enzymes, namely aminotransferases (2.6.1), have been reported to act on multiple substrates. Aspartate aminotransferase (aspAT) from *Pyrococcus fursious* has been identified, expressed in *E. coli* and the recombinant protein characterized to demonstrate that the enzyme has the highest activities towards aspartate and alpha-ketoglutarate but lower, yet significant activities towards alanine, glutamate and the aromatic amino acids (Ward et al., *Archaea*. 1:133-141 (2002)). In another instance, an aminotransferase identified from *Leishmania mexicana* and expressed in *E. coli* Vernal et al., *FEMS Microbiol. Lett.* 229:217-222 (2003)) was reported to have a broad substrate specificity towards tyrosine (activity considered 100% on tyrosine), phenylalanine (90%), tryptophan (85%), aspartate (30%), leucine (25%) and methionine (25%) respectively (Vernal et al., *Mol. Biochem. Parasitol.* 96:83-92 (1998)). Similar broad specificity has been reported for a tyrosine aminotransferase from *Trypanosoma cruzi*, even though both of these enzymes have a sequence homology of only 6%. Note that the latter enzyme can accept leucine, methionine as well as tyrosine, phenylalanine, tryptophan and alanine as efficient amino donors (Nowicki et al., *Biochim. Biophys. Acta* 1546: 268-281 (2001)).

In contrast to these examples where the enzymes naturally have broad substrate specificities, numerous enzymes have been modified using directed evolution to broaden their specificity towards their non-natural substrates. Alternatively, the substrate preference of an enzyme has also been changed using directed evolution. For example, it has been reported that the enantioselectivity of a lipase from *Pseudomonas aeruginosa* was improved significantly. This enzyme hydrolyzed p-nitrophenyl 2-methyldecanoate with only 2% enantiomeric excess (ee) in favor of the (S)-acid. However, after four successive rounds of error-prone mutagenesis and screening, a variant was produced that catalyzed the requisite reaction with 81% ee Reetz et al., Angew. Chem. Int. Ed Engl. 36:2830-2832 (1997)).

Directed evolution methods have made possible the modification of an enzyme to function on an array of unnatural substrates. The substrate specificity of the lipase in *P. aeruginosa* was broadened by randomization of amino acid residues near the active site. This allowed for the acceptance of alpha-substituted carboxylic acid esters by this enzyme Reetz et al., Angew. Chem. Int. Ed Engl. 44:4192-4196 (2005)). In another successful attempt, DNA shuffling was employed to create an *Escherichia coli* aminotransferase that accepted β-branched substrates, which were poorly accepted by the wild-type enzyme (Yano et al., Proc. Natl. Acad. Sci. U. S. A 95:5511-5515 (1998)). Specifically, at the end of four rounds of shuffling, the activity of aspartate aminotransferase for valine and 2-oxovaline increased by up to five orders of magnitude, while decreasing the activity towards the natural substrate, aspartate, by up to 30-fold. Recently, an algorithm was used to design a retro-aldolase that could be used to catalyze the carbon-carbon bond cleavage in a non-natural and non-biological substrate, 4-hydroxy-4-(6-methoxy-2-naphthyl)-2-butanone. These algorithms used different combinations of four different catalytic motifs to design new enzymes and 20 of the selected designs for experimental characterization had four-fold improved rates over the uncatalyzed reaction (Jiang et al., Science 319:1387-1391 (2008)). Thus, not only are these engineering approaches capable of expanding the array of substrates on which an enzyme can act, but allow the design and construction of very efficient enzymes. For example, a method of DNA shuffling (random chimeragenesis on transient templates or RACHITT) was reported to lead to an engineered monooxygenase that had an improved rate of desulfurization on complex substrates as well as 20-fold faster conversion of a non-natural substrate (Coco et al. Nat. Biotechnol. 19:354-359 (2001)). Similarly, the specific activity of a sluggish mutant triosephosphate isomerase enzyme was improved up to 19-fold from 1.3 fold (Hermes et al., Proc. Natl. Acad. Sci. U. S. A 87:696-700 (1990)). This enhancement in specific activity was accomplished by using random mutagenesis over the whole length of the protein and the improvement could be traced back to mutations in six amino acid residues.

The effectiveness of protein engineering approaches to alter the substrate specificity of an enzyme for a desired substrate has also been demonstrated. Isopropylmalate dehydrogenase from *Thermus thermophilus* was modified by changing residues close to the active site so that it could now act on malate and D-lactate as substrates (Fujita et al., Biosci. Biotechnol Biochem. 65:2695-2700 (2001)). In this study as well as in others, it was pointed out that one or a few residues could be modified to alter the substrate specificity. A case in point is the dihydroflavonol 4-reductase for which a single amino acid was changed in the presumed substrate-binding region that could preferentially reduce dihydro-kaempferol Johnson et al., Plant J. 25:325-333 (2001)). The substrate specificity of a very specific isocitrate dehydrogenase from *Escherichia coli* was changed from isocitrate to isopropylmalate by changing one residue in the active site (Doyle et al., Biochemistry 40:4234-4241 (2001)). In a similar vein, the cofactor specificity of a NAD+-dependent 1,5-hydroxyprostaglandin dehydrogenase was altered to NADP+ by changing a few residues near the N-terminal end Cho et al., Arch. Biochem. Biophys. 419:139-146 (2003)). Sequence analysis and molecular modeling analysis were used to identify the key residues for modification, which were further studied by site-directed mutagenesis.

A fucosidase was evolved from a galactosidase in *E. coli* by DNA shuffling and screening (Zhang et al., Proc Natl Acad Sci U S. A 94:4504-4509 (1997)). Similarly, aspartate aminotransferase from *E. coli* was converted into a tyrosine aminotransferase using homology modeling and site-directed mutagenesis (Onuffer et al., Protein Sci. 4:1750-1757 (1995)). Site-directed mutagenesis of two residues in the active site of benzoylformate decarboxylase from *P. putida* reportedly altered the affinity (Km) towards natural and non-natural substrates Siegert et al., Protein Eng Des Sel 18:345-357 (2005)). Cytochrome c peroxidase (CCP) from *Saccharomyces cerevisiae* was subjected to directed molecular evolution to generate mutants with increased activity against the classical peroxidase substrate guaiacol, thus changing the substrate specificity of CCP from the protein cytochrome c to a small organic molecule. After three rounds of DNA shuffling and screening, mutants were isolated which possessed a 300-fold increased activity against guaiacol and up to 1000-fold increased specificity for this substrate relative to that for the natural substrate (Iffland et al., Biochemistry 39:10790-10798 (2000)).

In some cases, enzymes with different substrate preferences than both the parent enzymes have been obtained. For example, biphenyl-dioxygenase-mediated degradation of polychlorinated biphenyls was improved by shuffling genes from two bacteria, *Pseudomonas* pseudoalcaligens and Burkholderia cepacia (Kumamaru et al., Nat. Biotechnol 16, 663-666 (1998)). The resulting chimeric biphenyl oxygenases showed different substrate preferences than both the parental enzymes and enhanced the degradation activity towards related biphenyl compounds and single aromatic ring hydrocarbons such as toluene and benzene which were originally poor substrates for the enzyme.

It is not only possible to change the enzyme specificity but also to enhance the activities on those substrates on which the enzymes naturally have low activities. One study demonstrated that amino acid racemase from *P. putida* that had broad substrate specificity (on lysine, arginine, alanine, serine, methionine, cysteine, leucine and histidine among others) but low activity towards tryptophan could be improved significantly by random mutagenesis Kino et al., Appl. Microbiol. Biotechnol. 73:1299-1305 (2007)). Similarly, the active site of the bovine BCKAD was engineered to favor alternate substrate acetyl-CoA (Meng et al. Biochemistry 33:12879-12885 (1994)). An interesting aspect of these approaches is that even when random methods have been applied to generate these mutated enzymes with efficacious activities, the exact mutations or structural changes that confer the improvement in activity can be identified. For example, in the aforementioned study, the mutations that facilitated improved activity on tryptophan could be traced back to two different positions.

Directed evolution has also been used to express proteins that are difficult to express. For example, by subjecting the horseradish peroxidase to random mutagenesis and gene recombination, mutants could be extracted that had more than 14-fold activity than the wild type (Lin et al., Biotechnol. Prog. 15:467-471 (1999)).

A final example of directed evolution shows the extensive modifications to which an enzyme can be subjected to achieve a range of desired functions. The enzyme, lactate dehydrogenase from *Bacillus stearothermophilus* was subjected to site-directed mutagenesis, and three amino acid substitutions were made at sites that were indicated to determine the specificity towards different hydroxyacids (Clarke et al., Biochem. Biophys. Res. Commun. 148:15-23 (1987)). After these mutations, the specificity for oxaloacetate over pyruvate was increased to 500 in contrast to the wild type enzyme that had a catalytic specificity for pyruvate over oxaloacetate of 1000. This enzyme was further engineered using site-directed mutagenesis to have activity towards branched-chain substituted pyruvates (Wilks et al., Biochemistry 29:8587-8591 (1990)). Specifically, the enzyme had a 55-fold improvement in Kcat for alpha-ketoisocaproate. Three structural modifications were made in the same enzyme to change its substrate specificity from lactate to malate. The enzyme was highly active and specific towards malate (Wilks et al., Science 242:1541-1544 (1988)). The same enzyme from *B. stearothermophilus* was subsequently engineered to have high catalytic activity towards alpha-keto acids with positively charged side chains, such as those containing ammonium groups (Hogan et al., Biochemistry 34:4225-4230 (1995)). Mutants with acidic amino acids introduced at position 102 of the enzyme favored binding of such side chain ammonium groups. The results obtained proved that the mutants showed up to 25-fold improvements in kcat/Km values for omega-amino-alpha-keto acid substrates. This enzyme was also structurally modified to function as a phenyllactate dehydrogenase instead of a lactate dehydrogenase (Wilks et al., Biochemistry 31:7802-7806 (1992)). Restriction sites were introduced into the gene for the enzyme which allowed a region of the gene to be excised. This region coded for a mobile surface loop of polypeptide (residues 98-110) which normally seals the active site vacuole from bulk solvent and is a major determinant of substrate specificity. The variable length and sequence loops were inserted into the cut gene and used to synthesize hydroxyacid dehydrogenases with altered substrate specificities. With one longer loop construction, activity with pyruvate was reduced one-million-fold but activity with phenylpyruvate was largely unaltered. A switch in specificity (kcat/Km) of 390,000-fold was achieved. The 1700:1 selectivity of this enzyme for phenylpyruvate over pyruvate is that required in a phenyllactate dehydrogenase.

As indicated above, directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (e.g., >104). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened.

Numerous directed evolution technologies have been developed (for reviews, see Hibbert, E. G., F. Baganz, H. C. Hailes, J. M. Ward, G. J. Lye, J. M. Woodley, and P. A. Dalby, 2005, Directed evolution of biocatalytic processes. Biomol. Eng 22:11-19; Huisman, G. W. and J. J. Lalonde, 2007, Enzyme evolution for chemical process applications, p. 717-742. In R. N. Patel (ed.), Biocatalysis in the pharmaceutical and biotechnology industries. CRC Press; Otten, L. G. and W. J. Quax. 2005. Directed evolution: selecting today's biocatalysts. Biomol. Eng 22:1-9; and Sen, S., D. Venkata, V, and B. Mandal, 2007, Developments in directed evolution for improving enzyme functions. Appl Biochem. Biotechnol 143:212-223.) to be effective at creating diverse variant libraries and these methods have been successfully applied to the improvement of a wide range of properties across many enzyme classes.

Enzyme characteristics that have been improved and/or altered by directed evolution technologies include, for example, selectivity/specificity—for conversion of non-natural substrates; temperature stability—for robust high temperature processing; pH stability—for bioprocessing under lower or higher pH conditions; substrate or product tolerance—so that high product titers can be achieved; binding (Km)—broadens substrate binding to include non-natural substrates; inhibition (Ki)—to remove inhibition by products, substrates, or key intermediates; activity (kcat)—increases enzymatic reaction rates to achieve desired flux; expression levels—increases protein yields and overall pathway flux; oxygen stability—for operation of air sensitive enzymes under aerobic conditions; and anaerobic activity—for operation of an aerobic enzyme in the absence of oxygen.

The following exemplary methods have been developed for the mutagenesis and diversification of genes to target desired properties of specific enzymes. Any of these can be used to alter/optimize activity of a decarboxylase enzyme.

EpPCR (Pritchard, L., D. Corne, D. Kell, J. Rowland, and M. Winson, 2005, A general model of error-prone PCR. J Theor. Biol 234:497-509.) introduces random point mutations by reducing the fidelity of DNA polymerase in PCR reactions by the addition of Mn2+ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful. A high number of mutants can be generated by EpPCR, so a high-throughput screening assay or a selection method (especially using robotics) is useful to identify those with desirable characteristics.

Error-prone Rolling Circle Amplification (epRCA) (Fujii, R., M. Kitaoka, and K. Hayashi, 2004, One-step random mutagenesis by error-prone rolling circle amplification. Nucleic Acids Res 32:e145; and Fujii, R., M. Kitaoka, and K. Hayashi, 2006, Error-prone rolling circle amplification: the simplest random mutagenesis protocol. Nat. Protoc. 1:2493-2497.) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the Mn2+ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a kit.

DNA or Family Shuffling (Stemmer, W. P. 1994, DNA shuffling by random fragmentation and reassembly: in vitro recombination for molecular evolution. Proc Natl Acad Sci US.A 91:10747-10751; and Stemmer, W. P. 1994. Rapid evolution of a protein in vitro by DNA shuffling. Nature 370:389-391.) typically involves digestion of 2 or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious random neutral mutations that might confer antigenicity.

Staggered Extension (StEP) (Zhao, H., L. Giver, Z. Shao, J. A. Affholter, and F. H. Arnold, 1998, Molecular evolution by staggered extension process (StEP) in vitro recombination. Nat. Biotechnol 16:258-261.) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template. (Shao, Z., H. Zhao, L. Giver, and F. H. Arnold, 1998, Random-priming in vitro recombination: an effective tool for directed evolution. Nucleic Acids Res 26:681-683.) Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair. (Volkov, A. A., Z. Shao, and F. H. Arnold. 1999. Recombination and chimeragenesis by in vitro heteroduplex formation and in vivo repair. Nucleic Acids Res 27:e18; and Volkov, A. A., Z. Shao, and F. H. Arnold. 2000. Random chimeragenesis by heteroduplex recombination. Methods Enzymol. 328:456-463.) The mismatch repair step is at least somewhat mutagenic. Heteroduplexes transform more efficiently than linear homoduplexes. This method is suitable for large genes and whole operons.

Random Chimeragenesis on Transient Templates (RACHITT) (Coco, W. M., W. E. Levinson, M. J. Crist, H. J. Hektor, A. Darzins, P. T. Pienkos, C. H. Squires, and D. J. Monticello, 2001, DNA shuffling method for generating highly recombined genes and evolved enzymes. Nat. Biotechnol 19:354-359.) employs Dnase I fragmentation and size fractionation of ssDNA. Homologous fragments are hybridized in the absence of polymerase to a complementary ssDNA scaffold. Any overlapping unhybridized fragment ends are trimmed down by an exonuclease. Gaps between fragments are filled in, and then ligated to give a pool of full-length diverse strands hybridized to the scaffold (that contains U to preclude amplification). The scaffold then is destroyed and is replaced by a new strand complementary to the diverse strand by PCR amplification. The method involves one strand (scaffold) that is from only one parent while the priming fragments derive from other genes; the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates. (Lee, S. H., E. J. Ryu, M. J. Kang, E.-S. Wang, Z. C. Y. Piao, K. J. J. Jung, and Y. Shin, 2003, A new approach to directed gene evolution by recombined extension on truncated templates (RETT). J. Molec. Catalysis 26:119-129.) No DNA endonucleases are used. Unidirectional ssDNA is made by DNA polymerase with random primers or serial deletion with exonuclease. Unidirectional ssDNA are only templates and not primers. Random priming and exonucleases don't introduce sequence bias as true of enzymatic cleavage of DNA shuffling/RACHITT. RETT can be easier to optimize than StEP because it uses normal PCR conditions instead of very short extensions. Recombination occurs as a component of the PCR steps—no direct shuffling. This method can also be more random than StEP due to the absence of pauses.

In Degenerate Oligonucleotide Gene Shuffling (DOGS) degenerate primers are used to control recombination between molecules; (Bergquist, P. L. and M. D. Gibbs, 2007, Degenerate oligonucleotide gene shuffling. Methods Mol. Biol 352:191-204; Bergquist, P. L., R. A. Reeves, and M. D. Gibbs, 2005, Degenerate oligonucleotide gene shuffling (DOGS) and random drift mutagenesis (RNDM): two complementary techniques for enzyme evolution. Biomol. Eng 22:63-72; Gibbs, M. D., K. M. Nevalainen, and P. L. Bergquist, 2001, Degenerate oligonucleotide gene shuffling (DOGS): a method for enhancing the frequency of recombination with family shuffling. Gene 271:13-20.) this can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest. (Ostermeier et al., Proc Natl Acad Sci US.A. 96:3562-3567 (1999); Ostermeier et al., 1999 Nat. Biotechnol. 17:1205-1209 (1999)) Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an E. coli and a human gene were created via ITCHY. When ITCHY libraries are made, all possible crossovers are captured.

Thio-Incremental Truncation for the Creation of Hybrid Enzymes (THIO-ITCHY) is almost the same as ITCHY except that phosphothioate dNTPs are used to generate truncations. (Lutz, S., M. Ostermeier, and S. J. Benkovic, 2001, Rapid generation of incremental truncation libraries for protein engineering using alpha-phosphothioate nucleotides. Nucleic Acids Res 29:E16.) Relative to ITCHY, THIO-ITCHY can be easier to optimize, provide more reproducibility, and adjustability.

SCRATCHY—ITCHY combined with DNA shuffling is a combination of DNA shuffling and ITCHY; therefore, allowing multiple crossovers. (Lutz et al., Proc Natl Acad Sci U S.A. 98:11248-11253 (2001).) SCRATCHY combines the best features of ITCHY and DNA shuffling. Computational predictions can be used in optimization. SCRATCHY is more effective than DNA shuffling when sequence identity is below 80%.

In Random Drift Mutagenesis (RNDM) mutations made via epPCR followed by screening/selection for those retaining usable activity. (Bergquist et al., Biomol. Eng. 22:63-72 (2005).) Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates pool of random length fragments using random incorporation of a phosphothioate nucleotide and cleavage; this pool is used as a template to 2) extend in the presence of "universal" bases such as inosine; 3) replication of a inosine-containing complement gives random base incorporation and, consequently, mutagenesis. (Wong et al., Biotechnol J. 3:74-82 (2008); Wong Nucleic Acids Res 32:e26; Wong et al., Anal. Biochem. 341:187-189 (2005).) Using this technique it can be possible to generate a large library of mutants within 2-3 days using simple methods. This is very non-directed compared to mutational bias of DNA polymerases. Differences in this approach makes this technique complementary (or alternative) to epPCR.

In Synthetic Shuffling, overlapping oligonucleotides are designed to encode "all genetic diversity in targets" and allow a very high diversity for the shuffled progeny. (Ness, et al., Nat. Biotechnol 20:1251-1255 (2002).) In this technique, one can design the fragments to be shuffled. This aids in increasing the resulting diversity of the progeny. One can design sequence/codon biases to make more distantly related sequences recombine at rates approaching more closely related sequences and it doesn't require possessing the template genes physically.

Nucleotide Exchange and Excision Technology NexT exploits a combination of dUTP incorporation followed by treatment with uracil DNA glycosylase and then piperidine to perform endpoint DNA fragmentation. (Muller et al., Nucleic Acids Res 33:e117 (2005)) The gene is reassembled using internal PCR primer extension with proofreading polymerase. The sizes for shuffling are directly controllable using varying dUPT::dTTP ratios. This is an end point reaction using simple methods for uracil incorporation and cleavage. One can use other nucleotide analogs such as 8-oxo-guanine with this method. Additionally, the technique works well with very short fragments (86 bp) and has a low error rate. Chemical cleavage of DNA means very few unshuffled clones.

In Sequence Homology-Independent Protein Recombination (SHIPREC) a linker is used to facilitate fusion between 2 distantly/unrelated genes; nuclease treatment is used to generate a range of chimeras between the two. Result is a single crossover library of these fusions. (Sieber, V., C. A.

Martinez, and F. H. Arnold. 2001. Libraries of hybrid proteins from distantly related sequences. Nat. Biotechnol 19:456-460.) This produces a limited type of shuffling; mutagenesis is a separate process. This technique can create a library of chimeras with varying fractions of each of 2 unrelated parent genes. No homology is needed. SHIPREC was tested with a heme-binding domain of a bacterial CP450 fused to N-terminal regions of a mammalian CP450; this produced mammalian activity in a more soluble enzyme.

In Gene Site Saturation Mutagenesis (GSSM) the starting materials are a supercoiled dsDNA plasmid with insert and 2 primers degenerate at the desired site for mutations. (Kretz, K. A., T. H. Richardson, K. A. Gray, D. E. Robertson, X. Tan, and J. M. Short, 2004, Gene site saturation mutagenesis: a comprehensive mutagenesis approach. Methods Enzymol. 388:3-11.) Primers carry the mutation of interest and anneal to the same sequence on opposite strands of DNA; mutation in the middle of the primer and ~20 nucleotides of correct sequence flanking on each side. The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (i.e., one codon). The technique facilitates the generation of all possible replacements at one site with no nonsense codons and equal or near-equal representation of most possible alleles. It does not require prior knowledge of structure, mechanism, or domains of the target enzyme. If followed by shuffling or Gene Reassembly, this technology creates a diverse library of recombinants containing all possible combinations of single-site up-mutations. The utility of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations. (Reidhaar-Olson, J. F., J. U. Bowie, R. M. Breyer, J. C. Hu, K. L. Knight, W. A. Lim, M. C. Mossing, D. A. Parsell, K. R. Shoemaker, and R. T. Sauer, 1991, Random mutagenesis of protein sequences using oligonucleotide cassettes. Methods Enzymol. 208:564-586; and Reidhaar-Olson, J. F. and R. T. Sauer, 1988, Combinatorial cassette mutagenesis as a probe of the informational content of protein sequences. Science 241:53-57.) Simultaneous substitutions at 2 or 3 sites are possible using this technique. Additionally, the method tests a large multiplicity of possible sequence changes at a limited range of sites. It has been used to explore the information content of lambda repressor DNA-binding domain.

Combinatorial Multiple Cassette Mutagenesis (CMCM) is essentially similar to CCM except it is employed as part of a larger program: 1) Use of epPCR at high mutation rate to 2) ID hot spots and hot regions and then 3) extension by CMCM to cover a defined region of protein sequence space. (Reetz, M. T., S. Wilensek, D. Zha, and K. E. Jaeger, 2001, Directed Evolution of an Enantioselective Enzyme through Combinatorial Multiple-Cassette Mutagenesis. Angew. Chem. Int. Ed Engl. 40:3589-3591.) As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique conditional is mutator plasmids allow increases of 20- to 4000-X in random and natural mutation frequency during selection and to block accumulation of deleterious mutations when selection is not required. (Selifonova, O., F. Valle, and V. Schellenberger, 2001, Rapid evolution of novel traits in microorganisms. Appl Environ Microbiol 67:3645-3649.) This technology is based on a plasmid-derived mutD5 gene, which encodes a mutant subunit of DNA polymerase III. This subunit binds to endogenous DNA polymerase III and compromises the proofreading ability of polymerase III in any of the strain that harbors the plasmid. A broad-spectrum of base substitutions and frameshift mutations occur. In order for effective use, the mutator plasmid should be removed once the desired phenotype is achieved; this is accomplished through a temperature sensitive origin of replication, which allows plasmid curing at 41° C. It should be noted that mutator strains have been explored for quite some time (e.g., see Winter and coworkers, 1996, J. Mol. Biol. 260, 359-3680. In this technique very high spontaneous mutation rates are observed. The conditional property minimizes non-desired background mutations. This technology could be combined with adaptive evolution to enhance mutagenesis rates and more rapidly achieve desired phenotypes.

"Look-Through Mutagenesis (LTM) is a multidimensional mutagenesis method that assesses and optimizes combinatorial mutations of selected amino acids." (Rajpal, A., N. Beyaz, L. Haber, G. Cappuccilli, H. Yee, R. R. Bhatt, T. Takeuchi, R. A. Lerner, and R. Crea, 2005, A general method for greatly improving the affinity of antibodies by using combinatorial libraries. Proc Natl Acad Sci US.A 102:8466-8471.) Rather than saturating each site with all possible amino acid changes, a set of 9 is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This is a rational approach to minimize the number of random combinations and should increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to creating a large library of chimeras (multiple mutations) of a single gene. (on the world-wide web at URL Verenium.com/Pages/Technology/EnzymeTech/TechEnzyTGR.html). Typically this technology is used in combination with ultra-high-throughput screening to query the represented sequence space for desired improvements. This technique allows multiple gene recombination independent of homology. The exact number and position of cross-over events can be pre-determined using fragments designed via bioinformatics analysis. This technology leads to a very high level of diversity with virtually no parental gene reformation and a low level of inactive genes. Combined with GSSM, a large range of mutations can be tested for improved activity. The method allows "blending" and "fine tuning" of DNA shuffling, e.g. codon usage can be optimized.

In Silico Protein Design Automation PDA is an optimization algorithm that anchors the structurally defined protein backbone possessing a particular fold, and searches sequence space for amino acid substitutions that can stabilize the fold and overall protein energetics. (Hayes, R. J., J. Bentzien, M. L. Ary, M. Y. Hwang, J. M. Jacinto, J.

Vielmetter, A. Kundu, and B. I. Dahiyat, 2002, Combining computational and experimental screening for rapid optimization of protein properties. Proc Natl Acad Sci US.A 99:15926-15931.) This technology allows in silico structure-based entropy predictions in order to search for structural tolerance toward protein amino acid variations. Statistical mechanics is applied to calculate coupling interactions at each position—structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants (1050). Choice of sequence variants to test is related to predictions based on most favorable thermodynamics and ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves 1) Use knowledge of structure/function to choose a likely site for enzyme improvement. 2) Saturation mutagenesis at chosen site using Stratagene QuikChange (or other suitable means). 3) Screen/select for desired properties. 4) With improved clone(s), start over at another site and continue repeating. (Reetz, M. T. and J. D. Carballeira, 2007, Iterative saturation mutagenesis (ISM) for rapid directed evolution of functional enzymes. Nat. Protoc. 2:891-903; and Reetz, M. T., J. D. Carballeira, and A. Vogel, 2006, Iterative saturation mutagenesis on the basis of B factors as a strategy for increasing protein thermostability. Angew. Chem. Int. Ed Engl. 45:7745-7751.) This is a proven methodology assures all possible replacements at a given position are made for screening/selection.

Any of the aforementioned methods for mutagenesis can be used alone or in any combination. Additionally, any one or combination of the directed evolution methods can be used in conjunction with adaptive evolution techniques.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 1,3-butanediol.

One computational method for identifying and designing metabolic alterations favoring biosynthesis of a desired product is the OptKnock computational framework (Burgard et al., Biotechnol. Bioeng. 84:647-657 (2003)). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation methods referred to herein as OptKnock are described in, for example, U.S. 2002/0168654, WO 2002/055995, and U.S. 2009/0047719.

Another computational method for identifying and designing metabolic alterations favoring biosynthetic production of a product is a metabolic modeling and simulation system termed SimPheny®. This computational method and system is described in, for example, U.S. 2003/0233218, filed Jun. 14, 2002, and in WO/2003/106998. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., Biotechnol. Prog. 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., Biotechnol. Bioeng. 84:647-657 (2003)).

An in silico stoichiometric model of *E. coli* metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a 1,3-butanediol pathway can be introduced into a host organism. In some cases, it can be desirable to modify an activity of a 1,3-butanediol pathway enzyme or protein to increase production of 1,3-butanediol. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme.

Improved and/or altered enzymes can be identified through the development and implementation of sensitive high-throughput screening assays that allow the automated screening of many enzyme variants (for example, >10⁴). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005).; and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a 1,3-butanediol pathway enzyme or protein. Such methods include, but are not limited to EpPCR, which introduces random point mutations by reducing the fidelity of DNA polymerase in PCR reactions (Pritchard et al., *J Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protoc.* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc Natl Acad Sci USA* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. USA* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res* 29:E16 (2001)); SCRATCHY, which combines two methods for recombining genes, ITCHY and DNA shuffling (Lutz et al., *Proc. Natl. Acad. Sci. USA* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzy-* mol. 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional is mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. USA* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. USA* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange (Stratagene; San Diego Calif.), screening/selecting for desired properties, and, using improved clone(s), starting over at another site and continue repeating until a desired activity is achieved (Reetz et al., *Nat. Protoc.* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

It is understood that modifications which do not substantially affect the activity of the various embodiments of this invention are also included within the definition of the invention provided herein. Accordingly, the following examples are intended to illustrate but not limit the present invention.

Example I

1,3-Butanediol Synthesis Via Alanine

This example describes the generation of a microbial organism capable of producing 1,3-butanediol using the alanine pathway in FIG. 1 via Steps A, B, C, D and H.

*Escherichia coli* is used as a target organism to engineer a 1,3-butanediol-producing pathway as shown in FIG. 1. *E. coli* provides a good host for generating a non-naturally occurring microorganism capable of producing 1,3-butanediol. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce 1,3-butanediol, nucleic acids encoding the enzymes utilized in the alanine pathway as described previously, are expressed in *E. coli* using well known molecular biology techniques (see, for example, Sambrook, supra, 2001; Ausubel supra, 1999; Roberts et al., supra, 1989).

In particular, the ortA (YP_001086914.1), ortB (YP_001086915.1), dat (P19938), and pdc (P06672) genes encoding the AKP thiolase, AKP aminotransferase and 2,4-dioxopentanoate decarboxylase activities, respectively, are cloned into the pZE13 vector (Expressys, Ruelzheim, Germany) under the PA1/lacO promoter. In addition, the yqhD (NP_417484.1) and adh (AAA23199.2) genes encoding 3-oxobutyraldehdye reductase (aldehyde reducing) and 4-hydroxy,2-butanone reductase, respectively are cloned into the pZA33 vector (Expressys, Ruelzheim, Germany) under the PA1/lacO promoter. The two sets of plasmids are transformed into *E. coli* strain MG1655 to express the proteins and enzymes required for 1,3-butanediol synthesis via the alanine pathway. Note that *E. coli* possesses the ability to form D-alanine.

The resulting genetically engineered organism is cultured in glucose containing medium following procedures well known in the art (see, for example, Sambrook et al., supra, 2001). The expression of alanine pathway genes is corroborated using methods well known in the art for determining polypeptide expression or enzymatic activity, including for example, Northern blots, PCR amplification of mRNA, immunoblotting. Enzymatic activities of the expressed enzymes are confirmed using assays specific for the individually activities. The ability of the engineered *E. coli* strain to produce 1,3-butanediol is confirmed using HPLC, gas chromatography-mass spectrometry (GCMS) or liquid chromatography-mass spectrometry (LCMS).

Microbial strains engineered to have a functional 1,3-butanediol synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of 1,3-butanediol. One modeling method is the bilevel optimization approach, OptKnock (Burgard et al., Biotechnol. Bioengineer. 84:647-657 (2003)), which is applied to select gene knockouts that collectively result in better production of 1,3-butanediol. Adaptive evolution also can be used to generate better producers of, for example, alanine or 2-amino-4-oxopentanoate intermediates or the 1,3-butanediol product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the 1,3-butanediol producer to further increase production.

For large-scale production of 1,3-butanediol, the above alanine pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., *Biotechnol. Bioeng.*, 775-779 (2005).

Example II 1,3-BDO Synthesis Using Acetoacetyl-CoA as the Intermediate

This Example describes the generation of a microbial organism capable of producing 1,3-butanediol using acetoacetyl-CoA as the precursor (Steps G, H and I in FIG. 2).

*Escherichia coli* is used as a target organism to engineer the pathway through Steps G (conversion of acetoacetyl-CoA into 3-hydroxybutyryl-CoA), H (conversion of 3-hydroxybutyryl-CoA into 3-hydroxybutyraldehyde) and I (conversion of 3-hydroxybutyraldehyde into 1,3-butanediol) in FIG. 2. *E. coli* provides a good host for generating a non-naturally occurring microorganism capable of producing 1,3-butanediol. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce 1,3-butanediol, nucleic acids encoding the enzymes utilized in the disclosed pathway (Steps G, H and I) as described previously, are expressed in *E. coli* using well known molecular biology techniques (see, for example, Sambrook, supra, 2001; *Ausubel supra*, 1999; Roberts et al., supra, 1989). Note that *E. coli* has a native thiolase encoded by atoB (Accession number: NP_416728.1) that condenses two molecules of acetyl-CoA to form acetoacetyl-CoA.

Further, hbd (NP_349314.1) encoding acetoacetyl-CoA reductase (ketone reducing), is cloned into the pZE13 vector (Expressys, Ruelzheim, Germany) under the PA1/lacO promoter. The plasmid is transformed into *E. coli* strain MG1655 to express the enzyme required for the formation of 3-hydroxybutyryl-CoA via acetoacetyl-CoA. An aldehyde dehydrogenase (selected from Table 75 below) that converts 3-hydroxybutyryl-CoA into 3-hydroxybutyraldehyde, and an alcohol dehydrogenase (selected from Table 76 below) that further reduces 3-hydroxybutyraldehyde into 1,3-BDO are also cloned into the pZE13 vector under the PA1/lacO promoter.

The resulting genetically engineered organism is cultured in glucose containing medium following procedures well known in the art (see, for example, Sambrook et al., supra, 2001). The expression of the pathway genes is corroborated using methods well known in the art for determining polypeptide expression or enzymatic activity, including, for example, Northern blots, PCR amplification of mRNA, immunoblotting. Enzymatic activities of the expressed enzymes are confirmed using assays specific for the individually activities. The ability of the engineered *E. coli* strain to produce 1,3-butanediol is confirmed using HPLC, gas chromatography-mass spectrometry (GCMS) or liquid chromatography-mass spectrometry (LCMS).

Microbial strains engineered to have a functional 1,3-butanediol synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of 1,3-butanediol. One modeling method is the bilevel optimization approach, OptKnock (Burgard et al., Biotechnol. Bioengineer. 84:647-657 (2003)), which is applied to select gene knockouts that collectively result in better production of 1,3-butanediol. Adaptive evolution also can be used to generate better producers of, for example, the acetyl-CoA intermediate or the 1,3-butanediol product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the 1,3-butanediol producer to further increase production.

For large-scale production of 1,3-butanediol, the recombinant organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids (Lin et al., Biotechnol. Bioeng., 90:775-779 (2005)).

Several aldehyde dehydrogenases were tested for activity on 3-hydroxybutyryl-CoA. Crude lysates of bacteria, each strain carrying one out of six genes listed in Table 75 below encoding for an aldehyde dehydrogenase was tested for activity on 3-hydroxybutyryl-CoA by measuring the release of CoA moiety. The genes that were tested and were found to have significant activity on 3-HBCoA encode the proteins with the following accession and GI numbers:

TABLE 75

| Protein | GenBank ID | GI Number | Organism |
| --- | --- | --- | --- |
| bld | AAP42563.1 | 31075383 | Clostridium saccharoperbutylacetonicum |
| ald | ACL06658.1 | 218764192 | Desulfatibacillum alkenivorans AK-01 |
| ald | YP_001452373 | 157145054 | Citrobacter koseri ATCC BAA-895 |
| pduP | NP_460996.1 | 16765381 | Salmonella enterica Typhimurium |
| pduP | ABJ64680.1 | 116099531 | Lactobacillus brevis ATCC 367 |
| BselDRAFT_1651 | ZP_02169447 | 163762382 | Bacillus selenitireducens MLS10 |

Figure 4:
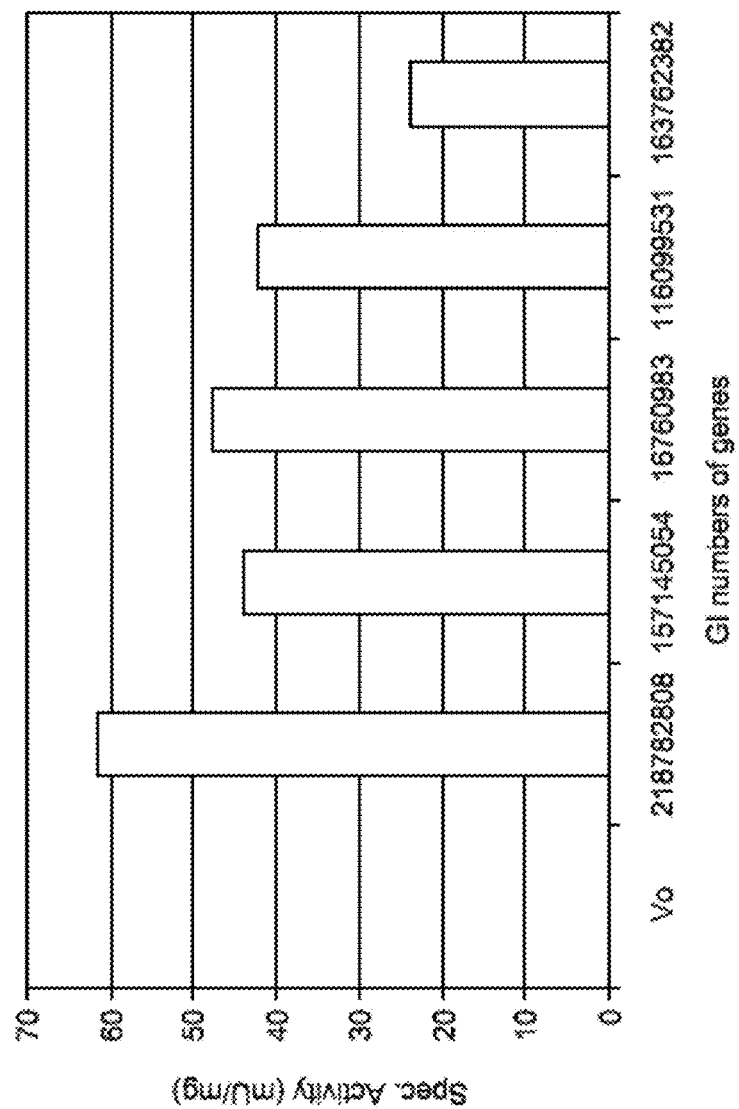
FIG. 4 shows aldehyde dehydrogenases showing significant activity on 3-hydroxybutyl-CoA.

To correct for background activity in the lysate, measured activities were compared to a negative control without ALD gene (vector only, "Vo"). FIG. 4 shows the specific activity of each of the tested genes on 3-hydroxybutyryl-CoA. The gene ids are shown on the x-axis.

Figure 5:
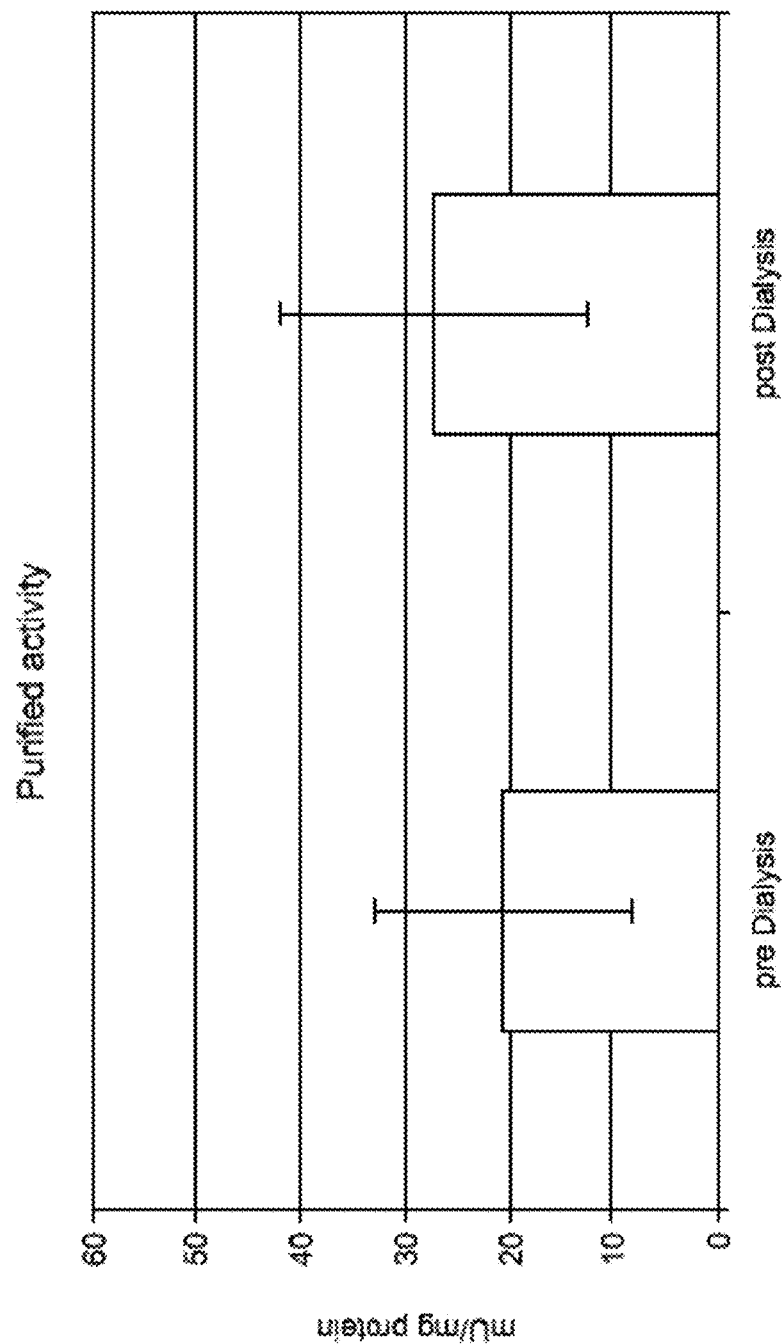
FIG. 5 shows the specific activity of bld from *Clostridium saccharoperbutylacetonicum* on 3-Hydroxybutyryl-CoA before and after dialysis.

Further, bld (GenBank ID: AAP42563.1, GI number: 31075383) was also tested for activity on 3-HBCoA. The following FIG. 5 shows the activity of the gene on 3-hydroxybutyryl-CoA before and after dialysis.

Alcohol dehydrogenases that were tested for activity on 3-hydroxybutyraldehyde and demonstrated to have significant activity are listed below.

TABLE 76

| Protein | GenBank ID | GI Number | Organism |
| --- | --- | --- | --- |
| Bdh (Cbei_2181) | YP_001309304 | 150017050 | Clostridium beijerinckii |
| Bdh (Cbei_1722) | YP_001309535.1 | 150016596 | Clostridium beijerinckii |
| Bdh (Cbei_2421) | YP_001309535.1 | 150017281 | Clostridium beijerinckii |

The following protocol was used to demonstrate alcohol dehydrogenase activity (i.e., conversion of 3-hydroxybutyraldehyde to 1,3-BDO) and combined aldehyde and alcohol dehydrogenase activities (i.e., conversion of 3-hydroxybutyryl-CoA into 1,3-BDO).

Chemically competent cells were transformed with plasmids containing either an aldehyde dehydrogenase or an alcohol dehydrogenase (listed in Tables 75 and 76 above). Colonies from the plates were picked and grown in LB plus 100 ug/ml carbenecillin overnight, then 0.6 mL was used to inoculate 60 mL culture of each alcohol dehydrogenase, or 1.5 mL was used to inoculate a 500 mL culture of each aldehyde dehydrogenase. Cells were grown at 37° C. to an O.D. of ~0.7 and induced with IPTG. The cultures were incubated at 30° C. during protein expression for 4 hours. The cell cultures were divided into 30 ml aliquots, centrifuged and the cell pellets were stored at −80° C. A sample of the cell culture was used to estimate final cell density.

Combinations of alcohol dehydrogenases and aldehyde dehydrogenases were screened in a 96-well plate format with 3-hydroxybutyryl-CoA as a substrate plus a control (no substrate). Alternatively, for testing the alcohol dehydrogenases activity, only the alcohol dehydrogenases were added with and without the substrate, 3-hydroxybutyraldehyde. Preparation of cell lysates was performed on ice in the coldroom (4° C.). Final cell density was used to calculate the quantity of Bug Buster cell lysis reagent for each cell pellet. Lysozyme (10 uL) and benzonase (10 uL) were added to 35 ml bugbuster and gently inverted to mix. First, 50 μm of dithiothreitol (100 mM stock) was added to the pellet, then 0.5 ml per O.D. of 1.0 (at 600 nm) of the Bug Buster plus enzyme mixture was added to the cell pellet and gently mixed to resuspend.

To each well, 50 ul of 1 M MOPS (pH=7.5), and 25 ul of cofactor mixture (4 mM NADH and 4 mM NADPH), both 100 uL aldehyde dehydrogenase cell lysate, 150 uL alcohol dehydrogenase cell lysate or only 150 uL alcohol dehydrogenase cell lysate was added and gently mixed. Then, the relevant substrate was added to the wells. 25 mg of 3-hydroxybutyryl CoA was resuspended in 250 uL water and 5 ul was added to each well testing for both alcohol and aldehyde dehydrogenase activities for a final concentration of 1.8 mM. For testing only the alcohol dehydrogenase activity, 50 uL of 3-hydroxybutyraldehyde (prepared by mixing 0.6 ml acetaldehyde in 5 ml water plus catalytic base (one pellet of NaOH) Guthrie, J. P. (reference attached) was added to each well. The final concentration of 3-hydroxybutyraldehyde in each well was approximately 50 mM. The 96-deepwell plate was sealed with a plastic PCR seal and incubated at 30° C. shaking overnight (18 hours total). Because protein and cell debris form precipitates during the incubation period, the plates were centrifuged for 10 min at 4500×g, and the supernate was filtered through a Whatman 96-well filter plate (0.45 μm) prior to LC-MS analysis. Samples were analyzed for 1,3-butanediol formation.

Figure 6:
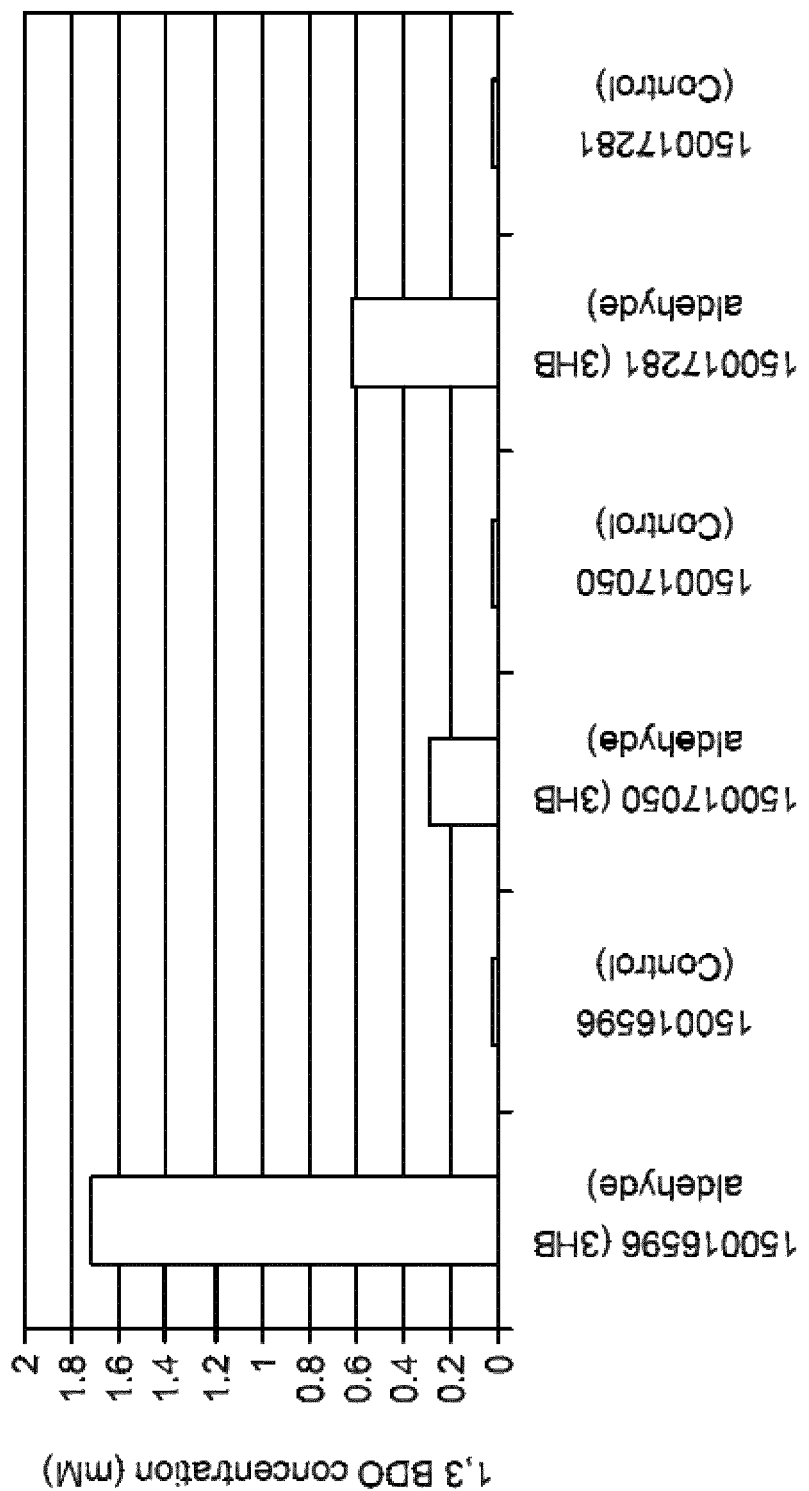
FIG. 6 shows 1,3-BDO concentrations when 3-hydroxybutyraldehyde was added as a substrate and in the control samples with no substrate. The GI numbers for the alcohol dehydrogenases are shown.

FIG. 6 shows 1,3-BDO concentrations when 3-hydroxybutyraldehyde was added as a substrate and in the control samples with no substrate. The GI numbers for the alcohol dehydrogenases are shown.

Figure 7:
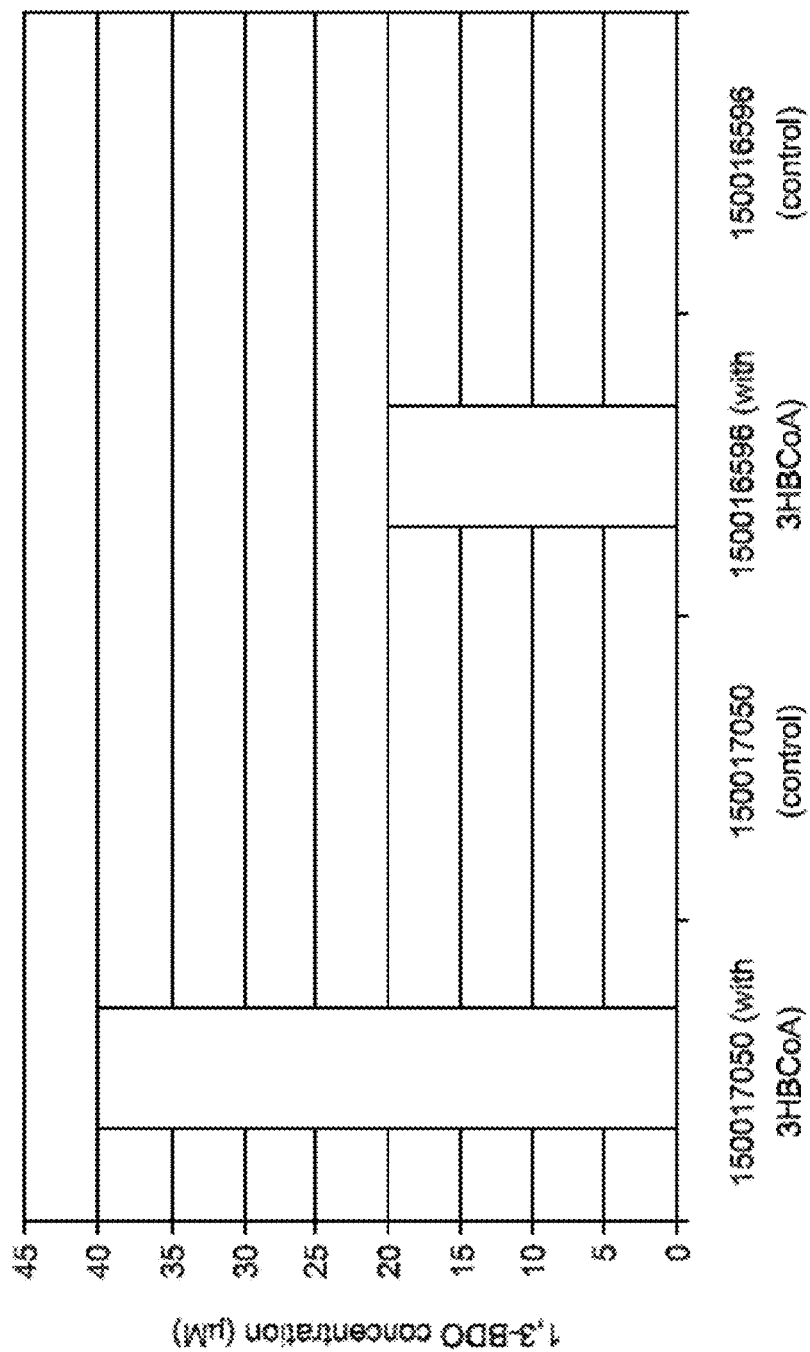
FIG. 7 shows 1,3-BDO concentrations when 3-hydroxybutyryl-CoA was added as a substrate and in the control samples with no substrate. The GI numbers for the alcohol dehydrogenases are shown. The GI number for the aldehyde dehydrogenase tested in conjunction is 163762382.

FIG. 7 shows 1,3-BDO concentrations when 3-hydroxybutyryl-CoA was added as a substrate and in the control samples with no substrate. The GI numbers for the alcohol dehydrogenases are shown. The GI number for the aldehyde dehydrogenase tested in conjunction is 163762382.

Example III 1,3-BDO Synthesis Using 4-Hydroxybutyryl-CoA as the Intermediate

This Example describes the generation of a microbial organism capable of producing 1,3-butanediol using 4-hydroxybutyryl-CoA as the precursor (Steps A, B and E in FIG. 3).

Escherichia coli is used as a target organism to engineer the pathway through Steps A, B and E in FIG. 3. E. coli provides a good host for generating a non-naturally occurring microorganism capable of producing 1,3-butanediol. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce 1,3-butanediol, nucleic acids encoding the enzymes utilized in the disclosed pathway (Steps A, B and E) as described previously, are expressed in *E. coli* using well known molecular biology techniques (see, for example, Sambrook, supra, 2001; Ausubel supra, 1999; Roberts et al., supra, 1989). A recombinant strain that has been engineered to produce significant quantities of 4-hydroxybutyryl-CoA has been described by the applicants previously (Burk et al. (US 20090075351) and will be used for inserting the proposed pathway to 1,3-butanediol.

Further, abfD (YP_3001396399.1), crt (NP_349318.1) and adhE2 (AAK09379.1) genes encoding 4-hydroxybutyryl-CoA dehydratase, crotonase and 3-hydroxybutyryl-CoA reductase (alcohol forming) activities respectively, are cloned into the pZE13 vector (Expressys, Ruelzheim, Germany) under the PA1/lacO promoter. The plasmid is transformed into the recombinant *E. coli* strain producing 4-hydroxybutyryl-CoA to express the proteins and enzymes required for 1,3-butanediol synthesis from this metabolite.

The resulting genetically engineered organism is cultured in glucose containing medium following procedures well known in the art (see, for example, Sambrook et al., supra, 2001). The expression of the pathway genes is corroborated using methods well known in the art for determining polypeptide expression or enzymatic activity, including, for example, Northern blots, PCR amplification of mRNA, immunoblotting. Enzymatic activities of the expressed enzymes are confirmed using assays specific for the individually activities. The ability of the engineered *E. coli* strain to produce 1,3-butanediol is confirmed using HPLC, gas chromatography-mass spectrometry (GCMS) or liquid chromatography-mass spectrometry (LCMS).

Microbial strains engineered to have a functional 1,3-butanediol synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of 1,3-butanediol. One modeling method is the bilevel optimization approach, OptKnock (Burgard et al., Biotechnol. Bioengineer. 84:647-657 (2003)), which is applied to select gene knockouts that collectively result in better production of 1,3-butanediol. Adaptive evolution also can be used to generate better producers of, for example, the acetyl-CoA intermediate or the 1,3-butanediol product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the 1,3-butanediol producer to further increase production.

For large-scale production of 1,3-butanediol, the recombinant organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as H2SO4. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids (Lin et al., Biotechnol Bioeng. 90:775-779 (2005)).

Example IV

Exemplary Hydrogenase and CO Dehydrogenase Enzymes for Extracting Reducing Equivalents from Syngas and Exemplary Reductive TCA Cycle Enzymes Enzymes of the reductive TCA cycle useful in the non-naturally occurring microbial organisms of the present invention include one or more of ATP-citrate lyase and three CO2-fixing enzymes: isocitrate dehydrogenase, alpha-ketoglutarate:ferredoxin oxidoreductase, pyruvate:ferredoxin oxidoreductase. The presence of ATP-citrate lyase or citrate lyase and alpha-ketoglutarate:ferredoxin oxidoreductase indicates the presence of an active reductive TCA cycle in an organism. Enzymes for each step of the reductive TCA cycle are shown below.

ATP-citrate lyase (ACL, EC 2.3.3.8), also called ATP citrate synthase, catalyzes the ATP-dependent cleavage of citrate to oxaloacetate and acetyl-CoA. ACL is an enzyme of the RTCA cycle that has been studied in green sulfur bacteria *Chlorobium limicola* and *Chlorobium tepidum*. The alpha(4)beta(4) heteromeric enzyme from *Chlorobium limicola* was cloned and characterized in *E. coli* (Kanao et al., Eur. J. Biochem. 269:3409-3416 (2002). The *C. limicola* enzyme, encoded by aclAB, is irreversible and activity of the enzyme is regulated by the ratio of ADP/ATP. A recombinant ACL from *Chlorobium tepidum* was also expressed in *E. coli* and the holoenzyme was reconstituted in vitro, in a study elucidating the role of the alpha and beta subunits in the catalytic mechanism (Kim and Tabita, J. Bacteriol. 188: 6544-6552 (2006). ACL enzymes have also been identified in *Balnearium lithotrophicum*, *Sulfurihydrogenibium subterraneum* and other members of the bacterial phylum Aquificae (Hugler et al., Environ. Microbiol. 9:81-92 (2007)). This activity has been reported in some fungi as well. Exemplary organisms include *Sordaria macrospora* (Nowrousian et al., Curr. Genet. 37:189-93 (2000), *Aspergillus nidulans*, *Yarrowia lipolytica* (Hynes and Murray, Eukaryotic Cell, July: 1039-1048, (2010) and *Aspergillus niger* (Meijer et al. J. Ind. Microbiol. Biotechnol. 36:1275-1280 (2009). Other candidates can be found based on sequence homology. Information related to these enzymes is tabulated below:

TABLE 77

| Protein | GenBank ID | GI Number | Organism |
|---|---|---|---|
| aclA | BAB21376.1 | 12407237 | Chlorobium limicola |
| aclB | BAB21375.1 | 12407235 | Chlorobium limicola |
| aclA | AAM72321.1 | 21647054 | Chlorobium tepidum |
| aclB | AAM72322.1 | 21647055 | Chlorobium tepidum |
| aclA | ABI50076.1 | 114054981 | Balnearium lithotrophicum |
| aclB | ABI50075.1 | 114054980 | Balnearium lithotrophicum |
| aclA | ABI50085.1 | 114055040 | Sulfurihydrogenibium subterraneum |
| aclB | ABI50084.1 | 114055039 | Sulfurihydrogenibium subterraneum |
| aclA | AAX76834.1 | 62199504 | Sulfurimonas denitrificans |
| aclB | AAX76835.1 | 62199506 | Sulfurimonas denitrificans |
| acl1 | XP_504787.1 | 50554757 | Yarrowia lipolytica |
| acl2 | XP_503231.1 | 50551515 | Yarrowia lipolytica |
| SPBC1703.07 | NP_596202.1 | 19112994 | Schizosaccharomyces pombe |
| SPAC22A12.16 | NP_593246.1 | 19114158 | Schizosaccharomyces pombe |
| acl1 | CAB76165.1 | 7160185 | Sordaria macrospora |
| acl2 | CAB76164.1 | 7160184 | Sordaria macrospora |
| aclA | CBF86850.1 | 259487849 | Aspergillus nidulans |
| aclB | CBF86848 | 259487848 | Aspergillus nidulans |

In some organisms the conversion of citrate to oxaloacetate and acetyl-CoA proceeds through a citryl-CoA intermediate and is catalyzed by two separate enzymes, citryl-CoA synthetase (EC 6.2.1.18) and citryl-CoA lyase (EC 4.1.3.34) (Aoshima, M., Appl. Microbiol. Biotechnol. 75:249-255 (2007). Citryl-CoA synthetase catalyzes the activation of citrate to citryl-CoA. The *Hydrogenobacter thermophilus* enzyme is composed of large and small subunits encoded by ccsA and ccsB, respectively (Aoshima et al., Mol. Micrbiol. 52:751-761 (2004)). The citryl-CoA synthetase of *Aquifex aeolicus* is composed of alpha and beta subunits encoded by sucC1 and sucD1 (Hugler et al., Environ. Microbiol. 9:81-92 (2007)). Citryl-CoA lyase splits citryl-CoA into oxaloacetate and acetyl-CoA. This enzyme is a homotrimer encoded by ccl in *Hydrogenobacter thermophilus* (Aoshima et al., Mol. Microbiol. 52:763-770 (2004)) and aq_150 in *Aquifex aeolicus* (Hugler et al., supra (2007)). The genes for this mechanism of converting citrate to oxaloacetate and citryl-CoA have also been reported recently in *Chlorobium tepidum* (Eisen et al., PNAS 99(14): 9509-14 (2002).

TABLE 78

| Protein | GenBank ID | GI Number | Organism |
|---|---|---|---|
| ccsA | BAD17844.1 | 46849514 | Hydrogenobacter thermophilus |
| ccsB | BAD17846.1 | 46849517 | Hydrogenobacter thermophilus |
| sucC1 | AAC07285 | 2983723 | Aquifex aeolicus |
| sucD1 | AAC07686 | 2984152 | Aquifex aeolicus |
| ccl | BAD17841.1 | 46849510 | Hydrogenobacter thermophilus |
| aq_150 | AAC06486 | 2982866 | Aquifex aeolicus |
| CT0380 | NP_661284 | 21673219 | Chlorobium tepidum |
| CT0269 | NP_661173.1 | 21673108 | Chlorobium tepidum |
| CT1834 | AAM73055.1 | 21647851 | Chlorobium tepidum |

Oxaloacetate is converted into malate by malate dehydrogenase (EC 1.1.1.37), an enzyme which functions in both the forward and reverse direction. *S. cerevisiae* possesses three copies of malate dehydrogenase, MDH1 (McAlister-Henn and Thompson, *J. Bacteriol.* 169:5157-5166 (1987), MDH2 (Minard and McAlister-Henn, *Mol. Cell. Biol.* 11:370-380 (1991); Gibson and McAlister-Henn, *J. Biol. Chem.* 278:25628-25636 (2003)), and MDH3 (Steffan and McAlister-Henn, *J. Biol. Chem.* 267:24708-24715 (1992)), which localize to the mitochondrion, cytosol, and peroxisome, respectively. *E. coli* is known to have an active malate dehydrogenase encoded by mdh.

TABLE 79

| Protein | GenBank ID | GI Number | Organism |
|---|---|---|---|
| MDH1 | NP_012838 | 6322765 | Saccharomyces cerevisiae |
| MDH2 | NP_014515 | 116006499 | Saccharomyces cerevisiae |
| MDH3 | NP_010205 | 6320125 | Saccharomyces cerevisiae |
| Mdh | NP_417703.1 | 16131126 | Escherichia coli |

Fumarate hydratase (EC 4.2.1.2) catalyzes the reversible hydration of fumarate to malate. The three fumarases of *E. coli*, encoded by fumA, fumB and fumC, are regulated under different conditions of oxygen availability. FumB is oxygen sensitive and is active under anaerobic conditions. FumA is active under microanaerobic conditions, and FumC is active under aerobic growth conditions (Tseng et al., *J. Bacteriol.* 183:461-467 (2001); Woods et al., *Biochim. Biophys. Acta* 954:14-26 (1988); Guest et al., *J. Gen. Microbiol.* 131:2971-2984 (1985)). *S. cerevisiae* contains one copy of a fumarase-encoding gene, FUM1, whose product localizes to both the cytosol and mitochondrion (Sass et al., *J. Biol. Chem.* 278:45109-45116 (2003)). Additional fumarase enzymes are found in *Campylobacter jejuni* (Smith et al., *Int. J. Biochem. Cell. Biol.* 31:961-975 (1999)), *Thermus thermophilus* (Mizobata et al., *Arch. Biochem. Biophys.* 355:49-55 (1998)) and *Rattus norvegicus* (Kobayashi et al., *J. Biochem.* 89:1923-1931 (1981)). Similar enzymes with high sequence homology include fum1 from *Arabidopsis thaliana* and fumC from *Corynebacterium glutamicum*. The MmcBC fumarase from *Pelotomaculum thermopropionicum* is another class of fumarase with two subunits (Shimoyama et al., *FEMS Microbiol. Lett.* 270:207-213 (2007)).

TABLE 80

| Protein | GenBank ID | GI Number | Organism |
|---|---|---|---|
| fumA | NP_416129.1 | 16129570 | Escherichia coli |
| fumB | NP_418546.1 | 16131948 | Escherichia coli |
| fumC | NP_416128.1 | 16129569 | Escherichia coli |
| FUM1 | NP_015061 | 6324993 | Saccharomyces cerevisiae |
| fumC | Q8NRN8.1 | 39931596 | Corynebacterium glutamicum |
| fumC | O69294.1 | 9789756 | Campylobacter jejuni |
| fumC | P84127 | 75427690 | Thermus thermophilus |
| fumH | P14408.1 | 120605 | Rattus norvegicus |
| MmcB | YP_001211906 | 147677691 | Pelotomaculum thermopropionicum |
| MmcC | YP_001211907 | 147677692 | Pelotomaculum thermopropionicum |

Fumarate reductase catalyzes the reduction of fumarate to succinate. The fumarate reductase of *E. coli*, composed of four subunits encoded by frdABCD, is membrane-bound and active under anaerobic conditions. The electron donor for this reaction is menaquinone and the two protons produced in this reaction do not contribute to the proton gradient (Iverson et al., *Science* 284:1961-1966 (1999)). The yeast genome encodes two soluble fumarate reductase isozymes encoded by FRDS1 (Enomoto et al., *DNA Res.* 3:263-267 (1996)) and FRDS2 (Muratsubaki et al., *Arch. Biochem. Biophys.* 352:175-181 (1998)), which localize to the cytosol and promitochondrion, respectively, and are used during anaerobic growth on glucose (Arikawa et al., *FEMS Microbiol. Lett.* 165:111-116 (1998)).

TABLE 81

| Protein | GenBank ID | GI Number | Organism |
|---|---|---|---|
| FRDS1 | P32614 | 418423 | *Saccharomyces cerevisiae* |
| FRDS2 | NP_012585 | 6322511 | *Saccharomyces cerevisiae* |
| frdA | NP_418578.1 | 16131979 | *Escherichia coli* |
| frdB | NP_418577.1 | 16131978 | *Escherichia coli* |
| frdC | NP_418576.1 | 16131977 | *Escherichia coli* |
| frdD | NP_418475.1 | 16131877 | *Escherichia coli* |

The ATP-dependent acylation of succinate to succinyl-CoA is catalyzed by succinyl-CoA synthetase (EC 6.2.1.5). The product of the LSC1 and LSC2 genes of *S. cerevisiae* and the sucC and sucD genes of *E. coli* naturally form a succinyl-CoA synthetase complex that catalyzes the formation of succinyl-CoA from succinate with the concomitant consumption of one ATP, a reaction which is reversible in vivo (Buck et al., Biochemistry 24:6245-6252 (1985)). These proteins are identified below:

TABLE 82

| Protein | GenBank ID | GI Number | Organism |
|---|---|---|---|
| LSC1 | NP_014785 | 6324716 | *Saccharomyces cerevisiae* |
| LSC2 | NP_011760 | 6321683 | *Saccharomyces cerevisiae* |
| sucC | NP_415256.1 | 16128703 | *Escherichia coli* |
| sucD | AAC73823.1 | 1786949 | *Escherichia coli* |

Alpha-ketoglutarate:ferredoxin oxidoreductase (EC 1.2.7.3), also known as 2-oxoglutarate synthase or 2-oxoglutarate:ferredoxin oxidoreductase (OFOR), forms alpha-ketoglutarate from CO2 and succinyl-CoA with concurrent consumption of two reduced ferredoxin equivalents. OFOR and pyruvate:ferredoxin oxidoreductase (PFOR) are members of a diverse family of 2-oxoacid:ferredoxin (flavodoxin) oxidoreductases which utilize thiamine pyrophosphate, CoA and iron-sulfur clusters as cofactors and ferredoxin, flavodoxin and FAD as electron carriers (Adams et al., Archaea. Adv. Protein Chem. 48:101-180 (1996)). Enzymes in this class are reversible and function in the carboxylation direction in organisms that fix carbon by the RTCA cycle such as *Hydrogenobacter thermophilus*, *Desulfobacter hydrogenophilus* and *Chlorobium* species (Shiba et al. 1985; Evans et al., Proc. Natl. Acad. Sci. U.S.A. 55:92934 (1966); Buchanan, 1971). The two-subunit enzyme from *H. thermophilus*, encoded by korAB, has been cloned and expressed in *E. coli* (Yun et al., Biochem. Biophys. Res. Commun. 282:589-594 (2001)). A five subunit OFOR from the same organism with strict substrate specificity for succinyl-CoA, encoded by forDABGE, was recently identified and expressed in *E. coli* (Yun et al. 2002). The kinetics of CO2 fixation of both *H. thermophilus* OFOR enzymes have been characterized (Yamamoto et al., Extremophiles 14:79-85 (2010)). A CO2-fixing OFOR from *Chlorobium thiosulfatophilum* has been purified and characterized but the genes encoding this enzyme have not been identified to date. Enzyme candidates in *Chlorobium* species can be inferred by sequence similarity to the *H. thermophilus* genes. For example, the *Chlorobium limicola* genome encodes two similar proteins. Acetogenic bacteria such as *Moorella* thermoacetica are predicted to encode two OFOR enzymes. The enzyme encoded by Moth_0034 is predicted to function in the CO2-assimilating direction. The genes associated with this enzyme, Moth_0034 have not been experimentally validated to date but can be inferred by sequence similarity to known OFOR enzymes.

OFOR enzymes that function in the decarboxylation direction under physiological conditions can also catalyze the reverse reaction. The OFOR from the thermoacidophilic archaeon *Sulfolobus* sp. strain 7, encoded by ST2300, has been extensively studied (Zhang et al. 1996. A plasmid-based expression system has been developed for efficiently expressing this protein in *E. coli* (Fukuda et al., Eur. J. Biochem. 268:5639-5646 (2001)) and residues involved in substrate specificity were determined (Fukuda and Wakagi, Biochim. Biophys. Acta 1597:74-80 (2002)). The OFOR encoded by Ape1472/Ape1473 from *Aeropyrum pernix* str. K1 was recently cloned into *E. coli*, characterized, and found to react with 2-oxoglutarate and a broad range of 2-oxoacids (Nishizawa et al., FEBS Lett. 579:2319-2322 (2005)). Another exemplary OFOR is encoded by oorDABC in *Helicobacter pylori* (Hughes et al. 1998). An enzyme specific to alpha-ketoglutarate has been reported in *Thauera aromatics* (Dorner and Boll, J, Bacteriol. 184 (14), 3975-83 (2002). A similar enzyme can be found in *Rhodospirillum rubrum* by sequence homology. A two subunit enzyme has also been identified in *Chlorobium tepidum* (Eisen et al., PNAS 99(14): 9509-14 (2002)).

TABLE 83

| Protein | GenBank ID | GI Number | Organism |
|---|---|---|---|
| korA | BAB21494 | 12583691 | *Hydrogenobacter thermophilus* |
| korB | BAB21495 | 12583692 | *Hydrogenobacter thermophilus* |
| forD | BAB62132.1 | 14970994 | *Hydrogenobacter thermophilus* |
| forA | BAB62133.1 | 14970995 | *Hydrogenobacter thermophilus* |
| forB | BAB62134.1 | 14970996 | *Hydrogenobacter thermophilus* |
| forG | BAB62135.1 | 14970997 | *Hydrogenobacter thermophilus* |
| forE | BAB62136.1 | 14970998 | *Hydrogenobacter thermophilus* |
| Clim_0204 | ACD89303.1 | 189339900 | *Chlorobium limicola* |
| Clim_0205 | ACD89302.1 | 189339899 | *Chlorobium limicola* |
| Clim_1123 | ACD90192.1 | 189340789 | *Chlorobium limicola* |
| Clim_1124 | ACD90193.1 | 189340790 | *Chlorobium limicola* |
| Moth_1984 | YP_430825.1 | 83590816 | *Moorella thermoacetica* |
| Moth_1985 | YP_430826.1 | 83590817 | *Moorella thermoacetica* |
| Moth_0034 | YP_428917.1 | 83588908 | *Moorella thermoacetica* |
| ST2300 | NP_378302.1 | 15922633 | *Sulfolobus* sp. strain 7 |
| Ape1472 | BAA80470.1 | 5105156 | *Aeropyrum pernix* |
| Ape1473 | BAA80471.2 | 116062794 | *Aeropyrum pernix* |
| oorD | NP_207383.1 | 15645213 | *Helicobacter pylori* |
| oorA | NP_207384.1 | 15645214 | *Helicobacter pylori* |
| oorB | NP_207385.1 | 15645215 | *Helicobacter pylori* |
| oorC | NP_207386.1 | 15645216 | *Helicobacter pylori* |
| CT0163 | NP_661069.1 | 21673004 | *Chlorobium tepidum* |
| CT0162 | NP_661068.1 | 21673003 | *Chlorobium tepidum* |
| korA | CAA12243.2 | 19571179 | *Thauera aromatica* |
| korB | CAD27440.1 | 19571178 | *Thauera aromatica* |
| Rru_A2721 | YP_427805.1 | 83594053 | *Rhodospirillum rubrum* |
| Rru_A2722 | YP_427806.1 | 83594054 | *Rhodospirillum rubrum* |

Isocitrate dehydrogenase catalyzes the reversible decarboxylation of isocitrate to 2-oxoglutarate coupled to the reduction of NAD(P)$^+$. IDH enzymes in *Saccharomyces cerevisiae* and *Escherichia coli* are encoded by IDP1 and icd, respectively (Haselbeck and McAlister-Henn, J. Biol. Chem. 266:2339-2345 (1991); Nimmo, H. G., Biochem. J. 234:317-2332 (1986)). The reverse reaction in the reductive TCA cycle, the reductive carboxylation of 2-oxoglutarate to isocitrate, is favored by the NADPH-dependent $CO_2$-fixing IDH from *Chlorobium limicola* and was functionally expressed in *E. coli* (Kanao et al., Eur. J. Biochem. 269: 1926-1931 (2002)). A similar enzyme with 95% sequence identity is found in the *C. tepidum* genome in addition to some other candidates listed below.

TABLE 84

| Protein | GenBank ID | GI Number | Organism |
|---|---|---|---|
| Icd | ACI84720.1 | 209772816 | Escherichia coli |
| IDP1 | AAA34703.1 | 171749 | Saccharomyces cerevisiae |
| Idh | BAC00856.1 | 21396513 | Chlorobium limicola |
| Icd | AAM71597.1 | 21646271 | Chlorobium tepidum |
| icd | NP_952516.1 | 39996565 | Geobacter sulfurreducens |
| icd | YP_393560. | 78777245 | Sulfurimonas denitrificans |

In *H. thermophilus* the reductive carboxylation of 2-oxoglutarate to isocitrate is catalyzed by two enzymes: 2-oxoglutarate carboxylase and oxalosuccinate reductase. 2-Oxoglutarate carboxylase (EC 6.4.1.7) catalyzes the ATP-dependent carboxylation of alpha-ketoglutarate to oxalosuccinate (Aoshima and Igarashi, *Mol. Microbiol.* 62:748-759 (2006)). This enzyme is a large complex composed of two subunits. Biotinylation of the large (A) subunit is required for enzyme function (Aoshima et al., *Mol. Microbiol.* 51:791-798 (2004)). Oxalosuccinate reductase (EC 1.1.1.-) catalyzes the NAD-dependent conversion of oxalosuccinate to D-threo-isocitrate. The enzyme is a homodimer encoded by icd in *H. thermophilus*. The kinetic parameters of this enzyme indicate that the enzyme only operates in the reductive carboxylation direction in vivo, in contrast to isocitrate dehydrogenase enzymes in other organisms (Aoshima and Igarashi, *J. Bacteriol.* 190:2050-2055 (2008)). Based on sequence homology, gene candidates have also been found in *Thiobacillus denitrificans* and *Thermocrinis albus*.

TABLE 85

| Protein | GenBank ID | GI Number | Organism |
|---|---|---|---|
| cfiA | BAF34932.1 | 116234991 | Hydrogenobacter thermophilus |
| cifB | BAF34931.1 | 116234990 | Hydrogenobacter thermophilus |
| Icd | BAD02487.1 | 38602676 | Hydrogenobacter thermophilus |
| Tbd_1556 | YP_315314 | 74317574 | Thiobacillus denitrificans |
| Tbd_1555 | YP_315313 | 74317573 | Thiobacillus denitrificans |
| Tbd_0854 | YP_314612 | 74316872 | Thiobacillus denitrificans |
| Thal_0268 | YP_003473030 | 289548042 | Thermocrinis albus |
| Thal_0267 | YP_003473029 | 289548041 | Thermocrinis albus |
| Thal_0646 | YP_003473406 | 289548418 | Thermocrinis albus |

Aconitase (EC 4.2.1.3) is an iron-sulfur-containing protein catalyzing the reversible isomerization of citrate and iso-citrate via the intermediate cis-aconitate. Two aconitase enzymes are encoded in the *E. coli* genome by acnA and acnB. AcnB is the main catabolic enzyme, while AcnA is more stable and appears to be active under conditions of oxidative or acid stress (Cunningham et al., *Microbiology* 143 (Pt 12):3795-3805 (1997)). Two isozymes of aconitase in *Salmonella typhimurium* are encoded by acnA and acnB (Horswill and Escalante-Semerena, *Biochemistry* 40:4703-4713 (2001)). The *S. cerevisiae* aconitase, encoded by ACO1, is localized to the mitochondria where it participates in the TCA cycle (Gangloff et al., *Mol. Cell. Biol.* 10:3551-3561 (1990)) and the cytosol where it participates in the glyoxylate shunt (Regev-Rudzki et al., *Mol. Biol. Cell.* 16:4163-4171 (2005)).

TABLE 86

| Protein | GenBank ID | GI Number | Organism |
|---|---|---|---|
| acnA | AAC7438.1 | 1787531 | Escherichia coli |
| acnB | AAC73229.1 | 2367097 | Escherichia coli |
| HP0779 | NP_207572.1 | 15645398 | Helicobacter pylori 26695 |
| H16_B0568 | CAJ95365.1 | 113529018 | Ralstonia eutropha |
| DesfrDRAFT_3783 | ZP_07335307.1 | 303249064 | Desulfovibrio fructosovorans JJ |
| Suden_1040 (acnB) | ABB44318.1 | 78497778 | Sulfurimonas denitrificans |
| Hydth_0755 | ADO45152.1 | 308751669 | Hydrogenobacter thermophilus |
| CT0543 (acn) | AAM71785.1 | 21646475 | Chlorobium tepidum |
| Clim_2436 | YP_001944436.1 | 189347907 | Chlorobium limicola |
| Clim_0515 | ACD89607.1 | 189340204 | Chlorobium limicola |
| acnA | NP_460671.1 | 16765056 | Salmonella typhimurium |
| acnB | NP_459163.1 | 16763548 | Salmonella typhimurium |
| ACO1 | AAA34389.1 | 170982 | Saccharomyces cerevisiae |

Pyruvate:ferredoxin oxidoreductase (PFOR) catalyzes the reversible oxidation of pyruvate to form acetyl-CoA. The PFOR from *Desulfovibrio africanus* has been cloned and expressed in *E. coli* resulting in an active recombinant enzyme that was stable for several days in the presence of oxygen (Pieulle et al., *J. Bacteriol.* 179:5684-5692 (1997)). Oxygen stability is relatively uncommon in PFORs and is believed to be conferred by a 60 residue extension in the polypeptide chain of the *D. africanus* enzyme. Two cysteine residues in this enzyme form a disulfide bond that prtotects it against inactivation in the form of oxygen. This disulfide bond and the stability in the presence of oxygen has been found in other *Desulfovibrio* species also (Vita et al., Biochemistry, 47: 957-64 (2008)). The *M. thermoacetica* PFOR is also well characterized (Menon and Ragsdale, *Biochemistry* 36:8484-8494 (1997)) and was shown to have high activity in the direction of pyruvate synthesis during autotrophic growth (Furdui and Ragsdale, *J. Biol. Chem.* 275: 28494-28499 (2000)). Further, *E. coli* possesses an uncharacterized open reading frame, ydbK, encoding a protein that is 51% identical to the *M. thermoacetica* PFOR. Evidence for pyruvate oxidoreductase activity in *E. coli* has been described (Blaschkowski et al., *Eur. J. Biochem.* 123:563-569 (1982)). PFORs have also been described in other organisms, including *Rhodobacter capsulatas* (Yakunin and Hallenbeck, Biochimica et Biophysica Acta 1409 (1998) 39-49 (1998)) and *Choloboum tepidum* (Eisen et al., PNAS 99(14): 9509-14 (2002)). The five subunit PFOR from *H. thermophilus*, encoded by porEDABG, was cloned into *E. coli* and shown to function in both the decarboxylating and $CO_2$-assimilating directions (Ikeda et al. 2006; Yamamoto et al., *Extremophiles* 14:79-85 (2010)). Homologs also exist in *C. carboxidivorans* P7. Several additional PFOR enzymes are described in the following review (Ragsdale, S. W., *Chem. Rev.* 103:2333-2346 (2003)). Finally, flavodoxin reductases (e.g., fqrB from *Helicobacter pylori* or *Campylobacter jejuni*) (St Maurice et al., *J. Bacteriol.* 189:4764-4773 (2007)) or Rnf-type proteins (Seedorf et al., *Proc. Natl. Acad. Sci. U.S.A.* 105:2128-2133 (2008); and Herrmann, *J. Bacteriol* 190:784-791 (2008)) provide a means to generate NADH or NADPH from the reduced ferredoxin generated by PFOR. These proteins are identified below.

TABLE 87

| Protein | GenBank ID | GI Number | Organism |
| --- | --- | --- | --- |
| DesfrDRAFT_0121 | ZP_07331646.1 | 303245362 | Desulfovibrio fructosovorans JJ |
| Por | CAA70873.1 | 1770208 | Desulfovibrio africanus |
| por | YP_012236.1 | 46581428 | Desulfovibrio vulgaris str. Hildenborough |
| Dde_3237 | ABB40031.1 | 78220682 | DesulfoVibrio desulfuricans G20 |
| Ddes_0298 | YP_002478891.1 | 220903579 | Desulfovibrio desulfuricans subsp. desulfuricans str. ATCC 27774 |
| Por | YP_428946.1 | 83588937 | Moorella thermoacetica |
| YdbK | NP_415896.1 | 16129339 | Escherichia coli |
| nifJ (CT1628) | NP_662511.1 | 21674446 | Chlorobium tepidum |
| CJE1649 | YP_179630.1 | 57238499 | Campylobacter jejuni |
| nifJ | ADE85473.1 | 294476085 | Rhodobacter capsulatus |
| porE | BAA95603.1 | 7768912 | Hydrogenobacter thermophilus |
| porD | BAA95604.1 | 7768913 | Hydrogenobacter thermophilus |
| porA | BAA95605.1 | 7768914 | Hydrogenobacter thermophilus |
| porB | BAA95606.1 | 776891 | Hydrogenobacter thermophilus |
| porG | BAA95607.1 | 7768916 | Hydrogenobacter thermophilus |
| FqrB | YP_001482096.1 | 157414840 | Campylobacter jejuni |
| HP1164 | NP_207955.1 | 15645778 | Helicobacter pylori |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |

The conversion of pyruvate into acetyl-CoA can be catalyzed by several other enzymes or their combinations thereof. For example, pyruvate dehydrogenase can transform pyruvate into acetyl-CoA with the concomitant reduction of a molecule of NAD into NADH. It is a multi-enzyme complex that catalyzes a series of partial reactions which results in acylating oxidative decarboxylation of pyruvate. The enzyme comprises of three subunits: the pyruvate decarboxylase (E1), dihydrolipoamide acyltransferase (E2) and dihydrolipoamide dehydrogenase (E3). This enzyme is naturally present in several organisms, including E. coli and S. cerevisiae. In the E. coli enzyme, specific residues in the E1 component are responsible for substrate specificity (Bisswanger, H., J. Biol. Chem. 256:815-82 (1981); Bremer, J., Eur. J. Biochem. 8:535-540 (1969); Gong et al., J. Biol. Chem. 275:13645-13653 (2000)). Enzyme engineering efforts have improved the E. coli PDH enzyme activity under anaerobic conditions (Kim et al., J. Bacteriol. 190: 3851-3858 (2008); Kim et al., Appl. Environ. Microbiol. 73:1766-1771 (2007); Zhou et al., Biotechnol. Lett. 30:335-342 (2008)). In contrast to the E. coli PDH, the B. subtilis complex is active and required for growth under anaerobic conditions (Nakano et al., J. Bacteriol. 179:6749-6755 (1997)). The Klebsiella pneumoniae PDH, characterized during growth on glycerol, is also active under anaerobic conditions (5). Crystal structures of the enzyme complex from bovine kidney (18) and the E2 catalytic domain from Azotobacter vinelandii are available (4). Yet another enzyme that can catalyze this conversion is pyruvate formate lyase. This enzyme catalyzes the conversion of pyruvate and CoA into acetyl-CoA and formate. Pyruvate formate lyase is a common enzyme in prokaryotic organisms that is used to help modulate anaerobic redox balance. Exemplary enzymes can be found in Escherichia coli encoded by pflB (Knappe and Sawers, FEMS. Microbiol Rev. 6:383-398 (1990)), Lactococcus lactis (Melchiorsen et al., Appl Microbiol Biotechnol 58:338-344 (2002)), and Streptococcus mutans (Takahashi-Abbe et al., Oral. Microbiol Immunol. 18:293-297 (2003)). E. coli possesses an additional pyruvate formate lyase, encoded by tdcE, that catalyzes the conversion of pyruvate or 2-oxobutanoate to acetyl-CoA or propionyl-CoA, respectively (Hesslinger et al., Mol. Microbiol 27:477-492 (1998)). Both pflB and tdcE from E. coli require the presence of pyruvate formate lyase activating enzyme, encoded by pflA. Further, a short protein encoded by yfiD in E. coli can associate with and restore activity to oxygen-cleaved pyruvate formate lyase (Vey et al., Proc. Natl. Acad. Sci. U.S.A. 105:16137-16141 (2008). Note that pflA and pflB from E. coli were expressed in S. cerevisiae as a means to increase cytosolic acetyl-CoA for butanol production as described in WO/2008/080124]. Additional pyruvate formate lyase and activating enzyme candidates, encoded by pfl and act, respectively, are found in Clostridium pasteurianum (Weidner et al., J Bacteriol. 178:2440-2444 (1996)).

Further, different enzymes can be used in combination to convert pyruvate into acetyl-CoA. For example, in S. cerevisiae, acetyl-CoA is obtained in the cytosol by first decarboxylating pyruvate to form acetaldehyde; the latter is oxidized to acetate by acetaldehyde dehydrogenase and subsequently activated to form acetyl-CoA by acetyl-CoA synthetase. Acetyl-CoA synthetase is a native enzyme in several other organisms including E. coli (Kumari et al., J. Bacteriol. 177:2878-2886 (1995)), Salmonella enterica (Starai et al., Microbiology 151:3793-3801 (2005); Starai et al., J. Biol. Chem. 280:26200-26205 (2005)), and Moorella thermoacetica (described already). Alternatively, acetate can be activated to form acetyl-CoA by acetate kinase and phosphotransacetylase. Acetate kinase first converts acetate into acetyl-phosphate with the accompanying use of an ATP molecule. Acetyl-phosphate and CoA are next converted into acetyl-CoA with the release of one phosphate by phosphotransacetylase. Both acetate kinase and phosphotransacetylase are well-studied enzymes in several Clostridia and Methanosarcina thermophila.

Yet another way of converting pyruvate to acetyl-CoA is via pyruvate oxidase. Pyruvate oxidase converts pyruvate into acetate, using ubiquione as the electron acceptor. In E. coli, this activity is encoded by poxB. PoxB has similarity to pyruvate decarboxylase of S. cerevisiae and Zymomonas mobilis. The enzyme has a thiamin pyrophosphate cofactor (Koland and Gennis, Biochemistry 21:4438-4442 (1982)); O'Brien et al., Biochemistry 16:3105-3109 (1977); O'Brien and Gennis, J. Biol. Chem. 255:3302-3307 (1980)) and a flavin adenine dinucleotide (FAD) cofactor. Acetate can then be converted into acetyl-CoA by either acetyl-CoA synthetase or by acetate kinase and phosphotransacetylase, as described earlier. Some of these enzymes can also catalyze the reverse reaction from acetyl-CoA to pyruvate.

For enzymes that use reducing equivalents in the form of NADH or NADPH, these reduced carriers can be generated by transferring electrons from reduced ferredoxin. Two enzymes catalyze the reversible transfer of electrons from reduced ferredoxins to NAD(P)+, ferredoxin:NAD+ oxidoreductase (EC 1.18.1.3) and ferredoxin:NADP+ oxidoreductase (FNR, EC 1.18.1.2). Ferredoxin:NADP+ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., Eur. J. Biochem. 123:563-569 (1982); Fujii et al., 1977). The *Helicobacter pylori* FNR, encoded by HP1164 (fqrB), is coupled to the activity of pyruvate:ferredoxin oxidoreductase (PFOR) resulting in the pyruvate-dependent production of NADPH (St et al. 2007). An analogous enzyme is found in *Campylobacter jejuni* (St et al. 2007). A ferredoxin:NADP+ oxidoreductase enzyme is encoded in the *E. coli* genome by fpr (Bianchi et al. 1993). Ferredoxin:NAD+ oxidoreductase utilizes reduced ferredoxin to generate NADH from NAD+. In several organisms, including *E. coli*, this enzyme is a component of multifunctional dioxygenase enzyme complexes. The ferredoxin:NAD+ oxidoreductase of *E. coli*, encoded by hcaD, is a component of the 3-phenylproppionate dioxygenase system involved in involved in aromatic acid utilization (Diaz et al. 1998). NADH:ferredoxin reductase activity was detected in cell extracts of *Hydrogenobacter thermophilus* strain TK-6, although a gene with this activity has not yet been indicated (Yoon et al. 2006). NADP oxidoreductase of *C. kluyveri*, encoded by nfnAB, catalyzes the concomitant reduction of ferredoxin and NAD+ with two equivalents of NADPH (Wang et al, J Bacteriol 192: 5115-5123 (2010)). Finally, the energy-conserving membrane-associated Rnf-type proteins (Seedorf et al., Proc. Natl. Acad. Sci. U.S.A. 105:2128-2133 (2008); Herrmann et al., J. Bacteriol. 190:784-791 (2008)) provide a means to generate NADH or NADPH from reduced ferredoxin. Additional ferredoxin:NAD(P)+ oxidoreductases have been annotated in *Clostridium carboxydivorans* P7 and *Clostridium ljungdahli*.

TABLE 88

| Protein | GenBank ID | GI Number | Organism |
|---|---|---|---|
| HP1164 | NP_207955.1 | 15645778 | Helicobacter pylori |
| RPA3954 | CAE29395.1 | 39650872 | Rhodopseudomonas palustris |
| fpr | BAH29712.1 | 225320633 | Hydrogenobacter thermophilus |
| yumC | NP_391091.2 | 255767736 | Bacillus subtilis |
| CJE0663 | AAW35824.1 | 57167045 | Campylobacter jejuni |
| fpr | P28861.4 | 399486 | Escherichia coli |
| hcaD | AAC75595.1 | 1788892 | Escherichia coli |
| LOC100282643 | NP_001149023.1 | 226497434 | Zea mays |
| NfnA | YP_001393861.1 | 153953096 | Clostridium kluyveri |
| NfnB | YP_001393862.1 | 153953097 | Clostridium kluyveri |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |
| CcarbDRAFT_2639 | ZP_05392639.1 | 255525707 | Clostridium carboxidivorans P7 |
| CcarbDRAFT_2638 | ZP_05392638.1 | 255525706 | Clostridium carboxidivorans P7 |
| CcarbDRAFT_2636 | ZP_05392636.1 | 255525704 | Clostridium carboxidivorans P7 |
| CcarbDRAFT_5060 | ZP_05395060.1 | 255528241 | Clostridium carboxidivorans P7 |
| CcarbDRAFT_2450 | ZP_05392450.1 | 255525514 | Clostridium carboxidivorans P7 |
| CcarbDRAFT_1084 | ZP_05391084.1 | 255524124 | Clostridium carboxidivorans P7 |
| CLJU_c11410 (RnfB) | ADK14209.1 | 300434442 | Clostridium ljungdahli |
| CLJU_c11400 (RnfA) | ADK14208.1 | 300434441 | Clostridium ljungdahli |
| CLJU_c11390 (RnfE) | ADK14207.1 | 300434440 | Clostridium ljungdahli |
| CLJU_c11380 (RnfG) | ADK14206.1 | 300434439 | Clostridium ljungdahli |
| CLJU_c11370 (RnfD) | ADK14205.1 | 300434438 | Clostridium ljungdahli |
| CLJU_c11360 (RnfC) | ADK14204.1 | 300434437 | Clostridium ljungdahli |

Ferredoxins are small acidic proteins containing one or more iron-sulfur clusters that function as intracellular electron carriers with a low reduction potential. Reduced ferredoxins donate electrons to Fe-dependent enzymes such as ferredoxin-NADP+ oxidoreductase, pyruvate:ferredoxin oxidoreductase (PFOR) and 2-oxoglutarate:ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., Extremophiles 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, 1999). Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thermoacetica, Clostridium carboxidivorans P7, Clostridium ljungdahli* and *Rhodospirillum rubrum* are predicted to encode several ferredoxins, listed in the table below.

Succinyl-CoA transferase catalyzes the conversion of succinyl-CoA to succinate while transferring the CoA moiety to a CoA acceptor molecule. Many transferases have broad specificity and can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, and butyrate, among others.

The conversion of succinate to succinyl-CoA can be carried by a transferase which does not require the direct consumption of an ATP or GTP. This type of reaction is common in a number of organisms. The conversion of succinate to succinyl-CoA can also be catalyzed by succinyl-CoA:Acetyl-CoA transferase. The gene product of cat1 of *Clostridium kluyveri* has been shown to exhibit succinyl-CoA: acetyl-CoA transferase activity (Sohling and Gottschalk, J. Bacteriol. 178:871-880 (1996)). In addition, the activity is present in *Trichomonas vaginalis* (van Grinsven et al. 2008) and *Trypanosoma brucei* (Riviere et al. 2004). The succinyl-CoA:acetate CoA-transferase from *Acetobacter aceti*, encoded by aarC, replaces succinyl-CoA synthetase in a variant TCA cycle (Mullins et al. 2008). Similar succinyl-CoA transferase activities are also present

TABLE 89

| Protein | GenBank ID | GI Number | Organism |
|---|---|---|---|
| fdx1 | BAE02673.1 | 68163284 | *Hydrogenobacter thermophilus* |
| M11214.1 | AAA83524.1 | 144806 | *Clostridium pasteurianum* |
| Zfx | AAY79867.1 | 68566938 | *Sulfolobus acidocalarius* |
| Fdx | AAC75578.1 | 1788874 | *Escherichia coli* |
| hp_0277 | AAD07340.1 | 2313367 | *Helicobacter pylori* |
| fdxA | CAL34484.1 | 112359698 | *Campylobacter jejuni* |
| Moth_0061 | ABC18400.1 | 83571848 | *Moorella thermoacetica* |
| Moth_1200 | ABC19514.1 | 83572962 | *Moorella thermoacetica* |
| Moth_1888 | ABC20188.1 | 83573636 | *Moorella thermoacetica* |
| Moth_2112 | ABC20404.1 | 83573852 | *Moorella thermoacetica* |
| Moth_1037 | ABC19351.1 | 83572799 | *Moorella thermoacetica* |
| CcarbDRAFT_4383 | ZP_05394383.1 | 255527515 | *Clostridium carboxidivorans P7* |
| CcarbDRAFT_2958 | ZP_05392958.1 | 255526034 | *Clostridium carboxidivorans P7* |
| CcarbDRAFT_2281 | ZP_05392281.1 | 255525342 | *Clostridium carboxidivorans P7* |
| CcarbDRAFT_5296 | ZP_05395295.1 | 255528511 | *Clostridium carboxidivorans P7* |
| CcarbDRAFT_1615 | ZP_05391615.1 | 255524662 | *Clostridium carboxidivorans P7* |
| CcarbDRAFT_1304 | ZP_05391304.1 | 255524347 | *Clostridium carboxidivorans P7* |
| cooF | AAG29808.1 | 11095245 | *Carboxydothermus hydrogenoformans* |
| fdxN | CAA35699.1 | 46143 | *Rhodobacter capsulatus* |
| Rru_A2264 | ABC23064.1 | 83576513 | *Rhodospirillum rubrum* |
| Rru_A1916 | ABC22716.1 | 83576165 | *Rhodospirillum rubrum* |
| Rru_A2026 | ABC22826.1 | 83576275 | *Rhodospirillum rubrum* |
| cooF | AAC45122.1 | 1498747 | *Rhodospirillum rubrum* |
| fdxN | AAA26460.1 | 152605 | *Rhodospirillum rubrum* |
| Alvin_2884 | ADC63789.1 | 288897953 | *Allochromatium vinosum* DSM 180 |
| fdx | YP_002801146.1 | 226946073 | *Azotobacter vinelandii* DJ |
| CKL_3790 | YP_001397146.1 | 153956381 | *Clostridium kluyveri* DSM 555 |
| fer1 | NP_949965.1 | 39937689 | *Rhodopseudomonas palustris* CGA009 |
| fdx | CAA12251.1 | 3724172 | *Thauera aromatica* |
| CHY_2405 | YP_361202.1 | 78044690 | *Carboxydothermus hydrogenoformans* |
| fer | YP_359966.1 | 78045103 | *Carboxydothermus hydrogenoformans* |
| fer | AAC83945.1 | 1146198 | *Bacillus subtilis* |
| fdx1 | NP_249053.1 | 15595559 | *Pseudomonas aeruginosa* PA01 |
| yfhL | AP_003148.1 | 89109368 | *Escherichia coli* K-12 |
| CLJU_c00930 | ADK13195.1 | 300433428 | *Clostridium ljungdahli* |
| CLJU_c00010 | ADK13115.1 | 300433348 | *Clostridium ljungdahli* |
| CLJU_c01820 | ADK13272.1 | 300433505 | *Clostridium ljungdahli* |
| CLJU_c17980 | ADK14861.1 | 300435094 | *Clostridium ljungdahli* |
| CLJU_c17970 | ADK14860.1 | 300435093 | *Clostridium ljungdahli* |
| CLJU_c22510 | ADK15311.1 | 300435544 | *Clostridium ljungdahli* |
| CLJU_c26680 | ADK15726.1 | 300435959 | *Clostridium ljungdahli* |
| CLJU_c29400 | ADK15988.1 | 300436221 | *Clostridium ljungdahli* | in *Trichomonas vaginalis* (van Grinsven et al. 2008), *Trypanosoma brucei* (Riviere et al. 2004) and *Clostridium kluyveri* (Sohling and Gottschalk, 1996c). The beta-ketoadipate:succinyl-CoA transferase encoded by pcaI and pcaJ in *Pseudomonas putida* is yet another candidate (Kaschabek et al. 2002). The aforementioned proteins are identified below.

TABLE 90

| Protein | GenBank ID | GI Number | Organism |
| --- | --- | --- | --- |
| cat1 | P38946.1 | 729048 | *Clostridium kluyveri* |
| TVAG_395550 | XP_001330176 | 123975034 | *Trichomonas vaginalis* G3 |
| Tb11.02.0290 | XP_828352 | 71754875 | *Trypanosoma brucei* |
| pcaI | AAN69545.1 | 24985644 | *Pseudomonas putida* |
| pcaJ | NP_746082.1 | 26990657 | *Pseudomonas putida* |
| aarC | ACD85596.1 | 189233555 | *Acetobacter aceti* |

An additional exemplary transferase that converts succinate to succinyl-CoA while converting a 3-ketoacyl-CoA to a 3-ketoacid is succinyl-CoA:3:ketoacid-CoA transferase (EC 2.8.3.5). Exemplary succinyl-CoA:3:ketoacid-CoA transferases are present in *Helicobacter pylori* (Corthesy-Theulaz et al. 1997), *Bacillus subtilis*, and *Homo sapiens* (Fukao et al. 2000; Tanaka et al. 2002). The aforementioned proteins are identified below.

TABLE 91

| Protein | GenBank ID | GI Number | Organism |
| --- | --- | --- | --- |
| HPAG1_0676 | YP_627417 | 108563101 | *Helicobacter pylori* |
| HPAG1_0677 | YP_627418 | 108563102 | *Helicobacter pylori* |
| ScoA | NP_391778 | 16080950 | *Bacillus subtilis* |
| ScoB | NP_391777 | 16080949 | *Bacillus subtilis* |
| OXCT1 | NP_000427 | 4557817 | *Homo sapiens* |
| OXCT2 | NP_071403 | 11545841 | *Homo sapiens* |

Converting succinate to succinyl-CoA by succinyl-CoA:3:ketoacid-CoA transferase requires the simultaneous conversion of a 3-ketoacyl-CoA such as acetoacetyl-CoA to a 3-ketoacid such as acetoacetate. Conversion of a 3-ketoacid back to a 3-ketoacyl-CoA can be catalyzed by an acetoacetyl-CoA: acetate: CoA transferase. Acetoacetyl-CoA: acetate: CoA transferase converts acetoacetyl-CoA and acetate to acetoacetate and acetyl-CoA, or vice versa. Exemplary enzymes include the gene products of atoAD from *E. coli* (Hanai et al., Appl Environ Microbiol 73:7814-7818 (2007), ctfAB from *C. acetobutylicum* (Jojima et al., Appl Microbiol Biotechnol 77:1219-1224 (2008), and ctfAB from *Clostridium saccharoperbutylacetonicum* (Kosaka et al., *Biosci. Biotechnol Biochem.* 71:58-68 (2007)) are shown below.

TABLE 92

| Protein | GenBank ID | GI Number | Organism |
| --- | --- | --- | --- |
| AtoA | NP_416726.1 | 2492994 | *Escherichia coli* |
| AtoD | NP_416725.1 | 2492990 | *Escherichia coli* |
| CtfA | NP_149326.1 | 15004866 | *Clostridium acetobutylicum* |
| CtfB | NP_149327.1 | 15004867 | *Clostridium acetobutylicum* |
| CtfA | AAP42564.1 | 31075384 | *Clostridium saccharoperbutylacetonicum* |
| CtfB | AAP42565.1 | 31075385 | *Clostridium saccharoperbutylacetonicum* |

Yet another possible CoA acceptor is benzylsuccinate. Succinyl-CoA:(R)-Benzylsuccinate CoA-Transferase functions as part of an anaerobic degradation pathway for toluene in organisms such as *Thauera aromatics* (Leutwein and Heider, *J. Bact.* 183(14) 4288-4295 (2001)). Homologs can be found in *Azoarcus* sp. T, *Aromatoleum aromaticum* EbN1, and *Geobacter metallireducens* GS-15. The aforementioned proteins are identified below.

TABLE 93

| Protein | GenBank ID | GI Number | Organism |
| --- | --- | --- | --- |
| bbsE | AAF89840 | 9622535 | *Thauera aromatica* |
| Bbsf | AAF89841 | 9622536 | *Thauera aromatica* |
| bbsE | AAU45405.1 | 52421824 | *Azoarcus* sp. T |
| bbsF | AAU45406.1 | 52421825 | *Azoarcus* sp. T |
| bbsE | YP_158075.1 | 56476486 | *Aromatoleum aromaticum* EbN1 |
| bbsF | YP_158074.1 | 56476485 | *Aromatoleum aromaticum* EbN1 |
| Gmet_1521 | YP_384480.1 | 78222733 | *Geobacter metallireducens* GS-15 |
| Gmet_1522 | YP_384481.1 | 78222734 | *Geobacter metallireducens* GS-15 |

Additionally, ygfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae serovar*, and *Yersinia intermedia* ATCC 29909. The aforementioned proteins are identified below.

TABLE 94

| Protein | GenBank ID | GI Number | Organism |
| --- | --- | --- | --- |
| ygfH | NP_417395.1 | 16130821 | *Escherichia coli* str. K-12 substr. MG1655 |
| CIT292_04485 | ZP_03838384.1 | 227334728 | *Citrobacter youngae* ATCC 29220 |
| SARI_04582 | YP_001573497.1 | 161506385 | *Salmonella enterica* subsp. *arizonae serovar* |
| yinte0001_14430 | ZP_04635364.1 | 238791727 | *Yersinia intermedia* ATCC 29909 |

Citrate lyase (EC 4.1.3.6) catalyzes a series of reactions resulting in the cleavage of citrate to acetate and oxaloacetate. The enzyme is active under anaerobic conditions and is composed of three subunits: an acyl-carrier protein (ACP, gamma), an ACP transferase (alpha), and a acyl lyase (beta). Enzyme activation uses covalent binding and acetylation of an unusual prosthetic group, 2'-(5"-phosphoribosyl)-3-'-dephospho-CoA, which is similar in structure to acetyl-CoA. Acylation is catalyzed by CitC, a citrate lyase synthetase. Two additional proteins, CitG and CitX, are used to convert the apo enzyme into the active holo enzyme (Schneider et al., *Biochemistry* 39:9438-9450 (2000)). Wild type *E. coli* does not have citrate lyase activity; however, mutants deficient in molybdenum cofactor synthesis have an active citrate lyase (Clark, *FEMS Microbiol. Lett.* 55:245-249 (1990)). The *E. coli* enzyme is encoded by citEFD and the citrate lyase synthetase is encoded by citC (Nilekani and SivaRaman, *Biochemistry* 22:4657-4663 (1983)). The *Leuconostoc mesenteroides* citrate lyase has been cloned, characterized and expressed in *E. coli* (Bekal et al., *J. Bacteriol.* 180:647-654 (1998)). Citrate lyase enzymes have also been identified in enterobacteria that utilize citrate as a carbon and energy source, including *Salmonella typhimurium* and *Klebsiella pneumoniae* (Bott, *Arch. Microbiol.* 167: 78-88

(1997); Bott and Dimroth, *Mol. Microbiol.* 14:347-356 (1994)). The aforementioned proteins are tabulated below.

TABLE 95

| Protein | GenBank ID | GI Number | Organism |
|---|---|---|---|
| citF | AAC73716.1 | 1786832 | *Escherichia coli* |
| Cite | AAC73717.2 | 87081764 | *Escherichia coli* |
| citD | AAC73718.1 | 1786834 | *Escherichia coli* |
| citC | AAC73719.2 | 87081765 | *Escherichia coli* |
| citG | AAC73714.1 | 1786830 | *Escherichia coli* |
| citX | AAC73715.1 | 1786831 | *Escherichia coli* |
| citF | CAA71633.1 | 2842397 | *Leuconostoc mesenteroides* |
| Cite | CAA71632.1 | 2842396 | *Leuconostoc mesenteroides* |
| citD | CAA71635.1 | 2842395 | *Leuconostoc mesenteroides* |
| citC | CAA71636.1 | 3413797 | *Leuconostoc mesenteroides* |
| citG | CAA71634.1 | 2842398 | *Leuconostoc mesenteroides* |
| citX | CAA71634.1 | 2842398 | *Leuconostoc mesenteroides* |
| citF | NP_459613.1 | 16763998 | *Salmonella typhimurium* |
| cite | AAL19573.1 | 16419133 | *Salmonella typhimurium* |
| citD | NP_459064.1 | 16763449 | *Salmonella typhimurium* |
| citC | NP_459616.1 | 16764001 | *Salmonella typhimurium* |
| citG | NP_459611.1 | 16763996 | *Salmonella typhimurium* |
| citX | NP_459612.1 | 16763997 | *Salmonella typhimurium* |
| citF | CAA56217.1 | 565619 | *Klebsiella pneumoniae* |
| cite | CAA56216.1 | 565618 | *Klebsiella pneumoniae* |
| citD | CAA56215.1 | 565617 | *Klebsiella pneumoniae* |
| citC | BAH66541.1 | 238774045 | *Klebsiella pneumoniae* |
| citG | CAA56218.1 | 565620 | *Klebsiella pneumoniae* |
| citX | AAL60463.1 | 18140907 | *Klebsiella pneumoniae* |

Acetate kinase (EC 2.7.2.1) catalyzes the reversible ATP-dependent phosphorylation of acetate to acetylphosphate. Exemplary acetate kinase enzymes have been characterized in many organisms including *E. coli, Clostridium acetobutylicum* and *Methanosarcina thermophila* (Ingram-Smith et al., *J. Bacteriol.* 187:2386-2394 (2005); Fox and Roseman, *J. Biol. Chem.* 261:13487-13497 (1986); Winzer et al., *Microbioloy* 143 (Pt 10):3279-3286 (1997)). Acetate kinase activity has also been demonstrated in the gene product of *E. coli* purT (Marolewski et al., *Biochemistry* 33:2531-2537 (1994). Some butyrate kinase enzymes (EC 2.7.2.7), for example buk1 and buk2 from *Clostridium acetobutylicum*, also accept acetate as a substrate (Hartmanis, M. G., *J. Biol. Chem.* 262:617-621 (1987)).

TABLE 96

| Protein | GenBank ID | GI Number | Organism |
|---|---|---|---|
| ackA | NP_416799.1 | 16130231 | *Escherichia coli* |
| Ack | AAB18301.1 | 1491790 | *Clostridium acetobutylicum* |
| Ack | AAA72042.1 | 349834 | *Methanosarcina thermophila* |
| purT | AAC74919.1 | 1788155 | *Escherichia coli* |
| buk1 | NP_349675 | 15896326 | *Clostridium acetobutylicum* |
| buk2 | Q97II1 | 20137415 | *Clostridium acetobutylicum* |

The formation of acetyl-CoA from acetylphosphate is catalyzed by phosphotransacetylase (EC 2.3.1.8). The pta gene from *E. coli* encodes an enzyme that reversibly converts acetyl-CoA into acetyl-phosphate (Suzuki, T., *Biochim. Biophys. Acta* 191:559-569 (969)). Additional acetyltransferase enzymes have been characterized in *Bacillus subtilis* (Rado and Hoch, *Biochim. Biophys. Acta* 321:114-125 (1973), *Clostridium kluyveri* (Stadtman, E., *Methods Enzymol.* 1:5896-599 (1955), and *Thermotoga maritima* (Bock et al., *J. Bacteriol.* 181:1861-1867 (1999)). This reaction is also catalyzed by some phosphotranbutyrylase enzymes (EC 2.3.1.19) including the ptb gene products from *Clostridium acetobutylicum* (Wiesenborn et al., *App. Environ. Microbiol.* 55:317-322 (1989); Walter et al., *Gene* 134:107-111 (1993)). Additional ptb genes are found in butyrate-producing bacterium L2-50 (Louis et al., *J. Bacteriol.* 186:2099-2106 (2004) and *Bacillus megaterium* (Vazquez et al., *Curr. Microbiol.* 42:345-349 (2001).

TABLE 97

| Protein | GenBank ID | GI Number | Organism |
|---|---|---|---|
| Pta | NP_416800.1 | 71152910 | *Escherichia coli* |
| Pta | P39646 | 730415 | *Bacillus subtilis* |
| Pta | A5N801 | 146346896 | *Clostridium kluyveri* |
| Pta | Q9X0L4 | 6685776 | *Thermotoga maritima* |
| Ptb | NP_349676 | 34540484 | *Clostridium acetobutylicum* |
| Ptb | AAR19757.1 | 38425288 | butyrate-producing bacterium L2-50 |
| Ptb | CAC07932.1 | 10046659 | *Bacillus megaterium* |

The acylation of acetate to acetyl-CoA is catalyzed by enzymes with acetyl-CoA synthetase activity. Two enzymes that catalyze this reaction are AMP-forming acetyl-CoA synthetase (EC 6.2.1.1) and ADP-forming acetyl-CoA synthetase (EC 6.2.1.13). AMP-forming acetyl-CoA synthetase (ACS) is the predominant enzyme for activation of acetate to acetyl-CoA. Exemplary ACS enzymes are found in *E. coli* (Brown et al., *J. Gen. Microbiol.* 102:327-336 (1977)), *Ralstonia eutropha* (Priefert and Steinbuchel, *J. Bacteriol.* 174:6590-6599 (1992)), *Methanothermobacter thermautotrophicus* (Ingram-Smith and Smith, *Archaea* 2:95-107 (2007)), *Salmonella enterica* (Gulick et al., *Biochemistry* 42:2866-2873 (2003)) and *Saccharomyces cerevisiae* (Jogl and Tong, *Biochemistry* 43:1425-1431 (2004)). ADP-forming acetyl-CoA synthetases are reversible enzymes with a generally broad substrate range (Musfeldt and Schonheit, *J. Bacteriol.* 184:636-644 (2002)). Two isozymes of ADP-forming acetyl-CoA synthetases are encoded in the *Archaeoglobus fulgidus* genome by are encoded by AF1211 and AF1983 (Musfeldt and Schonheit, supra (2002)). The enzyme from *Haloarcula marismortui* (annotated as a succinyl-CoA synthetase) also accepts acetate as a substrate and reversibility of the enzyme was demonstrated (Brasen and Schonheit, *Arch. Microbiol.* 182:277-287 (2004)). The ACD encoded by PAE3250 from hyperthermophilic crenarchaeon *Pyrobaculum aerophilum* showed the broadest substrate range of all characterized ACDs, reacting with acetate, isobutyryl-CoA (preferred substrate) and phenylacetyl-CoA (Brasen and Schonheit, supra (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra (2004); Musfeldt and Schonheit, supra (2002)). Additional candidates include the succinyl-CoA synthetase encoded by sucCD in *E. coli* (Buck et al., *Biochemistry* 24:6245-6252 (1985)) and the acyl-CoA ligase from *Pseudomonas putida* (Fernandez-Valverde et al., *Appl. Environ. Microbiol.* 59:1149-1154 (1993)). The aforementioned proteins are tabulated below.

TABLE 98

| Protein | GenBank ID | GI Number | Organism |
|---|---|---|---|
| acs | AAC77039.1 | 1790505 | *Escherichia coli* |
| acoE | AAA21945.1 | 141890 | *Ralstonia eutropha* |
| acs1 | ABC87079.1 | 86169671 | *Methanothermobacter thermautotrophicus* |
| acs1 | AAL23099.1 | 16422835 | *Salmonella enterica* |
| ACS1 | Q01574.2 | 257050994 | *Saccharomyces cerevisiae* |

TABLE 98-continued

| Protein | GenBank ID | GI Number | Organism |
|---|---|---|---|
| AF1211 | NP_070039.1 | 11498810 | *Archaeoglobus fulgidus* |
| AF1983 | NP_070807.1 | 11499565 | *Archaeoglobus fulgidus* |
| scs | YP_135572.1 | 55377722 | *Haloarcula marismortui* |
| PAE3250 | NP_560604.1 | 18313937 | *Pyrobaculum aerophilum* str. IM2 |
| sucC | NP_415256.1 | 16128703 | *Escherichia coli* |
| sucD | AAC73823.1 | 1786949 | *Escherichia coli* |
| paaF | AAC24333.2 | 22711873 | *Pseudomonas putida* |

The product yields per C-mol of substrate of microbial cells synthesizing reduced fermentation products such as 1,3-butanediol, are limited by insufficient reducing equivalents in the carbohydrate feedstock. Reducing equivalents, or electrons, can be extracted from synthesis gas components such as CO and H2 using carbon monoxide dehydrogenase (CODH) and hydrogenase enzymes, respectively. The reducing equivalents are then passed to acceptors such as oxidized ferredoxins, oxidized quinones, oxidized cytochromes, NAD(P)+, water, or hydrogen peroxide to form reduced ferredoxin, reduced quinones, reduced cytochromes, NAD(P)H, H2, or water, respectively. Reduced ferredoxin and NAD(P)H are particularly useful as they can serve as redox carriers for various Wood-Ljungdahl pathway and reductive TCA cycle enzymes.

Here, we show specific examples of how additional redox availability from CO and/or H2 can improve the yields of reduced products such as 1,3-butanediol. The maximum theoretical yield to produce 1,3-butanediol from glucose is 1.09 mole 1,3-butanediol per mole of glucose under aerobic conditions via the pathways shown in FIG. 8B or 1.09 mole 1,3-butanediol per mole of glucose under aerobic conditions via the pathways shown in FIG. 9B. Gasification of glucose to form syngas will result in the maximum theoretical yield of 1.09 moles of 1,3-BDO per mole of glucose consumed, assuming that 6 moles of CO and 6 moles of H2 are obtained from glucose.

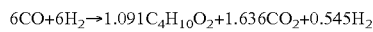

$6CO+6H_2 \rightarrow 1.091C_4H_{10}O_2+1.636CO_2+0.545H_2$

When additional reducing equivalents are provided, the yield can be improved to 2 mol/mol glucose.

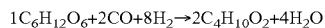

$1C_6H_{12}O_6+2CO+8H_2 \rightarrow 2C_4H_{10}O_2+4H_2O$

When both feedstocks of sugar and syngas are available, the syngas components CO and $H_2$ can be utilized together or separately (from any source) to generate reducing equivalents by employing the hydrogenase and/or CO dehydrogenase. The reducing equivalents generated from CO and/or hydrogen will be utilized to power the glucose to 1,3-butanediol production pathways. Theoretically, all carbons in glucose will be conserved, thus resulting in a maximal theoretical yield to produce 1,3-butanediol from glucose.

As shown in above example, a combined feedstock strategy where syngas is combined with a sugar-based feedstock or other carbon substrate can greatly improve the theoretical yields. In this co-feeding approach, syngas components H2 and/or CO can be utilized by the hydrogenase and CO dehydrogenase to generate reducing equivalents, that can be used to power chemical production pathways in which the carbons from sugar or other carbon substrates will be maximally conserved and the theoretical yields improved. Such improvements provide environmental and economic benefits and greatly enhance sustainable chemical production.

As shown in above example, a combined feedstock strategy where syngas is combined with a sugar-based feedstock or other carbon substrate can greatly improve the theoretical yields. In this co-feeding approach, syngas components H2 and CO can be utilized by the hydrogenase and CO dehydrogenase to generate reducing equivalents, that can be used to power chemical production pathways in which the carbons from sugar or other carbon substrates will be maximally conserved and the theoretical yields improved. In case of 1,3-butanediol production from glucose or sugar, the theoretical yields improve from 1.09 mol 1,3-butanediol per mol of glucose to 2 mol 1,3-butanediol per mol of glucose. Such improvements provide environmental and economic benefits and greatly enhance sustainable chemical production.

Herein below the enzymes and the corresponding genes used for extracting redox from syngas components are described. CODH is a reversible enzyme that interconverts CO and CO2 at the expense or gain of electrons. The natural physiological role of the CODH in ACS/CODH complexes is to convert CO2 to CO for incorporation into acetyl-CoA by acetyl-CoA synthase. Nevertheless, such CODH enzymes are suitable for the extraction of reducing equivalents from CO due to the reversible nature of such enzymes. Expressing such CODH enzymes in the absence of ACS allows them to operate in the direction opposite to their natural physiological role (i.e., CO oxidation).

In *M. thermoacetica, C. hydrogenoformans, C. carboxidivorans* P7, and several other organisms, additional CODH encoding genes are located outside of the ACS/CODH operons. These enzymes provide a means for extracting electrons (or reducing equivalents) from the conversion of carbon monoxide to carbon dioxide. The *M. thermoacetica* gene (GenBank Accession Number: YP_430813) is expressed by itself in an operon and is believed to transfer electrons from CO to an external mediator like ferredoxin in a "Ping-pong" reaction. The reduced mediator then couples to other reduced nicotinamide adenine dinucleotide phosphate (NAD(P)H) carriers or ferredoxin-dependent cellular processes (Ragsdale, *Annals of the New York Academy of Sciences* 1125: 129-136 (2008)). The genes encoding the *C. hydrogenoformans* CODH-II and CooF, a neighboring protein, were cloned and sequenced (Gonzalez and Robb, *FEMS Microbiol Lett.* 191:243-247 (2000)). The resulting complex was membrane-bound, although cytoplasmic fractions of CODH-II were shown to catalyze the formation of NADPH suggesting an anabolic role (Svetlitchnyi et al., *J Bacteriol.* 183:5134-5144 (2001)). The crystal structure of the CODH-II is also available (Dobbek et al., *Science* 293:1281-1285 (2001)). Similar ACS-free CODH enzymes can be found in a diverse array of organisms including *Geobacter metallireducens* GS-15, *Chlorobium phaeobacteroides* DSM 266, *Clostridium cellulolyticum* H10, *Desulfovibrio desulfuricans* subsp. *desulfuricans* str. ATCC 27774, *Pelobacter carbinolicus* DSM 2380, and *Campylobacter curvus* 525.92.

TABLE 99

| Protein | GenBank ID | GI Number | Organism |
|---|---|---|---|
| CODH (putative) | YP_430813 | 83590804 | Moorella thermoacetica |
| CODH-II (CooS-II) | YP_358957 | 78044574 | Carboxydothermus hydrogenoformans |
| CooF | YP_358958 | 78045112 | Carboxydothermus hydrogenoformans |
| CODH (putative) | ZP_05390164.1 | 255523193 | Clostridium carboxidivorans P7 |
| CcarbDRAFT_0341 | ZP_05390341.1 | 255523371 | Clostridium carboxidivorans P7 |
| CcarbDRAFT_1756 | ZP_05391756.1 | 255524806 | Clostridium carboxidivorans P7 |
| CcarbDRAFT_2944 | ZP_05392944.1 | 255526020 | Clostridium carboxidivorans P7 |
| CODH | YP_384856.1 | 78223109 | Geobacter metallireducens GS-15 |
| Cpha266_0148 (cytochrome c) | YP_910642.1 | 119355998 | Chlorobium phaeobacteroides DSM 266 |
| Cpha266_0149 (CODH) | YP_910643.1 | 119355999 | Chlorobium phaeobacteroides DSM 266 |
| Ccel_0438 | YP_002504800.1 | 220927891 | Clostridium cellulolyticum H10 |
| Ddes_0382 (CODH) | YP_002478973.1 | 220903661 | Desulfovibrio desulfuricans subsp. desulfuricans str. ATCC 27774 |
| Ddes_0381 (CooC) | YP_002478972.1 | 220903660 | Desulfovibrio desulfuricans subsp. desulfuricans str. ATCC 27774 |
| Pcar_0057 (CODH) | YP_355490.1 | 7791767 | Pelobacter carbinolicus DSM 2380 |
| Pcar_0058 (CooC) | YP_355491.1 | 7791766 | Pelobacter carbinolicus DSM 2380 |
| Pcar_0058 (HypA) | YP_355492.1 | 7791765 | Pelobacter carbinolicus DSM 2380 |
| CooS (CODH) | YP_001407343.1 | 154175407 | Campylobacter curvus 525.92 |
| CLJU_c09110 | ADK13979.1 | 300434212 | Clostridium ljungdahli |
| CLJU_c09100 | ADK13978.1 | 300434211 | Clostridium ljungdahli |
| CLJU_c09090 | ADK13977.1 | 300434210 | Clostridium ljungdahli |

In some cases, hydrogenase encoding genes are located adjacent to a CODH. In Rhodospirillum rubrum, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., J Bacteriol. 178:6200-6208 (1996)). The CODH-I of C. hydrogenoformans and its adjacent genes have been proposed to catalyze a similar functional role based on their similarity to the R. rubrum CODH/hydrogenase gene cluster (Wu et al., PLoS Genet. 1:e65 (2005)). The C. hydrogenoformans CODH-I was also shown to exhibit intense CO oxidation and $CO_2$ reduction activities when linked to an electrode (Parkin et al., J Am. Chem. Soc. 129:10328-10329 (2007)). The protein sequences of exemplary CODH and hydrogenase genes can be identified by the following GenBank accession numbers.

TABLE 100

| Protein | GenBank ID | GI Number | Organism |
|---|---|---|---|
| CODH-I (CooS-I) | YP_360644 | 78043418 | Carboxydothermus hydrogenoformans |
| CooF | YP_360645 | 78044791 | Carboxydothermus hydrogenoformans |
| HypA | YP_360646 | 78044340 | Carboxydothermus hydrogenoformans |
| CooH | YP_360647 | 78043871 | Carboxydothermus hydrogenoformans |
| CooU | YP_360648 | 78044023 | Carboxydothermus hydrogenoformans |
| CooX | YP_360649 | 78043124 | Carboxydothermus hydrogenoformans |
| CooL | YP_360650 | 78043938 | Carboxydothermus hydrogenoformans |
| CooK | YP_360651 | 78044700 | Carboxydothermus hydrogenoformans |
| CooM | YP_360652 | 78043942 | Carboxydothermus hydrogenoformans |

TABLE 100-continued

| Protein | GenBank ID | GI Number | Organism |
|---|---|---|---|
| CooC | YP_360654.1 | 78043296 | Carboxydothermus hydrogenoformans |
| CooA-1 | YP_360655.1 | 78044021 | Carboxydothermus hydrogenoformans |
| CooL | AAC45118 | 1515468 | Rhodospirillum rubrum |
| CooX | AAC45119 | 1515469 | Rhodospirillum rubrum |
| CooU | AAC45120 | 1515470 | Rhodospirillum rubrum |
| CooH | AAC45121 | 1498746 | Rhodospirillum rubrum |
| CooF | AAC45122 | 1498747 | Rhodospirillum rubrum |
| CODH (CooS) | AAC45123 | 1498748 | Rhodospirillum rubrum |
| CooC | AAC45124 | 1498749 | Rhodospirillum rubrum |
| CooT | AAC45125 | 1498750 | Rhodospirillum rubrum |
| CooJ | AAC45126 | 1498751 | Rhodospirillum rubrum |

Native to E. coli and other enteric bacteria are multiple genes encoding up to four hydrogenases (Sawers, G., Antonie Van Leeuwenhoek 66:57-88 (1994); Sawers et al., J Bacteriol. 164:1324-1331 (1985); Sawers and Boxer, Eur. J Biochem. 156:265-275 (1986); Sawers et al., J Bacteriol. 168:398-404 (1986)). Given the multiplicity of enzyme activities, E. coli or another host organism can provide sufficient hydrogenase activity to split incoming molecular hydrogen and reduce the corresponding acceptor. E. coli possesses two uptake hydrogenases, Hyd-1 and Hyd-2, encoded by the hyaABCDEF and hybOABCDEFG gene clusters, respectively (Lukey et al., How E. coli is equipped to oxidize hydrogen under different redox conditions, J Biol Chem published online Nov. 16, 2009). Hyd-1 is oxygen-tolerant, irreversible, and is coupled to quinone reduction via the hyaC cytochrome. Hyd-2 is sensitive to $O_2$, reversible, and transfers electrons to the periplasmic ferredoxin hybA which, in turn, reduces a quinone via the hybB integral membrane protein. Reduced quinones can serve as the source of electrons for fumarate reductase in the reductive branch of the TCA cycle. Reduced ferredoxins can be used by enzymes such as NAD(P)H:ferredoxin oxidoreductases to generate NADPH or NADH. They can alternatively be used as the electron donor for reactions such as pyruvate ferredoxin oxidoreductase, AKG ferredoxin oxidoreductase, and 5,10-methylene-H4folate reductase.

TABLE 101

| Protein | GenBank ID | GI Number | Organism |
|---|---|---|---|
| HyaA | AAC74057.1 | 1787206 | *Escherichia coli* |
| HyaB | AAC74058.1 | 1787207 | *Escherichia coli* |
| HyaC | AAC74059.1 | 1787208 | *Escherichia coli* |
| HyaD | AAC74060.1 | 1787209 | *Escherichia coli* |
| HyaE | AAC74061.1 | 1787210 | *Escherichia coli* |
| HyaF | AAC74062.1 | 1787211 | *Escherichia coli* |

TABLE 102

| Protein | GenBank ID | GI Number | Organism |
|---|---|---|---|
| HybO | AAC76033.1 | 1789371 | *Escherichia coli* |
| HybA | AAC76032.1 | 1789370 | *Escherichia coli* |
| HybB | AAC76031.1 | 2367183 | *Escherichia coli* |
| HybC | AAC76030.1 | 1789368 | *Escherichia coli* |
| HybD | AAC76029.1 | 1789367 | *Escherichia coli* |
| HybE | AAC76028.1 | 1789366 | *Escherichia coli* |
| HybF | AAC76027.1 | 1789365 | *Escherichia coli* |
| HybG | AAC76026.1 | 1789364 | *Escherichia coli* |

The hydrogen-lyase systems of *E. coli* include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. Hydrogenase 3 has been shown to be a reversible enzyme (Maeda et al., *Appl Microbiol Biotechnol* 76(5):1035-42 (2007)). Hydrogenase activity in *E. coli* is also dependent upon the expression of the hyp genes whose corresponding proteins are involved in the assembly of the hydrogenase complexes (Jacobi et al., *Arch. Microbiol* 158:444-451 (1992); Rangarajan et al., *J. Bacteriol.* 190:1447-1458 (2008)).

TABLE 103

| Protein | GenBank ID | GI Number | Organism |
|---|---|---|---|
| HycA | NP_417205 | 16130632 | *Escherichia coli* |
| HycB | NP_417204 | 16130631 | *Escherichia coli* |
| HycC | NP_417203 | 16130630 | *Escherichia coli* |
| HycD | NP_417202 | 16130629 | *Escherichia coli* |
| HycE | NP_417201 | 16130628 | *Escherichia coli* |
| HycF | NP_417200 | 16130627 | *Escherichia coli* |
| HycG | NP_417199 | 16130626 | *Escherichia coli* |
| HycH | NP_417198 | 16130625 | *Escherichia coli* |
| HycI | NP_417197 | 16130624 | *Escherichia coli* |

TABLE 104

| Protein | GenBank ID | GI Number | Organism |
|---|---|---|---|
| HyfA | NP_416976 | 90111444 | *Escherichia coli* |
| HyfB | NP_416977 | 16130407 | *Escherichia coli* |
| HyfC | NP_416978 | 90111445 | *Escherichia coli* |
| HyfD | NP_416979 | 16130409 | *Escherichia coli* |
| HyfE | NP_416980 | 16130410 | *Escherichia coli* |
| HyfF | NP_416981 | 16130411 | *Escherichia coli* |
| HyfG | NP_416982 | 16130412 | *Escherichia coli* |
| HyfH | NP_416983 | 16130413 | *Escherichia coli* |
| HyfI | NP_416984 | 16130414 | *Escherichia coli* |
| HyfJ | NP_416985 | 90111446 | *Escherichia coli* |
| HyfR | NP_416986 | 90111447 | *Escherichia coli* |

TABLE 105

| Protein | GenBank ID | GI Number | Organism |
|---|---|---|---|
| HypA | NP_417206 | 16130633 | *Escherichia coli* |
| HypB | NP_417207 | 16130634 | *Escherichia coli* |
| HypC | NP_417208 | 16130635 | *Escherichia coli* |
| HypD | NP_417209 | 16130636 | *Escherichia coli* |
| HypE | NP_417210 | 226524740 | *Escherichia coli* |
| HypF | NP_417192 | 16130619 | *Escherichia coli* |

The *M. thermoacetica* hydrogenases are suitable for a host that lacks sufficient endogenous hydrogenase activity. *M. thermoacetica* can grow with CO2 as the exclusive carbon source indicating that reducing equivalents are extracted from H2 to enable acetyl-CoA synthesis via the Wood-Ljungdahl pathway (Drake, H. L., *J. Bacteriol.* 150: 702-709 (1982); Drake and Daniel, *Res. Microbiol.* 155: 869-883 (2004); Kellum and Drake, *J. Bacteriol.* 160:466-469 (1984)). *M. thermoacetica* has homologs to several hyp, hyc, and hyf genes from *E. coli*. The protein sequences encoded for by these genes are identified by the following GenBank accession numbers.

Proteins in *M. thermoacetica* whose genes are homologous to the *E. coli* hyp genes are shown below.

TABLE 106

| Protein | GenBank ID | GI Number | Organism |
|---|---|---|---|
| Moth_2175 | YP_431007 | 83590998 | *Moorella thermoacetica* |
| Moth_2176 | YP_431008 | 83590999 | *Moorella thermoacetica* |
| Moth_2177 | YP_431009 | 83591000 | *Moorella thermoacetica* |
| Moth_2178 | YP_431010 | 83591001 | *Moorella thermoacetica* |
| Moth_2179 | YP_431011 | 83591002 | *Moorella thermoacetica* |
| Moth_2180 | YP_431012 | 83591003 | *Moorella thermoacetica* |
| Moth_2181 | YP_431013 | 83591004 | *Moorella thermoacetica* |

Proteins in *M. thermoacetica* that are homologous to the *E. coli* Hydrogenase 3 and/or 4 proteins are listed in the following table.

TABLE 107

| Protein | GenBank ID | GI Number | Organism |
|---|---|---|---|
| Moth_2182 | YP_431014 | 83591005 | *Moorella thermoacetica* |
| Moth_2183 | YP_431015 | 83591006 | *Moorella thermoacetica* |
| Moth_2184 | YP_431016 | 83591007 | *Moorella thermoacetica* |
| Moth_2185 | YP_431017 | 83591008 | *Moorella thermoacetica* |
| Moth_2186 | YP_431018 | 83591009 | *Moorella thermoacetica* |
| Moth_2187 | YP_431019 | 83591010 | *Moorella thermoacetica* |
| Moth_2188 | YP_431020 | 83591011 | *Moorella thermoacetica* |
| Moth_2189 | YP_431021 | 83591012 | *Moorella thermoacetica* |
| Moth_2190 | YP_431022 | 83591013 | *Moorella thermoacetica* |
| Moth_2191 | YP_431023 | 83591014 | *Moorella thermoacetica* |
| Moth_2192 | YP_431024 | 83591015 | *Moorella thermoacetica* |

In addition, several gene clusters encoding hydrogenase functionality are present in *M. thermoacetica* and their corresponding protein sequences are provided below.

TABLE 108A

| Protein | GenBank ID | GI Number | Organism |
|---|---|---|---|
| Moth_0439 | YP_429313 | 83589304 | *Moorella thermoacetica* |
| Moth_0440 | YP_429314 | 83589305 | *Moorella thermoacetica* |
| Moth_0441 | YP_429315 | 83589306 | *Moorella thermoacetica* |
| Moth_0442 | YP_429316 | 83589307 | *Moorella thermoacetica* |
| Moth_0809 | YP_429670 | 83589661 | *Moorella thermoacetica* |
| Moth_0810 | YP_429671 | 83589662 | *Moorella thermoacetica* |
| Moth_0811 | YP_429672 | 83589663 | *Moorella thermoacetica* |

TABLE 108A-continued

| Protein | GenBank ID | GI Number | Organism |
|---|---|---|---|
| Moth_0812 | YP_429673 | 83589664 | *Moorella thermoacetica* |
| Moth_0814 | YP_429674 | 83589665 | *Moorella thermoacetica* |
| Moth_0815 | YP_429675 | 83589666 | *Moorella thermoacetica* |
| Moth_0816 | YP_429676 | 83589667 | *Moorella thermoacetica* |
| Moth_1193 | YP_430050 | 83590041 | *Moorella thermoacetica* |
| Moth_1194 | YP_430051 | 83590042 | *Moorella thermoacetica* |
| Moth_1195 | YP_430052 | 83590043 | *Moorella thermoacetica* |
| Moth_1196 | YP_430053 | 83590044 | *Moorella thermoacetica* |
| Moth_1717 | YP_430562 | 83590553 | *Moorella thermoacetica* |
| Moth_1718 | YP_430563 | 83590554 | *Moorella thermoacetica* |
| Moth_1719 | YP_430564 | 83590555 | *Moorella thermoacetica* |
| Moth_1883 | YP_430726 | 83590717 | *Moorella thermoacetica* |
| Moth_1884 | YP_430727 | 83590718 | *Moorella thermoacetica* |
| Moth_1885 | YP_430728 | 83590719 | *Moorella thermoacetica* |
| Moth_1886 | YP_430729 | 83590720 | *Moorella thermoacetica* |
| Moth_1887 | YP_430730 | 83590721 | *Moorella thermoacetica* |
| Moth_1888 | YP_430731 | 83590722 | *Moorella thermoacetica* |
| Moth_1452 | YP_430305 | 83590296 | *Moorella thermoacetica* |
| Moth_1453 | YP_430306 | 83590297 | *Moorella thermoacetica* |
| Moth_1454 | YP_430307 | 83590298 | *Moorella thermoacetica* |

Genes encoding hydrogenase enzymes from *C. ljungdahli* are shown below.

TABLE 108B

| Protein | GenBank ID | GI Number | Organism |
|---|---|---|---|
| CLJU_c20290 | ADK15091.1 | 300435324 | *Clostridium ljungdahli* |
| CLJU_c07030 | ADK13773.1 | 300434006 | *Clostridium ljungdahli* |
| CLJU_c07040 | ADK13774.1 | 300434007 | *Clostridium ljungdahli* |
| CLJU_c07050 | ADK13775.1 | 300434008 | *Clostridium ljungdahli* |
| CLJU_c07060 | ADK13776.1 | 300434009 | *Clostridium ljungdahli* |
| CLJU_c07070 | ADK13777.1 | 300434010 | *Clostridium ljungdahli* |
| CLJU_c07080 | ADK13778.1 | 300434011 | *Clostridium ljungdahli* |
| CLJU_c14730 | ADK14541.1 | 300434774 | *Clostridium ljungdahli* |
| CLJU_c14720 | ADK14540.1 | 300434773 | *Clostridium ljungdahli* |
| CLJU_c14710 | ADK14539.1 | 300434772 | *Clostridium ljungdahli* |
| CLJU_c14700 | ADK14538.1 | 300434771 | *Clostridium ljungdahli* |
| CLJU_c28670 | ADK15915.1 | 300436148 | *Clostridium ljungdahli* |
| CLJU_c28660 | ADK15914.1 | 300436147 | *Clostridium ljungdahli* |
| CLJU_c28650 | ADK15913.1 | 300436146 | *Clostridium ljungdahli* |
| CLJU_c28640 | ADK15912.1 | 300436145 | *Clostridium ljungdahli* |

*Ralstonia eutropha* H16 uses hydrogen as an energy source with oxygen as a terminal electron acceptor. Its membrane-bound uptake [NiFe]-hydrogenase is an "O2-tolerant" hydrogenase (Cracknell, et al. Proc Nat Acad Sci, 106(49) 20681-20686 (2009)) that is periplasmically-oriented and connected to the respiratory chain via a b-type cytochrome (Schink and Schlegel, *Biochim. Biophys. Acta*, 567, 315-324 (1979); Bernhard et al., *Eur. J. Biochem.* 248, 179-186 (1997)). *R. eutropha* also contains an $O_2$-tolerant soluble hydrogenase encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132 (2005)). Soluble hydrogenase enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.*, 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased hydrogenase activity compared to expression of the Hox genes alone (Germer, *J. Biol. Chem.* 284(52), 36462-36472 (2009)).

TABLE 109

| Protein | GenBank ID | GI Number | Organism |
|---|---|---|---|
| HoxF | NP_942727.1 | 38637753 | *Ralstonia eutropha* H16 |
| HoxU | NP_942728.1 | 38637754 | *Ralstonia eutropha* H16 |
| HoxY | NP_942729.1 | 38637755 | *Ralstonia eutropha* H16 |
| HoxH | NP_942730.1 | 38637756 | *Ralstonia eutropha* H16 |
| HoxW | NP_942731.1 | 38637757 | *Ralstonia eutropha* H16 |
| HoxI | NP_942732.1 | 38637758 | *Ralstonia eutropha* H16 |
| HoxE | NP_953767.1 | 39997816 | *Geobacter sulfurreducens* |
| HoxF | NP_953766.1 | 39997815 | *Geobacter sulfurreducens* |
| HoxU | NP_953765.1 | 39997814 | *Geobacter sulfurreducens* |
| HoxY | NP_953764.1 | 39997813 | *Geobacter sulfurreducens* |
| HoxH | NP_953763.1 | 39997812 | *Geobacter sulfurreducens* |
| GSU2717 | NP_953762.1 | 39997811 | *Geobacter sulfurreducens* |
| HoxE | NP_441418.1 | 16330690 | *Synechocystis* str. PCC 6803 |
| HoxF | NP_441417.1 | 16330689 | *Synechocystis* str. PCC 6803 |
| Unknown function | NP_441416.1 | 16330688 | *Synechocystis* str. PCC 6803 |
| HoxU | NP_441415.1 | 16330687 | *Synechocystis* str. PCC 6803 |
| HoxY | NP_441414.1 | 16330686 | *Synechocystis* str. PCC 6803 |
| Unknown function | NP_441413.1 | 16330685 | *Synechocystis* str. PCC 6803 |
| Unknown function | NP_441412.1 | 16330684 | *Synechocystis* str. PCC 6803 |
| HoxH | NP_441411.1 | 16330683 | *Synechocystis* str. PCC 6803 |
| HypF | NP_484737.1 | 17228189 | *Nostoc* sp. PCC 7120 |
| HypC | NP_484738.1 | 17228190 | *Nostoc* sp. PCC 7120 |
| HypD | NP_484739.1 | 17228191 | *Nostoc* sp. PCC 7120 |
| Unknown function | NP_484740.1 | 17228192 | *Nostoc* sp. PCC 7120 |
| HypE | NP_484741.1 | 17228193 | *Nostoc* sp. PCC 7120 |
| HypA | NP_484742.1 | 17228194 | *Nostoc* sp. PCC 7120 |
| HypB | NP_484743.1 | 17228195 | *Nostoc* sp. PCC 7120 |
| Hox1E | AAP50519.1 | 37787351 | *Thiocapsa roseopersicina* |
| Hox1F | AAP50520.1 | 37787352 | *Thiocapsa roseopersicina* |
| Hox1U | AAP50521.1 | 37787353 | *Thiocapsa roseopersicina* |
| Hox1Y | AAP50522.1 | 37787354 | *Thiocapsa roseopersicina* |
| Hox1H | AAP50523.1 | 37787355 | *Thiocapsa roseopersicina* |

Several enzymes and the corresponding genes used for fixing carbon dioxide to either pyruvate or phosphoenolpyruvate to form the TCA cycle intermediates, oxaloacetate or malate are described below.

Carboxylation of phosphoenolpyruvate to oxaloacetate is catalyzed by phosphoenolpyruvate carboxylase. Exemplary PEP carboxylase enzymes are encoded by ppc in *E. coli* (Kai et al., Arch. Biochem. Biophys. 414:170-179 (2003), ppcA in *Methylobacterium extorquens* AM1 (Arps et al., J. Bacteriol. 175:3776-3783 (1993), and ppc in *Corynebacterium glutamicum* (Eikmanns et al., Mol. Gen. Genet. 218:330-339 (1989).

TABLE 110

| Protein | GenBank ID | GI Number | Organism |
|---|---|---|---|
| Ppc | NP_418391 | 16131794 | *Escherichia coli* |
| ppcA | AAB58883 | 28572162 | *Methylobacterium extorquens* |
| Ppc | ABB53270 | 80973080 | *Corynebacterium glutamicum* |

An alternative enzyme for converting phosphoenolpyruvate to oxaloacetate is PEP carboxykinase, which simultaneously forms an ATP while carboxylating PEP. In most organisms PEP carboxykinase serves a gluconeogenic function and converts oxaloacetate to PEP at the expense of one ATP. *S. cerevisiae* is one such organism whose native PEP carboxykinase, PCKJ, serves a gluconeogenic role (Valdes-Hevia et al., *FEBS Lett.* 258:313-316 (1989). *E. coli* is another such organism, as the role of PEP carboxykinase in producing oxaloacetate is believed to be minor when compared to PEP carboxylase, which does not form ATP, possibly due to the higher $K_m$ for bicarbonate of PEP carboxykinase (Kim et al., *Appl. Environ. Microbiol.* 70:1238-1241 (2004)). Nevertheless, activity of the native *E. coli* PEP carboxykinase from PEP towards oxaloacetate has been recently demonstrated in ppc mutants of *E. coli* K-12 (Kwon et al., *J. Microbiol. Biotechnol.* 16:1448-1452 (2006)). These strains exhibited no growth defects and had increased succinate production at high $NaHCO_3$ concentrations. Mutant strains of *E. coli* can adopt Pck as the dominant CO2-fixing enzyme following adaptive evolution (Zhang et al. 2009). In some organisms, particularly rumen bacteria, PEP carboxykinase is quite efficient in producing oxaloacetate from PEP and generating ATP. Examples of PEP carboxykinase genes that have been cloned into *E. coli* include those from *Mannheimia succiniciproducens* (Lee et al., *Biotechnol. Bioprocess Eng.* 7:95-99 (2002)), *Anaerobiospirillum succiniciproducens* (Laivenieks et al., *Appi. Environ. Microbiol.* 63:2273-2280 (1997), and *Actinobacillus succinogenes* (Kim et al. supra). The PEP carboxykinase enzyme encoded by *Haemophilus influenza* is effective at forming oxaloacetate from PEP.

TABLE 111

| Protein | GenBank ID | GI Number | Organism |
|---|---|---|---|
| PCK1 | NP_013023 | 6322950 | *Saccharomyces cerevisiae* |
| pck | NP_417862.1 | 16131280 | *Escherichia coli* |
| pckA | YP_089485.1 | 52426348 | *Mannheimia succiniciproducens* |
| pckA | O09460.1 | 3122621 | *Anaerobiospirillum succiniciproducens* |
| pckA | Q6W6X5 | 75440571 | *Actinobacillus succinogenes* |
| pckA | P43923.1 | 1172573 | *Haemophilus influenza* |

Pyruvate carboxylase (EC 6.4.1.1) directly converts pyruvate to oxaloacetate at the cost of one ATP. Pyruvate carboxylase enzymes are encoded by PYC1 (Walker et al., *Biochem. Biophys. Res. Commun.* 176:1210-1217 (1991) and PYC2 (Walker et al., supra) in *Saccharomyces cerevisiae*, and pyc in *Mycobacterium smegmatis* (Mukhopadhyay and Purwantini, *Biochim. Biophys. Acta* 1475:191-206 (2000)).

TABLE 112

| Protein | GenBank ID | GI Number | Organism |
|---|---|---|---|
| PYC1 | NP_011453 | 6321376 | *Saccharomyces cerevisiae* |
| PYC2 | NP_009777 | 6319695 | *Saccharomyces cerevisiae* |
| Pyc | YP_890857.1 | 118470447 | *Mycobacterium smegmatis* |

Malic enzyme can be applied to convert $CO_2$ and pyruvate to malate at the expense of one reducing equivalent. Malic enzymes for this purpose can include, without limitation, malic enzyme (NAD-dependent) and malic enzyme (NADP-dependent). For example, one of the *E. coli* malic enzymes (Takeo, *J. Biochem.* 66:379-387 (1969)) or a similar enzyme with higher activity can be expressed to enable the conversion of pyruvate and $CO_2$ to malate. By fixing carbon to pyruvate as opposed to PEP, malic enzyme allows the high-energy phosphate bond from PEP to be conserved by pyruvate kinase whereby ATP is generated in the formation of pyruvate or by the phosphotransferase system for glucose transport. Although malic enzyme is typically assumed to operate in the direction of pyruvate formation from malate, overexpression of the NAD-dependent enzyme, encoded by maeA, has been demonstrated to increase succinate production in *E. coli* while restoring the lethal Δpfl-ΔldhA phenotype under anaerobic conditions by operating in the carbon-fixing direction (Stols and Donnelly, *Appl. Environ. Microbiol.* 63(7) 2695-2701 (1997)). A similar observation was made upon overexpressing the malic enzyme from *Ascaris suum* in *E. coli* (Stols et al., *Appl. Biochem. Biotechnol.* 63-65(1), 153-158 (1997)). The second *E. coli* malic enzyme, encoded by maeB, is NADP-dependent and also decarboxylates oxaloacetate and other alpha-keto acids (Iwakura et al., *J. Biochem.* 85(5):1355-65 (1979)).

TABLE 113

| Protein | GenBank ID | GI Number | Organism |
|---|---|---|---|
| maeA | NP_415996 | 90111281 | *Escherichia coli* |
| maeB | NP_416958 | 16130388 | *Escherichia coli* |
| NAD-ME | P27443 | 126732 | *Ascaris suum* |

The enzymes used for converting oxaloacetate (formed from, for example, PEP carboxylase, PEP carboxykinase, or pyruvate carboxylase) or malate (formed from, for example, malic enzyme or malate dehydrogenase) to succinyl-CoA via the reductive branch of the TCA cycle are malate dehydrogenase, fumarate dehydratase (fumarase), fumarate reductase, and succinyl-CoA transferase. The genes for each of the enzymes are described herein above.

Enzymes, genes and methods for engineering pathways from succinyl-CoA to various products into a microorganism are now known in the art. The additional reducing equivalents obtained from CO and/or H2, as disclosed herein, improve the yields of 1,3-butanediol when utilizing carbohydrate-based feedstock. For example, 1,3-butanediol can be produced from succinyl-CoA via succinate semialdehyde, 4-hydroxybutyrate, 4-hydroxybutyryl-phosphate, 4-hydroxybutyrl-CoA, crotonyl-CoA, 3-hydroxybutyryl-CoA, 3-hydroxybutanal, and/or 3-hydroxybutryate. Exemplary enzymes for the conversion succinyl-CoA to 1,3-butanediol include: A. Succinyl-CoA transferase, or Succinyl-CoA synthetase (or succinyl-CoA ligase), B. Succinyl-CoA reductase (aldehyde forming), C. 4-Hydroxybutyrate dehydrogenase, D. 4-Hydroxybutyrate kinase, E. Phosphotrans-4-hydroxybutyrylase, F. Succinate reductase, G. Succinyl-CoA reductase (alcohol forming), H. 4-Hydroxybutyryl-CoA transferase, or 4-Hydroxybutyryl-CoA synthetase, I. Alpha-ketoglutarate decarboxylase or (Q. Glutamate dehydrogenase and/or R. Glutamate transaminase; S. Glutamate decarboxylase; T. 4-aminobutyrate dehydrogenase and/or U. 4-aminobutyrate transaminase), J. 4-hydroxybutyryl-CoA dehydratase, K. crotonase, L. 3-hydroxybutyryl-CoA reductase (aldehyde forming), M. 3-hydroxybutanal reductase, N. 3-hydroxybutyryl-CoA reductase (alcohol forming), O. 3-hydroxybutyryl-CoA hydrolase, transferase, or synthetase, P. 3-hydroxybutyrate reductase.

Enzymes, genes and methods for engineering pathways from glycolysis intermediates to various products into a microorganism are known in the art. The additional reducing equivalents obtained from CO and H2, as described herein, improve the yields of all these products on carbohydrates. For example, 1,3-butanediol can be produced from the glycolysis intermediate, pyruvate. Exemplary enzymes for the conversion of pyruvate to 1,3-butanediol include alanine dehydrogenase alanine aminotransferase; the remaining enzymatic transformations shown are carried out by the following enzymes: A) AKP thiolase, B) AKP aminotransferase or AKP oxidoreductase (deaminating), C) 2,4-dioxopentanoate decarboxylase, D) 3-oxobutyraldehyde reductase (aldehyde reducing), E) AKP decarboxylase, F) 4-aminobutan-2-one ammonia-lyase, G) Butenone hydratase, H) 4-hydroxy,2-butanone reductase, I) AKP ammonia-lyase, J) acetylacrylate decarboxylase, K) 4-aminobutan-2-one aminotransferase or 4-aminobutan-2-one oxidoreductase (deaminating), L) AKP dehydrogenase, M) 2-amino-4-hydroxypentanoate aminotransferase or 2-amino-4-hydroxypentanoate oxidoreductase (deaminating), N) 2-oxo-4-hydroxypentanoate decarboxylase, O) 3-oxobutyraldehyde reductase (ketone reducing), and P) 3-hydroxybutyraldehyde reductase.

Example V

Methods for Handling CO and Anaerobic Cultures

This example describes methods used in handling CO and anaerobic cultures.

A. Handling of CO in small quantities for assays and small cultures. CO is an odorless, colorless and tasteless gas that is a poison. Therefore, cultures and assays that utilized CO required special handling. Several assays, including CO oxidation, acetyl-CoA synthesis, CO concentration using myoglobin, and CO tolerance/utilization in small batch cultures, called for small quantities of the CO gas that were dispensed and handled within a fume hood. Biochemical assays called for saturating very small quantities (<2 mL) of the biochemical assay medium or buffer with CO and then performing the assay. All of the CO handling steps were performed in a fume hood with the sash set at the proper height and blower turned on; CO was dispensed from a compressed gas cylinder and the regulator connected to a Schlenk line. The latter ensures that equal concentrations of CO were dispensed to each of several possible cuvettes or vials. The Schlenk line was set up containing an oxygen scrubber on the input side and an oil pressure release bubbler and vent on the other side. Assay cuvettes were both anaerobic and CO-containing. Therefore, the assay cuvettes were tightly sealed with a rubber stopper and reagents were added or removed using gas-tight needles and syringes. Secondly, small (~50 mL) cultures were grown with saturating CO in tightly stoppered serum bottles. As with the biochemical assays, the CO-saturated microbial cultures were equilibrated in the fume hood using the Schlenk line setup. Both the biochemical assays and microbial cultures were in portable, sealed containers and in small volumes making for safe handling outside of the fume hood. The compressed CO tank was adjacent to the fume hood.

Typically, a Schlenk line was used to dispense CO to cuvettes, each vented. Rubber stoppers on the cuvettes were pierced with 19 or 20 gage disposable syringe needles and were vented with the same. An oil bubbler was used with a CO tank and oxygen scrubber. The glass or quartz spectrophotometer cuvettes have a circular hole on top into which a Kontes stopper sleeve, Sz7 774250-0007 was fitted. The CO detector unit was positioned proximal to the fume hood.

B. Handling of CO in larger quantities fed to large-scale cultures. Fermentation cultures are fed either CO or a mixture of CO and H2 to simulate syngas as a feedstock in fermentative production. Therefore, quantities of cells ranging from 1 liter to several liters can include the addition of CO gas to increase the dissolved concentration of CO in the medium. In these circumstances, fairly large and continuously administered quantities of CO gas are added to the cultures. At different points, the cultures are harvested or samples removed. Alternatively, cells are harvested with an integrated continuous flow centrifuge that is part of the fermenter.

The fermentative processes are carried out under anaerobic conditions. In some cases, it is uneconomical to pump oxygen or air into fermenters to ensure adequate oxygen saturation to provide a respiratory environment. In addition, the reducing power generated during anaerobic fermentation may be needed in product formation rather than respiration. Furthermore, many of the enzymes for various pathways are oxygen-sensitive to varying degrees. Classic acetogens such as *M. thermoacetica* are obligate anaerobes and the enzymes in the Wood-Ljungdahl pathway are highly sensitive to irreversible inactivation by molecular oxygen. While there are oxygen-tolerant acetogens, the repertoire of enzymes in the Wood-Ljungdahl pathway might be incompatible in the presence of oxygen because most are metallo-enzymes, key components are ferredoxins, and regulation can divert metabolism away from the Wood-Ljungdahl pathway to maximize energy acquisition. At the same time, cells in culture act as oxygen scavengers that moderate the need for extreme measures in the presence of large cell growth.

C. Anaerobic chamber and conditions. Exemplary anaerobic chambers are available commercially (see, for example, Vacuum Atmospheres Company, Hawthorne Calif.; MBraun, Newburyport Mass.). Conditions included an O2 concentration of 1 ppm or less and 1 atm pure N2. In one example, 3 oxygen scrubbers/catalyst regenerators were used, and the chamber included an O2 electrode (such as Teledyne; City of Industry Calif.). Nearly all items and reagents were cycled four times in the airlock of the chamber prior to opening the inner chamber door. Reagents with a volume >5 mL were sparged with pure N2 prior to introduction into the chamber. Gloves are changed twice/yr and the catalyst containers were regenerated periodically when the chamber displays increasingly sluggish response to changes in oxygen levels. The chamber's pressure was controlled through one-way valves activated by solenoids. This feature allowed setting the chamber pressure at a level higher than the surroundings to allow transfer of very small tubes through the purge valve.

The anaerobic chambers achieved levels of O2 that were consistently very low and were needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release can be controlled by a bubbler. Instead of using instrument-based O2 monitoring, test strips can be used instead.

D. Anaerobic microbiology. Small cultures were handled as described above for CO handling. In particular, serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step, each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl is added. This is made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle is stoppered immediately as the sodium sulfide solution generates hydrogen sulfide gas upon contact with the cysteine. When injecting into the culture, a syringe filter is used to sterilize the solution. Other components are added through syringe needles, such as B12 (10 M cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 M—made as 100-1000× stock solution in anaerobic water in the chamber and sterilized by autoclaving or by using a syringe filter upon injection into the culture). To facilitate faster growth under anaerobic conditions, the 1 liter bottles were inoculated with 50 mL of a preculture grown anaerobically. Induction of the pA1-lacO1 promoter in the vectors was performed by addition of isopropyl β-D-1-thiogalactopyranoside (IPTG) to a final concentration of 0.2 mM and was carried out for about 3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

Example VI

CO Oxidation (CODH) Assay

This example describes assay methods for measuring CO oxidation (CO dehydrogenase; CODH).

The 7 gene CODH/ACS operon of *Moorella thermoacetica* was cloned into *E. coli* expression vectors. The intact ~10 kbp DNA fragment was cloned, and it is likely that some of the genes in this region are expressed from their own endogenous promoters and all contain endogenous ribosomal binding sites. These clones were assayed for CO oxidation, using an assay that quantitatively measures CODH activity. Antisera to the *M. thermoacetica* gene products was used for Western blots to estimate specific activity. *M. thermoacetica* is Gram positive, and ribosome binding site elements are expected to work well in *E. coli*. This activity, described below in more detail, was estimated to be ~1/50th of the *M. thermoacetica* specific activity. It is possible that CODH activity of recombinant *E. coli* cells could be limited by the fact that *M. thermoacetica* enzymes have temperature optima around 55° C. Therefore, a mesophilic CODH/ACS pathway could be advantageous such as the close relative of *Moorella* that is mesophilic and does have an apparently intact CODH/ACS operon and a Wood-Ljungdahl pathway, *Desulfitobacterium hafniense*. Acetogens as potential host organisms include, but are not limited to, *Rhodospirillum rubrum, Moorella thermoacetica* and *Desulfitobacterium hafniense*.

CO oxidation is both the most sensitive and most robust of the CODH/ACS assays. It is likely that an *E. coli*-based syngas using system will ultimately need to be about as anaerobic as *Clostridial* (i.e., *Moorella*) systems, especially for maximal activity. Improvement in CODH should be possible but will ultimately be limited by the solubility of CO gas in water.

Initially, each of the genes was cloned individually into expression vectors. Combined expression units for multiple subunits/1 complex were generated. Expression in *E. coli* at the protein level was determined. Both combined *M. thermoacetica* CODH/ACS operons and individual expression clones were made.

CO oxidation assay. This assay is one of the simpler, reliable, and more versatile assays of enzymatic activities within the Wood-Ljungdahl pathway and tests CODH (Seravalli et al., Biochemistry 43:3944-3955 (2004)). A typical activity of *M. thermoacetica* CODH specific activity is 500 U at 55° C. or ~60 U at 25° C. This assay employs reduction of methyl viologen in the presence of CO. This is measured at 578 nm in stoppered, anaerobic, glass cuvettes.

In more detail, glass rubber stoppered cuvettes were prepared after first washing the cuvette four times in deionized water and one time with acetone. A small amount of vacuum grease was smeared on the top of the rubber gasket. The cuvette was gassed with CO, dried 10 min with a 22 Ga. needle plus an exhaust needle. A volume of 0.98 mlL of reaction buffer (50 mM Hepes, pH 8.5, 2 mM dithiothreitol (DTT) was added using a 22 Ga. needle, with exhaust needled, and 100% CO. Methyl viologen (CH3 viologen) stock was 1 M in water. Each assay used 20 microliters for 20 mM final concentration. When methyl viologen was added, an 18 Ga needle (partial) was used as a jacket to facilitate use of a Hamilton syringe to withdraw the CH3 viologen. 4-5 aliquots were drawn up and discarded to wash and gas equilibrate the syringe. A small amount of sodium dithionite (0.1 M stock) was added when making up the CH3 viologen stock to slightly reduce the CH3 viologen. The temperature was equilibrated to 55° C. in a heated Olis spectrophotometer (Bogart GA). A blank reaction (CH3 viologen+buffer) was run first to measure the base rate of CH3 viologen reduction. Crude *E. coli* cell extracts of ACS90 and ACS91 (CODH-ACS operon of *M. thermoacetica* with and without, respectively, the first cooC). 10 microliters of extract were added at a time, mixed and assayed. Reduced CH3 viologen turns purple. The results of an assay are shown in Table 114.

TABLE 114

Crude extract CO Oxidation Activities.

| ACS90 | 7.7 mg/ml | ACS91 | 11.8 mg/ml |
| Mta98 | 9.8 mg/ml | Mta99 | 11.2 mg/ml |

| Extract | Vol | OD/ | U/ml | U/mg |
|---|---|---|---|---|
| ACS90 | 10 microliters | 0.073 | 0.376 | 0.049 |
| ACS91 | 10 microliters | 0.096 | 0.494 | 0.042 |
| Mta99 | 10 microliters | 0.0031 | 0.016 | 0.0014 |
| ACS90 | 10 microliters | 0.099 | 0.51 | 0.066 |
| Mta99 | 25 microliters | 0.012 | 0.025 | 0.0022 |
| ACS91 | 25 microliters | 0.215 | 0.443 | 0.037 |
| Mta98 | 25 microliters | 0.019 | 0.039 | 0.004 |
| ACS91 | 10 microliters | 0.129 | 0.66 | 0.056 |

TABLE 114-continued

Crude extract CO Oxidation Activities.

| Averages | |
|---|---|
| ACS90 | 0.057 U/mg |
| ACS91 | 0.045 U/mg |
| Mta99 | 0.0018 U/mg |

Mta98/Mta99 are *E. coli* MG1655 strains that express methanol methyltransferase genes from *M. thermoacetia* and, therefore, are negative controls for the ACS90 ACS91 *E. coli* strains that contain *M. thermoacetica* CODH operons.

If ~1% of the cellular protein is CODH, then these figures would be approximately 100× less than the 500 U/mg activity of pure *M. thermoacetica* CODH. Actual estimates based on Western blots are 0.5% of the cellular protein, so the activity is about 50× less than for *M. thermoacetica* CODH. Nevertheless, this experiment demonstrates CO oxidation activity in recombinant *E. coli* with a much smaller amount in the negative controls. The small amount of CO oxidation (CH3 viologen reduction) seen in the negative controls indicates that *E. coli* may have a limited ability to reduce CH3 viologen.

To estimate the final concentrations of CODH and Mtr proteins, SDS-PAGE followed by Western blot analyses were performed on the same cell extracts used in the CO oxidation, ACS, methyltransferase, and corrinoid Fe—S assays. The antisera used were polyclonal to purified *M. thermoacetica* CODH-ACS and Mtr proteins and were visualized using an alkaline phosphatase-linked goat-anti-rabbit secondary antibody. The Westerns were performed and results are shown in FIG. 9. The amounts of CODH in ACS90 and ACS91 were estimated at 50 ng by comparison to the control lanes. Expression of CODH-ACS operon genes including 2 CODH subunits and the methyltransferase were confirmed via Western blot analysis. Therefore, the recombinant *E. coli* cells express multiple components of a 7 gene operon. In addition, both the methyltransferase and corrinoid iron sulfur protein were active in the same recombinant *E. coli* cells. These proteins are part of the same operon cloned into the same cells.

Figure 11:
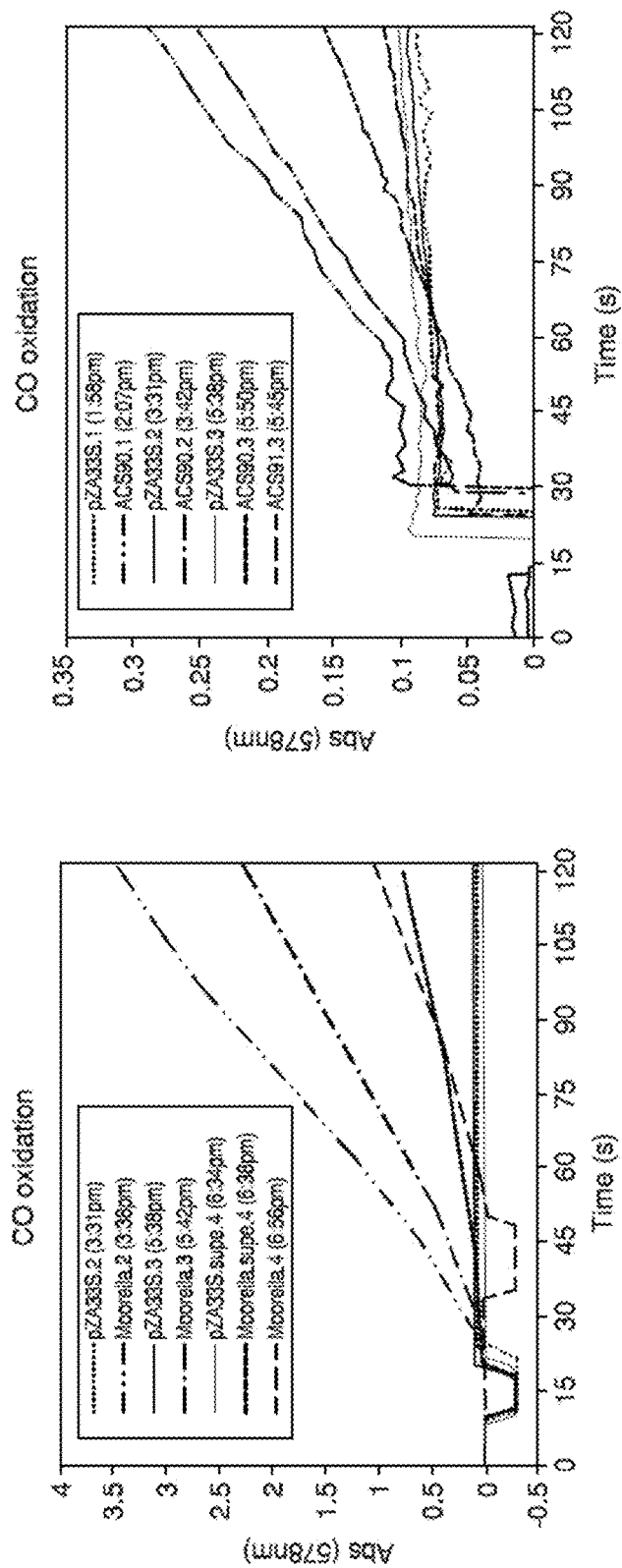
FIG. 11 shows CO oxidation assay results. Cells (*M. thermoacetica* or *E. coli* with the CODH/ACS operon; ACS90 or ACS91 or empty vector: pZA33S) were grown and extracts prepared. Assays were performed at 55° C. at various times on the day the extracts were prepared. Reduction of methylviologen was followed at 578 nm over a 120 sec time course.

The CO oxidation assays were repeated using extracts of *Moorella thermoacetica* cells for the positive controls. Though CODH activity in *E. coli* ACS90 and ACS91 was measurable, it was at about 130-150× lower than the *M. thermoacetica* control. The results of the assay are shown in FIG. 11. Briefly, cells (*M. thermoacetica* or *E. coli* with the CODH/ACS operon; ACS90 or ACS91 or empty vector: pZA33S) were grown and extracts prepared as described above. Assays were performed as described above at 55° C. at various times on the day the extracts were prepared. Reduction of methylviologen was followed at 578 nm over a 120 sec time course.

These results describe the CO oxidation (CODH) assay and results. Recombinant *E. coli* cells expressed CO oxidation activity as measured by the methyl viologen reduction assay.

Example VII

*E. coli* CO Tolerance Experiment and CO Concentration Assay (Myoglobin Assay)

This example describes the tolerance of *E. coli* for high concentrations of CO.

To test whether or not *E. coli* can grow anaerobically in the presence of saturating amounts of CO, cultures were set up in 120 ml serum bottles with 50 ml of Terrific Broth medium (plus reducing solution, NiCl2, Fe(II)NH4SO4, cyanocobalamin, IPTG, and chloramphenicol) as described above for anaerobic microbiology in small volumes. One half of these bottles were equilibrated with nitrogen gas for 30 min. and one half was equilibrated with CO gas for 30 min. An empty vector (pZA33) was used as a control, and cultures containing the pZA33 empty vector as well as both ACS90 and ACS91 were tested with both N2 and CO. All were inoculated and grown for 36 hrs with shaking (250 rpm) at 37° C. At the end of the 36 hour period, examination of the flasks showed high amounts of growth in all. The bulk of the observed growth occurred overnight with a long lag.

Given that all cultures appeared to grow well in the presence of CO, the final CO concentrations were confirmed. This was performed using an assay of the spectral shift of myoglobin upon exposure to CO. Myoglobin reduced with sodium dithionite has an absorbance peak at 435 nm; this peak is shifted to 423 nm with CO. Due to the low wavelength and need to record a whole spectrum from 300 nm on upwards, quartz cuvettes must be used. CO concentration is measured against a standard curve and depends upon the Henry's Law constant for CO of maximum water solubility=970 micromolar at 20° C. and 1 atm.

For the myoglobin test of CO concentration, cuvettes were washed 10× with water, 1× with acetone, and then stoppered as with the CODH assay. N2 was blown into the cuvettes for ~10 min. A volume of 1 ml of anaerobic buffer (HEPES, pH 8.0, 2 mM DTT) was added to the blank (not equilibrated with CO) with a Hamilton syringe. A volume of 10 microliter myoglobin (~1 mM—can be varied, just need a fairly large amount) and 1 microliter dithionite (20 mM stock) were added. A CO standard curve was made using CO saturated buffer added at 1 microliter increments. Peak height and shift was recorded for each increment. The cultures tested were pZA33/CO, ACS90/CO, and ACS91/CO. Each of these was added in 1 microliter increments to the same cuvette. Midway through the experiment a second cuvette was set up and used. The results are shown in Table 115.

TABLE 115

Carbon Monoxide Concentrations, 36 hrs.

| Strain and Growth Conditions | Final CO concentration (micromolar) |
|---|---|
| pZA33-CO | 930 |
| ACS90-CO | 638 |
|  | 494 |
|  | 734 |
|  | 883 |
| ave | 687 |
| SD | 164 |
| ACS91-CO | 728 |
|  | 812 |
|  | 760 |
|  | 611 |
| ave. | 728 |
| SD | 85 |

The results shown in Table 115 indicate that the cultures grew whether or not a strain was cultured in the presence of CO or not. These results indicate that *E. coli* can tolerate exposure to CO under anaerobic conditions and that *E. coli* cells expressing the CODH-ACS operon can metabolize some of the CO.

These results demonstrate that *E. coli* cells, whether expressing CODH/ACS or not, were able to grow in the presence of saturating amounts of CO. Furthermore, these grew equally well as the controls in nitrogen in place of CO.

This experiment demonstrated that laboratory strains of *E. coli* are insensitive to CO at the levels achievable in a syngas project performed at normal atmospheric pressure. In addition, preliminary experiments indicated that the recombinant *E. coli* cells expressing CODH/ACS actually consumed some CO, probably by oxidation to carbon dioxide.

Example VIII

Exemplary Carboxylic Acid Reductases

This example describes the use of carboxylic acid reductases (CAR) to carry out the conversion of a carboxylic acid to an aldehyde.

Any intermediate carboxylic acid in a 1,3-butanediol pathway (or accessible carboxylic acid via its CoA derivative) can be converted to an aldehyde, if so desired. The conversion of unactivated acids to aldehydes can be carried out by an acid reductase. Examples of such conversions include, but are not limited, the conversion of 4-hydroxybutyrate, succinate, alpha-ketoglutarate, and 4-aminobutyrate to 4-hydroxybutanal, succinate semialdehyde, 2,5-dioxopentanoate, and 4-aminobutanal, respectively. One notable carboxylic acid reductase can be found in *Nocardia iowensis* which catalyzes the magnesium, ATP and NADPH-dependent reduction of carboxylic acids to their corresponding aldehydes (Venkitasubramanian et al., *J. Biol. Chem.* 282:478-485 (2007)). This enzyme is encoded by the car gene and was cloned and functionally expressed in *E. coli* (Venkitasubramanian et al., *J. Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid, and the enzyme exhibits broad acceptance of aromatic and aliphatic substrates (Venkitasubramanian et al., in Biocatalysis in the Pharmaceutical and Biotechnology Industires, ed. R. N. Patel, Chapter 15, pp. 425-440, CRC Press LLC, Boca Raton, Fla. (2006)).

TABLE 116

| Gene | Accession No. | GI No. | Organism |
|---|---|---|---|
| car | AAR91681.1 | 40796035 | *Nocardia iowensis* (sp. NRRL 5646) |
| npt | ABI83656.1 | 114848891 | *Nocardia iowensis* (sp. NRRL 5646) |

Additional car and npt genes can be identified based on sequence homology.

TABLE 117

| Gene | Accession No. | GI No. | Organism |
|---|---|---|---|
| fadD9 | YP_978699.1 | 121638475 | *Mycobacterium bovis* BCG |
| BCG_2812c | YP_978898.1 | 121638674 | *Mycobacterium bovis* BCG |
| nfa20150 | YP_118225.1 | 54023983 | *Nocardia farcinica* IFM 10152 |
| nfa40540 | YP_120266.1 | 54026024 | *Nocardia farcinica* IFM 10152 |
| SGR_6790 | YP_001828302.1 | 182440583 | *Streptomyces griseus* subsp. *griseus* NBRC 13350 |
| SGR_665 | YP_001822177.1 | 182434458 | *Streptomyces griseus* subsp. *griseus* NBRC 13350 |

An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of griC and griD with SGR_665, an enzyme similar in sequence to the *Nocardia iowensis* npt, can be beneficial.

TABLE 118

| Gene | Accession No. | GI No. | Organism |
|---|---|---|---|
| griC | 182438036 | YP_001825755.1 | *Streptomyces griseus* subsp. *griseus* NBRC 13350 |
| griD | 182438037 | YP_001825756.1 | *Streptomyces griseus* subsp. *griseus* NBRC 13350 |
| MSMEG_2956 | YP_887275.1 | YP_887275.1 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | 227979396 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J. Biol. Chem.* 278:8250-8256 (2003)). The gene encoding the *P. chrysogenum* PPTase has not been identified to date.

TABLE 119

| Gene | Accession No. | GI No. | Organism |
| --- | --- | --- | --- |
| LYS2 | AAA34747.1 | 171867 | Saccharomyces cerevisiae |
| LYS5 | P50113.1 | 1708896 | Saccharomyces cerevisiae |
| LYS2 | AAC02241.1 | 2853226 | Candida albicans |
| LYS5 | AAO26020.1 | 28136195 | Candida albicans |
| Lys1p | P40976.3 | 13124791 | Schizosaccharomyces pombe |
| Lys7p | Q10474.1 | 1723561 | Schizosaccharomyces pombe |
| Lys2 | CAA74300.1 | 3282044 | Penicillium chrysogenum |

Cloning and Expression of Carboxylic Acid Reductase.

*Escherichia coli* is used as a target organism to engineer the pathway for 1,3-butanediol. *E. coli* provides a good host for generating a non-naturally occurring microorganism capable of producing 1,3-butanediol. *E. coli* is amenable to genetic manipulation and is known to be capable of producing various intermediates and products effectively under various oxygenation conditions.

To generate a microbial organism strain such as an *E. coli* strain engineered to produce 1,3-butanediol, nucleic acids encoding a carboxylic acid reductase and phosphopantetheine transferase are expressed in *E. coli* using well known molecular biology techniques (see, for example, Sambrook, supra, 2001; *Ausubel supra*, 1999). In particular, car genes from *Nocardia iowensis* (designated 720), *Mycobacterium smegmatis* mc(2)155 (designated 890), *Mycobacterium avium* subspecies *paratuberculosis* K-10 (designated 891) and *Mycobacterium marinum* M (designated 892) were cloned into pZS*13 vectors (Expressys, Ruelzheim, Germany) under control of PA1/lacO promoters. The npt (ABI83656.1) gene (i.e., 721) was cloned into the pKJL33S vector, a derivative of the original mini-F plasmid vector PML31 under control of promoters and ribosomal binding sites similar to those used in pZS*13.

The car gene (GNM_720) was cloned by PCR from *Nocardia* genomic DNA. Its nucleic acid and protein sequences are shown in FIGS. 12A and 12B, respectively. A codon-optimized version of the npt gene (GNM_721) was synthesized by GeneArt (Regensburg, Germany). Its nucleic acid and protein sequences are shown in FIGS. 13A and 13B, respectively. The nucleic acid and protein sequences for the *Mycobacterium smegmatis* mc(2)155 (designated 890), *Mycobacterium avium* subspecies *paratuberculosis* K-10 (designated 891) and *Mycobacterium marinum* M (designated 892) genes and enzymes can be found in FIGS. 14, 15, and 16, respectively. The plasmids are transformed into a host cell to express the proteins and enzymes required for 1,3-butanediol production.

Additional CAR variants were generated. A codon optimized version of CAR 891 was generated and designated 891 GA. The nucleic acid and amino acid sequences of CAR 891GA are shown in FIGS. 17A and 17B, respectively. Over 2000 CAR variants were generated. In particular, all 20 amino acid combinations were made at positions V295, M296, G297, G391, G421, D413, G414, Y415, G416, and S417, and additional variants were tested as well. Exemplary CAR variants include: E16K; Q95L; L100M; A1011T; K823E; T941S; H15Q; D198E; G446C; S392N; F699L; V883I; F467S; T987S; R12H; V295G; V295A; V295S; V295T; V295C; V295V; V295L; V295I; V295M; V295P; V295F; V295Y; V295W; V295D; V295E; V295N; V295Q; V295H; V295K; V295R; M296G; M296A; M296S; M296T; M296C; M296V; M296L; M296I; M296M; M296P; M296F; M296Y; M296W; M296D; M296E; M296N; M296Q; M296H; M296K; M296R; G297G; G297A; G297S; G297T; G297C; G297V; G297L; G297I; G297M; G297P; G297F; G297Y; G297W; G297D; G297E; G297N; G297Q; G297H; G297K; G297R; G391G; G391A; G391S; G391T; G391C; G391V; G391L; G391I; G391M; G391P; G391F; G391Y; G391W; G391D; G391E; G391N; G391Q; G391H; G391K; G391R; G421G; G421A; G421S; G421T; G421C; G421V; G421L; G421I G421M; G421P; G421F; G421Y; G421W; G421D; G421E; G421N; G421Q; G421H; G421K; G421R; D413G; D413A; D413S; D413T; D413C; D413V; D413L; D413I; D413M; D413P; D413F; D413Y; D413W; D413D; D413E; D413N; D413Q; D413H; D413K; D413R; G414G; G414A; G414S; G414T; G414C; G414V; G414L; G414I; G414M; G414P; G414F; G414Y; G414W; G414D; G414E; G414N; G414Q; G414H; G414K; G414R; Y415G; Y415A; Y415S; Y415T; Y415C; Y415V; Y415L; Y415I; Y415M; Y415P; Y415F; Y415Y; Y415W; Y415D; Y415E; Y415N; Y415Q; Y415H; Y415K; Y415R; G416G; G416A; G416S; G416T; G416C; G416V; G416L; G416I; G416M; G416P; G416F; G416Y; G416W; G416D; G416E; G416N; G416Q; G416H; G416K; G416R; S417G; S417A; S417S; S417T; S417C; S417V S417L; S417I; S417M; S417P; S417F; S417Y; S417W; S417D; S417E; S417N; S417Q; S417H; S417K; and S417R.

The CAR variants were screened for activity, and numerous CAR variants were found to exhibit CAR activity. This example describes the use of CAR for converting carboxylic acids to aldehydes.

TABLE 120
(Ref. FIG. 1)

| Step | EC class | Desired substrate | Desired product | Enzyme name | Gene name | GenBank ID (if available) | Organism | Known Substrates |
|---|---|---|---|---|---|---|---|---|
| A | 2.3.1.b | D-alanine | 2-amino-4-oxopentanoate | AKP Thiolase | ortA | YP_001086914.1 | Clostridium difficile 630 | D-alanine |
| | | | | | ortB | YP_001086915.1 | Clostridium difficile 630 | D-alanine |
| | | | | | Amet_2368 | YP_001320181.1 | Alkaliphilus metalliredigenes QYF | D-alanine |
| | | | | | Amet_2369 | YP_001320182.1 | Alkaliphilus metalliredigenes QYF | D-alanine |
| | | | | | Teth514_1478 | YP_001663101.1 | Thermoanaerobacter sp. X514 | D-alanine |
| | | | | | Teth514_1479 | YP_001663102.1 | Thermoanaerobacter sp. X514 | D-alanine |
| B | 2.6.1.a | 2-amino-4-oxopentanoate | 2,4-dioxopentanoate | 2-amino-4-oxopentanoate aminotransferase or oxidoreductase (deaminating) | aspC | NP_415448.1 | Escherichia coli | L-aspartate |
| | | | | | avtA | YP_026231.1 | Escherichia coli | L-alanine, L-valine |
| | | | | | AAT2 | P23542.3 | Saccharomyces cerevisae | L-aspartate |
| | | | | | dat | P19938 | Bacillus sp. YM-1 | D-alanine, D-2-aminobutanoate, D-aspartate |
| | | | | | dat | O07597 | Bacillus subtilis | D-alanine, D-2-aminobutanoate, D-aspartate |
| | | | | | ldh | P0A393 | Bacillus cereus | L-leucine, L-valine, 2-aminobutanoate, L-isoleucine |
| | | | | | nadX | NP_229443.1 | Thermotoga maritima | L-aspartate |
| C | 4.1.1.a | 2,4-dioxopentanoate | 3-oxobutyraldehyde (3-oxobutanal) | 2,4-dioxopentanoate decarboxylase | pdc | P06672.1 | Zymomonas mobilis | 2-ketobutyrate |
| | | | | | pdc1 | P06169 | Saccharomyces cerevisae | 2-ketobutyrate, 3-hydroxypyruvate |
| | | | | | mdlC | P20906.2 | Pseudomonas putida | 2-ketobutyrate |
| | | | | | kgd | O50463.4 | Mycobacterium tuberculosis | alpha-ketoglutarate |

TABLE 120-continued (Ref: FIG. 1)

| Step | EC class | Desired substrate | Desired product | Enzyme name | Gene name | GenBank ID (if available) | Organism | Known Substrates |
|---|---|---|---|---|---|---|---|---|
| D | 1.1.1.a | 3-oxobutyraldehyde | 4-hydroxy,2-butanone | 3-oxobutyraldehyde reductase (aldehyde reducing) | alrA | BAB12273.1 | Acinetobacter sp. Strain M-1 | C2-C14 aldehydes |
| | | | | | ADH2 | NP_014032.1 | Saccharomyces cerevisiae | propionaldehyde, isobutyraldehyde, butyraldehyde, 2-methylbutyraldehyde, 3-methylbutyraldehyde, 2-phenylacetaldehyde |
| | | | | | yqhD | NP_417484.1 | Escherichia coli | acetaldehyde, malondialdehyde, propanaldehyde, butanaldehyde, and acrolein |
| | | | | | bdh I | NP_349892.1 | Clostridium acetobutylicum | butyraldehyde |
| | | | | | bdh II | NP_349891.1 | Clostridium acetobutylicum | butyraldehyde |
| | | | | | 4hbd | YP_726053.1 | Ralstonia eutropha H16 | succinate semialdehyde |
| | | | | | ADHI | AAR91477.1 | Geobacillus thermoglucosidasius M10EXG | ethanol, 1-butanol, 1-pentanol, 1-heptanol, 1-hexanol, 1-octanol, 2-propanol |
| | | | | | mmsb | P28811.1 | Pseudomonas aeruginosa | 3-hydroxybutyraldehyde, malonic semialdehyde, methylmalonate semialdehyde |
| | | | | | P84067 | P84067 | Thermus thermophilus | methylmalonate semialdehyde |
| E | 4.1.1.a | 2-amino-4-oxopentanoate | 4-aminobutan-2-one | 2-amino-4-oxopentanoate decarboxylase | lysA | NP_417315.1 | Escherichia coli | meso-diaminopimelate |
| | | | | | lysA | AAA25361.1 | Mycobacterium tuberculosis | meso-diaminopimelate |
| | | | | | lysA | BAC92756.1 | Methylophilus methylotrophus | meso-diaminopimelate |
| | | | | | odc1 | AAS99967.1 | Homo sapiens | D-ornithine |
| | | | | | panD | P0A790 | Escherichia coli | L-aspartate |
| | | | | | panD | Q9X4N0 | Corynebacterium glutamicum | L-aspartate |
| | | | | | panD | P65660 | Mycobacterium tuberculosis | L-aspartate |

TABLE 120-continued (Ref: FIG. 1)

| Step | EC class | Desired substrate | Desired product | Enzyme name | Gene name | GenBank ID (if available) | Organism | Known Substrates |
|---|---|---|---|---|---|---|---|---|
| F | 4.3.1.a | 4-aminobutan-2-one | butenone | 4-aminobutan-2-one ammonia lyase | aspA | NP_418562 | Escherichia coli K12 subsp. MG1655 | L-aspartate |
| | | | | | aspA | P44324.1 | Haemophilus influenzae | L-aspartate |
| | | | | | aspA | P07346.1 | Pseudomonas fluorescens | L-aspartate |
| | | | | | ansB | P26899.1 | Bacillus subtilis | L-aspartate |
| | | | | | aspA | P33109.1 | Serratia marcescens | L-aspartate |
| G | 4.2.1.a | butenone | 4-hydroxy,2-butanone | butenone hydratase | fumA | P0AC33 | Escherichia coli K12 | fumarate |
| | | | | | fumC | P05042 | Escherichia coli K12 | fumarate |
| | | | | | fumC | O69294 | Campylobacter jejuni | fumarate |
| | | | | | fumC | P84127 | Thermus thermophilus | fumarate |
| | | | | | fumH | P14408 | Rattus norvegicus | fumarate |
| | | | | | hmd | ABC88407.1 | Eubacterium barkeri | 2-methylene-glutarate |
| | | | | | dmdA | ABC88408 | Eubacterium barkeri | dimethylmaleate |
| | | | | | dmdB | ABC88409.1 | Eubacterium barkeri | dimethylmaleate |
| H | 1.1.1.a | 4-hydroxy,2-butanone | 1,3-butanediol | 4-hydroxy,2-butanone reductase | bdh | AAA58352.1 | Homo sapiens | 3-oxobutyrate |
| | | | | | adh | AAA23199.2 | Clostridium beijerinckii NRRL B593 | acetone |
| | | | | | adhA | AAC25556 | Pyrococcus furiosus | 2-pentanaol, pyruvaldehyde |
| | | | | | ldh | YP_725182.1 | Ralstonia eutropha | lactate, 2-oxobutyrate, 2-oxopentaonotae, 2-oxoglutarate |
| | | | | | adh | P14941.1 | Thermoanaerobacter brockii HTD4 | acetone |
| I | 4.3.1.a | 2-amino-4-oxopentanoate | acetylacrylate | 2-amino-4-oxopentanoate ammonia lyase | aspA | NP_418562 | Escherichia coli K12 subsp. MG1655 | L-aspartate |
| | | | | | aspA | P44324.1 | Haemophilus influenzae | L-aspartate |
| | | | | | aspA | P07346.1 | Pseudomonas fluorescens | L-aspartate |
| | | | | | ansB | P26899.1 | Bacillus subtilis | L-aspartate |
| | | | | | aspA | P33109.1 | Serratia marcescens | L-aspartate |

TABLE 120-continued (Ref: FIG. 1)

| Step | EC class | Desired substrate | Desired product | Enzyme name | Gene name | GenBank ID (if available) | Organism | Known Substrates |
|---|---|---|---|---|---|---|---|---|
| J | 4.1.1.a | acetylacrylate | butenone | acetylacrylate decarboxylase | xylII | YP_709328.1 | Pseudomonas putida | 4-oxalocrotonate |
| | | | | | xylIII | YP_709353.1 | Pseudomonas putida | 4-oxalocrotonate |
| | | | | | dmpH | CAA43228.1 | Pseudomonas sp. CF600 | 4-oxalocrotonate |
| | | | | | dmpE | CAA43225.1 | Pseudomonas sp. CF600 | 4-oxalocrotonate |
| | | | | | pdc | U63827 | Lactobacillus plantarum | cinnamate and derivatives |
| | | | | | pad | AB330293 | Klebsiella oxytoca | cinnamate and derivatives |
| K | 2.6.1.a | 4-aminobutan-2-one | 3-oxobutyr-aldehyde (3-oxobutanal) | 4-aminobutan-2-one aminotransferase or oxidoreductase (deaminating) | SkyPYD4 | ABF58893 | Saccharomyces kluyveri | beta-alanine |
| | | | | | gabT | P22256 | Escherichia coli | 4-aminobutyrate |
| | | | | | Abat | P50554 | Rattus norvegicus | 3-amino-2-methylpropionate |
| | | | | | UGA1 | NP_011533 | Saccharomyces cerevisae | 4-aminobutyrate |
| | | | | | kdd | AAL93966.1 | Fusobacterium nucleatum | 3,5-diaminohexanoate |
| | | | | | lysDH | BAB39707 | Geobacillus stearothermophilus | L-lysine |
| L | 1.1.1.a | 2-amino-4-oxopentanoate | 2-amino-4-hydroxypentanoate | 2-amino-4-oxopentanoate dehydrogenase | thrA | AAC73113 | Escherichia coli | aspartate semialdehyde |
| | | | | | hom6 | CAA89671 | Saccharomyces cerevisae | aspartate semialdehyde |
| | | | | | hom2 | CAD63186 | Lactobacillus plantarum | aspartate semialdehyde |
| | | | | | akthr2 | O81852 | Arabidopsis thaliana | aspartate semialdehyde |
| | | | | | hom1 | CAD64819 | Lactobacillus plantarum | aspartate semialdehyde |

TABLE 120-continued (Ref: FIG. 1)

| Step | EC class | Desired substrate | Desired product | Enzyme name | Gene name | GenBank ID (if available) | Organism | Known Substrates |
|---|---|---|---|---|---|---|---|---|
| M | 2.6.1.a | 2-amino-4-hydroxypentanoate | 2-oxo-4-hydroxypentanoate | 2-amino-4-hydroxypentanoate aminotransferase or oxidoreductase (deaminating) | aspC | NP_415448.1 | Escherichia coli | L-aspartate |
| | | | | | avtA | YP_026231.1 | Escherichia coli | L-alanine, L-valine |
| | | | | | AAT2 | P23542.3 | Saccharomyces cerevisiae | L-aspartate |
| | | | | | dat | Bacillus sp. YM-1 P19938 | | D-alanine, D-2-aminobutanoate, D-aspartate |
| | | | | | dat | O07597 | Bacillus subtilis | D-alanine, D-2-aminobutanoate, D-aspartate |
| | | | | | ldh | P0A393 | Bacillus cereus | L-leucine, L-valine, 2-aminobutanoate, L-isoleucine |
| | | | | | nadX | NP_229443.1 | Thermotoga maritima | L-aspartate |
| N | 4.1.1.a | 2-oxo-4-hydroxypentanoate | 3-hydroxybutyr-aldehyde (3-hydroxybutanal) | 2-oxo-4-hydroxypentanoate | pdc | P06672.1 | Zymomonas mobilis | 2-ketobutyrate |
| | | | | | pdc1 | P06169 | Saccharomyces cerevisiae | 2-ketobutyrate, 3-hydroxypyruvate |
| | | | | | mdlC | P20906.2 | Pseudomonas putida | 2-ketobutyrate |
| | | | | | kgd | O50463.4 | Mycobacterium tuberculosis | alpha-ketoglutarate |
| O | 1.1.1.a | 3-oxobutyraldehyde | 3-hydroxybutyr-aldehyde | 3-oxobutyraldehyde reductase (ketone reducing) | bdh | AAA58352.1 | Homo sapiens | 3-oxobutyrate |
| | | | | | adh | AAA23199.2 | Clostridium beijerinckii NRRL B593 | acetone |
| | | | | | adhA | AAC25556 | Pyrococcus furiosus | 2-pentanaol, pyruvaldehyde |
| | | | | | ldh | YP_725182.1 | Ralstonia eutropha | lactate, 2-oxobutyrate, 2-oxopentaonotae, 2-oxoglutarate |
| | | | | | adh | P14941.1 | Thermoanaerobacter brockii HTD4 | acetone |

TABLE 120-continued (Ref: FIG. 1)

| Step | EC class | Desired substrate | Desired product | Enzyme name | Gene name | GenBank ID (if available) | Organism | Known Substrates |
|---|---|---|---|---|---|---|---|---|
| P | 1.1.1.a | 3-hydroxybutyr-aldehyde | 1,3-butanediol | 3-hydroxybutyr-aldehyde reductase | alrA | BAB12273.1 | *Acinetobacter* sp. Strain M-1 | C2-C14 aldehydes |
| | | | | | ADH2 | NP_014032.1 | *Saccharomyces cerevisiae* | propionaldehyde, isobutyraldehyde, butyraldehyde, 2-methylbutyr-aldehyde, 3-methylbutyr-aldehyde, 2-phenylacetaldehyde |
| | | | | | yqhD | NP_417484.1 | *Escherichia coli* | acetaldehyde, malondialdehyde, propanaldehyde, butanaldehyde, and acrolein |
| | | | | | bdh I | NP_349892.1 | *Clostridium acetobutylicum* | butyraldehyde |
| | | | | | bdh II | NP_349891.1 | *Clostridium acetobutylicum* | butyraldehyde |
| | | | | | 4hbd | YP_726053.1 | *Ralstonia eutropha* H16 | succinate semialdehyde |
| | | | | | ADHI | AAR91477.1 | *Geobacillus thermoglucosidasius* M10EXG | ethanol, 1-butanol, 1-pentanol, 1-heptanol, 1-hexanol, 1-octanol, 2-propanol |
| | | | | | mmsb | P28811.1 | *Pseudomonas aeruginosa* | 3-hydroxybutyraldehyde, malonic semialdehyde, methylmalonate semialdehyde |
| | | | | | P84067 | P84067 | *Thermus thermophilus* | methylmalonate semialdehyde |

TABLE 121

(Ref: FIG. 2)

| Step | EC class | Desired substrate | Desired product | Enzyme name | Gene name | GenBank ID (if available) | Organism | Known Substrates |
|---|---|---|---|---|---|---|---|---|
| A | 1.2.1.b | acetoacetyl-CoA | 3-oxobutyraldehyde | acetoacetyl-CoA reductase (aldehdye forming) | Ald | AAT66436 | Clostridium beijerinckii | butyryl-CoA |
| | | | | | sucD | NP_904963.1 | Porphyromonas gingivalis | succinyl-CoA |
| | | | | | bphG | BAA03892.1 | Pseudomonas sp | acetaldehyde, propionaldehyde, butyraldehyde, isobutyraldehyde and formaldehyde |
| | | | | | Msed_0709 | YP_001190808.1 | Metallosphaera sedula | malonyl-CoA |
| | | | | | mcr | NP_378167 | Sulfolobus tokodaii | malonyl-CoA, methylmalonyl-CoA |
| B | 1.1.1.a | 3-oxobutyraldehyde | 3-hydroxybutyraldehyde | 3-oxobutyraldehyde reductase (ketone-reducing) | bdh | AAA58352.1 | Homo sapiens | 3-oxobutyrate |
| | | | | | adh | AAA23199.2 | Clostridium beijerinckii NRRL B593 | acetone |
| | | | | | adhA | AAC25556 | Pyrococuus furiosus | 2-pentanaol, pyruvaldehyde |
| | | | | | ldh | YP_725182.1 | Ralstonia eutropha | lactate, 2-oxobutyrate, 2-oxopentaonotae, 2-oxoglutarate |
| | | | | | adh | P14941.1 | Thermoanaerobacter brockii HTD4 | acetone |
| C | 1.1.1.a | 3-hydroxybutyraldehyde | 1,3-butanediol | 3-hydroxybutyraldehyde reductase | alrA | BAB12273.1 | Acinetobacter sp. Strain M-1 | C2-C14 aldehydes |
| | | | | | ADH2 | NP_014032.1 | Saccharymyces cerevisiae | propionaldehyde, isobutyraldehyde, butyraldehyde, 2-methylbutyraldehyde, 3-methylbutyraldehyde, 2-phenylacetaldehyde |
| | | | | | yqhD | NP_417484.1 | Escherichia coli | acetaldehyde, malondialdehyde, propanaldehyde, butanaldehyde, and acrolein |
| | | | | | bdh I | NP_349892.1 | Clostridium acetobutylicum | butyraldehyde |
| | | | | | bdh II | NP_349891.1 | Clostridium acetobutylicum | butyraldehyde |
| | | | | | 4hbd | YP_726053.1 | Ralstonia eutropha H16 | succinate semialdehyde |
| | | | | | ADHI | AAR91477.1 | Geobacillus thermoglucosidasius M10EXG | ethanol, 1-butanol, 1-pentanol, 1-heptanol, 1-hexanol, 1-octanol, 2-propanol |
| | | | | | mmsb | P28811.1 | Pseudomonas aeruginosa | 3-hydroxybutyraldehyde, malonic semialdehyde, methylmalonate semialdehyde |
| | | | | | P84067 | P84067 | Thermus thermophilus | methylmalonate semialdehyde |
| D | 1.1.1.c | acetoacetyl-CoA | 4-hydroxy,2-butanone | acetoacetyl-CoA reductase (alcohol-forming) | adhE2 | AAK09379.1 | Clostridium acetobutylicum | butanoyl-CoA |
| | | | | | mcr | AAS20429.1 | Chloroflexus aurantiacus | malonyl-CoA |

TABLE 121-continued (Ref: FIG. 2)

| Step | EC class | Desired substrate | Desired product | Enzyme name | Gene name | GenBank ID (if available) | Organism | Known Substrates |
|---|---|---|---|---|---|---|---|---|
| | | | | | FAR | AAD38039.1 | *Simmondsia chinensis* | long chain acyl-CoA |
| E | 1.1.1.a | 3-oxobutyr-aldehyde | 4-hydroxy,2-butanone | 3-oxobutyraldehdye reductase (aldehyde reducing) | alrA | BAB12273.1 | *Acinetobacter* sp. Strain M-1 | C2-C14 aldehydes |
| | | | | | ADH2 | NP_014032.1 | *Saccharymyces cerevisiae* | propionaldehyde, isobutyraldehyde, butyraldehyde, 2-methylbutyraldehyde, 3-methylbutyr-aldehyde, 2-phenylacetaldehyde |
| | | | | | yqhD | NP_417484.1 | *Escherichia coli* | acetaldehyde, malondialdehyde, propanaldehyde, butanaldehyde, and acrolein |
| | | | | | bdh I | NP_349892.1 | *Clostridium acetobutylicum* | butyraldehyde |
| | | | | | bdh II | NP_349891.1 | *Clostridium acetobutylicum* | butyraldehyde |
| | | | | | 4hbd | YP_726053.1 | *Ralstonia eutropha* H16 | succinate semialdehyde |
| | | | | | ADHI | AAR91477.1 | *Geobacillus thermoglucosidasius* M10EXG | ethanol, 1-butanol, 1-pentanol, 1-heptanol, 1-hexanol, 1-octanol, 2-propanol |
| | | | | | mmsb | P28811.1 | *Pseudomonas aeruginosa* | 3-hydroxybutyraldehyde, malonic semialdehyde, methylmalonate semialdehyde |
| | | | | | P84067 | P84067 | *Thermus thermophilus* | methylmalonate semialdehyde |
| F | 1.1.1.a | 4-hydroxy, 2-butanone | 1,3-butanediol | 4-hydroxy,2-butanone reductase | bdh | AAA58352.1 | *Homo sapiens* | 3-oxobutyrate |
| | | | | | adh | AAA23199.2 | *Clostridium beijerinckii* NRRL B593 | acetone |
| | | | | | adhA | AAC25556 | *Pyrococuus furiosus* | 2-pentanaol, pyruvaldehyde |
| | | | | | ldh | YP_725182.1 | *Ralstonia eutropha* | lactate, 2-oxobutyrate, 2-oxopentaonotae, 2-oxoglutarate |
| | | | | | adh | P14941.1 | *Thermoanaerobacter brockii* HTD4 | acetone |
| G | 1.1.1.a | acetoacetyl-CoA | 3-hydroxy-butyryl-CoA | acetoacetyl CoA reductase (ketone reducing) | hbd | NP_349314.1 | *Clostridium acetobutylicum* | acetoacetyl-CoA |
| | | | | | hbd | AAM14586.1 | *Clostridium beijerinckii* | acetoacetyl-CoA |
| | | | | | Hbd2 | EDK34807.1 | *Clostridium kluyveri* | acetoacetyl-CoA |
| | | | | | Hbd1 | EDK32512.1 | *Clostridium kluyveri* | acetoacetyl-CoA |
| | | | | | Msed_1423 | YP_001191505 | *Metallosphaera sedula* | 3-hydroxybutyryl-CoA (suspected) |
| | | | | | Msed_0399 | YP_001190500 | *Metallosphaera sedula* | 3-hydroxybutyryl-CoA (suspected) |
| | | | | | Msed_0389 | YP_001190490 | *Metallosphaera sedula* | 3-hydroxybutyryl-CoA (suspected) |
| | | | | | Msed_1993 | YP_001192057 | *Metallosphaera sedula* | 3-hydroxybutyryl-CoA (suspected) |
| | | | | | fadB | P21177.2 | *Escherichia coli* | 3-oxoacyl-CoA |
| | | | | | fadJ | P77399.1 | *Escherichia coli* | 3-oxoacyl-CoA |
| H | 1.2.1.b | 3-hydroxybutyryl-CoA | 3-hydroxy-butyral- | 3-hydroxy-butyryl-CoA | Ald | AAT66436 | *Clostridium beijerinckii* | butyryl-CoA |

TABLE 121-continued (Ref: FIG. 2)

| Step | EC class | Desired substrate | Desired product | Enzyme name | Gene name | GenBank ID (if available) | Organism | Known Substrates |
|---|---|---|---|---|---|---|---|---|
| | | | dehyde | redcutase (aldehyde forming) | | | | |
| | | | | | sucD | NP_904963.1 | Porphyromonas gingivalis | succinyl-CoA |
| | | | | | bphG | BAA03892.1 | Pseudomonas sp | acetaldehyde, propionaldehyde, butyraldehyde, isobutyraldehyde and formaldehyde |
| | | | | | Msed_0709 | YP_001190808.1 | Metallosphaera sedula | malonyl-CoA |
| | | | | | mcr | NP_378167 | Sulfolobus tokodaii | malonyl-CoA, methylmalonyl-CoA |
| I | 1.1.1.c | 3-hydroxybutyryl-CoA | 1,3-butanediol | 3-hydroxy-butyryl-CoA reductase (alcohol forming) | adhE2 | AAK09379.1 | Clostridium acetobutylicum | butanoyl-CoA |
| | | | | | mcr | AAS20429.1 | Chloroflexus aurantiacus | malonyl-CoA |
| | | | | | FAR | AAD38039.1 | Simmondsia chinensis | long chain acyl-CoA |

TABLE 122

(Ref: FIG. 3)

| Step | EC class | Desired substrate | Desired product | Enzyme name | Gene name | GenBank ID (if available) | Organism | Known Substrates |
|---|---|---|---|---|---|---|---|---|
| A | 4.2.1.a | 4-hydroxybutyryl-CoA | crotonyl-CoA | 4-hydroxy-butyryl-CoA dehydratase | abfD | YP_001396399.1 | Clostridium kluyveri DSM 555 | 4-hydroxybutyryl-CoA |
| | | | | | abfD | P55792 | Clostridium aminobutyricum | 4-hydroxybutyryl-CoA |
| | | | | | abfD | YP_001928843 | Porphyromonas gingivalis ATCC 33277 | 4-hydroxybutyryl-CoA |
| B | 4.2.1.a | crotonyl-CoA | 3-hydroxybutyryl-CoA | crotonase | crt | NP_349318.1 | Clostridium acetobutylicum | 3-hydroxybutyryl-CoA |
| | | | | | crt1 | YP_001393856 | Clostridium kluyveri DSM 555 | 3-hydroxybutyryl-CoA |
| | | | | | crt | YP_001929291.1 | Porphyromonas gingivalis ATCC 33277 | example based on sequence similarity |
| | | | | | paaA | NP_745427.1 | Pseudomonas putida | enoyl-CoA, cis-dihydrodiol derivative of phenylacetyl-CoA |
| | | | | | paaB | NP_745426.1 | Pseudomonas putida | enoyl-CoA, cis-dihydrodiol derivative of phenylacetyl-CoA |
| | | | | | phaA | ABF82233.1 | Pseudomonas fluorescens | enoyl-CoA, cis-dihydrodiol derivative of phenylacetyl-CoA |
| | | | | | phaB | ABF82234.1 | Pseudomonas fluorescens | enoyl-CoA, cis-dihydrodiol derivative of phenylacetyl-CoA |
| | | | | | maoC | NP_415905.1 | Escherichia coli | enoyl-CoA, cis-dihydrodiol derivative of phenylacetyl-CoA |
| | | | | | paaF | NP_415911.1 | Escherichia coli | enoyl-CoA, cis-dihydrodiol derivative of phenylacetyl-CoA |
| | | | | | paaG | NP_415912.1 | Escherichia coli | enoyl-CoA, |

TABLE 122-continued (Ref: FIG. 3)

| Step | EC class | Desired substrate | Desired product | Enzyme name | Gene name | GenBank ID (if available) | Organism | Known Substrates |
|---|---|---|---|---|---|---|---|---|
| C | 1.2.1.b | 3-hydroxybutyryl-CoA | 3-hydroxy-butyraldehyde | 3-hydroxy-butyryl-CoA reductase (aldehyde forming) | Ald | AAT66436 | *Clostridium beijerinckii* | cis-dihydrodiol derivative of phenylacetyl-CoA butyryl-CoA |
| | | | | | sucD | NP_904963.1 | *Porphyromonas gingivalis* | succinyl-CoA |
| | | | | | bphG | BAA03892.1 | *Pseudomonas* sp | acetaldehyde, propionaldehyde, butyraldehyde, isobutyraldehyde and formaldehyde |
| | | | | | Msed_0709 | YP_001190808.1 | *Metallosphaera sedula* | malonyl-CoA |
| | | | | | mcr | NP_378167 | *Sulfolobus tokodaii* | malonyl-CoA, methylmalonyl-CoA |
| D | 1.1.1.a | 3-hydroxy-butyraldehyde | 1,3-butanediol | 3-hydroxy-butyraldehyde reductase | alrA | BAB12273.1 | *Acinetobacter* sp. Strain M-1 | C2-C14 aldehydes |
| | | | | | ADH2 | NP_014032.1 | *Saccharymyces cerevisiae* | propionaldehyde, isobutyraldehyde, butyraldehyde, 2-methylbutyr-aldehyde, 3-methylbutyraldehyde, 2-phenylacetaldehyde |
| | | | | | yqhD | NP_417484.1 | *Escherichia coli* | acetaldehyde, malondialdehyde, propanaldehyde, butanaldehyde, and acrolein |
| | | | | | bdh I | NP_349892.1 | *Clostridium acetobutylicum* | butyraldehyde |
| | | | | | bdh II | NP_349891.1 | *Clostridium acetobutylicum* | butyraldehyde |
| | | | | | 4hbd | YP_726053.1 | *Ralstonia eutropha* H16 | succinate semialdehyde |
| | | | | | ADHI | AAR91477.1 | *Geobacillus thermoglucosidasius* M10EXG | ethanol, 1-butanol, 1-pentanol, 1-heptanol, 1-hexanol, 1-octanol, 2-propanol |
| | | | | | mmsb | P28811.1 | *Pseudomonas aeruginosa* | 3-hydroxy-butyraldehyde, malonic semialdehyde, methylmalonate semialdehyde |
| | | | | | P84067 | P84067 | *Thermus thermophilus* | methylmalonate semialdehyde |
| E | 1.1.1.c | 3-hydroxybutyryl-CoA | 1,3-butanediol | 3-hydroxy-butyryl-CoA reductase (alcohol forming) | adhE2 | AAK09379.1 | *Clostridium acetobutylicum* | butanoyl-CoA |
| | | | | | mcr | AAS20429.1 | *Chloroflexus aurantiacus* | malonyl-CoA |
| | | | | | FAR | AAD38039.1 | *Simmondsia chinensis* | long chain acyl-CoA |

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples and embodiments provided above, it should be understood that various modifications can be made without departing from the spirit of the invention.

SEQUENCE LISTING

<160> NUMBER OF SEQ ID NOS: 12

<210> SEQ ID NO 1
<211> LENGTH: 3525
<212> TYPE: DNA
<213> ORGANISM: Nocardia iowensis

<400> SEQUENCE: 1

| | |
|---|---:|
| atggcagtgg attcaccgga tgagcggcta cagcgccgca ttgcacagtt gtttgcagaa | 60 |
| gatgagcagg tcaaggccgc acgtccgctc gaagcggtga gcgcggcggt gagcgcgccc | 120 |
| ggtatgcggc tggcgcagat cgccgccact gttatggcgg ttacgccga ccgcccggcc | 180 |
| gccgggcagc gtgcgttcga actgaacacc gacgacgcga cgggccgcac ctcgctgcgg | 240 |
| ttacttcccc gattcgagac catcacctat cgcgaactgt ggcagcgagt cggcgaggtt | 300 |
| gccgcggcct ggcatcatga tcccgagaac cccttgcgcg caggtgattt cgtcgccctg | 360 |
| ctcggcttca ccagcatcga ctacgccacc ctcgacctgg ccgatatcca cctcggcgcg | 420 |
| gttaccgtgc cgttgcaggc cagcgcggcg gtgtcccagc tgatcgctat cctcaccgag | 480 |
| acttcgccgc ggctgctcgc ctcgaccccg gagcacctcg atgcggcggt cgagtgccta | 540 |
| ctcgcgggca ccacaccgga acgactggtg gtcttcgact accaccccga ggacgacgac | 600 |
| cagcgtgcgg ccttcgaatc cgcccgccgc gccttgccg acgcgggcag cttggtgatc | 660 |
| gtcgaaacgc tcgatgccgt gcgtgcccgg ggccgcgact accggccgc gccactgttc | 720 |
| gttcccgaca ccgacgacga cccgctggcc ctgctgatct acacctccgg cagcaccgga | 780 |
| acgccgaagg gcgcgatgta caccaatcgg ttggccgcca cgatgtggca ggggaactcg | 840 |
| atgctgcagg gaactcgca acgggtcggg atcaatctca actacatgcc gatgagccac | 900 |
| atcgccggtc gcatatcgct gttcggcgtg ctcgctcgcg gtggcaccgc atacttcgcg | 960 |
| gccaagagcg acatgtcgac actgttcgaa gacatcggct tggtacgtcc caccgagatc | 1020 |
| ttcttcgtcc cgcgcgtgtg cgacatggtc ttccagcgct atcagagcga gctggaccgg | 1080 |
| cgctcggtgg cgggcgccga cctggacacg ctcgatcggg aagtgaaagc cgacctccgg | 1140 |
| cagaactacc tcggtgggcg cttcctggtg gcggtcgtcg gcagcgcgcc gctggccgcg | 1200 |
| gagatgaaga cgttcatgga gtccgtcctc gatctgccac tgcacgacgg gtacgggtcg | 1260 |
| accgaggcgg gcgcaagcgt gctgctcgac aaccagatcc agcggccgcc ggtgctcgat | 1320 |
| tacaagctcg tcgacgtgcc cgaactgggt tacttccgca ccgaccggcc gcatccgcgc | 1380 |
| ggtgagctgt tgttgaaggc ggagaccacg attccgggct actacaagcg gcccgaggtc | 1440 |
| accgcggaga tcttcgacga ggacggcttc tacaagaccg gcgatatcgt ggccgagctc | 1500 |
| gagcacgatc ggctggtcta tgtcgaccgt cgcaacaatg tgctcaaact gtcgcagggc | 1560 |
| gagttcgtga ccgtcgccca tctcgaggcc gtgttcgcca gcagcccgct gatccggcag | 1620 |
| atcttcatct acggcagcag cgaacgttcc tatctgctcg cggtgatcgt ccccaccgac | 1680 |
| gacgcgctgc gcggccgcga caccgccacc ttgaaatcgg cactggccga atcgattcag | 1740 |
| cgcatcgcca aggacgcgaa cctgcagccc tacgagattc cgcgcgattt cctgatcgag | 1800 |
| accgagccgt tcaccatcgc caacggactg ctctccggca tcgcgaagct gctgcgcccc | 1860 |
| aatctgaagg aacgctacgg cgctcagctg gagcagatgt acaccgatct cgcgacaggc | 1920 |
| caggccgatg agctgctcgc cctcgccgc gaagccgccg acctgccggt gctcgaaacc | 1980 |
| gtcagccggg cagcgaaagc gatgctcggc gtcgcctccg ccgatatgcg tcccgacgcg | 2040 |
| cacttcaccg acctgggcgg cgattccctt tccgcgctgt cgttctcgaa cctgctgcac | 2100 |

```
gagatcttcg gggtcgaggt gccggtgggt gtcgtcgtca gcccggcgaa cgagctgcgc    2160
gatctggcga attacattga ggcggaacgc aactcgggcg cgaagcgtcc caccttcacc    2220
tcggtgcacg gcggcggttc cgagatccgc gccgccgatc tgaccctcga caagttcatc    2280
gatgcccgca ccctggccgc cgccgacagc attccgcacg cgccggtgcc agcgcagacg    2340
gtgctgctga ccggcgcgaa cggctacctc ggccggttcc tgtgcctgga atggctggag    2400
cggctggaca agacgggtgg cacgctgatc tgcgtcgtgc gcggtagtga cgcggccgcg    2460
gcccgtaaac ggctggactc ggcgttcgac agcggcgatc ccggcctgct cgagcactac    2520
cagcaactgg ccgcacggac cctggaagtc ctcgccggtg atatcggcga cccgaatctc    2580
ggtctggacg acgcgacttg gcagcggttg gccgaaaccg tcgacctgat cgtccatccc    2640
gccgcgttgg tcaaccacgt ccttccctac acccagctgt tcggcccaa tgtcgtcggc    2700 accgccgaaa tcgtccggtt ggcgatcacg gcgcggcgca agccggtcac ctacctgtcg    2760
accgtcggag tggccgacca ggtcgacccg cggagtatc aggaggacag cgacgtccgc    2820
gagatgagcg cggtgcgcgt cgtgcgcgag agttacgcca acggctacgg caacagcaag    2880
tgggcggggg aggtcctgct cgcgcgaagca cacgatctgt gtggcttgcc ggtcgcggtg    2940
ttccgttcgg acatgatcct ggcgcacagc cggtacgcgg gtcagctcaa cgtccaggac    3000
gtgttcaccc ggctgatcct cagcctggtc gccaccggca tcgcgccgta ctcgttctac    3060
cgaaccgacg cggacggcaa ccggcagcgg gcccactatg acggcttgcc ggcggacttc    3120
acggcggcgg cgatcaccgc gctcggcatc caagccaccg aaggcttccg gacctacgac    3180
gtgctcaatc cgtacgacga tggcatctcc ctcgatgaat cgtcgactg gctcgtcgaa    3240 tccggccacc cgatccagcg catcaccgac tacagcgact ggttccaccg tttcgagacg    3300
gcgatccgcg cgctgccgga aaagcaacgc caggcctcgg tgctgccgtt gctggacgcc    3360
taccgcaacc cctgcccggc ggtccgcggc gcgatactcc cggccaagga gttccaagcg    3420
gcggtgcaaa cagccaaaat cggtccggaa caggacatcc cgcatttgtc cgcgccactg    3480
atcgataagt acgtcagcga tctggaactg cttcagctgc tctaa    3525
```

<210> SEQ ID NO 2
<211> LENGTH: 1174
<212> TYPE: PRT
<213> ORGANISM: Nocardia iowensis

<400> SEQUENCE: 2

```
Met Ala Val Asp Ser Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
            20                  25                  30

Val Ser Ala Ala Val Ser Ala Pro Gly Met Arg Leu Ala Gln Ile Ala
        35                  40                  45

Ala Thr Val Met Ala Gly Tyr Ala Asp Arg Pro Ala Ala Gly Gln Arg
    50                  55                  60

Ala Phe Glu Leu Asn Thr Asp Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
```

-continued

```
            115                 120                 125
Ala Thr Leu Asp Leu Ala Asp Ile His Leu Gly Ala Val Thr Val Pro
        130                 135                 140
Leu Gln Ala Ser Ala Ala Val Ser Gln Leu Ile Ala Ile Leu Thr Glu
145                 150                 155                 160
Thr Ser Pro Arg Leu Leu Ala Ser Thr Pro Glu His Leu Asp Ala Ala
                165                 170                 175
Val Glu Cys Leu Leu Ala Gly Thr Thr Pro Glu Arg Leu Val Val Phe
                180                 185                 190
Asp Tyr His Pro Glu Asp Asp Gln Arg Ala Ala Phe Glu Ser Ala
                195                 200                 205
Arg Arg Arg Leu Ala Asp Ala Gly Ser Leu Val Ile Val Glu Thr Leu
        210                 215                 220
Asp Ala Val Arg Ala Arg Gly Arg Asp Leu Pro Ala Ala Pro Leu Phe
225                 230                 235                 240
Val Pro Asp Thr Asp Asp Pro Leu Ala Leu Leu Ile Tyr Thr Ser
                245                 250                 255
Gly Ser Thr Gly Thr Pro Lys Gly Ala Met Tyr Thr Asn Arg Leu Ala
                260                 265                 270
Ala Thr Met Trp Gln Gly Asn Ser Met Leu Gln Gly Asn Ser Gln Arg
        275                 280                 285
Val Gly Ile Asn Leu Asn Tyr Met Pro Met Ser His Ile Ala Gly Arg
        290                 295                 300
Ile Ser Leu Phe Gly Val Leu Ala Arg Gly Gly Thr Ala Tyr Phe Ala
305                 310                 315                 320
Ala Lys Ser Asp Met Ser Thr Leu Phe Glu Asp Ile Gly Leu Val Arg
                325                 330                 335
Pro Thr Glu Ile Phe Phe Val Pro Arg Val Cys Asp Met Val Phe Gln
                340                 345                 350
Arg Tyr Gln Ser Glu Leu Asp Arg Arg Ser Val Ala Gly Ala Asp Leu
                355                 360                 365
Asp Thr Leu Asp Arg Glu Val Lys Ala Asp Leu Arg Gln Asn Tyr Leu
        370                 375                 380
Gly Gly Arg Phe Leu Val Ala Val Val Gly Ser Ala Pro Leu Ala Ala
385                 390                 395                 400
Glu Met Lys Thr Phe Met Glu Ser Val Leu Asp Leu Pro Leu His Asp
                405                 410                 415
Gly Tyr Gly Ser Thr Glu Ala Gly Ala Ser Val Leu Leu Asp Asn Gln
                420                 425                 430
Ile Gln Arg Pro Pro Val Leu Asp Tyr Lys Leu Val Asp Val Pro Glu
        435                 440                 445
Leu Gly Tyr Phe Arg Thr Asp Arg Pro His Pro Arg Gly Glu Leu Leu
        450                 455                 460
Leu Lys Ala Glu Thr Thr Ile Pro Gly Tyr Tyr Lys Arg Pro Glu Val
465                 470                 475                 480
Thr Ala Glu Ile Phe Asp Glu Asp Gly Phe Tyr Lys Thr Gly Asp Ile
                485                 490                 495
Val Ala Glu Leu Glu His Asp Arg Leu Val Tyr Val Asp Arg Arg Asn
                500                 505                 510
Asn Val Leu Lys Leu Ser Gln Gly Glu Phe Val Thr Val Ala His Leu
        515                 520                 525
Glu Ala Val Phe Ala Ser Ser Pro Leu Ile Arg Gln Ile Phe Ile Tyr
        530                 535                 540
```

```
Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
                565                 570                 575

Glu Ser Ile Gln Arg Ile Ala Lys Asp Ala Asn Leu Gln Pro Tyr Glu
            580                 585                 590

Ile Pro Arg Asp Phe Leu Ile Glu Thr Glu Pro Phe Thr Ile Ala Asn
        595                 600                 605

Gly Leu Leu Ser Gly Ile Ala Lys Leu Leu Arg Pro Asn Leu Lys Glu
610                 615                 620

Arg Tyr Gly Ala Gln Leu Glu Gln Met Tyr Thr Asp Leu Ala Thr Gly
625                 630                 635                 640

Gln Ala Asp Glu Leu Leu Ala Leu Arg Arg Glu Ala Ala Asp Leu Pro
                645                 650                 655

Val Leu Glu Thr Val Ser Arg Ala Ala Lys Ala Met Leu Gly Val Ala
            660                 665                 670

Ser Ala Asp Met Arg Pro Asp Ala His Phe Thr Asp Leu Gly Gly Asp
        675                 680                 685

Ser Leu Ser Ala Leu Ser Phe Ser Asn Leu Leu His Glu Ile Phe Gly
690                 695                 700

Val Glu Val Pro Val Gly Val Val Ser Pro Ala Asn Glu Leu Arg
705                 710                 715                 720

Asp Leu Ala Asn Tyr Ile Glu Ala Glu Arg Asn Ser Gly Ala Lys Arg
            725                 730                 735

Pro Thr Phe Thr Ser Val His Gly Gly Ser Glu Ile Arg Ala Ala
                740                 745                 750

Asp Leu Thr Leu Asp Lys Phe Ile Asp Ala Arg Thr Leu Ala Ala Ala
            755                 760                 765

Asp Ser Ile Pro His Ala Pro Val Pro Ala Gln Thr Val Leu Leu Thr
        770                 775                 780

Gly Ala Asn Gly Tyr Leu Gly Arg Phe Leu Cys Leu Glu Trp Leu Glu
785                 790                 795                 800

Arg Leu Asp Lys Thr Gly Gly Thr Leu Ile Cys Val Val Arg Gly Ser
                805                 810                 815

Asp Ala Ala Ala Ala Arg Lys Arg Leu Asp Ser Ala Phe Asp Ser Gly
            820                 825                 830

Asp Pro Gly Leu Leu Glu His Tyr Gln Gln Leu Ala Ala Arg Thr Leu
        835                 840                 845

Glu Val Leu Ala Gly Asp Ile Gly Asp Pro Asn Leu Gly Leu Asp Asp
850                 855                 860

Ala Thr Trp Gln Arg Leu Ala Glu Thr Val Asp Leu Ile Val His Pro
865                 870                 875                 880

Ala Ala Leu Val Asn His Val Leu Pro Tyr Thr Gln Leu Phe Gly Pro
                885                 890                 895

Asn Val Val Gly Thr Ala Glu Ile Val Arg Leu Ala Ile Thr Ala Arg
            900                 905                 910

Arg Lys Pro Val Thr Tyr Leu Ser Thr Val Gly Val Ala Asp Gln Val
        915                 920                 925

Asp Pro Ala Glu Tyr Gln Glu Asp Ser Asp Val Arg Glu Met Ser Ala
        930                 935                 940

Val Arg Val Val Arg Glu Ser Tyr Ala Asn Gly Tyr Gly Asn Ser Lys
945                 950                 955                 960
```

```
Trp Ala Gly Glu Val Leu Leu Arg Glu Ala His Asp Leu Cys Gly Leu
                965                 970                 975
Pro Val Ala Val Phe Arg Ser Asp Met Ile Leu Ala His Ser Arg Tyr
            980                 985                 990
Ala Gly Gln Leu Asn Val Gln Asp  Val Phe Thr Arg Leu  Ile Leu Ser
        995                 1000                1005
Leu Val Ala Thr Gly Ile Ala  Pro Tyr Ser Phe Tyr  Arg Thr Asp
    1010                1015                1020
Ala Asp Gly Asn Arg Gln Arg  Ala His Tyr Asp Gly  Leu Pro Ala
    1025                1030                1035
Asp Phe Thr Ala Ala Ala Ile  Thr Ala Leu Gly Ile  Gln Ala Thr
    1040                1045                1050
Glu Gly Phe Arg Thr Tyr Asp  Val Leu Asn Pro Tyr  Asp Asp Gly
    1055                1060                1065
Ile Ser Leu Asp Glu Phe Val  Asp Trp Leu Val Glu  Ser Gly His
    1070                1075                1080
Pro Ile Gln Arg Ile Thr Asp  Tyr Ser Asp Trp Phe  His Arg Phe
    1085                1090                1095
Glu Thr Ala Ile Arg Ala Leu  Pro Glu Lys Gln Arg  Gln Ala Ser
    1100                1105                1110
Val Leu Pro Leu Leu Asp Ala  Tyr Arg Asn Pro Cys  Pro Ala Val
    1115                1120                1125
Arg Gly Ala Ile Leu Pro Ala  Lys Glu Phe Gln Ala  Ala Val Gln
    1130                1135                1140
Thr Ala Lys Ile Gly Pro Glu  Gln Asp Ile Pro His  Leu Ser Ala
    1145                1150                1155
Pro Leu Ile Asp Lys Tyr Val  Ser Asp Leu Glu Leu  Leu Gln Leu
    1160                1165                1170
Leu

<210> SEQ ID NO 3
<211> LENGTH: 669
<212> TYPE: DNA
<213> ORGANISM: Artificial Sequence
<220> FEATURE:
<223> OTHER INFORMATION: Description of Artificial Sequence: Synthetic
      codon optimized phosphpantetheine transferase
      polynucleotide

<400> SEQUENCE: 3
atgattgaaa ccattctgcc tgcaggcgtt gaaagcgcag aactgctgga atatccggaa      60
gatctgaaag cacatccggc agaagaacat ctgattgcca aaagcgttga aaaacgtcgt     120
cgtgatttta ttggtgcacg tcattgtgca cgtctggcac tggcagaact gggtgaacct     180
ccggttgcaa ttggtaaagg tgaacgtggt gcaccgattt ggcctcgtgg tgttgttggt     240
agcctgaccc cattgtgatgg ttatcgtgca gcagcagttg cacataaaat gcgctttcgc     300
agcattggta ttgatgcaga accgcatgca accctgccgg aaggtgttct ggatagcgtt     360
agcctgccgc cggaacgtga atggctgaaa accaccgata gcgcactgca tctggatcgt     420
ctgctgtttt gtgcaaaaga agccaccttat aaagcctggt ggccgctgac agcacgttgg     480
ctgggtttg aagaagccca tattacccttt gaaattgaag atggtagcgc agatagcggt     540
aatggcacct tcatagcga actgctggtt ccgggtcaga ccaatgatgg tggtacaccg     600
ctgctgagct tgatggtcg ttggctgatt gcagatggtt ttattctgac cgcaattgcc     660
tatgcctaa                                                              669
```

<210> SEQ ID NO 4
<211> LENGTH: 222
<212> TYPE: PRT
<213> ORGANISM: Artificial Sequence
<220> FEATURE:
<223> OTHER INFORMATION: Description of Artificial Sequence: Synthetic codon optimized phosphpantetheine transferase polypeptide

<400> SEQUENCE: 4

```
Met Ile Glu Thr Ile Leu Pro Ala Gly Val Glu Ser Ala Glu Leu Leu
1               5                   10                  15
Glu Tyr Pro Glu Asp Leu Lys Ala His Pro Ala Glu Glu His Leu Ile
            20                  25                  30
Ala Lys Ser Val Glu Lys Arg Arg Asp Phe Ile Gly Ala Arg His
        35                  40                  45
Cys Ala Arg Leu Ala Leu Ala Glu Leu Gly Glu Pro Pro Val Ala Ile
    50                  55                  60
Gly Lys Gly Glu Arg Gly Ala Pro Ile Trp Pro Arg Gly Val Val Gly
65                  70                  75                  80
Ser Leu Thr His Cys Asp Gly Tyr Arg Ala Ala Val Ala His Lys
                85                  90                  95
Met Arg Phe Arg Ser Ile Gly Ile Asp Ala Glu Pro His Ala Thr Leu
            100                 105                 110
Pro Glu Gly Val Leu Asp Ser Val Ser Leu Pro Pro Glu Arg Glu Trp
        115                 120                 125
Leu Lys Thr Thr Asp Ser Ala Leu His Leu Asp Arg Leu Leu Phe Cys
    130                 135                 140
Ala Lys Glu Ala Thr Tyr Lys Ala Trp Trp Pro Leu Thr Ala Arg Trp
145                 150                 155                 160
Leu Gly Phe Glu Glu Ala His Ile Thr Phe Glu Ile Glu Asp Gly Ser
                165                 170                 175
Ala Asp Ser Gly Asn Gly Thr Phe His Ser Glu Leu Leu Val Pro Gly
            180                 185                 190
Gln Thr Asn Asp Gly Gly Thr Pro Leu Leu Ser Phe Asp Gly Arg Trp
        195                 200                 205
Leu Ile Ala Asp Gly Phe Ile Leu Thr Ala Ile Ala Tyr Ala
    210                 215                 220
```

<210> SEQ ID NO 5
<211> LENGTH: 3522
<212> TYPE: DNA
<213> ORGANISM: Mycobacterium smegmatis

<400> SEQUENCE: 5

```
atgaccagcg atgttcacga cgccacagac ggcgtcaccg aaaccgcact cgacgacgag    60
cagtcgaccc gccgcatcgc cgagctgtac gccaccgatc ccgagttcgc cgccgccgca   120
ccgttgcccg ccgtggtcga cgcggcgcac aaacccgggc tgcggctggc agagatcctg   180
cagaccctgt tcaccggcta cggtgaccgc ccggcgctgg ataccgcgc ccgtgaactg   240 gccaccgacg agggcgggcg caccgtgacg cgtctgctgc cgcggttcga caccctcacc   300
tacgcccagg tgtggtcgcg cgtgcaagcg gtcgccgcgg ccctgcgcca caacttcgcg   360
cagccgatct accccggcga cgccgtcgcg acgatcggtt cgcgagtcc cgattacctg   420 acgctggatc tcgtatgcgc ctacctgggc ctcgtgagtg ttccgctgca gcacaacgca   480
```

```
ccggtcagcc ggctcgcccc gatcctggcc gaggtcgaac cgcggatcct caccgtgagc    540
gccgaatacc tcgacctcgc agtcgaatcc gtgcgggacg tcaactcggt gtcgcagctc    600
gtggtgttcg accatcaccc cgaggtcgac gaccaccgcg acgcactggc ccgcgcgcgt    660
gaacaactcg ccggcaaggg catcgccgtc accaccctgg acgcgatcgc cgacgagggc    720
gccgggctgc cggccgaacc gatctacacc gccgaccatg atcagcgcct cgcgatgatc    780
ctgtacacct cgggttccac cggcgcaccc aagggtgcga tgtacaccga ggcgatggtg    840
gcgcggctgt ggaccatgtc gttcatcacg ggtgacccca cgccggtcat caacgtcaac    900
ttcatgccgc tcaaccacct gggcgggcgc atccccattt ccaccgccgt gcagaacggt    960
ggaaccagtt acttcgtacc ggaatccgac atgtccacgc tgttcgagga tctcgcgctg   1020
gtgcgcccga ccgaactcgg cctggttccg cgcgtcgccg acatgctcta ccagcaccac   1080
ctcgccaccg tcgaccgcct ggtcacgcag ggcgccgacg aactgaccgc cgagaagcag   1140
gccggtgccg aactgcgtga gcaggtgctc ggcggacgcg tgatcaccgg attcgtcagc   1200
accgcaccgc tggccgcgga gatgagggcg ttcctcgaca tcaccctggg cgcacacatc   1260
gtcgacggct acgggctcac cgagaccggc gccgtgacac gcgacggtgt gatcgtgcgg   1320
ccaccggtga tcgactacaa gctgatcgac gttcccgaac tcggctactt cagcaccgac   1380
aagccctacc cgcgtggcga actgctggtc aggtcgcaaa cgctgactcc cgggtactac   1440
aagcgccccg aggtcaccgc gagcgtcttc gaccgggacg gctactacca caccggcgac   1500
gtcatggccg agaccgcacc cgaccacctg gtgtacgtgg accgtcgcaa caacgtcctc   1560
aaactcgcgc agggcgagtt cgtggcggtc gccaacctgg aggcggtgtt ctccggcgcg   1620
gcgctggtgc gccagatctt cgtgtacggc aacagcgagc gcagtttcct tctggccgtg   1680
gtggtcccga cgccggaggc gctcgagcag tacgatccgg ccgcgctcaa ggccgcgctg   1740
gccgactcgc tgcagcgcac cgcacgcgac gccgaactgc aatcctacga ggtgccggcc   1800
gatttcatcg tcgagaccga gccgttcagc gccgccaacg ggctgctgtc gggtgtcgga   1860
aaactgctgc ggcccaacct caaagaccgc tacgggcagc gcctggagca gatgtacgcc   1920
gatatcgcgg ccacgcaggc caaccagttg cgcgaactgc ggcgcgcggc cgccacacaa   1980
ccggtgatcg acaccctcac ccaggccgct gccacgatcc tcggcaccgg gagcgaggtg   2040
gcatccgacg cccacttcac cgacctgggc ggggattccc tgtcggcgct gacactttcg   2100
aacctgctga gcgatttctt cggtttcgaa gttcccgtcg gcaccatcgt gaacccggcc   2160
accaacctcg cccaactcgc ccagcacatc gaggcgcagc gcaccgcggg tgaccgcagg   2220
ccgagtttca ccaccgtgca cggcgcggac gccaccgaga tccgggcgag tgagctgacc   2280
ctggacaagt tcatcgacgc cgaaacgctc cgggccgcac cgggtctgcc caaggtcacc   2340
accgagccac ggacggtgtt gctctcgggc gccaacggct ggctgggccg gttcctcacg   2400
ttgcagtggc tggaacgcct ggcacctgtc ggcggcaccc tcatcacgat cgtgcggggc   2460
cgcgacgacg ccgcggcccg cgcacggctg acccaggcct acgacaccga tcccgagttg   2520
tcccgccgct tcgccgagct ggccgaccgc cacctgcggg tggtcgccgg tgacatcggc   2580
gacccgaatc tgggcctcac acccgagatc tggcaccggc tcgccgccga ggtcgacctg   2640
gtggtgcatc cggcagcgct ggtcaaccac gtgctcccct accggcagct gttcggcccc   2700
aacgtcgtgg gcacggccga ggtgatcaag ctggccctca ccgaacggat caagcccgtc   2760
acgtacctgt ccaccgtgtc ggtggccatg gggatccccg acttcgagga ggacggcgac   2820
atccggaccg tgagcccggt gcgcccgctc gacggcggat acgccaacgg ctacggcaac   2880
```

-continued

```
agcaagtggg ccggcgaggt gctgctgcgg gaggcccacg atctgtgcgg gctgcccgtg   2940
gcgacgttcc gctcggacat gatcctggcg catccgcgct accgcggtca ggtcaacgtg   3000
ccagacatgt tcacgcgact cctgttgagc ctcttgatca ccggcgtcgc gccgcggtcg   3060
ttctacatcg gagacggtga gcgcccgcgg gcgcactacc ccggcctgac ggtcgatttc   3120
gtggccgagg cggtcacgac gctcggcgcg cagcagcgcg agggatacgt gtcctacgac   3180
gtgatgaacc cgcacgacga cgggatctcc ctggatgtgt tcgtggactg gctgatccgg   3240
gcgggccatc cgatcgaccg ggtcgacgac tacgacgact gggtgcgtcg gttcgagacc   3300
gcgttgaccg cgcttcccga gaagcgccgc gcacagaccg tactgccgct gctgcacgcg   3360
ttccgcgctc cgcaggcacc gttgcgcggc gcacccgaac ccacggaggt gttccacgcc   3420
gcggtgcgca ccgcgaaggt gggcccggga gacatcccgc acctcgacga ggcgctgatc   3480
gacaagtaca tacgcgatct gcgtgagttc ggtctgatct aa                      3522
```

<210> SEQ ID NO 6
<211> LENGTH: 1173
<212> TYPE: PRT
<213> ORGANISM: Mycobacterium smegmatis

<400> SEQUENCE: 6

```
Met Thr Ser Asp Val His Asp Ala Thr Asp Gly Val Thr Glu Thr Ala
1               5                   10                  15

Leu Asp Asp Glu Gln Ser Thr Arg Arg Ile Ala Glu Leu Tyr Ala Thr
            20                  25                  30

Asp Pro Glu Phe Ala Ala Ala Ala Pro Leu Pro Ala Val Val Asp Ala
        35                  40                  45

Ala His Lys Pro Gly Leu Arg Leu Ala Glu Ile Leu Gln Thr Leu Phe
    50                  55                  60

Thr Gly Tyr Gly Asp Arg Pro Ala Leu Gly Tyr Arg Ala Arg Glu Leu
65                  70                  75                  80

Ala Thr Asp Glu Gly Gly Arg Thr Val Thr Arg Leu Leu Pro Arg Phe
                85                  90                  95

Asp Thr Leu Thr Tyr Ala Gln Val Trp Ser Arg Val Gln Ala Val Ala
            100                 105                 110

Ala Ala Leu Arg His Asn Phe Ala Gln Pro Ile Tyr Pro Gly Asp Ala
        115                 120                 125

Val Ala Thr Ile Gly Phe Ala Ser Pro Asp Tyr Leu Thr Leu Asp Leu
    130                 135                 140

Val Cys Ala Tyr Leu Gly Leu Val Ser Val Pro Leu Gln His Asn Ala
145                 150                 155                 160

Pro Val Ser Arg Leu Ala Pro Ile Leu Ala Glu Val Glu Pro Arg Ile
                165                 170                 175

Leu Thr Val Ser Ala Glu Tyr Leu Asp Leu Ala Val Glu Ser Val Arg
            180                 185                 190

Asp Val Asn Ser Val Ser Gln Leu Val Val Phe Asp His His Pro Glu
        195                 200                 205

Val Asp Asp His Arg Asp Ala Leu Ala Arg Ala Arg Glu Gln Leu Ala
    210                 215                 220

Gly Lys Gly Ile Ala Val Thr Thr Leu Asp Ala Ile Ala Asp Glu Gly
225                 230                 235                 240

Ala Gly Leu Pro Ala Glu Pro Ile Tyr Thr Ala Asp His Asp Gln Arg
                245                 250                 255
```

```
Leu Ala Met Ile Leu Tyr Thr Ser Gly Ser Thr Gly Ala Pro Lys Gly
            260                 265                 270

Ala Met Tyr Thr Glu Ala Met Val Ala Arg Leu Trp Thr Met Ser Phe
        275                 280                 285

Ile Thr Gly Asp Pro Thr Pro Val Ile Asn Val Asn Phe Met Pro Leu
    290                 295                 300

Asn His Leu Gly Gly Arg Ile Pro Ile Ser Thr Ala Val Gln Asn Gly
305                 310                 315                 320

Gly Thr Ser Tyr Phe Val Pro Glu Ser Asp Met Ser Thr Leu Phe Glu
                325                 330                 335

Asp Leu Ala Leu Val Arg Pro Thr Glu Leu Gly Leu Val Pro Arg Val
            340                 345                 350

Ala Asp Met Leu Tyr Gln His His Leu Ala Thr Val Asp Arg Leu Val
        355                 360                 365

Thr Gln Gly Ala Asp Glu Leu Thr Ala Glu Lys Gln Ala Gly Ala Glu
    370                 375                 380

Leu Arg Glu Gln Val Leu Gly Arg Val Ile Thr Gly Phe Val Ser
385                 390                 395                 400

Thr Ala Pro Leu Ala Ala Glu Met Arg Ala Phe Leu Asp Ile Thr Leu
                405                 410                 415

Gly Ala His Ile Val Asp Gly Tyr Gly Leu Thr Glu Thr Gly Ala Val
            420                 425                 430

Thr Arg Asp Gly Val Ile Val Arg Pro Val Ile Asp Tyr Lys Leu
    435                 440                 445

Ile Asp Val Pro Glu Leu Gly Tyr Phe Ser Thr Asp Lys Pro Tyr Pro
450                 455                 460

Arg Gly Glu Leu Leu Val Arg Ser Gln Thr Leu Thr Pro Gly Tyr Tyr
465                 470                 475                 480

Lys Arg Pro Glu Val Thr Ala Ser Val Phe Asp Arg Asp Gly Tyr Tyr
                485                 490                 495

His Thr Gly Asp Val Met Ala Glu Thr Ala Pro Asp His Leu Val Tyr
            500                 505                 510

Val Asp Arg Arg Asn Asn Val Leu Lys Leu Ala Gln Gly Glu Phe Val
    515                 520                 525

Ala Val Ala Asn Leu Glu Ala Val Phe Ser Gly Ala Ala Leu Val Arg
530                 535                 540

Gln Ile Phe Val Tyr Gly Asn Ser Glu Arg Ser Phe Leu Leu Ala Val
545                 550                 555                 560

Val Val Pro Thr Pro Glu Ala Leu Glu Gln Tyr Asp Pro Ala Ala Leu
                565                 570                 575

Lys Ala Ala Leu Ala Asp Ser Leu Gln Arg Thr Ala Arg Asp Ala Glu
            580                 585                 590

Leu Gln Ser Tyr Glu Val Pro Ala Asp Phe Ile Val Glu Thr Glu Pro
    595                 600                 605

Phe Ser Ala Ala Asn Gly Leu Leu Ser Gly Val Gly Lys Leu Leu Arg
610                 615                 620

Pro Asn Leu Lys Asp Arg Tyr Gly Gln Arg Leu Glu Gln Met Tyr Ala
625                 630                 635                 640

Asp Ile Ala Ala Thr Gln Ala Asn Gln Leu Arg Glu Leu Arg Arg Ala
                645                 650                 655

Ala Ala Thr Gln Pro Val Ile Asp Thr Leu Thr Gln Ala Ala Ala Thr
            660                 665                 670

Ile Leu Gly Thr Gly Ser Glu Val Ala Ser Asp Ala His Phe Thr Asp
```

```
                675                 680                 685
Leu Gly Gly Asp Ser Leu Ser Ala Leu Thr Leu Ser Asn Leu Leu Ser
690                 695                 700
Asp Phe Phe Gly Phe Glu Val Pro Val Gly Thr Ile Val Asn Pro Ala
705                 710                 715                 720
Thr Asn Leu Ala Gln Leu Ala Gln His Ile Glu Ala Gln Arg Thr Ala
                725                 730                 735
Gly Asp Arg Arg Pro Ser Phe Thr Thr Val His Gly Ala Asp Ala Thr
            740                 745                 750
Glu Ile Arg Ala Ser Glu Leu Thr Leu Asp Lys Phe Ile Asp Ala Glu
            755                 760                 765
Thr Leu Arg Ala Ala Pro Gly Leu Pro Lys Val Thr Thr Glu Pro Arg
770                 775                 780
Thr Val Leu Leu Ser Gly Ala Asn Gly Trp Leu Gly Arg Phe Leu Thr
785                 790                 795                 800
Leu Gln Trp Leu Glu Arg Leu Ala Pro Val Gly Gly Thr Leu Ile Thr
                805                 810                 815
Ile Val Arg Gly Arg Asp Asp Ala Ala Ala Arg Ala Arg Leu Thr Gln
            820                 825                 830
Ala Tyr Asp Thr Asp Pro Glu Leu Ser Arg Arg Phe Ala Glu Leu Ala
            835                 840                 845
Asp Arg His Leu Arg Val Val Ala Gly Asp Ile Gly Asp Pro Asn Leu
850                 855                 860
Gly Leu Thr Pro Glu Ile Trp His Arg Leu Ala Ala Glu Val Asp Leu
865                 870                 875                 880
Val Val His Pro Ala Ala Leu Val Asn His Val Leu Pro Tyr Arg Gln
                885                 890                 895
Leu Phe Gly Pro Asn Val Val Gly Thr Ala Glu Val Ile Lys Leu Ala
            900                 905                 910
Leu Thr Glu Arg Ile Lys Pro Val Thr Tyr Leu Ser Thr Val Ser Val
            915                 920                 925
Ala Met Gly Ile Pro Asp Phe Glu Glu Asp Gly Asp Ile Arg Thr Val
930                 935                 940
Ser Pro Val Arg Pro Leu Asp Gly Gly Tyr Ala Asn Gly Tyr Gly Asn
945                 950                 955                 960
Ser Lys Trp Ala Gly Glu Val Leu Leu Arg Glu Ala His Asp Leu Cys
                965                 970                 975
Gly Leu Pro Val Ala Thr Phe Arg Ser Asp Met Ile Leu Ala His Pro
            980                 985                 990
Arg Tyr Arg Gly Gln Val Asn Val Pro Asp Met Phe Thr Arg Leu Leu
            995                 1000                1005
Leu Ser Leu Leu Ile Thr Gly Val Ala Pro Arg Ser Phe Tyr Ile
        1010                1015                1020
Gly Asp Gly Glu Arg Pro Arg Ala His Tyr Pro Gly Leu Thr Val
        1025                1030                1035
Asp Phe Val Ala Glu Ala Val Thr Thr Leu Gly Ala Gln Gln Arg
        1040                1045                1050
Glu Gly Tyr Val Ser Tyr Asp Val Met Asn Pro His Asp Asp Gly
        1055                1060                1065
Ile Ser Leu Asp Val Phe Asp Trp Leu Ile Arg Ala Gly His
        1070                1075                1080
Pro Ile Asp Arg Val Asp Asp Tyr Asp Asp Trp Val Arg Arg Phe
        1085                1090                1095
```

```
Glu Thr  Ala Leu Thr Ala Leu  Pro Glu Lys Arg Arg  Ala Gln Thr
    1100                1105                1110

Val Leu  Pro Leu Leu His Ala  Phe Arg Ala Pro Gln  Ala Pro Leu
    1115                1120                1125

Arg Gly  Ala Pro Glu Pro Thr  Glu Val Phe His Ala  Ala Val Arg
    1130                1135                1140

Thr Ala  Lys Val Gly Pro Gly  Asp Ile Pro His Leu  Asp Glu Ala
    1145                1150                1155

Leu Ile  Asp Lys Tyr Ile Arg  Asp Leu Arg Glu Phe  Gly Leu Ile
    1160                1165                1170

<210> SEQ ID NO 7
<211> LENGTH: 3522
<212> TYPE: DNA
<213> ORGANISM: Mycobacterium avium

<400> SEQUENCE: 7
atgtcgactg ccacccatga cgaacgactc gaccgtcgcg tccacgaact catcgccacc     60
gacccgcaat tcgccgccgc ccaacccgac ccggcgatca ccgccgccct cgaacagccc    120
gggctgcggc tgccgcagat catccgcacc gtgctcgacg gctacgccga ccggccggcg    180
ctgggacagc gcgtggtgga gttcgtcacg gacgccaaga ccgggcgcac gtcggcgcag    240
ctgctccccc gcttcgagac catcacgtac agcgaagtag cgcagcgtgt ttcggcgctg    300
ggccgcgccc tgtccgacga cgcggtgcac cccggcgacc gggtgtgcgt gctgggcttc    360
aacagcgtcg actacgccac catcgacatg gcgctgggcg ccatcggcgc cgtctcggtg    420
ccgctgcaga ccagcgcggc aatcagctcg ctgcagccga tcgtggccga gaccgagccc    480
accctgatcg cgtccagcgt gaaccagctg tccgacgcgg tgcagctgat caccggcgcc    540
gagcaggcgc ccacccggct ggtggtgttc gactaccacc cgcaggtcga cgaccagcgc    600
gaggccgtcc aggacgccgc ggcgcggctg tccagcaccg gcgtggccgt ccagacgctg    660
gccgagctgc tggagcgcgg caaggacctg cccgccgtcg cggagccgcc cgccgacgag    720
gactcgctgg ccctgctgat ctacacctcc gggtccaccg gcgcccccaa gggcgcgatg    780
tacccacaga gcaacgtcgg caagatgtgg cgccgcggca gcaagaactg gttcggcgag    840
agcgccgcgt cgatcaccct gaacttcatg ccgatgagcc acgtgatggg ccgaagcatc    900
ctctacggca cgctgggcaa cggcggcacc gcctacttcg ccgcccgcag cgacctgtcc    960
accctgcttg aggacctcga gctggtgcgg cccaccgagc tcaacttcgt cccgcggatc   1020
tgggagacgc tgtacggcga attccagcgt caggtcgagc ggcggctctc cgaggccggg   1080
gacgccggcg aacgtcgcgc cgtcgaggcc gaggtgctgg ccgagcagcg ccagtacctg   1140
ctgggcgggc ggttcacctt cgcgatgacg ggctcggcgc ccatctcgcc ggagctgcgc   1200
aactgggtcg agtcgctgct cgaaatgcac ctgatggacg gctacggctc caccgaggcc   1260
ggaatggtgt tgttcgacgg ggagattcag cgcccgccgg tgatcgacta caagctggtc   1320
gacgtgccgg acctgggcta cttcagcacc gaccggccgc atccgcgcgg cgagctgctg   1380
ctgcgcaccg agaacatgtt cccgggctac tacaagcggg ccgaaaccac cgcgggcgtc   1440
ttcgacgagg acggctacta ccgcaccggc gacgtgttcg ccgagatcgc cccggaccgg   1500
ctggtctacg tcgaccgccg caacaacgtg ctcaagctgg cgcagggcga attcgtcacg   1560
ctggccaagc tggaggcggt gttcggcaac agcccgctga tccgccagat ctacgtctac   1620
ggcaacagcg cccagcccta cctgctggcg gtcgtggtgc ccaccgagga ggcgctggcc   1680
```

```
tcgggtgacc ccgagacgct caagcccaag atcgccgact cgctgcagca ggtcgccaag   1740
gaggccggcc tgcagtccta cgaggtgccg cgcgacttca tcatcgagac caccccgttc   1800
agcctggaaa acggtctgct gaccgggatc cggaagctgg cgtggccgaa actgaagcag   1860
cactacgggg aacggctgga gcagatgtac gccgacctgg ccgccggaca ggccaacgag   1920
ctggccgagc tgcgccgcaa cggtgcccag gcgccggtgt tgcagaccgt gagccgcgcc   1980
gcgggcgcca tgctgggttc ggccgcctcc gacctgtccc ccgacgccca cttcaccgat   2040
ctgggcggag actcgttgtc ggcgttgaca ttcggcaacc tgctgcgcga gatcttcgac   2100
gtcgacgtgc cggtaggcgt gatcgtcagc ccggccaacg acctggcggc catcgcgagc   2160
tacatcgagg ccgagcggca gggcagcaag cgcccgacgt tcgcctcggt gcacggccgg   2220
gacgcgaccg tggtgcgcgc cgccgacctg acgctggaca agttcctcga cgccgagacg   2280
ctggccgccg cgccgaacct gcccaagccg gccaccgagg tgcgcaccgt gctgctgacc   2340
ggcgccaccg gcttcctggg ccgctacctg gccctggaat ggctggagcg gatggacatg   2400
gtggacggca aggtcatcgc cctggtccgg gcccgctccg acgaggaggc acgcgcccgg   2460
ctggacaaga ccttcgacag cggcgacccg aaactgctcg cgcactacca gcagctggcc   2520
gccgatcacc tggaggtcat cgccggcgac aagggcgagg ccaatctggg cctgggccaa   2580
gacgtttggc aacgactggc cgacacggtc gacgtgatcg tcgaccccgc cgcgctggtc   2640
aaccacgtgt tgccgtacag cgagctgttc gggcccaacg ccctgggcac cgcggagctg   2700
atccggctgg cgctgacgtc caagcagaag ccgtacacct acgtgtccac catcggcgtg   2760
ggcgaccaga tcgagccggg caagttcgtc gagaacgccg acatccggca gatgagcgcc   2820
acccgggcga tcaacgacag ctacgccaac ggctatggca acagcaagtg ggccggcgag   2880
gtgctgctgc gcgaggcgca cgacctgtgc gggctgcccg tcgcggtgtt ccgctgcgac   2940
atgatcctgg ccgacaccac gtatgccggg cagctcaacc tgccggacat gttcacccgg   3000
ctgatgctga gcctggtggc caccgggatc gcgcccggct cgttctacga gctcgacgcc   3060
gacggcaacc ggcagcgggc gcactacgac ggcctgccgg tcgagttcat cgccgcggcg   3120
atctcgacgc tgggttcgca gatcaccgac agcgacaccg gcttccagac ctaccacgtg   3180
atgaacccct acgatgacgg cgtcggtctg gacgagtacg tcgattggct ggtggacgcc   3240
ggctattcga tcgagcggat cgccgactac tccgaatggc tgcggcggtt cgagacctcg   3300
ctgcgggccc tgccggaccg gcagcgccag tactcgctgc tgccgctgct gcacaactac   3360
cgcacgccgg agaagccgat caacgggtcg atagctccca ccgacgtgtt ccgggcagcg   3420
gtgcaggagg cgaaaatcgg ccccgacaaa gacattccgc acgtgtcgcc gccggtcatc   3480
gtcaagtaca tcaccgacct gcagctgctc gggctgctct aa                      3522
```

<210> SEQ ID NO 8
<211> LENGTH: 1173
<212> TYPE: PRT
<213> ORGANISM: Mycobacterium avium

<400> SEQUENCE: 8

```
Met Ser Thr Ala Thr His Asp Glu Arg Leu Asp Arg Arg Val His Glu
1               5                   10                  15

Leu Ile Ala Thr Asp Pro Gln Phe Ala Ala Ala Gln Pro Asp Pro Ala
            20                  25                  30

Ile Thr Ala Ala Leu Glu Gln Pro Gly Leu Arg Leu Pro Gln Ile Ile
        35                  40                  45
```

```
Arg Thr Val Leu Asp Gly Tyr Ala Asp Arg Pro Ala Leu Gly Gln Arg
    50                  55                  60

Val Val Glu Phe Val Thr Asp Ala Lys Thr Gly Arg Thr Ser Ala Gln
65                  70                  75                  80

Leu Leu Pro Arg Phe Glu Thr Ile Thr Tyr Ser Glu Val Ala Gln Arg
                85                  90                  95

Val Ser Ala Leu Gly Arg Ala Leu Ser Asp Ala Val His Pro Gly
            100                 105                 110

Asp Arg Val Cys Val Leu Gly Phe Asn Ser Val Asp Tyr Ala Thr Ile
            115                 120                 125

Asp Met Ala Leu Gly Ala Ile Gly Ala Val Ser Val Pro Leu Gln Thr
        130                 135                 140

Ser Ala Ala Ile Ser Ser Leu Gln Pro Ile Val Ala Glu Thr Glu Pro
145                 150                 155                 160

Thr Leu Ile Ala Ser Ser Val Asn Gln Leu Ser Asp Ala Val Gln Leu
                165                 170                 175

Ile Thr Gly Ala Glu Gln Ala Pro Thr Arg Leu Val Val Phe Asp Tyr
            180                 185                 190

His Pro Gln Val Asp Asp Gln Arg Glu Ala Val Gln Asp Ala Ala Ala
        195                 200                 205

Arg Leu Ser Ser Thr Gly Val Ala Val Gln Thr Leu Ala Glu Leu Leu
        210                 215                 220

Glu Arg Gly Lys Asp Leu Pro Ala Val Ala Glu Pro Pro Ala Asp Glu
225                 230                 235                 240

Asp Ser Leu Ala Leu Leu Ile Tyr Thr Ser Gly Ser Thr Gly Ala Pro
                245                 250                 255

Lys Gly Ala Met Tyr Pro Gln Ser Asn Val Gly Lys Met Trp Arg Arg
            260                 265                 270

Gly Ser Lys Asn Trp Phe Gly Glu Ser Ala Ala Ser Ile Thr Leu Asn
        275                 280                 285

Phe Met Pro Met Ser His Val Met Gly Arg Ser Ile Leu Tyr Gly Thr
        290                 295                 300

Leu Gly Asn Gly Gly Thr Ala Tyr Phe Ala Ala Arg Ser Asp Leu Ser
305                 310                 315                 320

Thr Leu Leu Glu Asp Leu Glu Leu Val Arg Pro Thr Glu Leu Asn Phe
                325                 330                 335

Val Pro Arg Ile Trp Glu Thr Leu Tyr Gly Glu Phe Gln Arg Gln Val
            340                 345                 350

Glu Arg Arg Leu Ser Glu Ala Gly Asp Ala Gly Glu Arg Arg Ala Val
        355                 360                 365

Glu Ala Glu Val Leu Ala Glu Gln Arg Gln Tyr Leu Leu Gly Gly Arg
        370                 375                 380

Phe Thr Phe Ala Met Thr Gly Ser Ala Pro Ile Ser Pro Glu Leu Arg
385                 390                 395                 400

Asn Trp Val Glu Ser Leu Leu Glu Met His Leu Met Asp Gly Tyr Gly
                405                 410                 415

Ser Thr Glu Ala Gly Met Val Leu Phe Asp Gly Glu Ile Gln Arg Pro
            420                 425                 430

Pro Val Ile Asp Tyr Lys Leu Val Asp Val Pro Asp Leu Gly Tyr Phe
        435                 440                 445

Ser Thr Asp Arg Pro His Pro Arg Gly Glu Leu Leu Leu Arg Thr Glu
        450                 455                 460
```

```
Asn Met Phe Pro Gly Tyr Tyr Lys Arg Ala Glu Thr Thr Ala Gly Val
465                 470                 475                 480

Phe Asp Glu Asp Gly Tyr Tyr Arg Thr Gly Asp Val Phe Ala Glu Ile
                485                 490                 495

Ala Pro Asp Arg Leu Val Tyr Val Asp Arg Arg Asn Asn Val Leu Lys
            500                 505                 510

Leu Ala Gln Gly Glu Phe Val Thr Leu Ala Lys Leu Glu Ala Val Phe
        515                 520                 525

Gly Asn Ser Pro Leu Ile Arg Gln Ile Tyr Val Tyr Gly Asn Ser Ala
    530                 535                 540

Gln Pro Tyr Leu Leu Ala Val Val Val Pro Thr Glu Glu Ala Leu Ala
545                 550                 555                 560

Ser Gly Asp Pro Glu Thr Leu Lys Pro Lys Ile Ala Asp Ser Leu Gln
                565                 570                 575

Gln Val Ala Lys Glu Ala Gly Leu Gln Ser Tyr Glu Val Pro Arg Asp
            580                 585                 590

Phe Ile Ile Glu Thr Thr Pro Phe Ser Leu Glu Asn Gly Leu Leu Thr
        595                 600                 605

Gly Ile Arg Lys Leu Ala Trp Pro Lys Leu Lys Gln His Tyr Gly Glu
    610                 615                 620

Arg Leu Glu Gln Met Tyr Ala Asp Leu Ala Ala Gly Gln Ala Asn Glu
625                 630                 635                 640

Leu Ala Glu Leu Arg Arg Asn Gly Ala Gln Ala Pro Val Leu Gln Thr
                645                 650                 655

Val Ser Arg Ala Ala Gly Ala Met Leu Gly Ser Ala Ala Ser Asp Leu
            660                 665                 670

Ser Pro Asp Ala His Phe Thr Asp Leu Gly Gly Asp Ser Leu Ser Ala
        675                 680                 685

Leu Thr Phe Gly Asn Leu Leu Arg Glu Ile Phe Asp Val Asp Val Pro
    690                 695                 700

Val Gly Val Ile Val Ser Pro Ala Asn Asp Leu Ala Ala Ile Ala Ser
705                 710                 715                 720

Tyr Ile Glu Ala Glu Arg Gln Gly Ser Lys Arg Pro Thr Phe Ala Ser
                725                 730                 735

Val His Gly Arg Asp Ala Thr Val Val Arg Ala Ala Asp Leu Thr Leu
            740                 745                 750

Asp Lys Phe Leu Asp Ala Glu Thr Leu Ala Ala Ala Pro Asn Leu Pro
        755                 760                 765

Lys Pro Ala Thr Glu Val Arg Thr Val Leu Leu Thr Gly Ala Thr Gly
770                 775                 780

Phe Leu Gly Arg Tyr Leu Ala Leu Glu Trp Leu Glu Arg Met Asp Met
785                 790                 795                 800

Val Asp Gly Lys Val Ile Ala Leu Val Arg Ala Arg Ser Asp Glu Glu
                805                 810                 815

Ala Arg Ala Arg Leu Asp Lys Thr Phe Asp Ser Gly Asp Pro Lys Leu
            820                 825                 830

Leu Ala His Tyr Gln Gln Leu Ala Ala Asp His Leu Glu Val Ile Ala
        835                 840                 845

Gly Asp Lys Gly Glu Ala Asn Leu Gly Leu Gly Gln Asp Val Trp Gln
    850                 855                 860

Arg Leu Ala Asp Thr Val Asp Val Ile Val Asp Pro Ala Ala Leu Val
865                 870                 875                 880

Asn His Val Leu Pro Tyr Ser Glu Leu Phe Gly Pro Asn Ala Leu Gly
```

```
                      885                 890                 895
Thr Ala Glu Leu Ile Arg Leu Ala Leu Thr Ser Lys Gln Lys Pro Tyr
            900                 905                 910
Thr Tyr Val Ser Thr Ile Gly Val Gly Asp Gln Ile Glu Pro Gly Lys
            915                 920                 925
Phe Val Glu Asn Ala Asp Ile Arg Gln Met Ser Ala Thr Arg Ala Ile
            930                 935                 940
Asn Asp Ser Tyr Ala Asn Gly Tyr Gly Asn Ser Lys Trp Ala Gly Glu
945                 950                 955                 960
Val Leu Leu Arg Glu Ala His Asp Leu Cys Gly Leu Pro Val Ala Val
                965                 970                 975
Phe Arg Cys Asp Met Ile Leu Ala Asp Thr Thr Tyr Ala Gly Gln Leu
            980                 985                 990
Asn Leu Pro Asp Met Phe Thr Arg Leu Met Leu Ser Leu Val Ala Thr
            995                 1000                1005
Gly Ile Ala Pro Gly Ser Phe Tyr Glu Leu Asp Ala Asp Gly Asn
            1010                1015                1020
Arg Gln Arg Ala His Tyr Asp Gly Leu Pro Val Glu Phe Ile Ala
            1025                1030                1035
Ala Ala Ile Ser Thr Leu Gly Ser Gln Ile Thr Asp Ser Asp Thr
            1040                1045                1050
Gly Phe Gln Thr Tyr His Val Met Asn Pro Tyr Asp Asp Gly Val
            1055                1060                1065
Gly Leu Asp Glu Tyr Val Asp Trp Leu Val Asp Ala Gly Tyr Ser
            1070                1075                1080
Ile Glu Arg Ile Ala Asp Tyr Ser Glu Trp Leu Arg Arg Phe Glu
            1085                1090                1095
Thr Ser Leu Arg Ala Leu Pro Asp Arg Gln Arg Gln Tyr Ser Leu
            1100                1105                1110
Leu Pro Leu Leu His Asn Tyr Arg Thr Pro Glu Lys Pro Ile Asn
            1115                1120                1125
Gly Ser Ile Ala Pro Thr Asp Val Phe Arg Ala Ala Val Gln Glu
            1130                1135                1140
Ala Lys Ile Gly Pro Asp Lys Asp Ile Pro His Val Ser Pro Pro
            1145                1150                1155
Val Ile Val Lys Tyr Ile Thr Asp Leu Gln Leu Leu Gly Leu Leu
            1160                1165                1170

<210> SEQ ID NO 9
<211> LENGTH: 3525
<212> TYPE: DNA
<213> ORGANISM: Mycobacterium marinum

<400> SEQUENCE: 9
atgtcgccaa tcacgcgtga agagcggctc gagcgccgca tccaggacct ctacgccaac      60
gacccgcagt tcgccgccgc caaacccgcc acggcgatca ccgcagcaat cgagcggccg     120
ggtctaccgc tacccagat catcgagacc gtcatgaccg atacgccga tcggccggct      180 ctcgctcagc gctcggtcga attcgtgacc gacgccggca ccggccacac cacgctgcga     240
ctgctccccc acttcgaaac catcagctac ggcgagcttt ggaccgcat cagcgcactg      300 gccgacgtgc tcagcaccga acagacggtg aaaccgggcg accgggtctg cttgttgggc     360
ttcaacagcg tcgactacgc cacgatcgac atgactttgg cgcggctggg cgcggtggcc     420
gtaccactgc agaccagcgc ggcgataacc cagctgcagc cgatcgtcgc cgagacccag     480
```

| | | | |
|---|---|---|---|
| cccaccatga | tcgcggccag | cgtcgacgca | ctcgctgacg ccaccgaatt ggctctgtcc | 540 |
| ggtcagaccg | ctacccgagt | cctggtgttc | gaccaccacc ggcaggttga cgcacaccgc | 600 |
| gcagcggtcg | aatccgcccg | ggagcgcctg | gccggctcgg cggtcgtcga accctggcc | 660 |
| gaggccatcg | cgcgcggcga | cgtgcccgc | ggtgcgtccg ccggctcggc gcccggcacc | 720 |
| gatgtgtccg | acgactcgct | cgcgctactg | atctacacct cgggcagcac gggtgcgccc | 780 |
| aagggcgcga | tgtaccccg | acgcaacgtt | gcgaccttct ggcgcaagcg cacctggttc | 840 |
| gaaggcggct | acgagccgtc | gatcacgctg | aacttcatgc caatgagcca cgtcatgggc | 900 |
| cgccaaatcc | tgtacggcac | gctgtgcaat | ggcggcaccg cctacttcgt ggcgaaaagc | 960 |
| gatctctcca | ccttgttcga | agacctggcg | ctggtgcggc ccaccgagct gaccttcgtg | 1020 |
| ccgcgcgtgt | gggacatggt | gttcgacgag | tttcagagtg aggtcgaccg ccgcctggtc | 1080 |
| gacggcgccg | accgggtcgc | gctcgaagcc | caggtcaagg ccgagatacg caacgacgtg | 1140 |
| ctcggtggac | ggtataccag | cgcactgacc | ggctccgccc ctatctccga cgagatgaag | 1200 |
| gcgtgggtcg | aggagctgct | cgacatgcat | ctggtcgagg gctacggctc caccgaggcc | 1260 |
| gggatgatcc | tgatcgacgg | agccattcgg | cgcccggcgg tactgactga caagctggtc | 1320 |
| gatgttcccg | acctgggtta | cttcctgacc | gaccggccac atccgcgggg cgagttgctg | 1380 |
| gtcaagaccg | atagtttgtt | cccgggctac | taccagcgag ccgaagtcac cgccgacgtg | 1440 |
| ttcgatgctg | acggcttcta | ccggaccggc | gacatcatgg ccgaggtcgg ccccgaacag | 1500 |
| ttcgtgtacc | tcgaccgccg | caacaacgtg | ttgaagctgt cgcagggcga gttcgtcacc | 1560 |
| gtctccaaac | tcgaagcggt | gtttggcgac | agcccactgg tacggcagat ctacatctac | 1620 |
| ggcaacagcg | cccgtgccta | cctgttggcg | gtgatcgtcc ccacccagga ggcgctggac | 1680 |
| gccgtgcctg | tcgaggagct | caaggcgcgg | ctgggcgact cgctgcaaga ggtcgcaaag | 1740 |
| gccgccggcc | tgcagtccta | cgagatcccg | cgcgacttca tcatcgaaac aacaccatgg | 1800 |
| acgctggaga | acggcctgct | caccggcatc | cgcaagttgg ccaggccgca gctgaaaaag | 1860 |
| cattacggcg | agcttctcga | gcagatctac | acggacctgg cacacggcca ggccgacgaa | 1920 |
| ctgcgctcgc | tgcgccaaag | cggtgccgat | gcgccggtgc tggtgacggt gtgccgtgcg | 1980 |
| gcggccgcgc | tgtttgggcgg | cagcgcctct | gacgtccagc ccgatgcgca cttcaccgat | 2040 |
| ttgggcggca | actcgctgtc | ggcgctgtcg | ttcaccaacc tgctgcacga gatcttcgac | 2100 |
| atcgaagtgc | cggtgggcgt | catcgtcagc | cccgccaacg acttgcaggc cctggccgac | 2160 |
| tacgtcgagg | cggctcgcaa | acccggctcg | tcacggccga ccttcgcctc ggtccacggc | 2220 |
| gcctcgaatg | ggcaggtcac | cgaggtgcat | gccggtgacc tgtccctgga caaattcatc | 2280 |
| gatgccgcaa | ccctggccga | agctccccgg | ctgcccgccg caaacaccca agtgcgcacc | 2340 |
| gtgctgctga | ccggcgccac | cggcttcctc | gggcgctacc tggccctgga atggctggag | 2400 |
| cggatggacc | tggtcgacgg | caaactgatc | tgcctggtcc gggccaagtc cgacaccgaa | 2460 |
| gcacgggcgc | ggctggacaa | gacgttcgac | agcggcgacc ccgaactgct ggcccactac | 2520 |
| cgcgcactgg | ccggcgacca | cctcgaggtg | ctcgccggtg acaagggcga agccgacctc | 2580 |
| ggactggacc | ggcagacctg | gcaacgcctg | gccgacacgg tcgacctgat cgtcgacccc | 2640 |
| gcggccctgg | tcaaccacgt | actgccatac | agccagctgt cgggcccaa cgcgctgggc | 2700 |
| accgccgagc | tgctgcggct | ggcgctcacc | tccaagatca gccctacag ctacacctcg | 2760 |
| acaatcggtg | tcgccgacca | gatcccgccg | tcggcgttca ccgaggacgc cgacatccgg | 2820 |

```
gtcatcagcg ccacccgcgc ggtcgacgac agctacgcca atggctactc gaacagcaag   2880
tgggccggcg aggtgctgtt gcgcgaggcg catgacctgt gtggcctgcc ggttgcggtg   2940
ttccgctgcg acatgatcct ggccgacacc acatgggcgg gacagctcaa tgtgccggac   3000
atgttcaccc ggatgatcct gagcctggcg gccaccggta tcgcgccggg ttcgttctat   3060
gagcttgcgg ccgacggcgc ccggcaacgc gcccactatg acggtctgcc cgtcgagttc   3120
atcgccgagg cgatttcgac tttgggtgcg cagagccagg atggtttcca cacgtatcac   3180
gtgatgaacc cctacgacga cggcatcgga ctcgacgagt tcgtcgactg gctcaacgag   3240
tccggttgcc ccatccagcg catcgctgac tatggcgact ggctgcagcg cttcgaaacc   3300
gcactgcgcg cactgcccga tcggcagcgg cacagctcac tgctgccgct gttgcacaac   3360
tatcggcagc cggagcggcc cgtccgcggg tcgatcgccc ctaccgatcg cttccgggca   3420
gcggtgcaag aggccaagat cggccccgac aaagacattc cgcacgtcgg cgcgccgatc   3480
atcgtgaagt acgtcagcga cctgcgccta ctcggcctgc tctaa                   3525
```

<210> SEQ ID NO 10
<211> LENGTH: 1174
<212> TYPE: PRT
<213> ORGANISM: Mycobacterium marinum

<400> SEQUENCE: 10

```
Met Ser Pro Ile Thr Arg Glu Glu Arg Leu Glu Arg Arg Ile Gln Asp
1               5                   10                  15

Leu Tyr Ala Asn Asp Pro Gln Phe Ala Ala Ala Lys Pro Ala Thr Ala
            20                  25                  30

Ile Thr Ala Ala Ile Glu Arg Pro Gly Leu Pro Leu Pro Gln Ile Ile
        35                  40                  45

Glu Thr Val Met Thr Gly Tyr Ala Asp Arg Pro Ala Leu Ala Gln Arg
    50                  55                  60

Ser Val Glu Phe Val Thr Asp Ala Gly Thr Gly His Thr Thr Leu Arg
65                  70                  75                  80

Leu Leu Pro His Phe Glu Thr Ile Ser Tyr Gly Glu Leu Trp Asp Arg
                85                  90                  95

Ile Ser Ala Leu Ala Asp Val Leu Ser Thr Glu Gln Thr Val Lys Pro
            100                 105                 110

Gly Asp Arg Val Cys Leu Leu Gly Phe Asn Ser Val Asp Tyr Ala Thr
        115                 120                 125

Ile Asp Met Thr Leu Ala Arg Leu Gly Ala Val Ala Val Pro Leu Gln
    130                 135                 140

Thr Ser Ala Ala Ile Thr Gln Leu Gln Pro Ile Val Ala Glu Thr Gln
145                 150                 155                 160

Pro Thr Met Ile Ala Ala Ser Val Asp Ala Leu Ala Asp Ala Thr Glu
                165                 170                 175

Leu Ala Leu Ser Gly Gln Thr Ala Thr Arg Val Leu Val Phe Asp His
            180                 185                 190

His Arg Gln Val Asp Ala His Arg Ala Ala Val Glu Ser Ala Arg Glu
        195                 200                 205

Arg Leu Ala Gly Ser Ala Val Val Glu Thr Leu Ala Glu Ala Ile Ala
    210                 215                 220

Arg Gly Asp Val Pro Arg Gly Ala Ser Ala Gly Ser Ala Pro Gly Thr
225                 230                 235                 240

Asp Val Ser Asp Asp Ser Leu Ala Leu Leu Ile Tyr Thr Ser Gly Ser
                245                 250                 255
```

```
Thr Gly Ala Pro Lys Gly Ala Met Tyr Pro Arg Arg Asn Val Ala Thr
            260                 265                 270

Phe Trp Arg Lys Arg Thr Trp Phe Glu Gly Gly Tyr Glu Pro Ser Ile
            275                 280                 285

Thr Leu Asn Phe Met Pro Met Ser His Val Met Gly Arg Gln Ile Leu
        290                 295                 300

Tyr Gly Thr Leu Cys Asn Gly Gly Thr Ala Tyr Phe Val Ala Lys Ser
305                 310                 315                 320

Asp Leu Ser Thr Leu Phe Glu Asp Leu Ala Leu Val Arg Pro Thr Glu
                325                 330                 335

Leu Thr Phe Val Pro Arg Val Trp Asp Met Val Phe Asp Glu Phe Gln
            340                 345                 350

Ser Glu Val Asp Arg Arg Leu Val Asp Gly Ala Asp Arg Val Ala Leu
            355                 360                 365

Glu Ala Gln Val Lys Ala Glu Ile Arg Asn Asp Val Leu Gly Gly Arg
    370                 375                 380

Tyr Thr Ser Ala Leu Thr Gly Ser Ala Pro Ile Ser Asp Glu Met Lys
385                 390                 395                 400

Ala Trp Val Glu Glu Leu Leu Asp Met His Leu Val Glu Gly Tyr Gly
            405                 410                 415

Ser Thr Glu Ala Gly Met Ile Leu Ile Asp Gly Ala Ile Arg Arg Pro
            420                 425                 430

Ala Val Leu Asp Tyr Lys Leu Val Asp Val Pro Asp Leu Gly Tyr Phe
            435                 440                 445

Leu Thr Asp Arg Pro His Pro Arg Gly Glu Leu Leu Val Lys Thr Asp
    450                 455                 460

Ser Leu Phe Pro Gly Tyr Tyr Gln Arg Ala Glu Val Thr Ala Asp Val
465                 470                 475                 480

Phe Asp Ala Asp Gly Phe Tyr Arg Thr Gly Asp Ile Met Ala Glu Val
            485                 490                 495

Gly Pro Glu Gln Phe Val Tyr Leu Asp Arg Arg Asn Asn Val Leu Lys
            500                 505                 510

Leu Ser Gln Gly Glu Phe Val Thr Val Ser Lys Leu Glu Ala Val Phe
            515                 520                 525

Gly Asp Ser Pro Leu Val Arg Gln Ile Tyr Ile Tyr Gly Asn Ser Ala
            530                 535                 540

Arg Ala Tyr Leu Leu Ala Val Ile Val Pro Thr Gln Glu Ala Leu Asp
545                 550                 555                 560

Ala Val Pro Val Glu Glu Leu Lys Ala Arg Leu Gly Asp Ser Leu Gln
            565                 570                 575

Glu Val Ala Lys Ala Ala Gly Leu Gln Ser Tyr Glu Ile Pro Arg Asp
            580                 585                 590

Phe Ile Ile Glu Thr Thr Pro Trp Thr Leu Glu Asn Gly Leu Leu Thr
            595                 600                 605

Gly Ile Arg Lys Leu Ala Arg Pro Gln Leu Lys Lys His Tyr Gly Glu
            610                 615                 620

Leu Leu Glu Gln Ile Tyr Thr Asp Leu Ala His Gly Gln Ala Asp Glu
625                 630                 635                 640

Leu Arg Ser Leu Arg Gln Ser Gly Ala Asp Ala Pro Val Leu Val Thr
                645                 650                 655

Val Cys Arg Ala Ala Ala Ala Leu Leu Gly Gly Ser Ala Ser Asp Val
            660                 665                 670
```

-continued

```
Gln Pro Asp Ala His Phe Thr Asp Leu Gly Gly Asp Ser Leu Ser Ala
            675                 680                 685

Leu Ser Phe Thr Asn Leu Leu His Glu Ile Phe Asp Ile Glu Val Pro
    690                 695                 700

Val Gly Val Ile Val Ser Pro Ala Asn Asp Leu Gln Ala Leu Ala Asp
705                 710                 715                 720

Tyr Val Glu Ala Ala Arg Lys Pro Gly Ser Ser Arg Pro Thr Phe Ala
                725                 730                 735

Ser Val His Gly Ala Ser Asn Gly Gln Val Thr Glu Val His Ala Gly
            740                 745                 750

Asp Leu Ser Leu Asp Lys Phe Ile Asp Ala Ala Thr Leu Ala Glu Ala
        755                 760                 765

Pro Arg Leu Pro Ala Ala Asn Thr Gln Val Arg Thr Val Leu Leu Thr
    770                 775                 780

Gly Ala Thr Gly Phe Leu Gly Arg Tyr Leu Ala Leu Glu Trp Leu Glu
785                 790                 795                 800

Arg Met Asp Leu Val Asp Gly Lys Leu Ile Cys Leu Val Arg Ala Lys
                805                 810                 815

Ser Asp Thr Glu Ala Arg Ala Arg Leu Asp Lys Thr Phe Asp Ser Gly
            820                 825                 830

Asp Pro Glu Leu Leu Ala His Tyr Arg Ala Leu Ala Gly Asp His Leu
        835                 840                 845

Glu Val Leu Ala Gly Asp Lys Gly Glu Ala Asp Leu Gly Leu Asp Arg
    850                 855                 860

Gln Thr Trp Gln Arg Leu Ala Asp Thr Val Asp Leu Ile Val Asp Pro
865                 870                 875                 880

Ala Ala Leu Val Asn His Val Leu Pro Tyr Ser Gln Leu Phe Gly Pro
                885                 890                 895

Asn Ala Leu Gly Thr Ala Glu Leu Leu Arg Leu Ala Leu Thr Ser Lys
            900                 905                 910

Ile Lys Pro Tyr Ser Tyr Thr Ser Thr Ile Gly Val Ala Asp Gln Ile
        915                 920                 925

Pro Pro Ser Ala Phe Thr Glu Asp Ala Asp Ile Arg Val Ile Ser Ala
    930                 935                 940

Thr Arg Ala Val Asp Asp Ser Tyr Ala Asn Gly Tyr Ser Asn Ser Lys
945                 950                 955                 960

Trp Ala Gly Glu Val Leu Leu Arg Glu Ala His Asp Leu Cys Gly Leu
                965                 970                 975

Pro Val Ala Val Phe Arg Cys Asp Met Ile Leu Ala Asp Thr Thr Trp
            980                 985                 990

Ala Gly Gln Leu Asn Val Pro Asp Met Phe Thr Arg Met Ile Leu Ser
        995                 1000                1005

Leu Ala Ala Thr Gly Ile Ala Pro Gly Ser Phe Tyr Glu Leu Ala
    1010                1015                1020

Ala Asp Gly Ala Arg Gln Arg Ala His Tyr Asp Gly Leu Pro Val
    1025                1030                1035

Glu Phe Ile Ala Glu Ala Ile Ser Thr Leu Gly Ala Gln Ser Gln
    1040                1045                1050

Asp Gly Phe His Thr Tyr His Val Met Asn Pro Tyr Asp Asp Gly
    1055                1060                1065

Ile Gly Leu Asp Glu Phe Val Asp Trp Leu Asn Glu Ser Gly Cys
    1070                1075                1080

Pro Ile Gln Arg Ile Ala Asp Tyr Gly Asp Trp Leu Gln Arg Phe
```

```
                1085                1090                1095
Glu Thr Ala Leu Arg Ala Leu Pro Asp Arg Gln Arg His Ser Ser
        1100                1105                1110

Leu Leu Pro Leu Leu His Asn Tyr Arg Gln Pro Glu Arg Pro Val
        1115                1120                1125

Arg Gly Ser Ile Ala Pro Thr Asp Arg Phe Arg Ala Ala Val Gln
        1130                1135                1140

Glu Ala Lys Ile Gly Pro Asp Lys Asp Ile Pro His Val Gly Ala
        1145                1150                1155

Pro Ile Ile Val Lys Tyr Val Ser Asp Leu Arg Leu Leu Gly Leu
        1160                1165                1170

Leu
```

<210> SEQ ID NO 11
<211> LENGTH: 3522
<212> TYPE: DNA
<213> ORGANISM: Artificial Sequence
<220> FEATURE:
<223> OTHER INFORMATION: Description of Artificial Sequence: Synthetic
      carboxylic acid reductase polynucleotide
      designated 891GA

<400> SEQUENCE: 11

```
atgagcaccg caacccatga tgaacgtctg gatcgtcgtg ttcatgaact gattgcaacc     60
gatccgcagt ttgcagcagc acagccggat cctgcaatta ccgcagcact ggaacagcct    120
ggtctgcgtc tgccgcagat tattcgtacc gttctggatg ttatgcaga tcgtccggca    180
ctgggtcagc gtgttgttga atttgttacc gatgcaaaaa ccggtcgtac cagcgcacag    240
ctgctgcctc gttttgaaac cattacctat agcgaagttg cacagcgtgt tagcgcactg    300
ggtcgtgcac tgagtgatga tgcagttcat ccgggtgatc gtgtttgtgt tctgggtttt    360
aatagcgttg attatgccac cattgatatg gcactgggtg caattggtgc agttagcgtt    420
ccgctgcaga ccagcgcagc aattagcagc ctgcagccga ttgttgcaga aaccgaaccg    480
accctgattg caagcagcgt taatcagctg tcagatgcag ttcagctgat taccggtgca    540
gaacaggcac cgacccgtct ggttgttttt gattatcatc gcaggttga tgatcagcgt    600
gaagcagttc aggatgcagc agcacgtctg agcagcaccg tgttgcagt tcagaccctg    660
gcagaactgc tggaacgtgg taaagatctg cctgcagttg cagaaccgcc tgcagatgaa    720
gatagcctgg cactgctgat ttataccagc ggtagcacag gtgcaccgaa aggtgcaatg    780
tatccgcaga gcaatgttgg taaaatgtgg cgtcgtggta caaaaattg gtttggtgaa    840
agcgcagcaa gcattaccct gaatttcatg ccgatgagcc atgttatggg tcgtagcatt    900
ctgtatggca ccctgggtaa tggtggcacc gcatattttg cagcacgtag cgatctgagc    960
accctgctgg aagatctgga actggttcgt ccgaccgaac tgaattttgt tccgcgtatt   1020
tgggaaaccc tgtatggtga atttcagcgt caggttgaac gtcgtctgag cgaagctggc   1080
gatgccggtg aacgtcgtgc agttgaagca gaagttctgg cagaacagcg tcagtatctg   1140
ctgggtggtc gttttaccct tgcaatgacc ggtagcgcac cgattagtcc ggaactgcgt   1200
aattgggttt aaagcctgct ggaaatgcat ctgatggatg ctatggtag caccgaagca   1260
ggtatggttc tgtttgatgg cgaaattcag cgtccgcctg tgattgatta taactggtt   1320
gatgttccgg atctgggtta ttttagcacc gatcgtccgc atccgcgtgg tgaactgctg   1380
ctgcgtaccg aaaatatgtt tccgggttat ataaacgtg cagaaccac cgcaggcgtt   1440
```

```
tttgatgaag atggttatta tcgtaccggt gatgtgtttg cagaaattgc accggatcgt    1500
ctggtttatg ttgatcgtcg taataatgtt ctgaaactgg cacagggtga atttgtgacc    1560
ctggccaaac tggaagcagt ttttggtaat agtccgctga ttcgtcagat ttatgtgtat    1620
ggtaatagcg cacagccgta tctgctggca gttgttgttc cgaccgaaga ggcactggca    1680
agcggtgatc cggaaaccct gaaaccgaaa attgcagata gcctgcagca ggttgcaaaa    1740
gaagcaggtc tgcagagcta tgaagttccg cgtgatttta ttattgaaac caccccgttt    1800
agcctggaaa atggtctgct gaccggtatt cgtaaactgg catggccgaa actgaaacag    1860
cattatggtg aacgcctgga acaaatgtat gcagatctgg cagcaggtca ggcaaatgaa    1920
ctggccgaac tgcgtcgtaa tggtgcacag gcaccggttc tgcagaccgt tagccgtgca    1980
gccggtgcaa tgctgggtag cgcagccagc gatctgagtc cggatgcaca ttttaccgat    2040
ctgggtggtg atagcctgag cgcactgacc tttggtaatc tgctgcgtga aatttttgat    2100
gttgatgtgc cggttggtgt tattgttagt ccggctaatg atctggcagc cattgcaagc    2160
tatattgaag cagaacgtca gggtagcaaa cgtccgacct tgcaagcgt tcatggtcgt    2220 gatgcaaccg ttgttcgtgc agcagatctg accctggata aatttctgga tgcagaaacc    2280
ctggcagcag caccgaatct gccgaaaccg gcaaccgaag ttcgtaccgt gctgctgaca    2340
ggtgcaaccg gttttctggg tcgttatctg gcactggaat ggctggaacg tatggatatg    2400
gttgatggta aagttattgc actggttcgt gcccgtagtg atgaagaagc acgcgcacgt    2460
ctggataaaa cctttgatag tggtgatccg aaactgctgg cacattatca gcagctggct    2520
gcagatcatc tggaagttat tgccggtgat aaaggtgaag caaatctggg tctgggtcag    2580
gatgtttggc agcgtctggc agataccgtt gatgttattg tggatccggc agcactggtt    2640
aatcatgttc tgccgtatag cgaactgttt ggtccgaatg cactgggcac cgcagaactg    2700
attcgtctgg cactgaccag caaacagaaa ccgtatacct atgttagcac cattggtgtt    2760
ggcgatcaga ttgaaccggg taaatttgtt gaaaatgccg atattcgtca gatgagcgca    2820
acccgtgcaa ttaatgatag ctatgcaaat ggctacggca atagcaaatg ggcaggcgaa    2880
gttctgctgc gcgaagcaca tgatctgtgt ggtctgccgg ttgcagtttt tcgttgtgat    2940
atgattctgg ccgataccac ctatgcaggt cagctgaatc tgccggatat gtttacccgt    3000
ctgatgctga gcctggttgc aaccggtatt gcaccgggta gcttttatga actggatgca    3060
gatggtaatc gtcagcgtgc acattatgat ggcctgccgg ttgaatttat tgcagcagcc    3120
attagcaccc tgggttcaca gattaccgat agcgatacccg ttttcagac ctatcatgtt    3180 atgaacccgt atgatgatgg tgttggtctg gatgaatatg ttgattggct ggttgatgcc    3240
ggttatagca ttgaacgtat tgcagattat agcgaatggc tgcgtcgctt tgaaacctca    3300
ctgcgtgcac tgccggatcg tcagcgccag tatagcctgc tgccgctgct gcacaattat    3360
cgtacaccgg aaaaaccgat taatggtagc attgcaccga ccgatgtttt tcgtgcagcc    3420
gttcaagaag ccaaaattgg tccggataaa gatattccgc atgttagccc tccggtgatt    3480
gttaaatata ttaccgatct gcagctgctg ggtctgctgt aa                      3522
```

<210> SEQ ID NO 12
<211> LENGTH: 1173
<212> TYPE: PRT
<213> ORGANISM: Artificial Sequence
<220> FEATURE:
<223> OTHER INFORMATION: Description of Artificial Sequence: Synthetic
      carboxylic acid reductase polypeptide
      designated 891GA

<400> SEQUENCE: 12

```
Met Ser Thr Ala Thr His Asp Glu Arg Leu Asp Arg Arg Val His Glu
1               5                   10                  15

Leu Ile Ala Thr Asp Pro Gln Phe Ala Ala Gln Pro Asp Pro Ala
            20                  25                  30

Ile Thr Ala Ala Leu Glu Gln Pro Gly Leu Arg Leu Pro Gln Ile Ile
            35                  40                  45

Arg Thr Val Leu Asp Gly Tyr Ala Asp Arg Pro Ala Leu Gly Gln Arg
    50                  55                  60

Val Val Glu Phe Val Thr Asp Ala Lys Thr Gly Arg Thr Ser Ala Gln
65                  70                  75                  80

Leu Leu Pro Arg Phe Glu Thr Ile Thr Tyr Ser Glu Val Ala Gln Arg
                85                  90                  95

Val Ser Ala Leu Gly Arg Ala Leu Ser Asp Asp Ala Val His Pro Gly
            100                 105                 110

Asp Arg Val Cys Val Leu Gly Phe Asn Ser Val Asp Tyr Ala Thr Ile
            115                 120                 125

Asp Met Ala Leu Gly Ala Ile Gly Ala Val Ser Val Pro Leu Gln Thr
    130                 135                 140

Ser Ala Ala Ile Ser Ser Leu Gln Pro Ile Val Ala Glu Thr Glu Pro
145                 150                 155                 160

Thr Leu Ile Ala Ser Ser Val Asn Gln Leu Ser Asp Ala Val Gln Leu
                165                 170                 175

Ile Thr Gly Ala Glu Gln Ala Pro Thr Arg Leu Val Val Phe Asp Tyr
            180                 185                 190

His Pro Gln Val Asp Asp Gln Arg Glu Ala Val Gln Asp Ala Ala Ala
            195                 200                 205

Arg Leu Ser Ser Thr Gly Val Ala Val Gln Thr Leu Ala Glu Leu Leu
    210                 215                 220

Glu Arg Gly Lys Asp Leu Pro Ala Val Ala Glu Pro Ala Asp Glu
225                 230                 235                 240

Asp Ser Leu Ala Leu Leu Ile Tyr Thr Ser Gly Ser Thr Gly Ala Pro
                245                 250                 255

Lys Gly Ala Met Tyr Pro Gln Ser Asn Val Gly Lys Met Trp Arg Arg
            260                 265                 270

Gly Ser Lys Asn Trp Phe Gly Glu Ser Ala Ala Ser Ile Thr Leu Asn
    275                 280                 285

Phe Met Pro Met Ser His Val Met Gly Arg Ser Ile Leu Tyr Gly Thr
290                 295                 300

Leu Gly Asn Gly Gly Thr Ala Tyr Phe Ala Ala Arg Ser Asp Leu Ser
305                 310                 315                 320

Thr Leu Leu Glu Asp Leu Glu Leu Val Arg Pro Thr Glu Leu Asn Phe
                325                 330                 335

Val Pro Arg Ile Trp Glu Thr Leu Tyr Gly Glu Phe Gln Arg Gln Val
            340                 345                 350

Glu Arg Arg Leu Ser Glu Ala Gly Asp Ala Gly Glu Arg Arg Ala Val
            355                 360                 365

Glu Ala Glu Val Leu Ala Glu Gln Arg Gln Tyr Leu Leu Gly Gly Arg
    370                 375                 380

Phe Thr Phe Ala Met Thr Gly Ser Ala Pro Ile Ser Pro Glu Leu Arg
385                 390                 395                 400

Asn Trp Val Glu Ser Leu Leu Glu Met His Leu Met Asp Gly Tyr Gly
```

-continued

```
                405                 410                 415
Ser Thr Glu Ala Gly Met Val Leu Phe Asp Gly Glu Ile Gln Arg Pro
            420                 425                 430

Pro Val Ile Asp Tyr Lys Leu Val Asp Val Pro Asp Leu Gly Tyr Phe
            435                 440                 445

Ser Thr Asp Arg Pro His Pro Arg Gly Glu Leu Leu Leu Arg Thr Glu
450                 455                 460

Asn Met Phe Pro Gly Tyr Tyr Lys Arg Ala Glu Thr Thr Ala Gly Val
465                 470                 475                 480

Phe Asp Glu Asp Gly Tyr Tyr Arg Thr Gly Asp Val Phe Ala Glu Ile
                485                 490                 495

Ala Pro Asp Arg Leu Val Tyr Val Asp Arg Arg Asn Asn Val Leu Lys
            500                 505                 510

Leu Ala Gln Gly Glu Phe Val Thr Leu Ala Lys Leu Glu Ala Val Phe
            515                 520                 525

Gly Asn Ser Pro Leu Ile Arg Gln Ile Tyr Val Tyr Gly Asn Ser Ala
530                 535                 540

Gln Pro Tyr Leu Leu Ala Val Val Pro Thr Glu Glu Ala Leu Ala
545                 550                 555                 560

Ser Gly Asp Pro Glu Thr Leu Lys Pro Lys Ile Ala Asp Ser Leu Gln
                565                 570                 575

Gln Val Ala Lys Glu Ala Gly Leu Gln Ser Tyr Glu Val Pro Arg Asp
            580                 585                 590

Phe Ile Ile Glu Thr Thr Pro Phe Ser Leu Glu Asn Gly Leu Leu Thr
595                 600                 605

Gly Ile Arg Lys Leu Ala Trp Pro Lys Leu Lys Gln His Tyr Gly Glu
610                 615                 620

Arg Leu Glu Gln Met Tyr Ala Asp Leu Ala Ala Gly Gln Ala Asn Glu
625                 630                 635                 640

Leu Ala Glu Leu Arg Arg Asn Gly Ala Gln Ala Pro Val Leu Gln Thr
                645                 650                 655

Val Ser Arg Ala Ala Gly Ala Met Leu Gly Ser Ala Ala Ser Asp Leu
            660                 665                 670

Ser Pro Asp Ala His Phe Thr Asp Leu Gly Gly Asp Ser Leu Ser Ala
            675                 680                 685

Leu Thr Phe Gly Asn Leu Leu Arg Glu Ile Phe Asp Val Asp Val Pro
            690                 695                 700

Val Gly Val Ile Val Ser Pro Ala Asn Asp Leu Ala Ala Ile Ala Ser
705                 710                 715                 720

Tyr Ile Glu Ala Glu Arg Gln Gly Ser Lys Arg Pro Thr Phe Ala Ser
                725                 730                 735

Val His Gly Arg Asp Ala Thr Val Val Arg Ala Ala Asp Leu Thr Leu
            740                 745                 750

Asp Lys Phe Leu Asp Ala Glu Thr Leu Ala Ala Pro Asn Leu Pro
            755                 760                 765

Lys Pro Ala Thr Glu Val Arg Thr Val Leu Leu Thr Gly Ala Thr Gly
            770                 775                 780

Phe Leu Gly Arg Tyr Leu Ala Leu Glu Trp Leu Glu Arg Met Asp Met
785                 790                 795                 800

Val Asp Gly Lys Val Ile Ala Leu Val Arg Ala Arg Ser Asp Glu Glu
                805                 810                 815

Ala Arg Ala Arg Leu Asp Lys Thr Phe Asp Ser Gly Asp Pro Lys Leu
            820                 825                 830
```

-continued

```
Leu Ala His Tyr Gln Gln Leu Ala Ala Asp His Leu Glu Val Ile Ala
            835                 840                 845
Gly Asp Lys Gly Glu Ala Asn Leu Gly Leu Gly Gln Asp Val Trp Gln
    850                 855                 860
Arg Leu Ala Asp Thr Val Asp Val Ile Val Asp Pro Ala Ala Leu Val
865                 870                 875                 880
Asn His Val Leu Pro Tyr Ser Glu Leu Phe Gly Pro Asn Ala Leu Gly
                885                 890                 895
Thr Ala Glu Leu Ile Arg Leu Ala Leu Thr Ser Lys Gln Lys Pro Tyr
            900                 905                 910
Thr Tyr Val Ser Thr Ile Gly Val Gly Asp Gln Ile Glu Pro Gly Lys
            915                 920                 925
Phe Val Glu Asn Ala Asp Ile Arg Gln Met Ser Ala Thr Arg Ala Ile
    930                 935                 940
Asn Asp Ser Tyr Ala Asn Gly Tyr Gly Asn Ser Lys Trp Ala Gly Glu
945                 950                 955                 960
Val Leu Leu Arg Glu Ala His Asp Leu Cys Gly Leu Pro Val Ala Val
                965                 970                 975
Phe Arg Cys Asp Met Ile Leu Ala Asp Thr Thr Tyr Ala Gly Gln Leu
            980                 985                 990
Asn Leu Pro Asp Met Phe Thr Arg Leu Met Leu Ser Leu Val Ala Thr
            995                1000                1005
Gly Ile Ala Pro Gly Ser Phe Tyr Glu Leu Asp Ala Asp Gly Asn
    1010                1015                1020
Arg Gln Arg Ala His Tyr Asp Gly Leu Pro Val Glu Phe Ile Ala
    1025                1030                1035
Ala Ala Ile Ser Thr Leu Gly Ser Gln Ile Thr Asp Ser Asp Thr
    1040                1045                1050
Gly Phe Gln Thr Tyr His Val Met Asn Pro Tyr Asp Asp Gly Val
    1055                1060                1065
Gly Leu Asp Glu Tyr Val Asp Trp Leu Val Asp Ala Gly Tyr Ser
    1070                1075                1080
Ile Glu Arg Ile Ala Asp Tyr Ser Glu Trp Leu Arg Arg Phe Glu
    1085                1090                1095
Thr Ser Leu Arg Ala Leu Pro Asp Arg Gln Arg Gln Tyr Ser Leu
    1100                1105                1110
Leu Pro Leu Leu His Asn Tyr Arg Thr Pro Glu Lys Pro Ile Asn
    1115                1120                1125
Gly Ser Ile Ala Pro Thr Asp Val Phe Arg Ala Ala Val Gln Glu
    1130                1135                1140
Ala Lys Ile Gly Pro Asp Lys Asp Ile Pro His Val Ser Pro Pro
    1145                1150                1155
Val Ile Val Lys Tyr Ile Thr Asp Leu Gln Leu Leu Gly Leu Leu
    1160                1165                1170
```

What is claimed is:

1. A non-naturally occurring microbial organism having a 1,3-butanediol (1,3-BDO) pathway, wherein said non-naturally occurring microbial organism comprises at least one exogenous nucleic acid encoding a 1,3-BDO pathway enzyme expressed in a sufficient amount to produce 1,3-BDO; said non-naturally occurring microbial organism further comprising:

(i) a reductive TCA pathway, wherein said microbial organism comprises at least one exogenous nucleic acid encoding a reductive TCA pathway enzyme selected from the group consisting of an ATP-citrate lyase, citrate lyase, a fumarate reductase, and an alpha-ketoglutarate:ferredoxin oxidoreductase; or (ii) a reductive TCA pathway, wherein said microbial organism comprises at least one exogenous nucleic acid encoding a reductive TCA pathway enzyme selected from the group consisting of a pyruvate:ferredoxin oxidoreductase, a phosphoenolpyruvate carboxylase, a phosphoenolpyruvate carboxykinase, a CO dehydrogenase, and an H$_2$ hydrogenase;
wherein said 1,3-BDO pathway comprises a pathway selected from the group consisting of:
(a) (1) a 2-amino-4-ketopentanoate (AKP) thiolase; (2) an AKP dehydrogenase; (3) a 2-amino-4-hydroxypentanoate aminotransferase or oxidoreductase (deaminating); (4) a 2-oxo-4-hydroxypentanoate decarboxylase; and (5) a 3-hydroxybutyraldehyde reductase;
(b) (1) an AKP thiolase; (2) an AKP aminotransferase or oxidoreductase (deaminating); (3) a 2,4-dioxopentanoate decarboxylase; (4) a 3-oxobutyraldehyde reductase (ketone reducing); and (5) a 3-hydroxybutyraldehyde reductase;
(c) (1) an AKP thiolase; (2) an AKP aminotransferase or oxidoreductase (deaminating); (3) a 2,4-dioxopentanoate decarboxylase; (4) a 3-oxobutyraldehyde reductase (aldehyde reducing); and (5) a 4-hydroxy-2-butanone reductase;
(d) (1) an AKP thiolase; (2) an AKP decarboxylase; (3) a 4-aminobutan-2-one aminotransferase or oxidoreductase (deaminating); (4) a 3-oxobutyraldehyde reductase (ketone reducing); and (5) a 3-hydroxybutyraldehyde reductase;
(e) (1) an AKP thiolase; (2) an AKP decarboxylase; (3) a 4-aminobutan-2-one aminotransferase or oxidoreductase (deaminating); (4) a 3-oxobutyraldehyde reductase (aldehyde reducing); and (5) a 4-hydroxy-2-butanone reductase;
(f) (1) an AKP thiolase; (2) an AKP decarboxylase; (3) a 4-aminobutan-2-one ammonia-lyase; (4) a butenone hydratase; and (5) a 4-hydroxy-2-butanone reductase;
(g) (1) an AKP thiolase; (2) an AKP ammonia-lyase; (3) an acetylacrylate decarboxylase; (4) a butenone hydratase; and (5) a 4-hydroxy-2-butanone reductase;
(h) (1) an acetoacetyl-CoA reductase (CoA-dependent, aldehyde forming); (2) a 3-oxobutyraldehyde reductase (ketone reducing); and (3) a 3-hydroxybutyraldehyde reductase;
(i) (1) an acetoacetyl-CoA reductase (CoA dependent, alcohol forming) and (2) a 4-hydroxy-2-butanone reductase;
(j) (1) an acetoacetyl-CoA reductase (CoA-dependent, aldehyde forming); (2) a 3-oxobutyraldehyde reductase (aldehyde reducing); and (3) a 4-hydroxy-2-butanone reductase;
(k) (1) an acetoacetyl-CoA reductase (ketone reducing) and (2) a 3-hydroxybutyryl-CoA reductase (alcohol forming);
(l) (1) an acetoacetyl-CoA reductase (ketone reducing); (2) a 3-hydroxybutyryl-CoA reductase (aldehyde forming); and (3) a 3-hydroxybutyraldehyde reductase;
(m) (1) a 4-hydroxybutyryl-CoA dehydratase; (2) a crotonase; and (3) a 3-hydroxybutyryl-CoA reductase (alcohol forming); and
(n) (1) a 4-hydroxybutyryl-CoA dehydratase; (2) a crotonase; (3) a 3-hydroxybutyryl-CoA reductase (aldehyde forming); and (4) a 3-hydroxybutyraldehyde reductase;
(o) (1) a succinyl-CoA transferase, a succinyl-CoA synthetase or a succinyl-CoA ligase, (2) a succinyl-CoA reductase (aldehyde forming), (3) a 4-hydroxybutyrate dehydrogenase, (4) a 4-hydroxybutyrate kinase, (5) a phosphotrans-4-hydroxybutyrylase, (6) a 4-hydroxybutyryl-CoA dehydratase, (7) a crotonase, (8) a 3-hydroxybutyryl-CoA reductase (aldehyde forming), and (9) a 3-hydroxybutanal reductase;

(p) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase; (6) a crotonase, (7) a 3-hydroxybutyryl-CoA reductase (aldehyde forming), and (8) a 3-hydroxybutanal reductase;
(q) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA reductase (aldehyde forming), and (7) a 3-hydroxybutanal reductase;
(r) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, and (7) a 3-hydroxybutyryl-CoA reductase (alcohol forming);
(s) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, and (6) a 3-hydroxybutyryl-CoA reductase (alcohol forming);
(t) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA hydrolase, transferase or synthetase, and (8) a 3-hydroxybutyrate reductase;
(u) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA hydrolase, transferase or synthetase, and (7) a 3-hydroxybutyrate reductase;
(v) (1) a succinate reductase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA reductase (aldehyde forming), and (8) a 3-hydroxybutanal reductase;
(w) (1) a succinate reductase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA reductase (aldehyde forming), (7) a 3-hydroxybutanal reductase;

(x) (1) a succinate reductase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, and (7) a 3-hydroxybutyryl-CoA reductase (alcohol forming);

(y) (1) a succinate reductase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, and (6) a 3-hydroxybutyryl-CoA reductase (alcohol forming);

(z) (1) a succinate reductase, (2) a 4-hydroxybutyrate dehydrogenase, (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA hydrolase, transferase or synthetase, and (8) a 3-hydroxybutyrate reductase;

(aa) (1) a succinate reductase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA hydrolase, transferase or synthetase, and (7) a 3-hydroxybutyrate reductase;

(bb) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (5) a 4-hydroxybutyrate kinase, (6) a pPhosphotrans-4-hydroxybutyrylase, (7) a 4-hydroxybutyryl-CoA dehydratase, (8) a crotonase, and (9) a 3-hydroxybutyryl-CoA reductase (alcohol forming);

(cc) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (4) a 4-hydroxybutyrate kinase, (5) a phosphotrans-4-hydroxybutyrylase, (6) a 4-hydroxybutyryl-CoA dehydratase, (7) a crotonase, (8) a 3-hydroxybutyryl-CoA hydrolase, transferase or synthetase, and (9) a 3-hydroxybutyrate reductase;

(dd) (1) a succinyl-CoA transferase, succinyl-CoA synthetase or succinyl-CoA ligase, (2) a succinyl-CoA reductase (alcohol forming), (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA reductase (aldehyde forming), and (8) a 3-hydroxybutanal reductase;

(ee) (1) a succinyl-CoA transferase, succinyl-CoA synthetase or succinyl-CoA ligase, (2) a succinyl-CoA reductase (alcohol forming), (3) a 4-hydroxybutyrate kinase, (4) a phosphotrans-4-hydroxybutyrylase, (5) a 4-hydroxybutyryl-CoA dehydratase, (6) a crotonase, and (7) a 3-hydroxybutyryl-CoA reductase (alcohol forming);

(ff) (1) a succinyl-CoA transferase, succinyl-CoA synthetase or succinyl-CoA ligase, (2) a succinyl-CoA reductase (alcohol forming), (3) a 4-hydroxybutyrate kinase, (4) a phosphotrans-4-hydroxybutyrylase, (5) a 4-hydroxybutyryl-CoA dehydratase, (6) a crotonase, (7) a 3-hydroxybutyryl-CoA hydrolase, transferase or synthetase, and (8) a 3-hydroxybutyrate reductase;

(gg) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (4) a 4-hydroxybutyryl-CoA transferase, or 4-hydroxybutyryl-CoA synthetase, (5) a 4-hydroxybutyryl-CoA dehydratase, (6) a crotonase, (7) a 3-hydroxybutyryl-CoA reductase (aldehyde forming), and (8) a 3-hydroxybutanal reductase;

(hh) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (4) a 4-hydroxybutyryl-CoA transferase or 4-hydroxybutyryl-CoA synthetase, (5) a 4-hydroxybutyryl-CoA dehydratase, (6) a crotonase, and (7) a 3-hydroxybutyryl-CoA reductase (alcohol forming);

(ii) (1) a succinyl-CoA transferase, succinyl-CoA synthetase or succinyl-CoA ligase, (2) a succinyl-CoA reductase (aldehyde forming), (3) a 4-hydroxybutyrate dehydrogenase, (4) a 4-hydroxybutyryl-CoA transferase or 4-hydroxybutyryl-CoA synthetase, (5) a 4-hydroxybutyryl-CoA dehydratase, (6) a crotonase, (7) a 3-hydroxybutyryl-CoA hydrolase, transferase or synthetase, (8) a 3-hydroxybutyrate reductase;

(jj) (1) a succinyl-CoA transferase, succinyl-CoA synthetase or succinyl-CoA ligase, (2) a succinyl-CoA reductase (alcohol forming), (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA reductase (aldehyde forming), and (7) a 3-hydroxybutanal reductase;

(kk) (1) a succinyl-CoA transferase, succinyl-CoA synthetase or succinyl-CoA ligase, (2) a succinyl-CoA reductase (alcohol forming), (3) a 4-hydroxybutyryl-CoA transferase or 4-hydroxybutyryl-CoA synthetase, (4) a 4-hydroxybutyryl-CoA dehydratase, (5) a crotonase, and (6) a 3-hydroxybutyryl-CoA reductase (alcohol forming);

(ll) (1) a succinyl-CoA transferase, succinyl-CoA synthetase or succinyl-CoA ligase, (2) a succinyl-CoA reductase (alcohol forming), (3) a 4-hydroxybutyryl-CoA transferase or 4-hydroxybutyryl-CoA synthetase, (5) a 4-hydroxybutyryl-CoA dehydratase, (6) a crotonase, (7) a 3-hydroxybutyryl-CoA hydrolase, transferase or synthetase, and (8) a 3-hydroxybutyrate reductase;

(mm) (1) (i) an alpha-ketoglutarate decarboxylase, or (ii) (a) a glutamate dehydrogenase and/or a glutamate transaminase, (b) a glutamate decarboxylase, and (c) a 4-aminobutyrate dehydrogenase and/or a 4-aminobutyrate transaminase, (2) a 4-hydroxybutyrate dehydrogenase, (3) a 4-hydroxybutyryl-CoA transferase or 4-hydroxybutyryl-CoA synthetase, (4) a 4-hydroxybutyryl-CoA dehydratase, (5) a crotonase, (6) a 3-hydroxybutyryl-CoA reductase (aldehyde forming), and (7) 3-hydroxybutyraldehyde reductase; and (nn) (1) a 4-hydroxybutyryl-CoA dehydratase, (2) a crotonase, (3) a 3-hydroxybutyryl-CoA hydrolase, transferase or synthetase, and (4) a 3-hydroxybutyrate reductase.

2. The non-naturally occurring microbial organism of claim 1, wherein said non-naturally occurring microbial organism further comprises an exogenous nucleic acid encoding an enzyme selected from the group consisting of a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, a ferredoxin, and combinations thereof.

3. The non-naturally occurring microbial organism of claim 1, wherein said non-naturally occurring microbial organism further comprises an exogenous nucleic acid encoding an enzyme selected from the group consisting of a succinyl-CoA synthetase, a succinyl-CoA transferase, a fumarase, a malate dehydrogenase, and combinations thereof.

4. The non-naturally occurring microbial organism of claim 1, wherein said non-naturally occurring microbial organism comprises two, three, four, five, six, seven, eight or nine exogenous nucleic acids, each encoding a 1,3-BDO pathway enzyme.

5. The non-naturally occurring microbial organism of claim 1, wherein said non-naturally occurring microbial organism comprises exogenous nucleic acids encoding each of the enzymes of at least one of the 1,3-BDO pathways selected from the group consisting of (a)-(mm), and (nn).

6. The non-naturally occurring microbial organism of claim 1, wherein said at least one exogenous nucleic acid is a heterologous nucleic acid.

7. The non-naturally occurring microbial organism of claim 1, wherein said non-naturally occurring microbial organism is in a substantially anaerobic culture medium.

8. A method for producing 1,3-BDO, comprising culturing a non-naturally occurring microbial organism according to claim 1, under conditions and for a sufficient period of time to produce 1,3-BDO.

9. The method of claim 8, wherein said non-naturally occurring microbial organism further comprises an exogenous nucleic acid encoding an enzyme selected from the group consisting of a pyruvate:ferredoxin oxidoreductase, an aconitase, an isocitrate dehydrogenase, a succinyl-CoA synthetase, a succinyl-CoA transferase, a fumarase, a malate dehydrogenase, an acetate kinase, a phosphotransacetylase, an acetyl-CoA synthetase, an NAD(P)H:ferredoxin oxidoreductase, ferredoxin, and combinations thereof.

10. The method of claim 8, wherein said non-naturally occurring microbial organism further comprises an exogenous nucleic acid encoding an enzyme selected from the group consisting of an aconitase, an isocitrate dehydrogenase, a succinyl-CoA synthetase, a succinyl-CoA transferase, a fumarase, a malate dehydrogenase, and combinations thereof.

11. The method of claim 8, wherein said non-naturally occurring microbial organism comprises two, three, four, five, six, seven, eight or nine exogenous nucleic acids, each encoding a 1,3-BDO pathway enzyme.

12. The method of claim 8, wherein said non-naturally occurring microbial organism comprises exogenous nucleic acids encoding each of the enzymes of at least one of the 1,3-BDO pathways selected from the group consisting of (a)-(mm), and (nn).

13. The method of claim 8, wherein said at least one exogenous nucleic acid is a heterologous nucleic acid.

14. The method of claim 8, wherein said non-naturally occurring microbial organism is in a substantially anaerobic culture medium.

* * * * *